(12) United States Patent
Volpe et al.

(10) Patent No.: US 12,115,176 B2
(45) Date of Patent: *Oct. 15, 2024

(54) METHODS AND COMPOSITIONS RELATING TO CLBP INHIBITION

(71) Applicant: PRESIDENT AND FELLOWS OF HARVARD COLLEGE, Cambridge, MA (US)

(72) Inventors: Matthew R. Volpe, Cambridge, MA (US); Emily Balskus, Cambridge, MA (US)

(73) Assignee: PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 20 days.

This patent is subject to a terminal disclaimer.

(21) Appl. No.: 18/108,164

(22) Filed: Feb. 10, 2023

(65) Prior Publication Data

US 2023/0190775 A1 Jun. 22, 2023

Related U.S. Application Data

(62) Division of application No. 17/771,949, filed as application No. PCT/US2022/011768 on Jan. 10, 2022, now Pat. No. 11,617,759.

(60) Provisional application No. 63/195,211, filed on Jun. 1, 2021, provisional application No. 63/135,825, filed on Jan. 11, 2021.

(51) Int. Cl.
*A61K 31/69* (2006.01)
(52) U.S. Cl.
CPC .................................. *A61K 31/69* (2013.01)
(58) Field of Classification Search
CPC ..................................................... A61K 31/69
See application file for complete search history.

(56) References Cited

U.S. PATENT DOCUMENTS

| | | | |
|---|---|---|---|
| 11,617,759 B2* | 4/2023 | Volpe | A61P 31/04 514/64 |
| 2020/0055836 A1 | 2/2020 | Volpe et al. | |
| 2021/0010051 A1 | 1/2021 | Watanabe et al. | |

FOREIGN PATENT DOCUMENTS

| | | |
|---|---|---|
| WO | 2013033461 A1 | 7/2013 |
| WO | 2020037009 A1 | 2/2020 |
| WO | 2021252640 A1 | 12/2021 |

OTHER PUBLICATIONS

Baker et al. "Therapeutic potential of boron-containing compounds." Future Medicinal Chemistry 1.7 (2009): 1275-1288.
Cougnoux et al. "Small-molecule inhibitors prevent the genotoxic and protumoural effects induced by colibactin-producing bacteria." Gut 65(2): 278-285 (2016).
Dziubanska-Kusibab et al. "Colibactin DNA damage signature indicates causative role in colorectal cancer." bioRxiv: 819854 (2019).
Lee-Six et al. "The landscape of somatic mutation in normal colorectal epithelial cells." Nature 574(7779): 532-537 (2019).
Volpe et al. "In vitro characterization of the colibactin-activating peptidase ClbP enables development of a fluorogenic activity probe." ACS Chemical Biology 14(6): 1097-1101 (2019).
Wisclicenus "Adolph Strecker's Short Textbook of Organic Chemistry." Spottiswoode: London, pp. 38-39 (1881).

* cited by examiner

*Primary Examiner* — James D. Anderson
(74) *Attorney, Agent, or Firm* — Nixon Peabody LLP; David S. Resnick; Nicole D. Kling

(57) ABSTRACT

The technology described herein is directed to methods and compositions for inhibition of ClbP and the treatment and/or prevention of cancer, e.g., colorectal cancer, a urinary tract cancer, a squamous cell carcinoma, an oral squamous cell carcinoma, or a head-and-neck cancer.

23 Claims, 33 Drawing Sheets

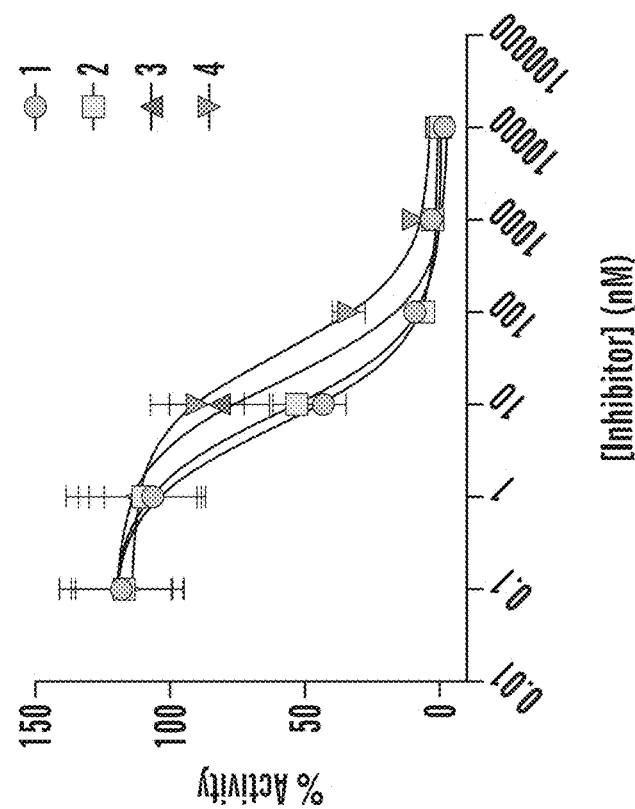
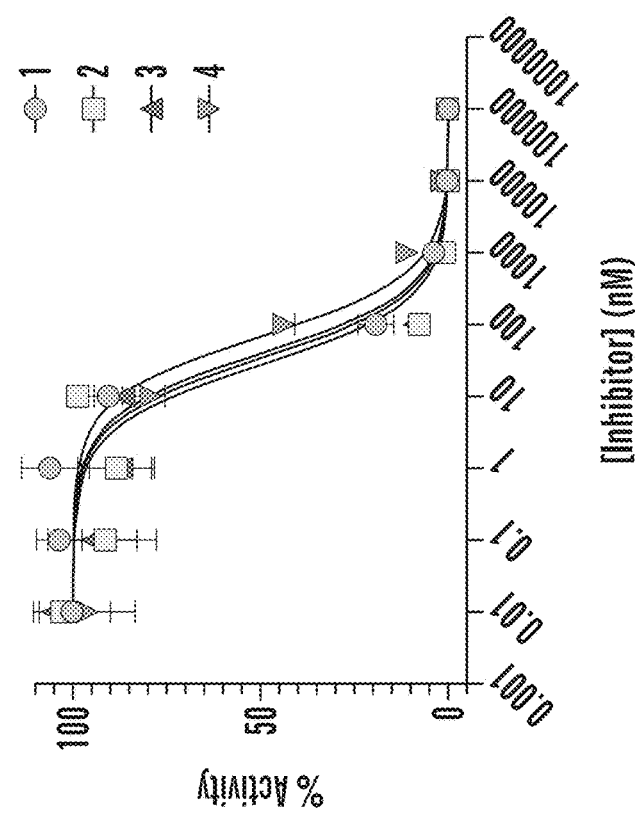
FIG. 2A
FIG. 2B

METHODS AND COMPOSITIONS RELATING TO CLBP INHIBITION

CROSS-REFERENCE TO RELATED APPLICATIONS

This application is a divisional under 35 U.S.C. § 121 of copending U.S. application Ser. No. 17/771,949 filed Apr. 26, 2022, which is a 35 U.S.C. § 371 National Phase Entry Application of International Application No. PCT/US2022/011768 filed Jan. 10, 2022, which designates the U.S. and claims benefit under 35 U.S.C. § 119(e) of U.S. Provisional Application No. 63/135,825 filed Jan. 11, 2021 and 63/195,211 filed Jun. 1, 2021, the contents of which are incorporated herein by reference in their entireties.

GOVERNMENT SUPPORT

This invention was made with government support under CA208834 and CA247069 awarded by the National Institutes of Health. The government has certain rights in the invention.

TECHNICAL FIELD

The technology described herein relates to inhibitors of ClbP.

BACKGROUND

Colibactin is produced by a non-ribosomal peptide synthetase-polyketide synthase (NRPS-PKS) assembly line encoded by the pks genomic island, which is carried by many strains of *E. coli* (pks$^+$ *E. coli*) and other proteobacteria. It was initially observed over a decade ago that pks$^+$ *E. coli* elicit a genotoxic phenotype and cause DNA double-strand breaks in cultured epithelial cells. Multiple lines of evidence have suggested colibactin-mediated DNA damage plays a role in cancer, e.g., colorectal cancer (CRC) development. Studies of human cohorts have found that pks$^+$ *E. coli* are found more frequently in patients with CRC relative to healthy controls. In addition, colonization with pks$^+$ *E. coli* increased tumor loads in multiple gnotobiotic mouse models of colitis-associated colorectal cancer. Recently, a pks-dependent mutational signature was detected in a colonic epithelial cell-derived organoid model and the same signatures were found in sequenced human cancer genomes, indicating a possible genetic basis for colibactin's carcinogenic potential.

Inhibitors of colibactin synthesis are desirable, both for further studying colibactin's role in carcinogenic mechanisms and for therapeutic use in treatment or prophylaxis (e.g., cancer prevention and/or chemoprevention). However, prior attempts to design ClbP inhibitors (Cougnoux et al. G I Cancer 2016 65:278-285) resulted in compounds that have anti-tumorogenesis effects, but which do not in fact inhibit ClbP (Volpe et al. ACS Chem Biol 2019 14:1097-1101).

SUMMARY

Provided herein are compounds which are demonstrated to directly inhibit ClbP. This is in contrast to prior art compounds (Cougnoux et al. G I Cancer 2016 65:278-285) which may bind ClbP, but which do not actually inhibit ClbP's activity, e.g., ClbP's catalytic activity.

In aspects of any of the embodiments described herein, there are provided ClbP inhibitors and/or a method of inhibiting ClbP, the method comprising contacting ClbP with one or more ClbP inhibitors, wherein the ClbP inhibitor(s) have the structure of:

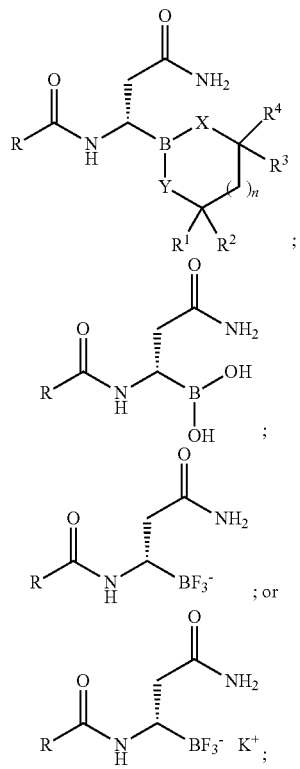

wherein R is selected from the group consisting of H, OH, alkyl, alkenyl, alkynyl, aryl, heteroaryl, cycloalkyl, or heterocycle; $R^1$, $R^2$, $R^3$ and $R^4$ independently are H, alkyl, alkenyl, alkynyl, aryl, heteroaryl, cycloalkyl or heterocycle, or $R^2$ and $R^3$, together with the carbons they are attached to, form an aryl, heteroaryl, cycloalkyl or heterocycle; X and Y independently are O, S or NH, and n is 0, or 1; or an R enantiomer of any of the foregoing. In some embodiments of any of the aspects, three of $R^1$, $R^2$, $R^3$ and $R^4$ are H and the other is methyl. In some embodiments of any of the aspects, $R^2$ and $R^3$, together with the carbon atoms they are attached to, form 2,3,4-trihydroxytetrahydropyran. In some embodiments of any of the aspects, n is 0, $R^1$ is methyl, $R^4$ is H, and $R^2$ and $R^3$, together with the carbon atoms they are attached to, form a 6,6-dimethylbicycle[3.1.1]heptane. In some embodiments of any of the aspects, n is 0, $R^1$ and $R^4$ are H, and $R^2$ and $R^3$, together with the carbon atoms they are attached to, form a benzene ring.

In some embodiments of any of the aspects, the ClbP inhibitor has the structure of:

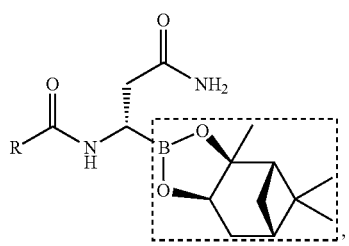

-continued

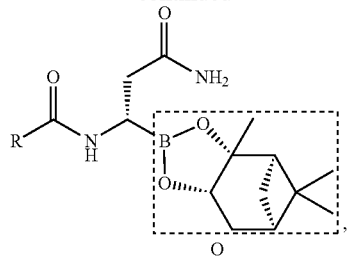

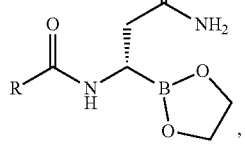

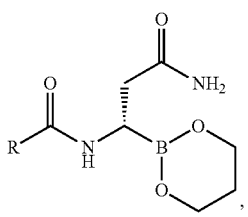

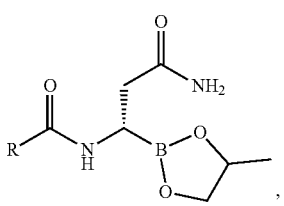

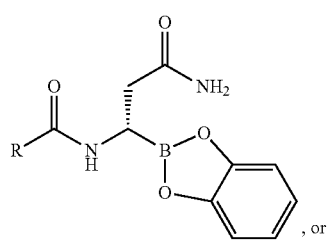

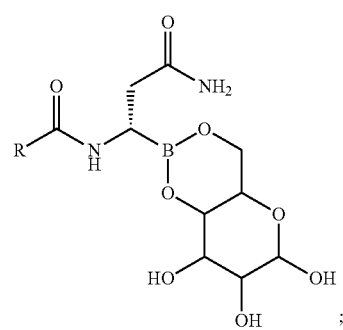

or an R enantiomer of any of the foregoing.

In some embodiments of any of the aspects, the ClbP inhibitor has the structure of:

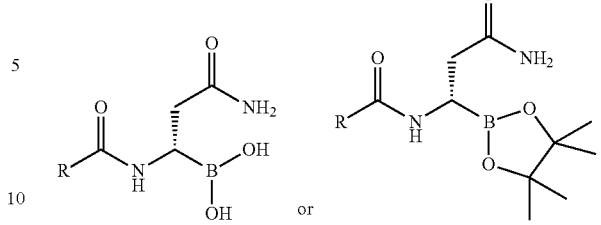

wherein R is, selected from the group consisting of H, OH, alkyl, alkenyl, alkynyl, aryl, heteroaryl, cycloalkyl, or heterocycle; wherein the alkyl, alkenyl, alkynyl, or cycloalkyl, whether alone or as part of a substituent group, is optionally substituted with one or more substituents independently selected from the group consisting of halogen, —OH, alkyl, O-alkyl, —NR$^A$R$^B$, —S-alkyl, —SO-alkyl, —SO$_2$-alkyl, alkenyl, alkynyl, aryl, heteroaryl, cycloalkyl or heterocycle; and the alkenyl, alkynyl, or optionally includes —O—, —S—, —SO$_2$—, —N(R$^C$)— substituting one or more carbons in the carbon chain, wherein the aryl or heteroaryl, whether alone or as part of a substituent group, is optionally substituted with one or more substituents independently selected from the group consisting of halogen, OH, alkyl, O-alkyl, —NR$^D$R$^E$, —S-alkyl, —SO-alkyl and —SO$_2$-alkyl, alkenyl, alkynyl, aryl, heteroaryl, cycloalkyl or heterocycle; wherein R$^A$, R$^B$, R$^C$, R$^D$, and R$^E$, are each independently selected from hydrogen and C$_{1-4}$ alkyl; or an R enantiomer of any of the foregoing.

In some embodiments of any of the aspects, R is alkyl or aryl. In some embodiments of any of the aspects, R is not a phenyl group. In some embodiments of any of the aspects, R is selected from the group consisting of:

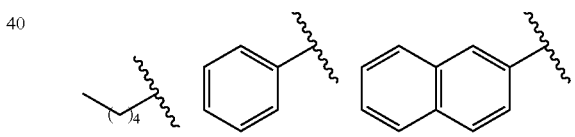

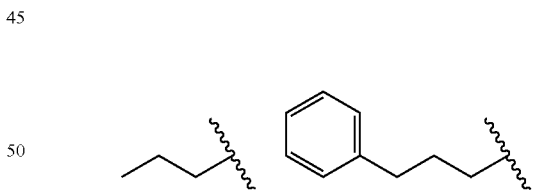

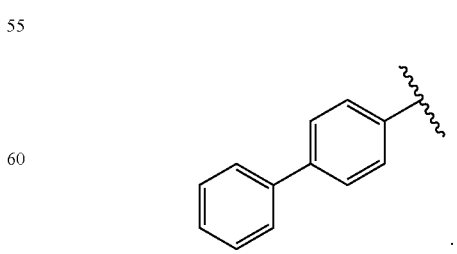

In some embodiments of any of the aspects, the ClbP inhibitor does not have the following structure:

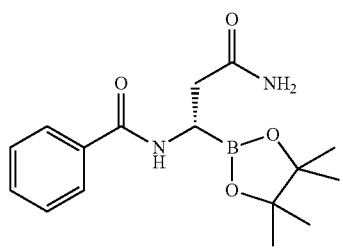

In some embodiments of any of the aspects, the ClbP inhibitor comprises a D-asparagine group and not an L-asparagine group. In some embodiments of any of the aspects, R is hydrophobic.

In some embodiments of any of the aspects, the ClbP inhibitor has a structure selected from the following:

Formula IV

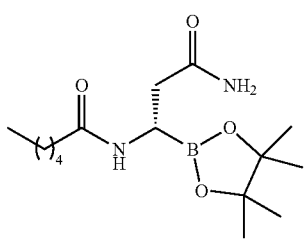

Hexanoyl-pinacalboro-Asn
(MRV03-037)

Formula V

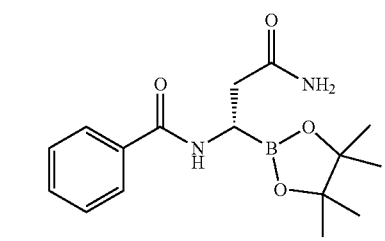

Formula VI

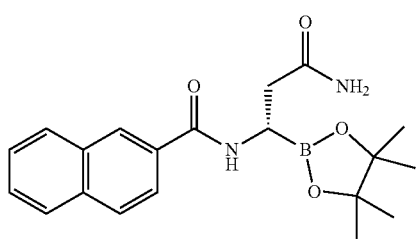

Formula VII

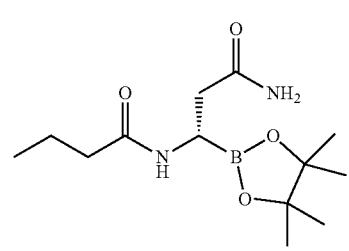

Formula VIII

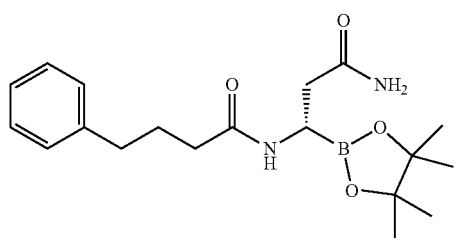

Formula IX

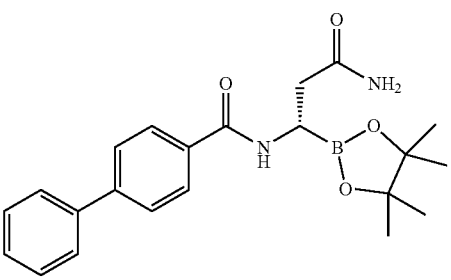

Formula X

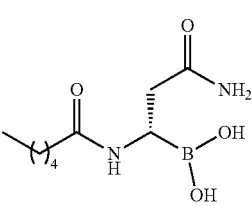

Formula XI

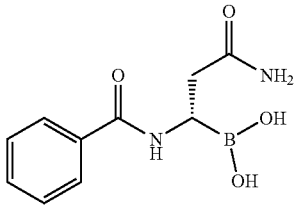

Formula XII

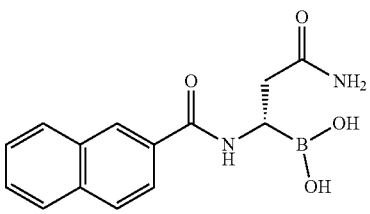

Formula XIII

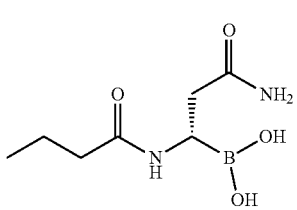

Formula XIV

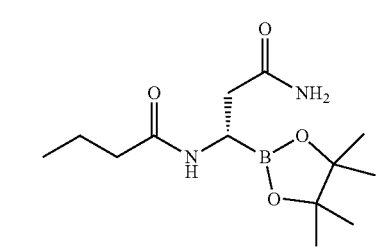

Formula XV
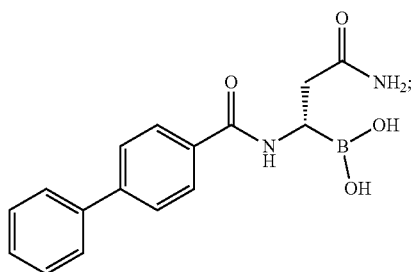
or an R enantiomer of any of the foregoing, e.g,
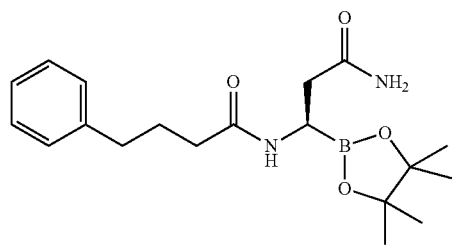
In some embodiments of any of the aspects, the ClbP inhibitor has a structure selected from the following:
Formula IV
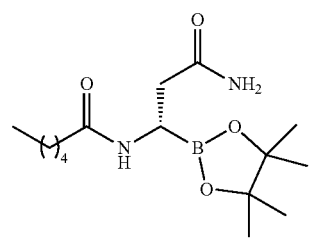
Hexanoyl-pinacalboro-Asn
(MRV03-037)
Formula VI
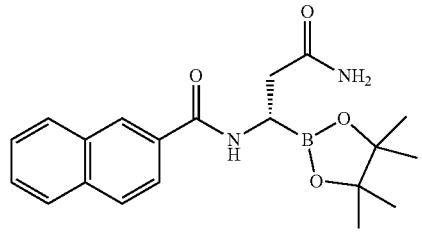
Formula VII
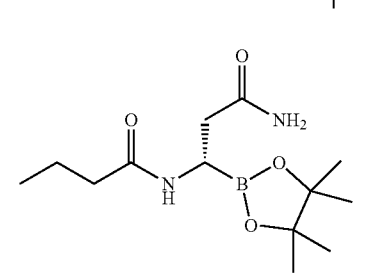
Formula VIII
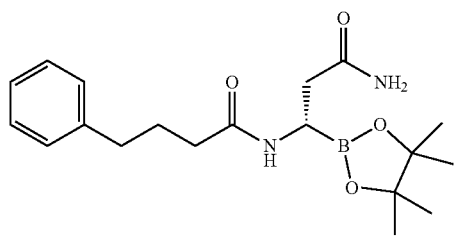
Formula IX
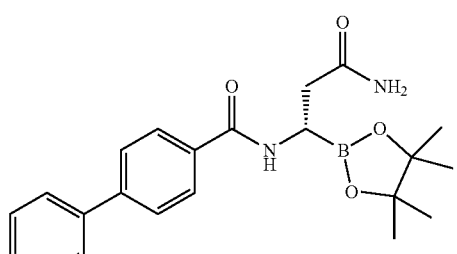
Formula X
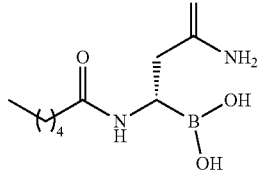
Formula XII
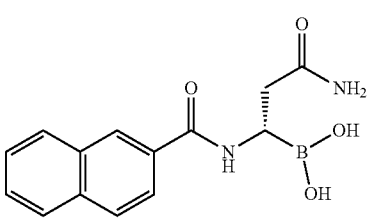
Formula XIII
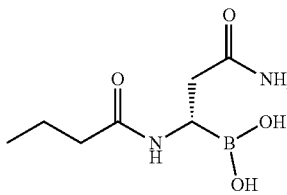
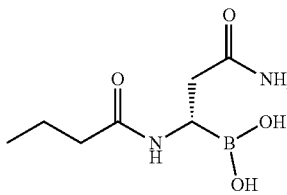
Formula XIV
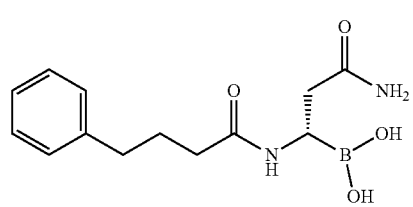

-continued

Formula XV

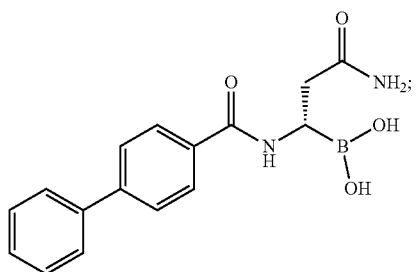

or an R enantiomer of any of the foregoing, e.g,

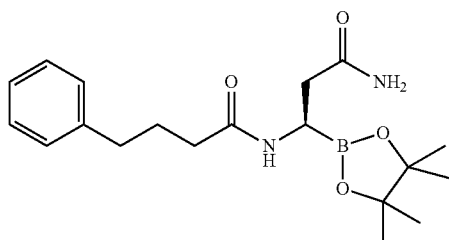

In one aspect of any of the embodiments, described herein is a ClbP inhibitor having the structure of:

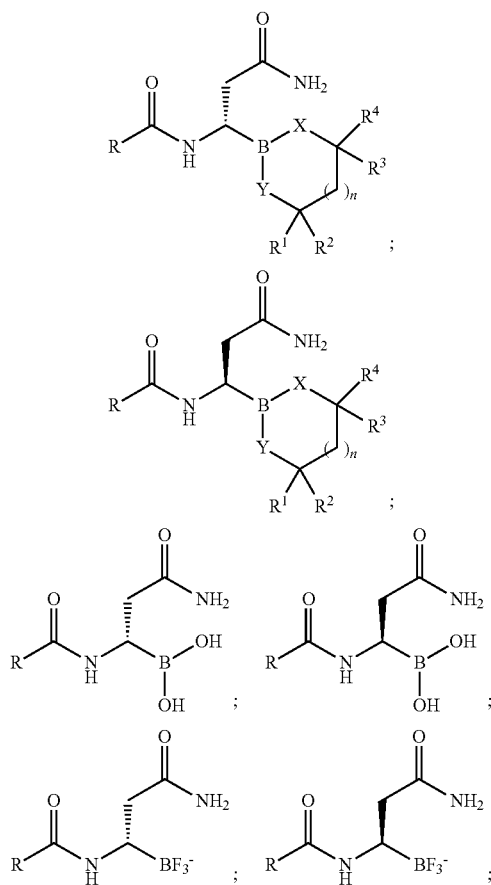

-continued

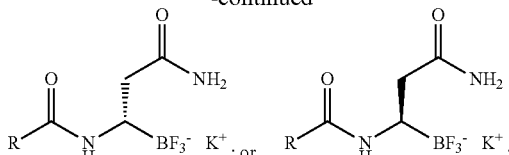

wherein R is selected from the group consisting of H, OH, alkyl, alkenyl, alkynyl, aryl, heteroaryl, cycloalkyl, or heterocycle; $R^1$, $R^2$, $R^3$ and $R^4$ independently are H, alkyl, alkenyl, alkynyl, aryl, heteroaryl, cycloalkyl or heterocycle, or $R^2$ and $R^3$, together with the carbons they are attached to, form an aryl, heteroaryl, cycloalkyl or heterocycle; X and Y independently are O, S or NH, and n is 0, or 1.

In one aspect of any of the embodiments, described herein is a ClbP inhibitor having the structure:

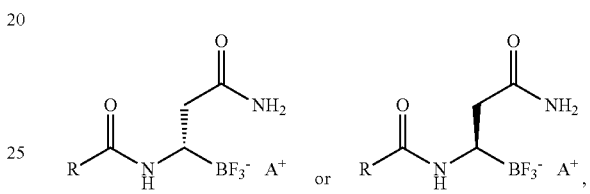

where A+ is absent or a cation and wherein R is selected from the group consisting of H, OH, alkyl, alkenyl, alkynyl, aryl, heteroaryl, cycloalkyl, or heterocycle; $R^1$, $R^2$, $R^3$ and $R^4$ independently are H, alkyl, alkenyl, alkynyl, aryl, heteroaryl, cycloalkyl or heterocycle, or $R^2$ and $R^3$, together with the carbons they are attached to, form an aryl, heteroaryl, cycloalkyl or heterocycle; X and Y independently are O, S or NH, and n is 0, or 1, or the R enantiomer thereof. In some embodiments of any of the aspects, the cation is selected from the group consisting of K+, Na+, ammonium (NH4+), pyridinium (C5H5NH+), and quaternary ammonium (R5R6R7R8N+), where R5, R6, R7, and R8 are independently selected from alkyl, cycloalkyl, phenyl, or benzyl, wherein the alkyl, cycloalkyl, phenyl, or benzyl is optionally substituted with one or more substitutents.

In some embodiments of any of the aspects, three of $R^1$, $R^2$, $R^3$ and $R^4$ are H and the other is methyl. In some embodiments of any of the aspects, $R^2$ and $R^3$, together with the carbon atoms they are attached to, form 2,3,4-trihydroxytetrahydropyran. In some embodiments of any of the aspects, n is 0, $R^1$ is methyl, $R^4$ is H, and $R^2$ and $R^3$, together with the carbon atoms they are attached to, form a 6,6-dimethylbicycle[3.1.1]heptane. In some embodiments of any of the aspects, n is 0, $R^1$ and $R^4$ are H, and $R^2$ and $R^3$, together with the carbon atoms they are attached to, form a benzene ring.

In some embodiments of any of the aspects, the ClbP inhibitor has the structure of:

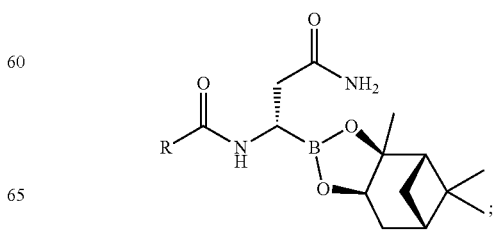

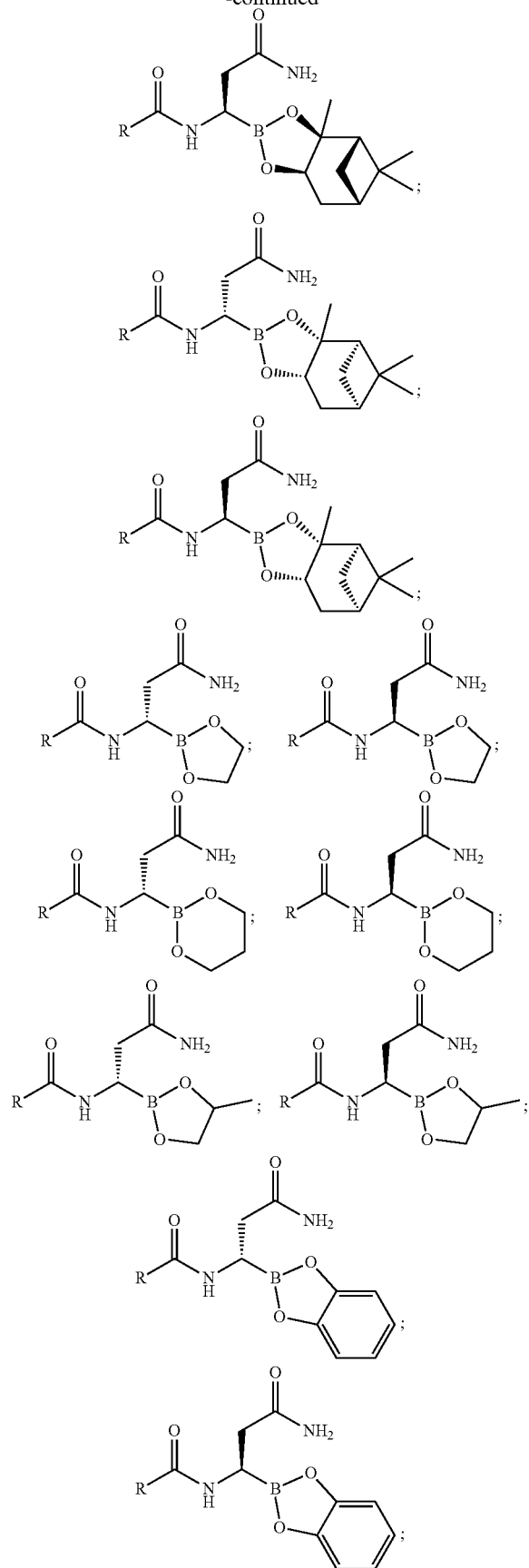

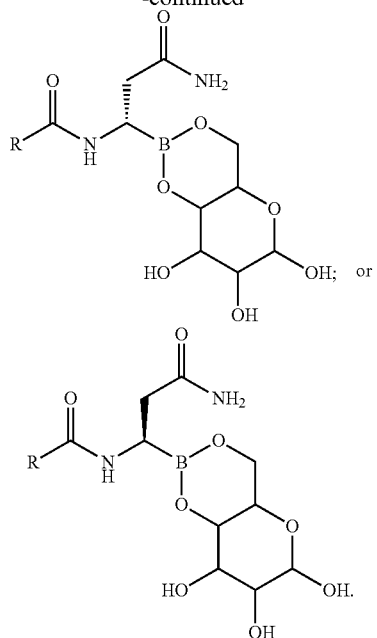

In some embodiments of any of the aspects, the ClbP inhibitor has the structure of:

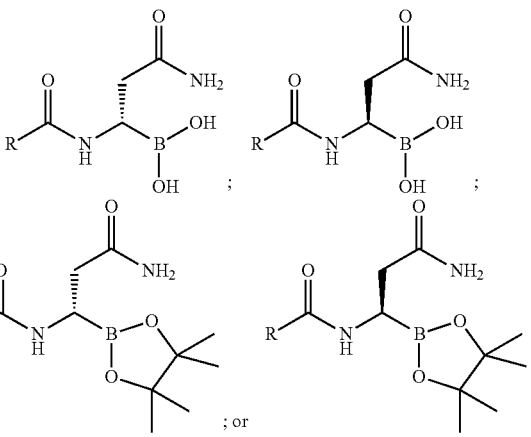

; or wherein R is, selected from the group consisting of H, OH, alkyl, alkenyl, alkynyl, aryl, heteroaryl, cycloalkyl, or heterocycle; wherein the alkyl, alkenyl, alkynyl, or cycloalkyl, whether alone or as part of a substituent group, is optionally substituted with one or more substituents independently selected from the group consisting of halogen, —OH, alkyl, O-alkyl, —NR$^A$R$^B$, —S-alkyl, —SO-alkyl, —SO$_2$-alkyl, alkenyl, alkynyl, aryl, heteroaryl, cycloalkyl or heterocycle; and the alkenyl, alkynyl, or optionally includes —O—, —S—, —SO$_2$—, —N(R$^C$)— substituting one or more carbons in the carbon chain, wherein the aryl or heteroaryl, whether alone or as part of a substituent group, is optionally substituted with one or more substituents independently selected from the group consisting of halogen, OH, alkyl, O-alkyl, —NR$^D$R$^E$, —S-alkyl, —SO-alkyl and —SO$_2$-alkyl, alkenyl, alkynyl, aryl, heteroaryl, cycloalkyl or heterocycle;

wherein R$^A$, R$^B$, R$^C$, R$^D$, and R$^E$, are each independently selected from hydrogen and C$_{1-4}$ alkyl. In some embodiments of any of the aspects, R is alkyl or aryl. In some embodiments of any of the aspects, R is not a phenyl group. In some embodiments of any of the aspects, R is selected from the group consisting of:

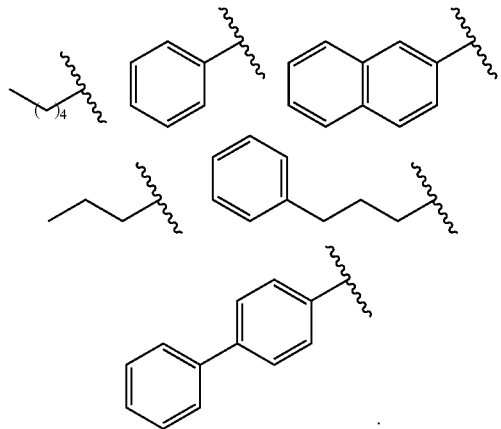

In some embodiments of any of the aspects, the ClbP inhibitor does not have the following structure:

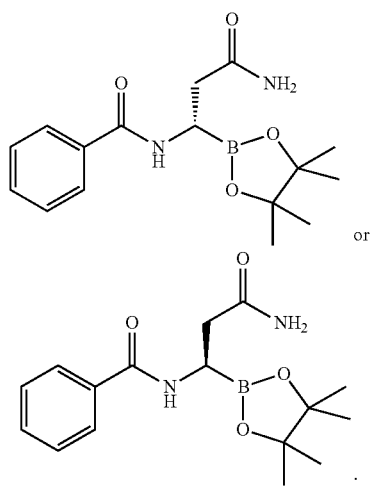

In some embodiments of any of the aspects, the ClbP inhibitor comprises a D-asparagine group and not an L-asparagine group. In some embodiments of any of the aspects, R is hydrophobic.

In some embodiments of any of the aspects, the ClbP inhibitor has a structure selected from the following:

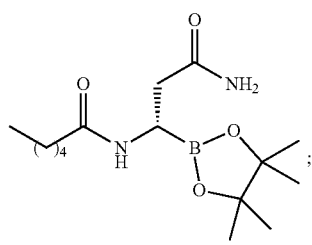

Hexanoyl-pinacolboro-Asn
(MRV03-037)

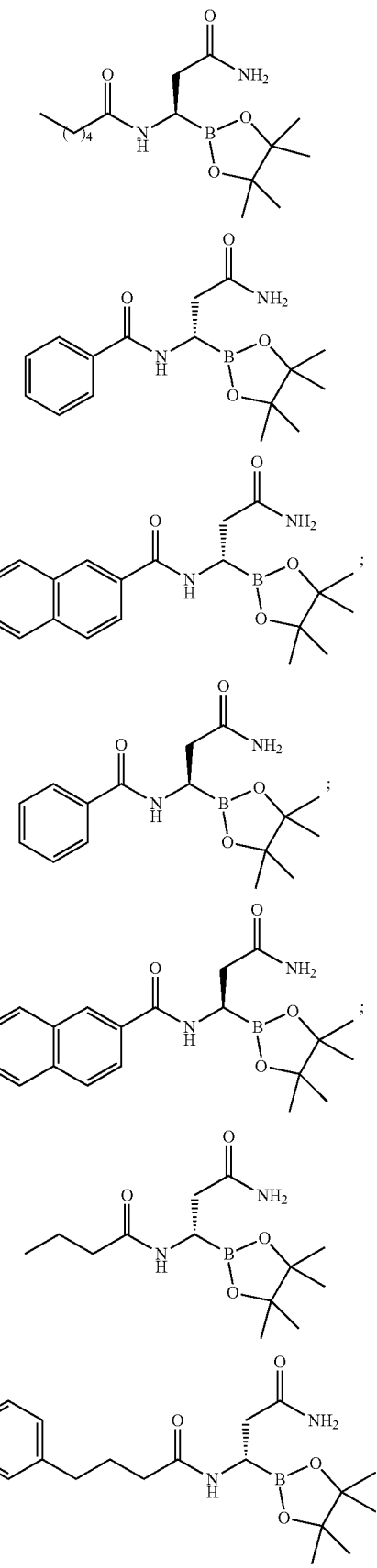

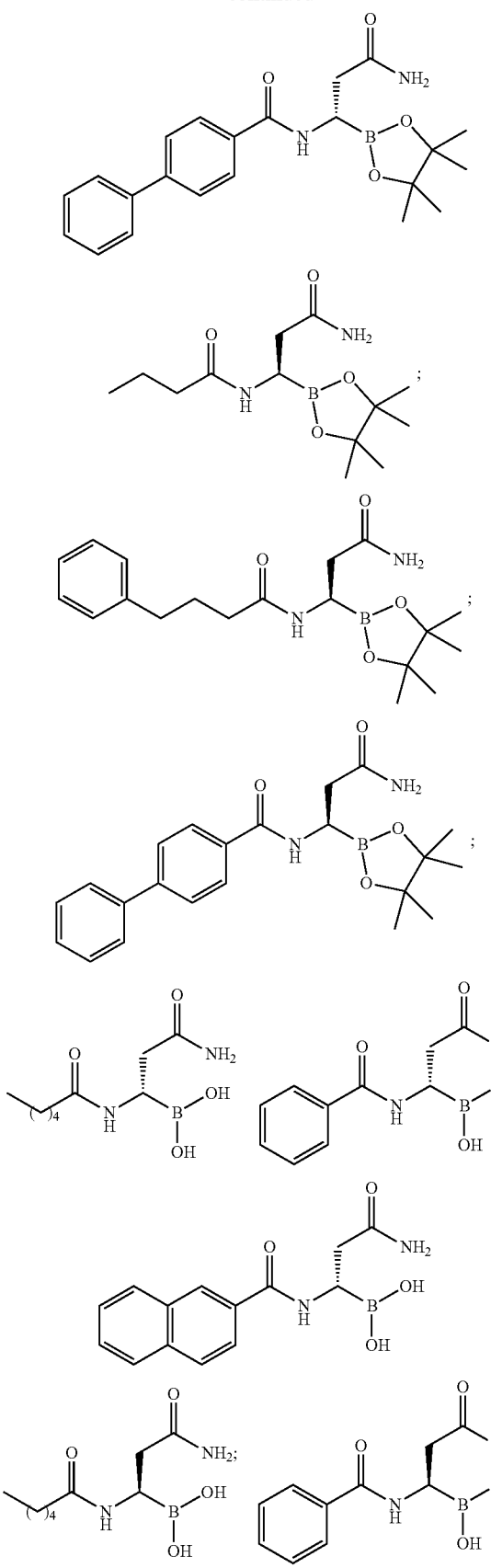
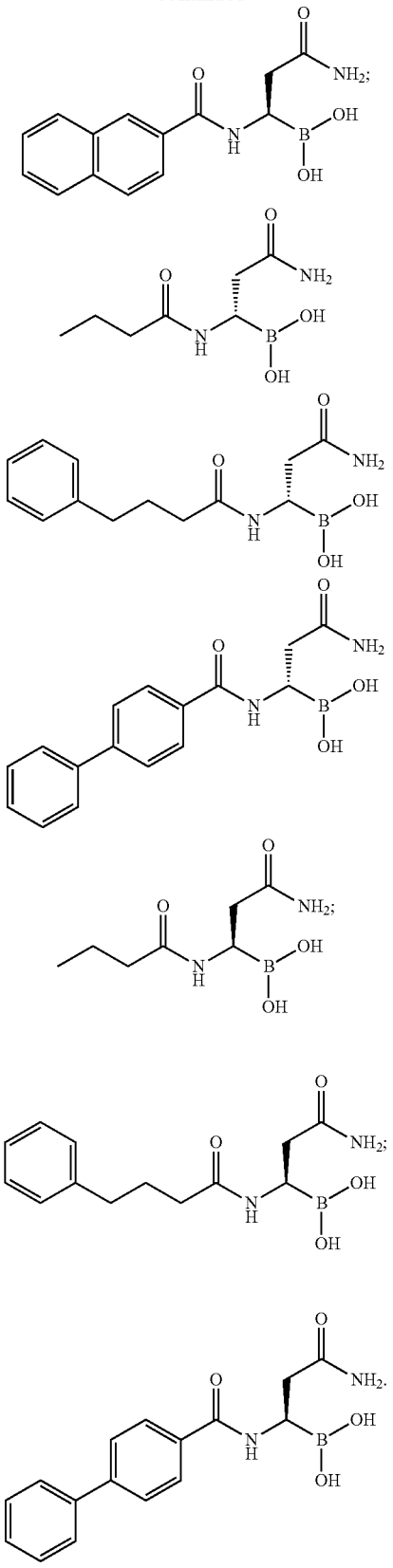
In some embodiments of any of the aspects, the ClbP inhibitor has a structure selected from the following:

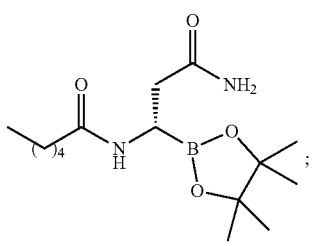
Hexanoyl-pinacolboro-Asn
(MRV03-037)
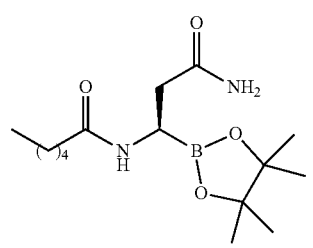
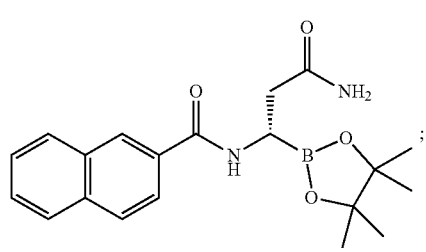
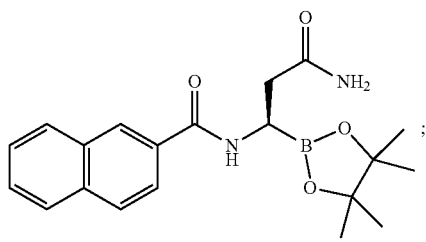
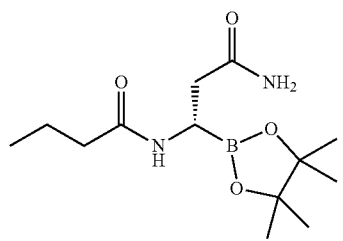
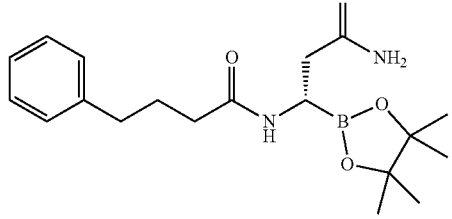
-continued
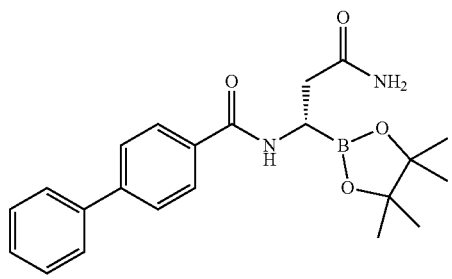
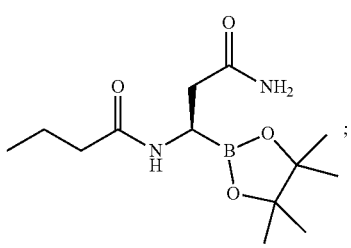
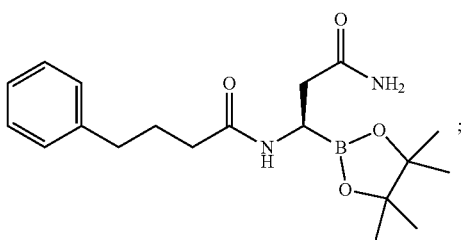
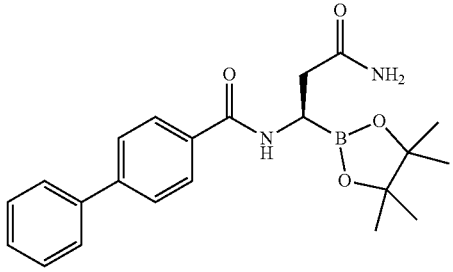
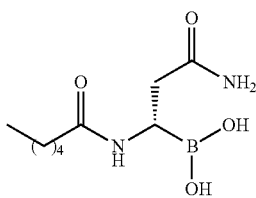
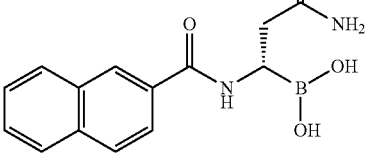
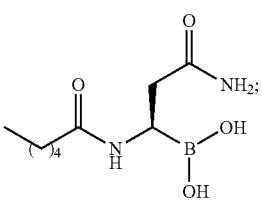

-continued

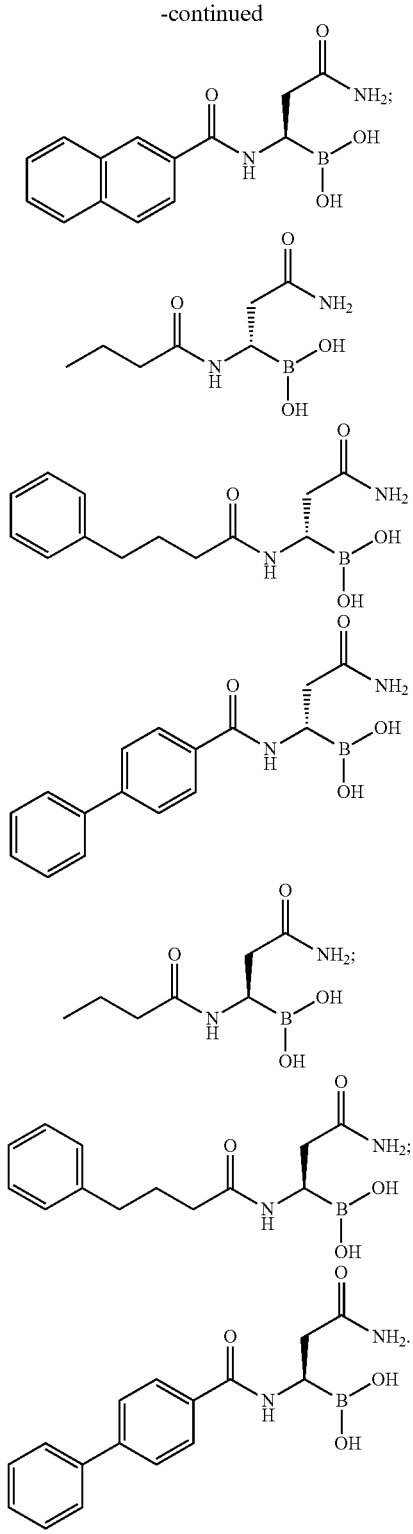

In some embodiments of any of the aspects, contacting comprises administering the ClbP inhibitor to a subject. In some embodiments of any of the aspects, the subject has a population and/or infection of pks+ bacteria. In some embodiments of any of the aspects, the bacteria is E. coli. In some embodiments of any of the aspects, the bacteria is a Proteobacteria, e.g., Citrobacter, Klebsiella, Eshcerichia, or E. coli. In some embodiments of any of the aspects, the level of genotoxin in a sample or subject is reduced and/or the production of genotoxin in a sample or subject is inhibited. In some embodiments of any of the aspects, the genotoxin is colibactin. In some embodiments of any of the aspects, the risk and/or progression of cancer in subject is reduced or inhibited. In some embodiments of any of the aspects, the cancer is colorectal cancer. In some embodiments of any of the aspects, the cancer is colorectal cancer, a urinary tract cancer, a squamous cell carcinoma, an oral squamous cell carcinoma, or a head-and-neck cancer.

In one aspect of any of the embodiments, described herein is a method of treating an infection of pks+ bacteria in a subject in need thereof, the method comprising administering a ClbP inhibitor described herein to the subject. In some embodiments of any of the aspects, the bacteria is E. coli. In some embodiments of any of the aspects, the bacteria is a Proteobacteria, e.g., Citrobacter, Klebsiella, Eshcerichia, or E. coli. In one aspect of any of the embodiments, described herein is a method of treating cancer (e.g., colorectal cancer) in a subject in need thereof, the method comprising administering a ClbP inhibitor described herein to the subject. In some embodiments of any of the aspects, the level of genotoxin in a sample or subject is reduced and/or the production of genotoxin in a sample or subject is inhibited. In some embodiments of any of the aspects, the genotoxin is colibactin.

BRIEF DESCRIPTION OF THE DRAWINGS

(FIG. 1A) ClbP activates colibactin by removing the myristoyl-D-Asn prodrug motif, which was the foundation for inhibitor design. Hydrolysis leads to the formation of two electrophilic warheads capable of DNA alkylation. (FIG. 1B) Synthesis of ClbP inhibitors (i) Pd(OAc)$_2$, NaOAc, TFA, PhMe, 80° C., 12 h (ii) CuCl (0.1 equiv), (R)-SegPhos (0.11 equiv), B$_2$pin$_2$ (1.1 equiv), KOt-Bu (1 equiv), MeOH (4 equiv), THF, 3 h (iii) NaCN (0.2 equiv), NH$_3$, MeOH, 1 h.

FIGS. 2A-2D depict screening for ClbP inhibition. Compounds 1-4 inhibit ClbP's activity with a fluorescent substrate analog in (FIG. 2A) an in vitro assay and (FIG. 2B) E. coli overexpressing ClbP; (FIG. 2C) 1-4 also block release of the prodrug motif from pks$^+$ E. coli (FIG. 2D). 1-4 exhibit slow-binding kinetics in an in vitro assay format. See Methods for calculations of % Activity.

(FIG. 3A) A 2.5 Å resolution structure of ClbP crystallized in the presence of 1 shows the compound bound in the expected pocket of the active site near the catalytic triad. Continuous electron density in the 2F$_o$-F$_c$ map contoured at 2σ (mesh) indicates the inhibitor is covalently bound to S95. (FIG. 3B) Key interactions determining specificity for the D-Asn sidechain. A 180° rotation relative to FIG. 3A shows hydrogen bonds (black dashed lines) with residues N331, S188, and H257 which mediate recognition of the D-Asn sidechain. (FIG. 3C) Interactions stabilizing the boronate mimic of the tetrahedral intermediate. The boronate ester, a structural mimic of the tetrahedral intermediates in colibactin hydrolysis, is stabilized by hydrogen bonds from Q330 and Y186.

FIG. 7A depicts flow cytometry analysis of HeLa cells infected with NC101 (a pks+*E. coli* strain) with or without inhibitor present, represented in violin plots. Width at each point on the vertical axis of each violin corresponds to population count at a given DNA content. ClbP inhibitor 3 can block the cell cycle arrest phenotype typical of colibactin's genotoxicity. Cells were fixed in ethanol before staining with propidium iodide. Data shown for a single replicate that is representative for three biological replicates. FIG. 7B depicts LCMS analysis for DNA adduct formation in HeLa cells infected with NC101 with or without inhibitor present, indicating that a ClbP inhibitor can block DNA adduct formation. Points shown are individual replicates, empty circles are below the limit of detection. FIG. 7C depicts LCMS quantification of N-myristoyl-Asn (prodrug motif) released from NC101 in the presence or absence of a complex microbial community from a mouse fecal sample, with or without inhibitor treatment. ClbP Inhibitor 3 can still effectively block colibactin production in the presence of a complex microbial community.

(FIG. 9A) ClbP activates colibactin by removing an N-myristoyl-D-Asn prodrug scaffold (dashed boxes). It is contemplated herein that hydrolysis of two amide bonds by two copies of ClbP leads to the formation of two electrophilic warheads (grey) capable of DNA alkylation. Inhibitor design was guided by the two key recognition features of the prodrug scaffold: a D-Asn sidechain, which is essential, and a lipid group, which can be modified. (FIG. 9B) Synthesis of ClbP inhibitors (i) Pd(OAc)$_2$, NaOAc, TFA, PhMe, 80° C., 12 h (ii) CuCl (0.1 equiv), (R)-SegPhos (0.11 equiv), B$_2$pin$_2$ (1.1 equiv), KOt-Bu (1 equiv), MeOH (4 equiv), THF, 3 h (iii) NaCN (0.2 equiv), NH$_3$, MeOH, 1 h.

(FIG. 10A) ClbP activity in vitro upon treatment with 1-4 using a fluorescent substrate analog. n=4 biological replicates for each condition, error bars are 1 standard deviation (s.d.) (FIG. 10B) ClbP activity in vitro upon treatment with 1-4 at 100 nM and varying incubation time before initiating the assay. n=4 biological replicates for each condition, error bars are 1 s.d. (FIG. 10C) Activity of *E. coli* overexpressing ClbP toward a fluorescent substrate analog after treatment with 1-4. n=4 biological replicates for each condition, error bars are 1 s.d. (FIG. 10D) LC-MS measurement of prodrug scaffold (FIG. 1a) released from BW pks after treatment with vehicle or 1-4. n=3 biological replicates; ****: P<0.0001; not significant (n.S): P>0.05, One-way ANOVA and Dunnett's multiple comparison test. See Methods in the Examples for calculation of % activity in fluorescence assays.

(FIG. 11A) LC-MS measurement of prodrug scaffold (FIG. 9A) released from BW pks after treatment with 3 or 3-(R). n=3 biological replicates, individual replicates shown. (FIG. 11B) Volcano plot representation of metabolites detected by LC-MS which are altered in BW pks treated with 1 μM of compound 3 versus untreated (left) and BW ΔP versus BW pks (right). Metabolites showing major changes are labeled with their mass-to-charge ratio (m/z). n=5 biological replicates for all conditions. (FIG. 11C) Gel-based ABPP using a fluorophosphonate-biotin probe (FP) to examine the reactivity of serine hydrolases in *E. coli* and HEK293T cell lysates does not identify any significant targets of compound 3. ClbP is not detected in this assay due to a lack of interaction between it and FP. (FIG. 11D) LC-MS measurement of the prodrug scaffold in extracts of *E. coli* NC101 and *E. coli* NC101ΔclbP cultured with and without compound 3 and with or without a community of organisms resuspended from fecal pellets of C57BL/6J mice. n=3 biological replicates for all conditions, individual replicates shown. Empty circles are below the limit of quantitation for this protocol (4 nM). ****: P<0.0001; *: P<0.05; n.s: P>0.05; One-way ANOVA and Bonferroni's multiple comparison test.

(FIG. 12A) Flow cytometry analysis of HeLa cells infected with NC101 and treated with 3. Cells were fixed in ethanol before staining with propidium iodide (PI) for DNA content. The increase in the fraction of the population with >2n DNA content indicates cell cycle arrest. Top shows raw histograms for PI fluorescence intensity in the population for one representative sample for each condition. Bottom shows the percentage of the population in G1 phase based on fitting histograms to the Watson cell cycle analysis model. Black symbols are individual replicates, bars show average value. All conditions run in 3 biological replicates. Shading indicates concentration of inhibitor. (FIG. 12B) Structure of two diastereomeric DNA adducts which are known to be derived from colibactin. LC-MS detection of these adducts (M+H$^+$ =m/z 540.1772) in hydrolyzed genomic DNA extracted from HeLa cells infected with NC101, 3 biological replicates shown. Empty circles indicate sample was below the detection limit. For (FIG. 12A) and (FIG. 12B) ****: P<0.0001; *: P<0.05; n.s: P>0.05; One-way ANOVA and Dunnett's multiple comparison test. (FIG. 12C) Western blot for FANCD2 in HeLa cell extracts. All conditions run in 3 biological replicates with one representative sample shown.

DETAILED DESCRIPTION

Figure 1A:
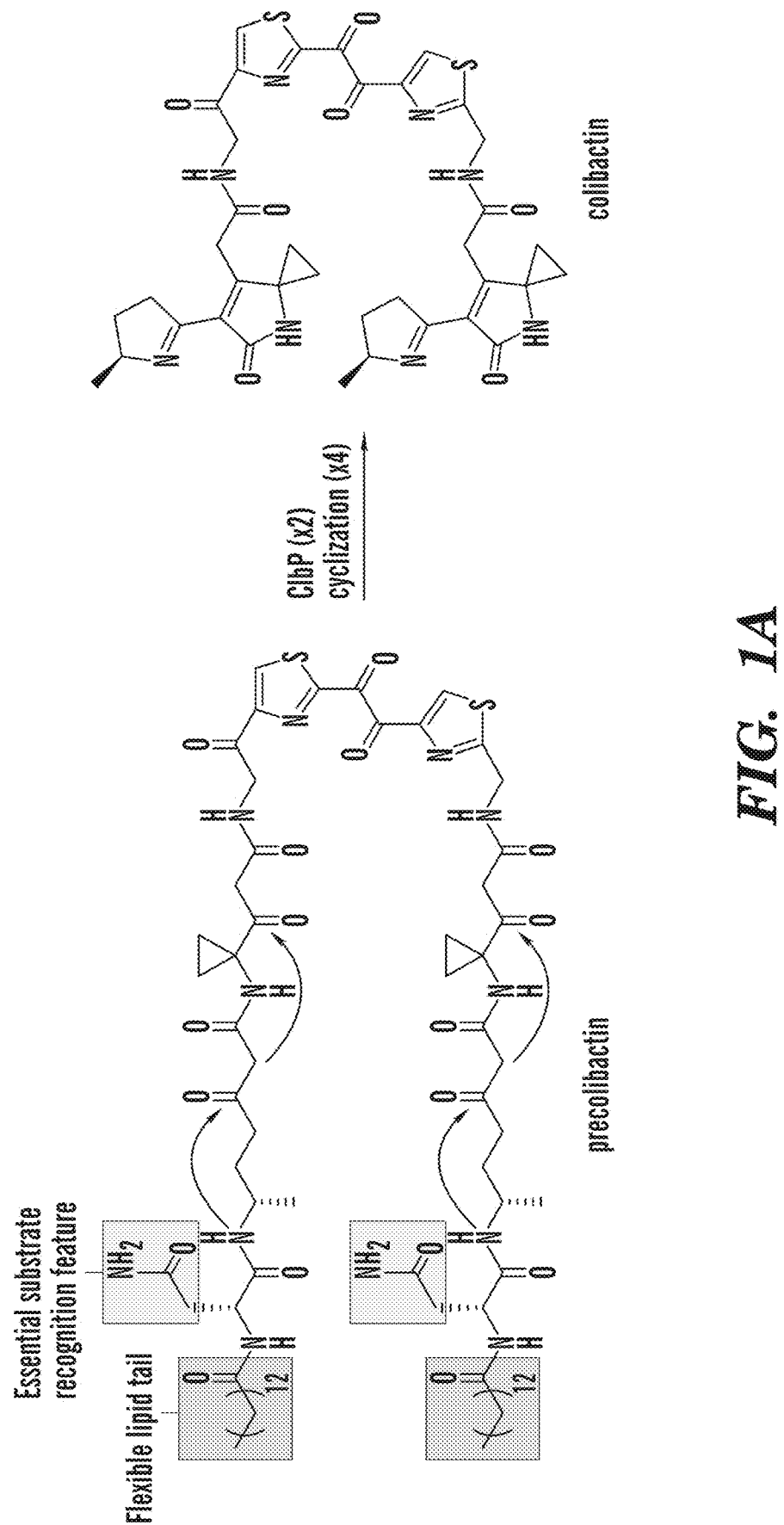
FIGS. 1A-1B depict rational design strategy and synthesis of ClbP inhibitors.

As demonstrated herein, the inventors have successfully produced ClbP inhibitors. Prior attempts to inhibit ClbP have failed to provide ClbP inhibitors. Instead, these prior attempts provided compounds which do affect pks+ bacteria, but through some other mechanism. These prior art compounds are demonstrated to not inhibit ClbP (Cougnoux et al. G I Cancer 2016 65:278-285; compounds 18 and 19 in Volpe et al. ACS Chem Biol 2019 14:1097-1101). However, using the assays used in Volpe et al. ACS Chem Biol 2019 14:1097-1101, and other assays/experiments described herein the inventors now demonstrate that the compounds provided herein do inhibit ClbP both in vitro and in cells.

In one aspect of any of the embodiments, provided herein is a method of inhibiting ClbP. As used herein "ClbP" or "colibactin P" refers to a membrane bound periplasmic peptidase that cleaves an N-acyl-D-asparagine motif (the 'prodrug scaffold' or 'prodrug motif') from the N-terminus of precolibactin to liberate the active colibactin. The sequences of ClbP are known in the art, e.g., the polypeptide sequence is available in the Uniprot database as accession number Q0P7K6 (SEQ ID NO: 1). In the final stages of colibactin biosynthesis, the inactive precursor (precolibactin) is activated via proteolytic cleavage by ClbP.

In some embodiments of any of the aspects, the methods relate to contacting ClbP, a sample, and/or a pks+ bacteria with a ClbP inhibitor. As used herein, the term "inhibitor" refers to an agent or compound which can reduce the activity of a target protein (i.e. ClbP).

In some embodiments, the ClbP inhibitor has the structure of

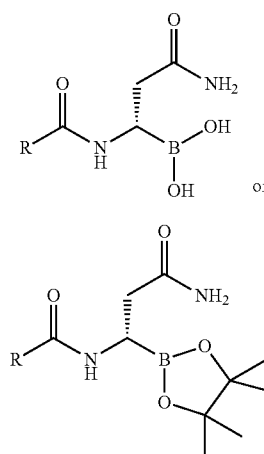

Formula I

Formula II wherein R is selected from the group consisting of H, OH, alkyl, alkenyl, alkynyl, aryl, heteroaryl, cycloalkyl, or heterocycle; or an R enantiomer of any of the foregoing. In some embodiments of any of the aspects, the ClbP inhibitor is a direct inhibitor of ClbP.

In some embodiments of any of the aspects, the alkyl, alkenyl, alkynyl, or cycloalkyl, whether alone or as part of a substituent group, is optionally substituted with one or more substituents independently selected from the group consisting of halogen, —OH, alkyl, O-alkyl, —NR$^A$R$^B$, —S-alkyl, —SO-alkyl, —SO$_2$-alkyl, alkenyl, alkynyl, aryl, heteroaryl, cycloalkyl or heterocycle; and the alkenyl, alkynyl, or optionally includes —O—, —S—, —SO$_2$—, —N(R$^C$)— substituting one or more carbons in the carbon chain, wherein the aryl or heteroaryl, whether alone or as part of a substituent group, is optionally substituted with one or more substituents independently selected from the group consisting of halogen, OH, alkyl, O-alkyl, —NR$^D$R$^E$, —S-alkyl, —SO-alkyl and —SO$_2$-alkyl, alkenyl, alkynyl, aryl, heteroaryl, cycloalkyl or heterocycle; and wherein R$^A$, R$^B$, R$^C$, R$^D$, and R$^E$, are each independently selected from hydrogen and C$_{1-4}$ alkyl.

In some embodiments of any of the aspects, R is alkyl or aryl. In some embodiments of any of the aspects, R is not a phenyl group. In some embodiments of any of the aspects, R is hydrophobic.

In some embodiments of any of the aspects, the ClbP inhibitor does not have the following structure:

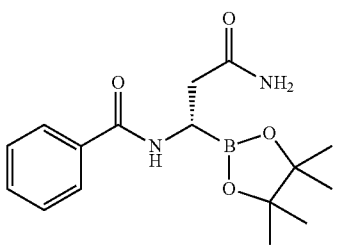

Formula V

In some embodiments of any of the aspects, the ClbP inhibitor comprises a D-asparagine group and not an L-asparagine group. As demonstrated herein, the D-asparagine group demonstrates surprisingly stronger inhibition than the L-asparagine group (see, e.g., FIG. 3).

In some embodiments of any of the aspects, the ClbP inhibitor or composition comprising at least one ClbP inhibitor comprises a mixture of individual molecules, each individual molecule comprising either a D-asparagine group or a L-asparagine groups, wherein the individual molecules comprising L-asparagine groups are no more than 50% of the total molecules (e.g., by weight, mass, or molar weight). In some embodiments of any of the aspects, the ClbP inhibitor or composition comprising at least one ClbP inhibitor comprises a mixture of individual molecules, each individual molecule comprising either a D-asparagine group or a L-asparagine groups, wherein the individual molecules comprising L-asparagine groups are no more than 40% of the total molecules (e.g., by weight, mass, or molar weight). In some embodiments of any of the aspects, the ClbP inhibitor or composition comprising at least one ClbP inhibitor comprises a mixture of individual molecules, each individual molecule comprising either a D-asparagine group or a L-asparagine groups, wherein the individual molecules comprising L-asparagine groups are no more than 30% of the total molecules (e.g., by weight, mass, or molar weight). In some embodiments of any of the aspects, the ClbP inhibitor or composition comprising at least one ClbP inhibitor comprises a mixture of individual molecules, each individual molecule comprising either a D-asparagine group or a L-asparagine groups, wherein the individual molecules comprising L-asparagine groups are no more than 20% of the total molecules (e.g., by weight, mass, or molar weight).

In some embodiments of any of the aspects, the ClbP inhibitor or composition comprising at least one ClbP inhibitor comprises a mixture of individual molecules, each individual molecule comprising either a D-asparagine group or a L-asparagine groups, wherein the individual molecules comprising L-asparagine groups are no more than 10% of the total molecules (e.g., by weight, mass, or molar weight). In some embodiments of any of the aspects, the ClbP inhibitor or composition comprising at least one ClbP inhibitor comprises a mixture of individual molecules, each individual molecule comprising either a D-asparagine group or a L-asparagine groups, wherein the individual molecules comprising L-asparagine groups are no more than 1% of the total molecules (e.g., by weight, mass, or molar weight). In some embodiments of any of the aspects, the ClbP inhibitor or composition comprising at least one ClbP inhibitor comprises a mixture of individual molecules, each individual molecule comprising either a D-asparagine group or a L-asparagine groups, wherein the individual molecules comprising L-asparagine groups are no more than 0.1% of the total molecules (e.g., by weight, mass, or molar weight).

In some embodiments of any of the aspects, ClbP inhibitor has a structure selected from the following:

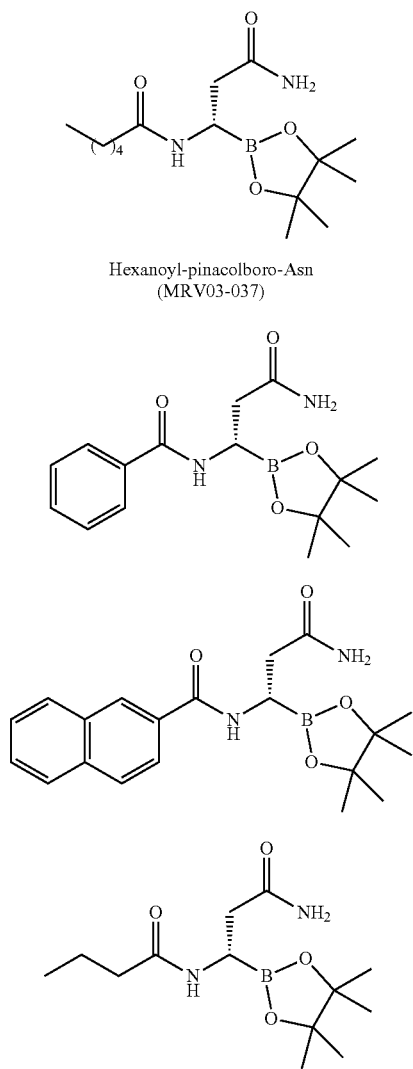

Hexanoyl-pinacolboro-Asn
(MRV03-037)

Formula IV

Formula V

Formula VI

Formula VII

-continued

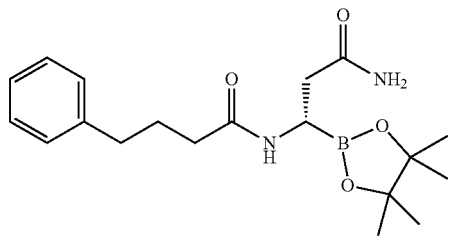

Formula VIII

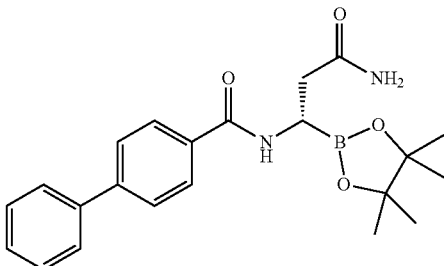

Formula IX

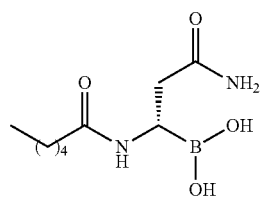

Formula X

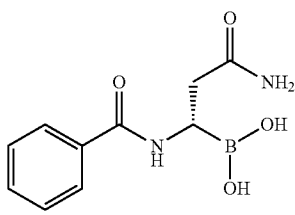

Formula XI

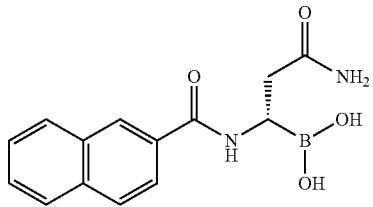

Formula XII

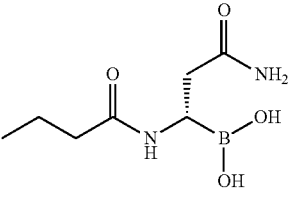

Formula XIII

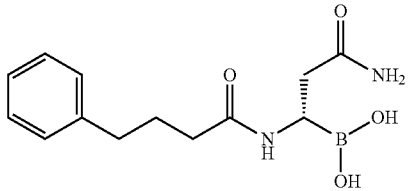

Formula XIV

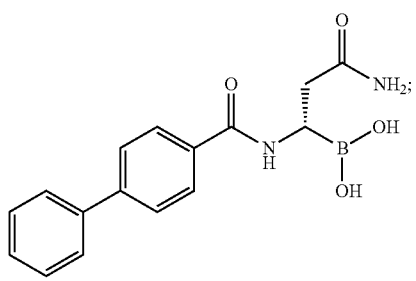
Formula XV
or an R enantiomer of any of the foregoing, e.g,
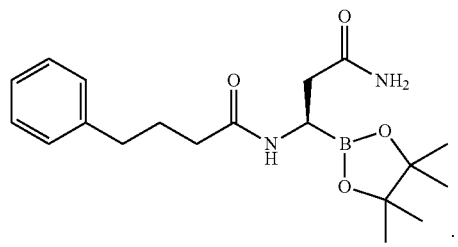 [SMILES: CC1(C)OB([C@H](CC(N)=O)NC(=O)CCCc2ccccc2)OC1(C)C]
In some embodiments of any of the aspects, ClbP inhibitor has a structure selected from the following:
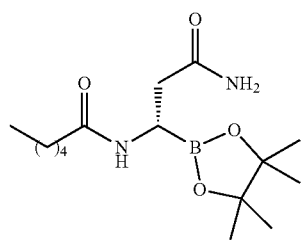
Hexanoyl-pinacolboro-Asn
(MRV03-037)
Formula IV
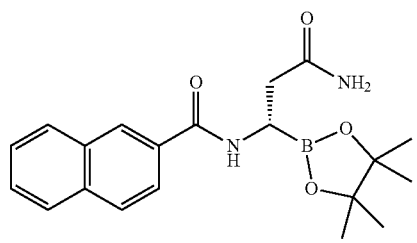
Formula VI
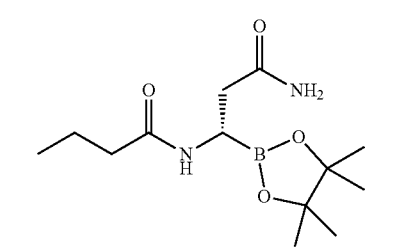
Formula VII
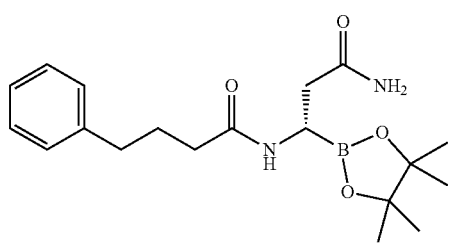
Formula VIII
Formula IX
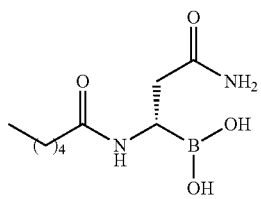
Formula X
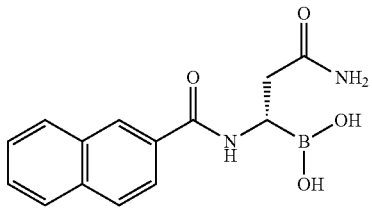
Formula XII
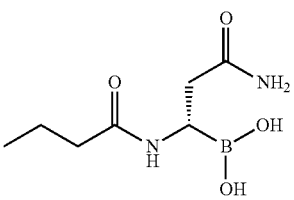
Formula XIII
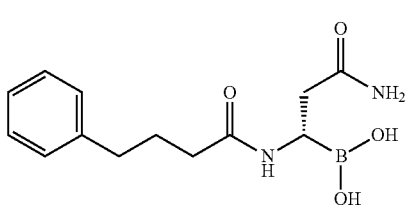
Formula XIV Formula XV

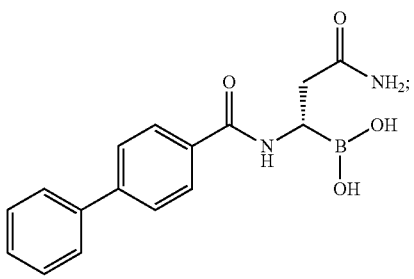

or an R enantiomer of any of the foregoing,

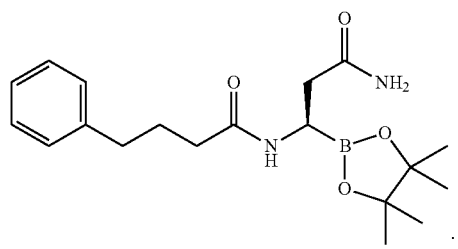 [SMILES: CC1(C)OB([C@H](CC(N)=O)NC(=O)CCCc2ccccc2)OC1(C)C]

In one aspect of any of the embodiments, described herein is a ClbP inhibitor having the structure of:

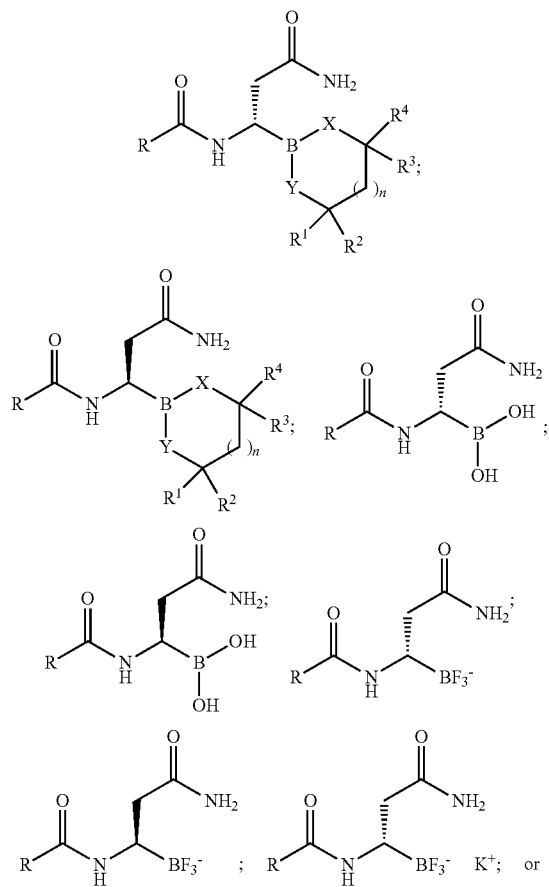

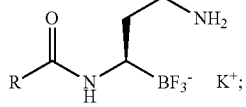

wherein R is selected from the group consisting of H, OH, alkyl, alkenyl, alkynyl, aryl, heteroaryl, cycloalkyl, or heterocycle; $R^1$, $R^2$, $R^3$ and $R^4$ independently are H, alkyl, alkenyl, alkynyl, aryl, heteroaryl, cycloalkyl or heterocycle, or $R^2$ and $R^3$, together with the carbons they are attached to, form an aryl, heteroaryl, cycloalkyl or heterocycle; X and Y independently are O, S or NH, and n is 0, or 1.

In one aspect of any of the embodiments, described herein is a ClbP inhibitor having the structure:

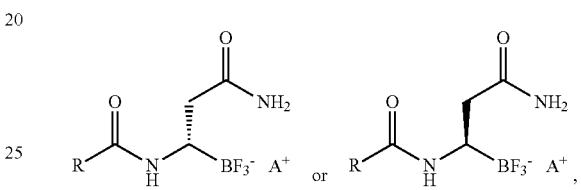

where A+ is absent or a cation and wherein R is selected from the group consisting of H, OH, alkyl, alkenyl, alkynyl, aryl, heteroaryl, cycloalkyl, or heterocycle; $R^1$, $R^2$, $R^3$ and $R^4$ independently are H, alkyl, alkenyl, alkynyl, aryl, heteroaryl, cycloalkyl or heterocycle, or $R^2$ and $R^3$, together with the carbons they are attached to, form an aryl, heteroaryl, cycloalkyl or heterocycle; X and Y independently are O, S or NH, and n is 0, or 1, or the R enantiomer thereof. In some embodiments of any of the aspects, the cation is selected from the group consisting of K+, Na+, ammonium (NH4+), pyridinium (C5H5NH+), and quaternary ammonium (R5R6R7R8N+), where R5, R6, R7, and R8 are independently selected from alkyl, cycloalkyl, phenyl, or benzyl, wherein the alkyl, cycloalkyl, phenyl, or benzyl is optionally substituted with one or more substitutents.

In some embodiments of any of the aspects, three of $R^1$, $R^2$, $R^3$ and $R^4$ are H and the other is methyl. In some embodiments of any of the aspects, $R^2$ and $R^3$, together with the carbon atoms they are attached to, form 2,3,4-trihydroxytetrahydropyran. In some embodiments of any of the aspects, n is 0, $R^1$ is methyl, $R^4$ is H, and $R^2$ and $R^3$, together with the carbon atoms they are attached to, form a 6,6-dimethylbicycle[3.1.1]heptane. In some embodiments of any of the aspects, n is 0, $R^1$ and $R^4$ are H, and $R^2$ and $R^3$, together with the carbon atoms they are attached to, form a benzene ring.

In some embodiments of any of the aspects, the ClbP inhibitor has the structure of:

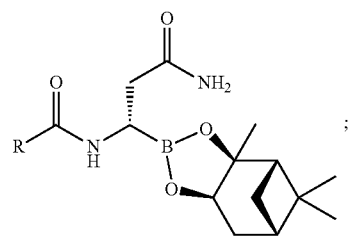

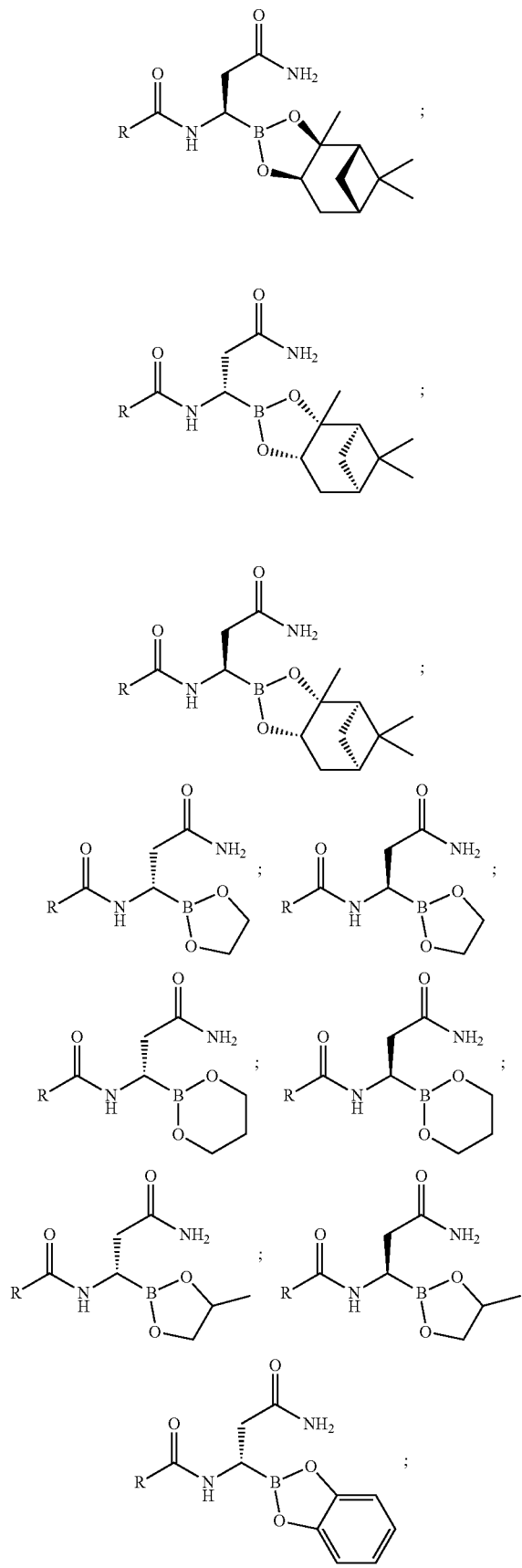

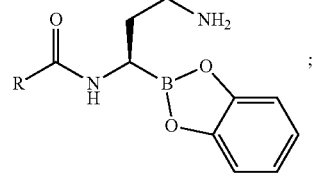

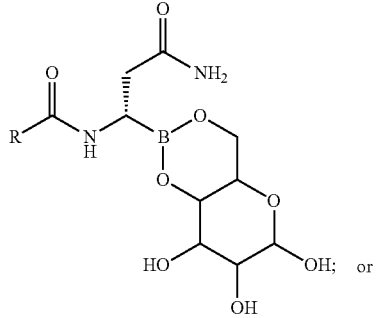

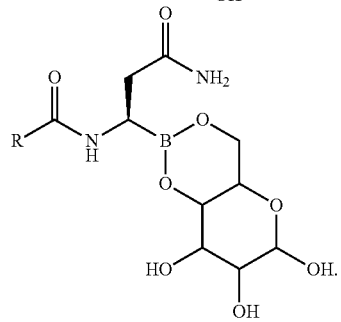

In some embodiments of any of the aspects, the ClbP inhibitor has the structure of:

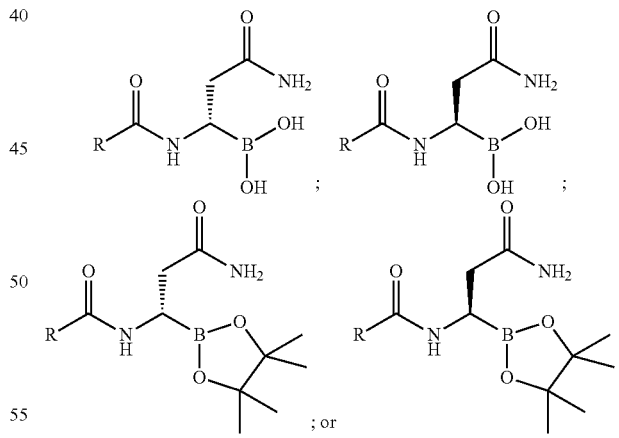

wherein R is, selected from the group consisting of H, OH, alkyl, alkenyl, alkynyl, aryl, heteroaryl, cycloalkyl, or heterocycle; wherein the alkyl, alkenyl, alkynyl, or cycloalkyl, whether alone or as part of a substituent group, is optionally substituted with one or more substituents independently selected from the group consisting of halogen, —OH, alkyl, O-alkyl, —NR$^A$R$^B$, —S-alkyl, —SO-alkyl, —SO$_2$-alkyl, alkenyl, alkynyl, aryl, heteroaryl, cycloalkyl or heterocycle; and the alkenyl, alkynyl, or optionally includes —O—, —S—, —SO$_2$—, —N(R$^C$)— substituting one or more carbons in the carbon chain, wherein the aryl or heteroaryl, whether alone or as part of a substituent group, is optionally substituted with one or more substituents independently selected from the group consisting of halogen, OH, alkyl, O-alkyl, —NR$^D$R$^E$, —S-alkyl, —SO-alkyl and —SO$_2$-alkyl, alkenyl, alkynyl, aryl, heteroaryl, cycloalkyl or heterocycle;

wherein R$^A$, R$^B$, R$^C$, R$^D$, and R$^E$, are each independently selected from hydrogen and C$_{1-4}$ alkyl. In some embodiments of any of the aspects, R is alkyl or aryl. In some embodiments of any of the aspects, R is not a phenyl group. In some embodiments of any of the aspects, R is selected from the group consisting of:

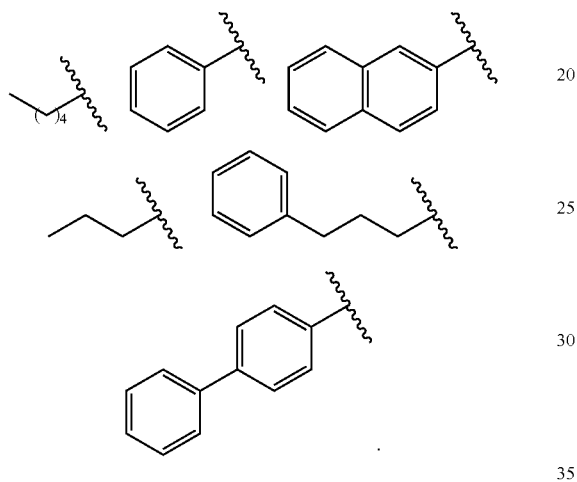

In some embodiments of any of the aspects, the ClbP inhibitor does not have the following structure:

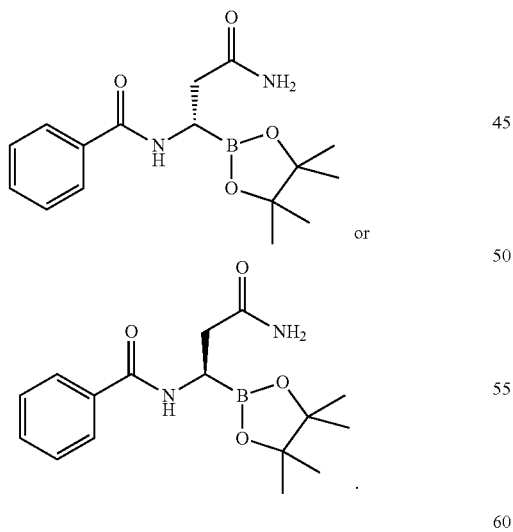

In some embodiments of any of the aspects, the ClbP inhibitor comprises a D-asparagine group and not an L-asparagine group. In some embodiments of any of the aspects, R is hydrophobic.

In some embodiments of any of the aspects, the ClbP inhibitor has a structure selected from the following:

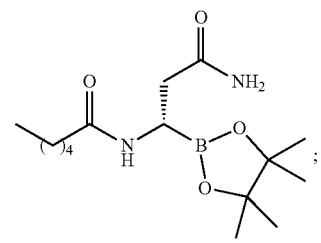

Hexanoyl-pinacolboro-Asn (MRV03-037)

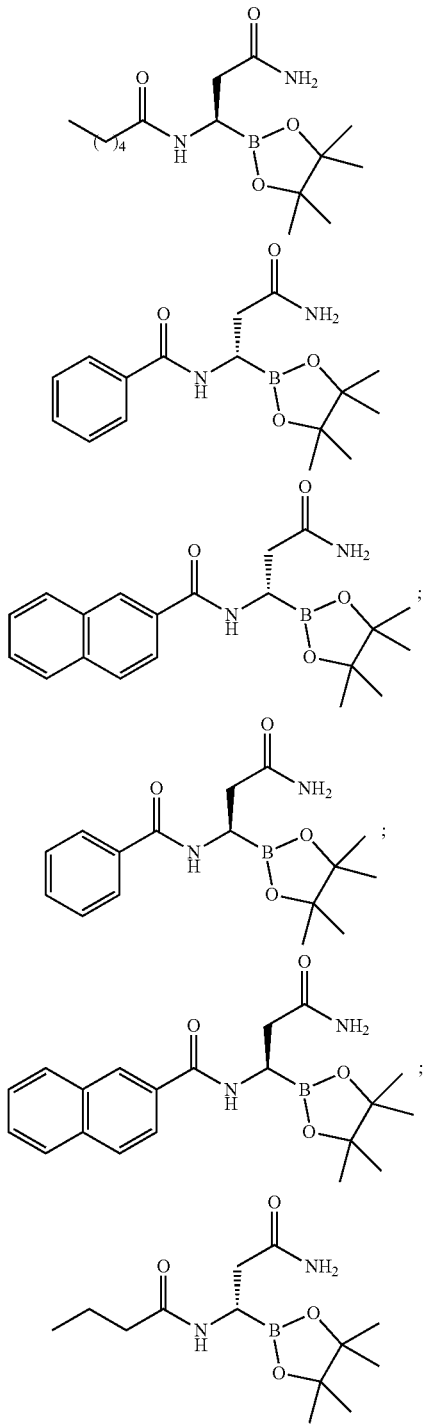

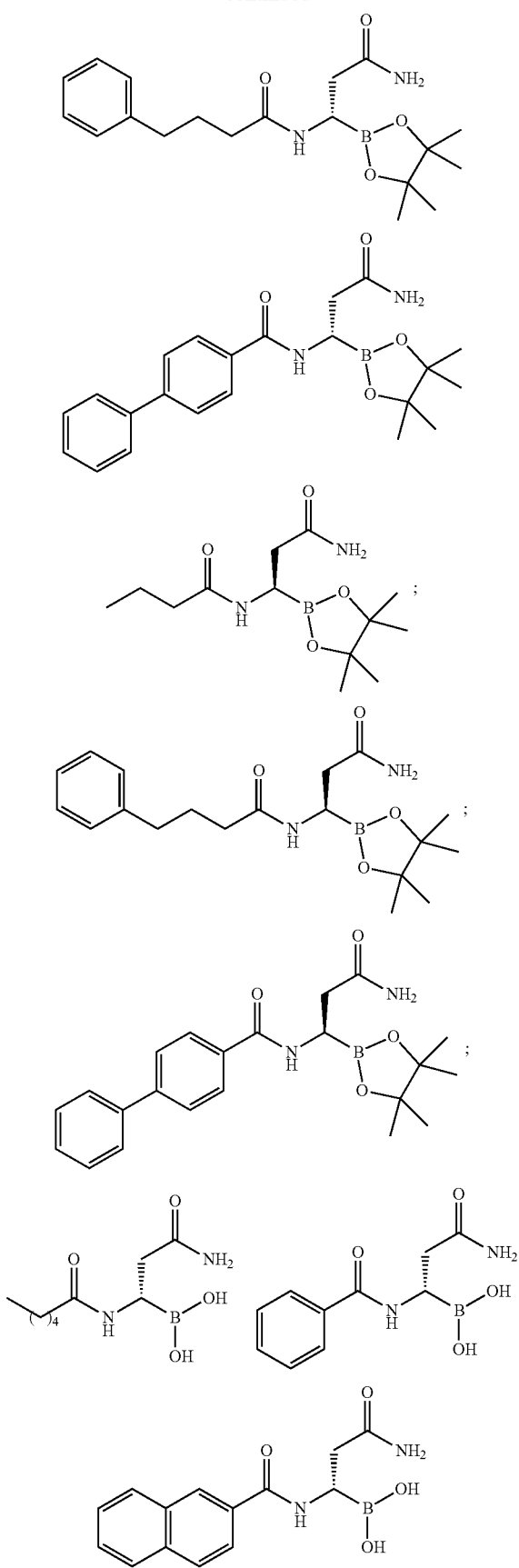

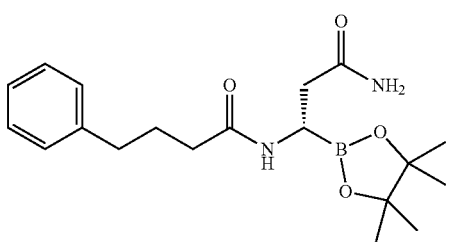
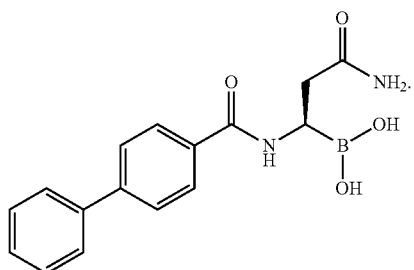
In some embodiments of any of the aspects, the ClbP inhibitor has a structure selected from the following:
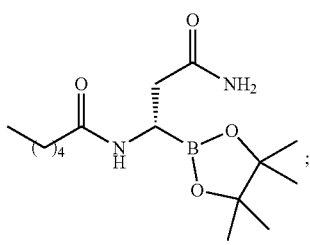
Hexanoyl-pinacolboro-Asn
(MRV03-037)
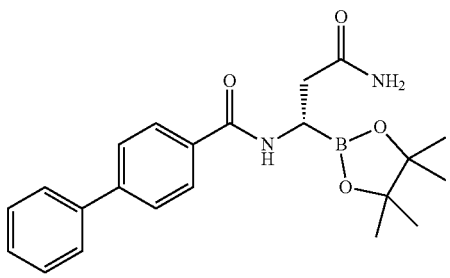
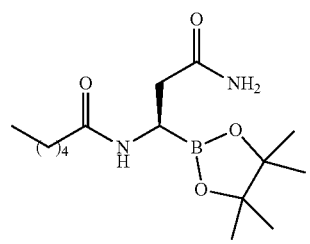
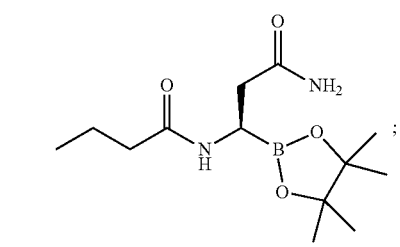
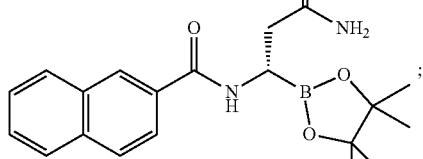
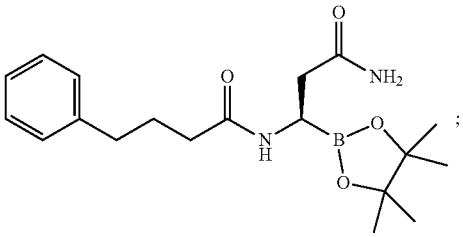
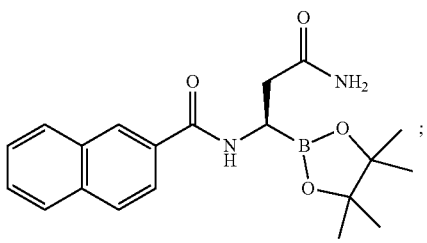
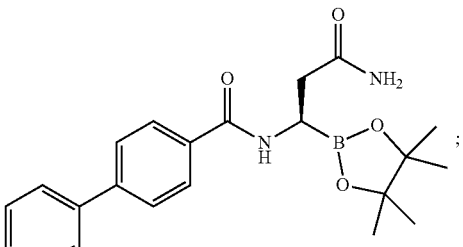
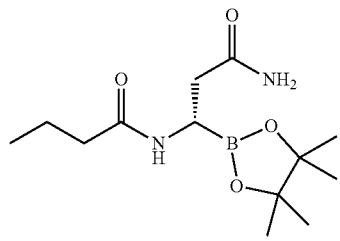
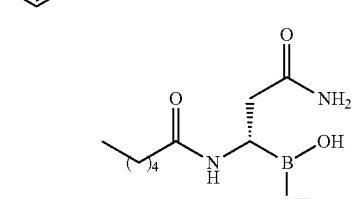
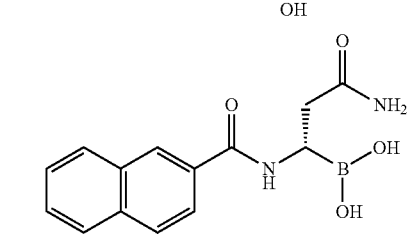

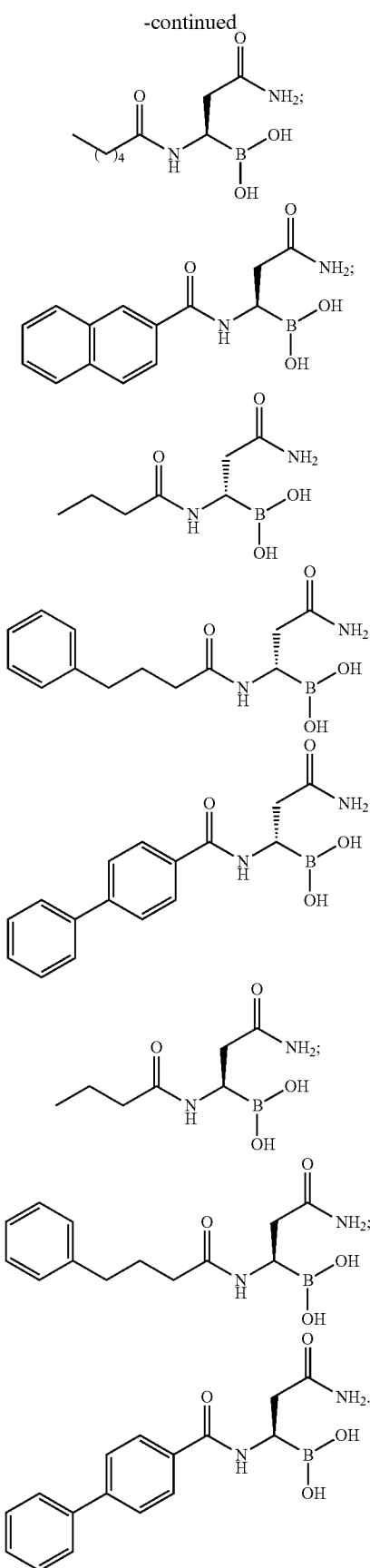

In some embodiments of any of the aspects, a ClbP inhibitor described herein, which includes a boronate ester, is first hydrolyzed to provide a free acid structure prior to inhibiting ClbP. This hydrolysis happens upon introduction to an aqueous environment, e.g., a subject, cell media, a cell, a solution of polypeptides/biomolecules, cell cytoplasm, stomach contents, blood, or others. In some of the foregoing embodiments, the described structures include a pinacol protecting group at the boronate ester group. However, it is known in the art that many boronate groups (esters and amides) readily undergo solvolysis in the presence of a nucleophilic solvent, such as alcohols or water, to produce the corresponding alcohol esters or free boronic acid, respectively. That is, protecting groups for boronate esters other than pincaol are known in the art to be labile and to hydrolyze upon contact with water, providing a free acid, e.g., according to some of the foregoing structures. Accordingly, a ClbP inhibitor compound comprising a protecting group other than pinacol can be administered and undergo hydrolysis in an aqueous environment, resulting in the corresponding free boronic acid. That is, compounds with different protecting groups each provide a species which is known to be an active inhibitor of ClbP. Exemplary protecting groups and their properties and uses are known in the art, e.g., see Bernardini et al. Chemistry Letters 2009 38(7)750-1; Hinkes and Klein Org. Lett. 2019 21:3048-52; Churches and Hutton "Chapter 11 Introduction, Interconversion, and Removal of Boron Protecting Groups" in Boron Reagents in Synthesis 2016; and Churches et al. Journal of Organic Chemistry 2015 80:5428-35; and U.S. Pat. No. 5,384,410; each of which is incorporated by reference herein in its entirety. It is noted that Bernardini et al. Chemistry Letters 2009 38(7)750-1 notes that pinanediol is one of the boronate ester protecting groups most resistant to hydrolysis. As demonstrated in the Example herein, a compound comprising this protecting group displays ClbP inhibition. Suitable protecting groups contemplated herein include pinacol; (+)-pinanediol; (−)-pinanediol; ethylene glycol; propylene glycol; 1,3 propanediol; catechol; any sugars; and 1,2 or 1,3 diols. Also contemplated herein are compounds where one or both of the alcohols (OH) of the boronate ester is replaced with an amine (NH2) or amide ((C=O)NH2). In general, any group with two primary nucleophiles (either alcohol or amine) that are 4 or 5 atoms apart is contemplated herein as a protecting group for a ClbP inhibitor as described herein.

Accordingly, in some embodiments, the ClbP has the structure of

Formula XVI

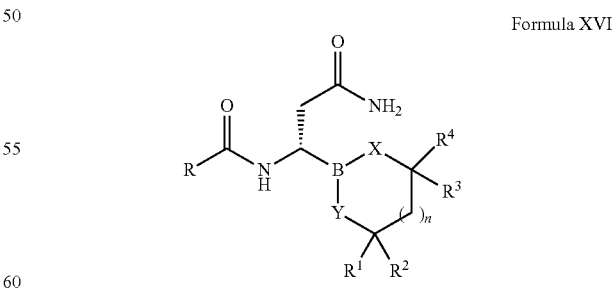

wherein R is selected from the group consisting of H, OH, alkyl, alkenyl, alkynyl, aryl, heteroaryl, cycloalkyl, or heterocycle and $R^1$, $R^2$, $R^3$ and $R^4$ independently are H, alkyl, alkenyl, alkynyl, aryl, heteroaryl, cycloalkyl or heterocycle, or $R^2$ and $R^3$, together with the carbons they are attached to, form an aryl, heteroaryl, cycloalkyl or heterocycle; X and Y independently are O, S or NH, and n is 0, or 1; or an R enantiomer of any of the foregoing.

In some embodiments, n is 0. In some other embodiments, n is 1.

In some embodiments, X is O. In some embodiments, Y is O. In some embodiments, X and Y are O.

In some embodiments, $R^1$ and $R^4$ are H. In some embodiments, at least one of $R^1$ and $R^4$ is a $C_1$-$C_6$alkyl. For example, at least one of $R^1$ and $R^4$ is methyl, ethyl, propyl, isopropyl, butyl, or pentyl. In some embodiments, one of $R^1$ and $R^4$ is H and the other of $R^1$ and $R^4$ is a $C_1$-$C_6$alkyl. For example, $R^1$ is H and $R^4$ is methyl, ethyl, propyl, isopropyl, butyl, or pentyl. In another example, $R^4$ is H and $R^1$ is methyl, ethyl, propyl, isopropyl, butyl, or pentyl.

In some embodiments, $R^2$ and $R^3$ are H. In some embodiments, at least one of $R^2$ and $R^3$ is a $C_1$-$C_6$alkyl. For example, at least one of $R^2$ and $R^3$ is methyl, ethyl, propyl, isopropyl, butyl, or pentyl. In some embodiments, one of $R^2$ and $R^3$ is H and the other of $R^2$ and $R^3$ is a $C_1$-$C_6$alkyl. For example, $R^2$ is H and $R^3$ is methyl, ethyl, propyl, isopropyl, butyl, or pentyl. In another example, $R^3$ is H and $R^2$ is methyl, ethyl, propyl, isopropyl, butyl, or pentyl.

In some embodiments, three of $R^1$, $R^2$, $R^3$ and $R^4$ are H and the other is a $C_1$-$C_6$alkyl. For example, three of $R^1$, $R^2$, $R^3$ and $R^4$ are H and the other is methyl, ethyl, propyl, isopropyl, butyl, or pentyl. In some embodiments, three of $R^1$, $R^2$, $R^3$ and $R^4$ are H and the other is methyl.

In some embodiments, $R^1$, $R^2$, $R^3$ and $R^4$ are H. For example, n is 0 and $R^1$, $R^2$, $R^3$ and $R^4$ are H. In another example, n is 1 and $R^1$, $R^2$, $R^3$ and $R^4$ are H.

In some embodiments, $R^2$ and $R^3$, together with the carbon atoms they are attached to, form a 5-8 membered cycloalkyl or heterocycle. For example, $R^2$ and $R^3$, together with the carbon atoms they are attached to, form a 5-8 membered monocyclic or 7-12 membered bicyclic cycloalkyl or heterocycle. In some embodiments, $R^2$ and $R^3$, together with the carbon atoms they are attached to, form a 5-8 membered monocyclic heterocycle comprising 1-3 heteroatoms. For example, $R^2$ and $R^3$, together with the carbon atoms they are attached to, form a six-membered heterocycle comprising an oxygen atom, i.e., tetrahydropyran. In some embodiments, $R^2$ and $R^3$, together with the carbon atoms they are attached to, form 2,3,4-trihydroxytetrahydropyran.

In some embodiments, $R^2$ and $R^3$, together with the carbon atoms they are attached to, form a 7-12 membered bicyclic cycloalkyl. For example, bicycloheptane, bicyclooctane, bicyclononane or bicyclodecane. In some embodiments, $R^2$ and $R^3$, together with the carbon atoms they are attached to, form a bicycle[3.1.1]heptane. For example, $R^2$ and $R^3$, together with the carbon atoms they are attached to, form a 6,6-dimethylbicycle[3.1.1]heptane. In some embodiments, n is 0, $R^1$ is methyl, $R^4$ is H, and $R^2$ and $R^3$, together with the carbon atoms they are attached to, form a 6,6-dimethylbicycle[3.1.1]heptane.

In some embodiments, $R^2$ and $R^3$, together with the carbon atoms they are attached to, form a 5-8 membered aryl. For example, n is 0 and $R^2$ and $R^3$, together with the carbon atoms they are attached to, form a 5-8 membered aryl. In some embodiments, n is 0, $R^1$ and $R^4$ are H, and $R^2$ and $R^3$, together with the carbon atoms they are attached to, form a benzene ring.

In some embodiments of any of the aspects, the alkyl, alkenyl, alkynyl, or cycloalkyl, whether alone or as part of a substituent group, is optionally substituted with one or more substituents independently selected from the group consisting of halogen, —OH, alkyl, O-alkyl, —$NR^AR^B$, —S-alkyl, —SO-alkyl, —$SO_2$-alkyl, alkenyl, alkynyl, aryl, heteroaryl, cycloalkyl or heterocycle; and the alkenyl, alkynyl, or optionally includes —O—, —S—, —$SO_2$—, —$N(R^C)$— substituting one or more carbons in the carbon chain, wherein the aryl or heteroaryl, whether alone or as part of a substituent group, is optionally substituted with one or more substituents independently selected from the group consisting of halogen, OH, alkyl, O-alkyl, —$NR^DR^E$, —S-alkyl, —SO-alkyl and —$SO_2$-alkyl, alkenyl, alkynyl, aryl, heteroaryl, cycloalkyl or heterocycle; and wherein $R^A$, $R^B$, $R^C$, $R^D$, and $R^E$, are each independently selected from hydrogen and $C_{1-4}$ alkyl. In some embodiments of any of the aspects, R is alkyl or aryl. In some embodiments of any of the aspects, R is not a phenyl group. In some embodiments of any of the aspects, R is hydrophobic. In some embodiments of any of the aspects R is selected from the group consisting of:

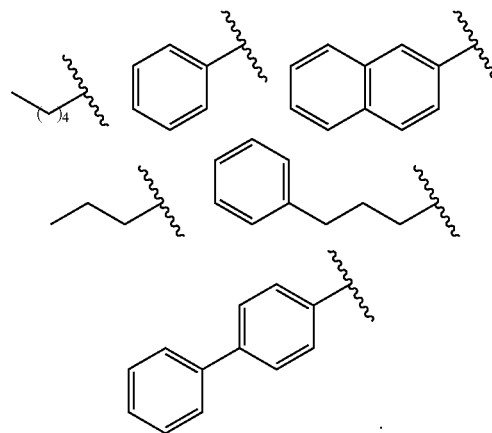

In some embodiments of any of the aspects, the ClbP inhibitor has the structure of:

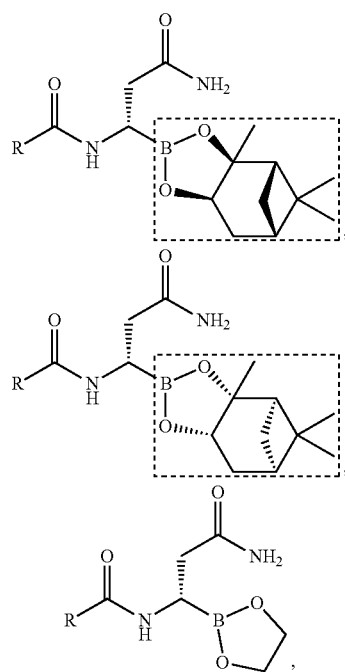

-continued

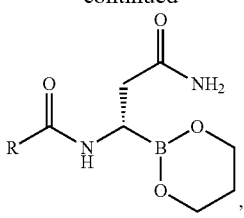

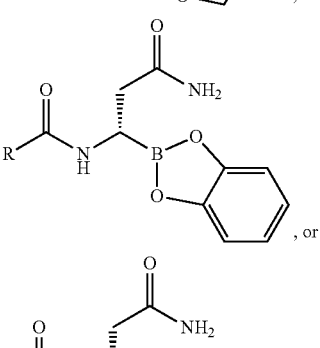

wherein R is selected from the group consisting of H, OH, alkyl, alkenyl, alkynyl, aryl, heteroaryl, cycloalkyl, or heterocycle. In some embodiments of any of the aspects, the alkyl, alkenyl, alkynyl, or cycloalkyl, whether alone or as part of a substituent group, is optionally substituted with one or more substituents independently selected from the group consisting of halogen, —OH, alkyl, O-alkyl, —NR$^A$R$^B$, —S-alkyl, —SO-alkyl, —SO$_2$-alkyl, alkenyl, alkynyl, aryl, heteroaryl, cycloalkyl or heterocycle; and the alkenyl, alkynyl, or optionally includes —O—, —S—, —SO$_2$—, —N(R$^C$)— substituting one or more carbons in the carbon chain, wherein the aryl or heteroaryl, whether alone or as part of a substituent group, is optionally substituted with one or more substituents independently selected from the group consisting of halogen, OH, alkyl, O-alkyl, —NR$^D$R$^E$, —S-alkyl, —SO-alkyl and —SO$_2$-alkyl, alkenyl, alkynyl, aryl, heteroaryl, cycloalkyl or heterocycle; and wherein R$^A$, R$^B$, R$^C$, R$^D$, and R$^E$, are each independently selected from hydrogen and C$_{1-4}$ alkyl; or an R enantiomer of any of the foregoing. In some embodiments of any of the aspects, R is alkyl or aryl. In some embodiments of any of the aspects, R is not a phenyl group. In some embodiments of any of the aspects, R is hydrophobic. In some of any of the aspects R is selected from the group consisting of:

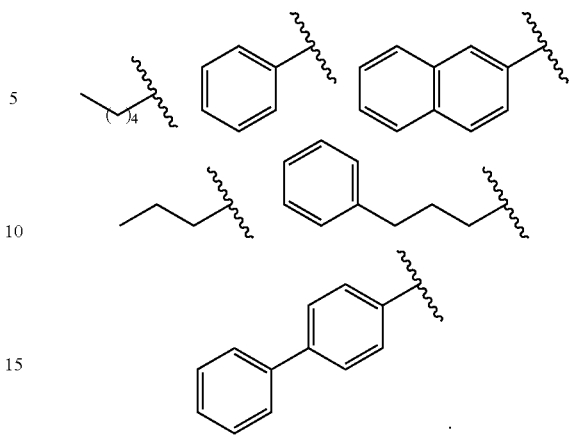

In some embodiments of any of the aspects, the ClbP inhibitor has the structure of:

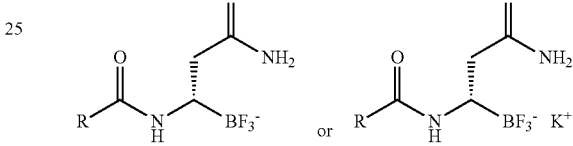

wherein R is selected from the group consisting of H, OH, alkyl, alkenyl, alkynyl, aryl, heteroaryl, cycloalkyl, or heterocycle. In some embodiments of any of the aspects, the alkyl, alkenyl, alkynyl, or cycloalkyl, whether alone or as part of a substituent group, is optionally substituted with one or more substituents independently selected from the group consisting of halogen, —OH, alkyl, O-alkyl, —NR$^A$R$^B$, —S-alkyl, —SO-alkyl, —SO$_2$-alkyl, alkenyl, alkynyl, aryl, heteroaryl, cycloalkyl or heterocycle; and the alkenyl, alkynyl, or optionally includes —O—, —S—, —SO$_2$—, —N(R$^C$)— substituting one or more carbons in the carbon chain, wherein the aryl or heteroaryl, whether alone or as part of a substituent group, is optionally substituted with one or more substituents independently selected from the group consisting of halogen, OH, alkyl, O-alkyl, —NR$^D$R$^E$, —S-alkyl, —SO-alkyl and —SO$_2$-alkyl, alkenyl, alkynyl, aryl, heteroaryl, cycloalkyl or heterocycle; and wherein R$^A$, R$^B$, R$^C$, R$^D$, and R$^E$, are each independently selected from hydrogen and C$_{1-4}$ alkyl; or an R enantiomer of any of the foregoing. In some embodiments of any of the aspects, R is alkyl or aryl. In some embodiments of any of the aspects, R is not a phenyl group. In some embodiments of any of the aspects, R is hydrophobic. In some embodiments of any of the aspects R is selected from the group consisting of:

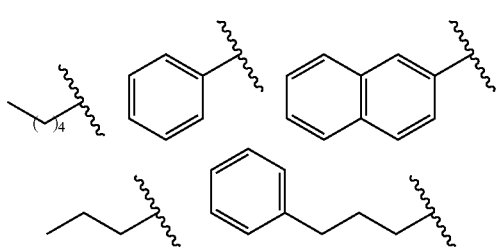

-continued

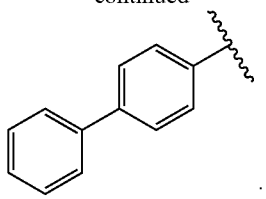

In some embodiments of any of the aspects, the ClbP inhibitor is a salt and further comprises a cation, e.g., K⁺, Na⁺, ammonium, pyridinium, or quaternary ammonium.

In some embodiments of any of the aspects, the ClbP inhibitor is a direct inhibitor of ClbP.

As noted above, ClbP functions in the production of colibactin. The genotoxin colibactin is produced by commensal and pathogenic strains of bacteria and has been linked to the development of certain cancers, e.g., colorectal cancer. The suite of genes necessary for colibactin biosynthesis (including clbP) are located in the biosynthetic gene cluster known as the pks island or clb gene cluster. Pks⁺ bacteria, e.g., *E. coli*, induce DNA double-strand breaks (DSBs) in eukaryotic cells, and mono-colonization with pks+ bacteria increases tumor load in genetically susceptible mouse models of colorectcal cancer. Pks⁺ bacteria, e.g., *E. coli*, are also found more frequently in patients with colorectal cancer than in healthy controls. Finally, mutational signatures arising from exposure of human cells to colibactin have been detected in sequenced cancer genomes, including colorectal cancer genomes. For example such signatures are discussed in more detail in Pleguezuelos-Manzano et al. Mutational signature in colorectal cancer caused by genotoxic pks⁺ *E. coli*. Nature 2020, 580, 269-273; Dziubańska-Kusibab et al. Colibactin DNA-damage signature indicates mutational impact in colorectal cancer. Nat. Med. 2020, 26, 1063-1069; and Boot, et al. Characterization of colibactin-associated mutational signature in an Asian oral squamous cell carcinoma and in other mucosal tumor types. Genome Res. 2020, 30, 803-813; each of which is incorporated by reference herein in its entirety. It should be noted that bacteria other than *E. coli* can be pks⁺. In some embodiments of any of the aspects, the pks+ bacteria is a Proteobacteria, e.g., *Citrobacter, Klebsiella, Eshcerichia*, or *E. coli*.

Colibactin-associated mutations have also been bound in other cancers e.g., in head-and-neck derived tumor, urinary tract tumors, and oral squamous-cell carcinoma. See, e.g., Pleguezuelos-Manzano Nature, 2020 580:269-273; which is incorporated by reference herein in its entirety. It is also known that certain cancer patients are susceptible to colibactin, e.g., cancer patients with Fanconi Anemia or Familial Adenomatous Polyposis. Accordingly, in some embodiments, the cancer is a colorectal cancer, a urinary tract cancer, a squamous cell carcinoma, an oral squamous cell carcinoma, or a head-and-neck cancer. In some embodiments, the subject is a subject having a disease known to increase susceptibility to colibactin. In some embodiments, the subject is a subject having Fanconi Anemia or Familial Adenomatous Polyposis.

Accordingly, in some embodiments, the methods described herein relate to inhibition in a subject, e.g., administering the ClbP inhibitor to a subject. In some embodiments of any of the aspects, the subject has a population of pks+ bacteria. In some embodiments of any of the aspects, the subject has an infection of pks+ bacteria. In some embodiments of any of the aspects, the subject has an infection of pks+ Proteobacteria, e.g., *Citrobacter, Klebsiella, Eshcerichia*, or *E. coli*. In some embodiments of any of the aspects, the subject has a population of pks+*E. coli*. In some embodiments of any of the aspects, the subject has an infection of pks+*E. coli*. In one aspect, described herein is a method of treating a pks+ bacterial infection in a subject in need thereof, the method comprising administering a ClbP inhibitor described herein to the subject.

Populations and/or infections of bacteria, e.g., pks+ bacteria can be detected by any method known in the art, e.g., by culuring bacteria from a sample obtained in a subject, or detecting bacteria in a sample obtained from a subject, e.g, using immunochemistry, PCR, sequencing technology, or other detection methods known in the art. Exemplary non-limiting methods are also described in US Patent Publication 2020/0055836, which is incorporated by reference herein in its entirety.

The methods described herein, by inhibiting ClbP, can reduce or inhibit the biosynthesis of a genotoxin, e.g., colibactin. In some embodiments of any of the aspects, the methods described herein reduct the level of one or more genotoxins in a sample, and/or reduce or inhibit the production of one or more genotoxins in the sample or subject. Genotoxin levels can be determined directly or indirectly by any method known in the art, e.g., mass spectrometry, immunochemistry, detection of DNA adducts caused by genotoxins, or detection of colibactin-related metabolites.

In some embodiments of any of the aspects, the subject has or has been diagnosed with cancer. In one aspect of any of the embodiments, described herein is a method of treating cancer in a subject in need thereof, the method comprising administering a ClbP inhibitor described herein to the subject. In one aspect of any of the embodiments, described herein is a method of reducing the risk and/or progression of cancer in a subject in need thereof, the method comprising administering a ClbP inhibitor described herein to the subject. In some embodiments of any of the aspects, the cancer is colorectal cancer.

In some embodiments of any of the aspects, two or more of the ClbP inhibitors described herein are administered. In some embodiments of any of the aspects, two, three, four, five, or more of the ClbP inhibitors described herein are administered. In some aspects, provided herein is a composition comprising two or more ClbP inhibitors for use in a method described herein, e.g., treatment of cancer of a pks+ bacterial infection. In some aspects, provided herein is a combination of two or more ClbP inhibitors (e.g., a kit comprising two or more ClbP inhibitors in the same or separate formulations) for use in a method described herein, e.g., treatment of cancer of a pks+ bacterial infection. The following table provides exemplary, non-limiting pairwise combinations.

|  | Formula | | | | | | | | | | | |
|---|---|---|---|---|---|---|---|---|---|---|---|---|
|  | IV | V | VI | VII | VIII | IX | X | XI | XII | XIII | XIV | XV |
| Formlua IV |  | x | x | x | x | x | x | x | x | x | x | X |
| V | X |  | x | x | x | x | x | x | x | x | x | x |
| VI | X | x |  | x | x | x | x | x | x | x | x | x |
| VII | X | x | X |  | x | x | x | x | x | x | x | X |
| VIII | X | x | x | X |  | x | x | x | x | x | x | x |
| IX | X | x | x | x | X |  | x | x | x | x | x | X |
| X | X | x | x | x | x | X |  | x | x | x | x | x |
| XI | X | x | x | x | x | x | X |  | x | x | x | x |
| XII | X | x | x | x | x | x | x | X |  | x | x | x |
| XIII | X | x | x | x | x | x | x | x | x |  | x | X |
| XIV | X | x | x | x | x | x | x | x | x | x |  | x |
| XV | x | x | x | x | x | x | x | x | x | x | x |  |

As used herein, the term "cancer" relates generally to a class of diseases or conditions in which abnormal cells divide without control and can invade nearby tissues. Cancer cells can also spread to other parts of the body through the blood and lymph systems. There are several main types of cancer. Carcinoma is a cancer that begins in the skin or in tissues that line or cover internal organs. Sarcoma is a cancer that begins in bone, cartilage, fat, muscle, blood vessels, or other connective or supportive tissue. Leukemia is a cancer that starts in blood-forming tissue such as the bone marrow, and causes large numbers of abnormal blood cells to be produced and enter the blood. Lymphoma and multiple myeloma are cancers that begin in the cells of the immune system. Central nervous system cancers are cancers that begin in the tissues of the brain and spinal cord.

In some embodiments of any of the aspects, the cancer is a primary cancer. In some embodiments of any of the aspects, the cancer is a malignant cancer. As used herein, the term "malignant" refers to a cancer in which a group of tumor cells display one or more of uncontrolled growth (i.e., division beyond normal limits), invasion (i.e., intrusion on and destruction of adjacent tissues), and metastasis (i.e., spread to other locations in the body via lymph or blood). As used herein, the term "metastasize" refers to the spread of cancer from one part of the body to another. A tumor formed by cells that have spread is called a "metastatic tumor" or a "metastasis." The metastatic tumor contains cells that are like those in the original (primary) tumor. As used herein, the term "benign" or "non-malignant" refers to tumors that may grow larger but do not spread to other parts of the body. Benign tumors are self-limited and typically do not invade or metastasize.

A "cancer cell" or "tumor cell" refers to an individual cell of a cancerous growth or tissue. A "cancer cell" is a cancerous, pre-cancerous, or transformed cell, either in vivo, ex vivo, or in tissue culture, that has spontaneous or induced phenotypic changes that do not necessarily involve the uptake of new genetic material. Although transformation can arise from infection with a transforming virus and incorporation of new genomic nucleic acid, or uptake of exogenous nucleic acid, it can also arise spontaneously or following exposure to a carcinogen, thereby mutating an endogenous gene. Transformation/cancer is associated with, e.g., morphological changes, immortalization of cells, aberrant growth control, foci formation, anchorage independence, malignancy, loss of contact inhibition and density limitation of growth, growth factor or serum independence, tumor specific markers, invasiveness or metastasis, and tumor growth in suitable animal hosts such as nude mice. A tumor refers generally to a swelling or lesion formed by an abnormal growth of cells, which may be benign, pre-malignant, or malignant. Most cancer cells form tumors, but some, e.g., leukemia, do not necessarily form tumors. For those cancer cells that form tumors, the terms cancer (cell) and tumor (cell) are used interchangeably.

As used herein the term "neoplasm" refers to any new and abnormal growth of tissue, e.g., an abnormal mass of tissue, the growth of which exceeds and is uncoordinated with that of the normal tissues. Thus, a neoplasm can be a benign neoplasm, premalignant neoplasm, or a malignant neoplasm.

A subject that has a cancer or a tumor is a subject having objectively measurable cancer cells present in the subject's body. Included in this definition are malignant, actively proliferative cancers, as well as potentially dormant tumors or micrometastatses. Cancers which migrate from their original location and seed other vital organs can eventually lead to the death of the subject through the functional deterioration of the affected organs.

Examples of cancer include but are not limited to, carcinoma, lymphoma, blastoma, sarcoma, leukemia, basal cell carcinoma, biliary tract cancer; bladder cancer; bone cancer; brain and CNS cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma (GBM); hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); lymphoma including Hodgkin's and non-Hodgkin's lymphoma; melanoma; myeloma; neuroblastoma; oral cavity cancer (e.g., lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; as well as other carcinomas and sarcomas; as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome.

In some embodiments, the methods described herein relate to treating a subject having or diagnosed as having cancer, e.g., colorectal cancer, or a pks+ bacterial population or infection with a ClbP inhibitor disclosed herein. Subjects having cancer, e.g., colorectal cancer, or a pks+ bacterial population or infection can be identified by a physician using current methods of diagnosing such conditions. For example, symptoms and/or complications of colorectal cancer which characterize these conditions and aid in diagnosis are well known in the art and include but are not limited to, a change in bowel habits, bleeding, abdominal discomfort, weakness, fatigue, or unexplained weight loss. Tests that may aid in a diagnosis of, e.g. colorectal cancer include, but are not limited to, a colonoscopy or CEA blood tests. A family history of cancer, or exposure to risk factors for cancer can also aid in determining if a subject is likely to have cancer or in making a diagnosis of cancer.

The compositions and methods described herein can be administered to a subject having or diagnosed as having cancer, e.g., colorectal cancer, or a pks+ bacterial population or infection. In some embodiments, the methods described herein comprise administering an effective amount of compositions described herein, e.g. a ClbP inhibitor to a subject in order to alleviate a symptom of a cancer, e.g., colorectal cancer, or a pks+ bacterial population or infection. As used herein, "alleviating a symptom" of a disease is ameliorating any condition or symptom associated with the disease. As compared with an equivalent untreated control, such reduction is by at least 5%, 10%, 20%, 40%, 50%, 60%, 80%, 90%, 95%, 99% or more as measured by any standard technique. A variety of means for administering the compositions described herein to subjects are known to those of skill in the art. Such methods can include, but are not limited to oral, parenteral, intravenous, intramuscular, subcutaneous, transdermal, airway (aerosol), pulmonary, cutaneous, topical, injection, or intratumoral administration. Administration can be local or systemic.

In some embodiments of any of the aspects, the term "effective amount" as used herein refers to the amount of a ClbP inhibitor needed to alleviate at least one or more symptom of the disease or disorder, and relates to a sufficient amount of pharmacological composition to provide the desired effect. In some embodiments of any of the aspects, the term "effective amount" as used herein refers to the amount of a ClbP inhibitor needed to inhibit the activity of ClbP in a bacterium or bacterial culture. The term "therapeutically effective amount" therefore refers to an amount of a ClbP inhibitor that is sufficient to provide a particular effect when administered to a typical subject. An effective amount as used herein, in various contexts, would also include an amount sufficient to delay the development of a symptom of the disease, alter the course of a symptom disease (for example but not limited to, slowing the progression of a symptom of the disease), or reverse a symptom of the disease. Thus, it is not generally practicable to specify an exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of a ClbP inhibitor which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay, e.g., assay for cancer cell growth or genotoxin production, among others. The dosage can be determined by a physician and adjusted, as necessary, to suit observed effects of the treatment.

In some embodiments, the technology described herein relates to a pharmaceutical composition comprising a ClbP inhibitor as described herein, and optionally a pharmaceutically acceptable carrier. In some embodiments, the active ingredients of the pharmaceutical composition comprise at least one ClbP inhibitor as described herein. In some embodiments, the active ingredients of the pharmaceutical composition consist essentially of at least one ClbP inhibitor as described herein. In some embodiments, the active ingredients of the pharmaceutical composition consist of at least one ClbP inhibitor as described herein. Pharmaceutically acceptable carriers and diluents include saline, aqueous buffer solutions, solvents and/or dispersion media. The use of such carriers and diluents is well known in the art. Some non-limiting examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein. In some embodiments, the carrier inhibits the degradation of the active agent, e.g. a ClbP inhibitor as described herein.

In some embodiments, the pharmaceutical composition comprising a ClbP inhibitor as described herein can be a parenteral dose form. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration of a patient, including, but not limited to, DUROS®-type dosage forms and dose-dumping.

Suitable vehicles that can be used to provide parenteral dosage forms of a ClbP inhibitor as disclosed within are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate. Compounds that alter or modify the solubility of a pharmaceutically acceptable salt of a ClbP inhibitor as disclosed herein can also be incorporated into the parenteral dosage forms of the disclosure, including conventional and controlled-release parenteral dosage forms.

Pharmaceutical compositions comprising at least one ClbP inhibitor can also be formulated to be suitable for oral administration, for example as discrete dosage forms, such as, but not limited to, tablets (including without limitation scored or coated tablets), pills, caplets, capsules, chewable tablets, powder packets, cachets, troches, wafers, aerosol sprays, or liquids, such as but not limited to, syrups, elixirs, solutions or suspensions in an aqueous liquid, a non-aqueous liquid, an oil-in-water emulsion, or a water-in-oil emulsion. Such compositions contain a predetermined amount of the pharmaceutically acceptable salt of the disclosed compounds, and may be prepared by methods of pharmacy well known to those skilled in the art. See generally, Remington: The Science and Practice of Pharmacy, 21st Ed., Lippincott, Williams, and Wilkins, Philadelphia PA (2005).

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under-dosing a drug (i.e., going below the minimum therapeutic levels) as well as exceeding the toxicity level for the drug. In some embodiments, the at least one ClbP inhibitor can be administered in a sustained release formulation.

Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. Kim, Cherng-ju, Controlled Release Dosage Form Design, 2 (Technomic Publishing, Lancaster, Pa.: 2000).

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the salts and compositions of the disclosure. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), or a combination thereof to provide the desired release profile in varying proportions.

In some embodiments of any of the aspects, the ClbP inhibitor described herein is administered as a monotherapy, e.g., another treatment for the cancer, e.g., colorectal cancer, or a pks+ bacterial population or infection is not administered to the subject.

In some embodiments of any of the aspects, the methods described herein can further comprise administering a second agent and/or treatment to the subject, e.g. as part of a combinatorial therapy. Non-limiting examples of a second agent and/or treatment can include radiation therapy, surgery, gemcitabine, cisplastin, paclitaxel, carboplatin, bortezomib, AMG479, vorinostat, rituximab, temozolomide, rapamycin, ABT-737, PI-103; alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin;

spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb®); inhibitors of PKC-alpha, Raf, H-Ras, EGFR (e.g., erlotinib (Tarceva®)) and VEGF-A that reduce cell proliferation and pharmaceutically acceptable salts, acids or derivatives of any of the above. Further, the methods of treatment can further include the use of surgical treatments.

In certain embodiments, an effective dose of a composition comprising at least one ClbP inhibitor as described herein can be administered to a patient once. In certain embodiments, an effective dose of a composition comprising at least one ClbP inhibitor can be administered to a patient repeatedly. For systemic administration, subjects can be administered a therapeutic amount of a composition comprising at least one ClbP inhibitor, such as, e.g. 0.1 mg/kg, 0.5 mg/kg, 1.0 mg/kg, 2.0 mg/kg, 2.5 mg/kg, 5 mg/kg, 10 mg/kg, 15 mg/kg, 20 mg/kg, 25 mg/kg, 30 mg/kg, 40 mg/kg, 50 mg/kg, or more.

In some embodiments, after an initial treatment regimen, the treatments can be administered on a less frequent basis. For example, after treatment biweekly for three months, treatment can be repeated once per month, for six months or a year or longer. Treatment according to the methods described herein can reduce levels of a marker or symptom of a condition, e.g. genotoxin production and/or cancer cell growth by at least 10%, at least 15%, at least 20%, at least 25%, at least 30%, at least 40%, at least 50%, at least 60%, at least 70%, at least 80% or at least 90% or more.

The dosage of a composition as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment, or make other alterations to the treatment regimen. The dosing schedule can vary from once a week to daily depending on a number of clinical factors, such as the subject's sensitivity to the active ingredient. The desired dose or amount of activation can be administered at one time or divided into subdoses, e.g., 2-4 subdoses and administered over a period of time, e.g., at appropriate intervals through the day or other appropriate schedule. In some embodiments, administration can be chronic, e.g., one or more doses and/or treatments daily over a period of weeks or months. Examples of dosing and/or treatment schedules are administration daily, twice daily, three times daily or four or more times daily over a period of 1 week, 2 weeks, 3 weeks, 4 weeks, 1 month, 2 months, 3 months, 4 months, 5 months, or 6 months, or more. A composition comprising at least one ClbP inhibitor can be administered over a period of time, such as over a 5 minute, 10 minute, 15 minute, 20 minute, or 25 minute period.

The dosage ranges for the administration of at least one ClbP inhibitor, according to the methods described herein depend upon, for example, the form of the ClbP inhibitor, its potency, and the extent to which symptoms, markers, or indicators of a condition described herein are desired to be reduced, for example the percentage reduction desired for ClbP activity. The dosage should not be so large as to cause adverse side effects. Generally, the dosage will vary with the age, condition, and sex of the patient and can be determined by one of skill in the art. The dosage can also be adjusted by the individual physician in the event of any complication.

The efficacy of a ClbP inhibitor in, e.g. the treatment of a condition described herein, or to induce a response as described herein can be determined by the skilled clinician. However, a treatment is considered "effective treatment," as the term is used herein, if one or more of the signs or symptoms of a condition described herein are altered in a beneficial manner, other clinically accepted symptoms are improved, or even ameliorated, or a desired response is induced e.g., by at least 10% following treatment according to the methods described herein. Efficacy can be assessed, for example, by measuring a marker, indicator, symptom, and/or the incidence of a condition treated according to the methods described herein or any other measurable parameter appropriate, e.g. genotoxin production and/or cancer cell growth. Efficacy can also be measured by a failure of an individual to worsen as assessed by hospitalization, or need for medical interventions (i.e., progression of the disease is halted). Methods of measuring these indicators are known to those of skill in the art and/or are described herein. Treatment includes any treatment of a disease in an individual or an animal (some non-limiting examples include a human or an animal) and includes: (1) inhibiting the disease, e.g., preventing a worsening of symptoms (e.g. pain or inflammation); or (2) relieving the severity of the disease, e.g., causing regression of symptoms. An effective amount for the treatment of a disease means that amount which, when administered to a subject in need thereof, is sufficient to result in effective treatment as that term is defined herein, for that disease. Efficacy of an agent can be determined by assessing physical indicators of a condition or desired response. It is well within the ability of one skilled in the art to monitor efficacy of administration and/or treatment by measuring any one of such parameters, or any combination of parameters. Efficacy can be assessed in animal models of a condition described herein, for example treatment of a murine model of colorectal cancer. When using an experimental animal model, efficacy of treatment is evidenced when a statistically significant change in a marker is observed, e.g. genotoxin production and/or cancer cell growth.

The efficacy of a given dosage combination can be assessed in an animal model, e.g. a mouse model of pks+ infection or colorectal cancer.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

"Alkyl" refers to an aliphatic hydrocarbon group which can be straight or branched having 1 to about 60 carbon atoms in the chain, and which preferably have about 6 to about 50 carbons in the chain. "Lower alkyl" refers to an alkyl group having 1 to about 8 carbon atoms. "Higher alkyl" refers to an alkyl group having about 10 to about 20 carbon atoms. The alkyl group can be optionally substituted with one or more alkyl group substituents which can be the same or different, where "alkyl group substituent" includes halo, amino, aryl, hydroxy, alkoxy, aryloxy, alkyloxy, alkylthio, arylthio, aralkyloxy, aralkylthio, carboxy, alkoxycarbonyl, oxo and cycloalkyl. "Branched" refers to an alkyl group in which a lower alkyl group, such as methyl, ethyl or propyl, is attached to a linear alkyl chain. Exemplary alkyl groups include methyl, ethyl, i-propyl, n-butyl, t-butyl, n-pentyl, heptyl, octyl, decyl, dodecyl, tridecyl, tetradecyl, pentadecyl and hexadecyl. Useful alkyl groups include branched or straight chain alkyl groups of 6 to 50 carbon, and also include the lower alkyl groups of 1 to about 4 carbons and the higher alkyl groups of about 12 to about 16 carbons. In some embodiments, alkyl is a $C_1$-$C_{20}$alkyl, optionally substituted with one, two, three, four or more independently selected substituents. For example, the $C_1$-$C_{20}$alkyl can be substituted at the terminal carbon by one substituent. In some preferred embodiments, alkyl is tridecyl, 1-propyl, 4-phenylprop-1-yl, methyl or 8-aminoheptyl.

"Alkenyl" refers to an alkyl group containing at least one carbon-carbon double bond. The alkenyl group can be optionally substituted with one or more "alkyl group substituents." Exemplary alkenyl groups include vinyl, allyl, n-pentenyl, decenyl, dodecenyl, tetradecadienyl, heptadec-8-en-1-yl and heptadec-8,11-dien-1-yl.

"Alkynyl" refers to an alkyl group containing a carbon-carbon triple bond. The alkynyl group can be optionally substituted with one or more "alkyl group substituents." Exemplary alkynyl groups include ethynyl, propargyl, n-pentynyl, decynyl and dodecynyl. Useful alkynyl groups include the lower alkynyl groups.

"Cycloalkyl" refers to a non-aromatic mono- or multicyclic ring system having 3 to 12 carbons, for example, 3 to 8 carbons, and, for example, 3 to 6 carbons. $C_x$cyclyl and $C_x$-$C_y$cylcyl are typically used where X and Y indicate the number of carbon atoms in the ring system. The cycloalkyl group additionally can be optionally substituted, e.g., with 1, 2, 3, or 4 substituents. Examples of cyclyl groups include, without limitation, cyclopropyl, cyclobutyl, cyclopentyl, cyclopentenyl, cyclohexyl, cyclohexenyl, 2,5-cyclohexadienyl, cycloheptyl, cyclooctyl, bicyclo[2.2.2]octyl, adamantan-1-yl, decahydronaphthyl, oxocyclohexyl, dioxocyclohexyl, thiocyclohexyl, 2-oxobicyclo [2.2.1]hept-1-yl, and the like.

"Heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively). $C_x$heterocyclyl and $C_x$-$C_y$heterocyclyl are typically used where X and Y indicate the number of carbon atoms in the ring system. In some embodiments, 1, 2 or 3 hydrogen atoms of each ring can be substituted by a substituent. Exemplary heterocyclyl groups include, but are not limited to piperazinyl, pyrrolidinyl, dioxanyl, morpholinyl, tetrahydrofuranyl, piperidyl, 4-morpholyl, 4-piperazinyl, pyrrolidinyl, perhydropyrrolizinyl, 1,4-diazaperhydroepinyl, 1,3-dioxanyl, 1,4-dioxanyland the like.

"Aryl" refers to an aromatic carbocyclic radical containing about 6 to about 10 carbon atoms. The aryl group can be optionally substituted with one or more aryl group substituents, which can be the same or different, where "aryl group substituent" includes alkyl, alkenyl, alkynyl, aryl, aralkyl, hydroxy, alkoxy, aryloxy, aralkoxy, carboxy, aroyl, halo, nitro, trihalomethyl, cyano, alkoxycarbonyl, aryloxycarbonyl, aralkoxycarbonyl, acyloxy, acylamino, aroylamino, carbamoyl, alkylcarbamoyl, dialkylcarbamoyl, arylthio, alkylthio, alkylene and —NRR', where R and R' are each independently hydrogen, alkyl, aryl and aralkyl. Exemplary aryl groups include substituted or unsubstituted phenyl and substituted or unsubstituted naphthyl.

"Heteroaryl" refers to an aromatic 5-8 membered monocyclic, 8-12 membered fused bicyclic, or 11-14 membered fused tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively.

Exemplary aryl and heteroaryls include, but are not limited to, phenyl, pyridinyl, pyrimidinyl, furanyl, thienyl, imidazolyl, thiazolyl, pyrazolyl, pyridazinyl, pyrazinyl, triazinyl, tetrazolyl, indolyl, benzyl, naphthyl, anthracenyl, azulenyl, fluorenyl, indanyl, indenyl, naphthyl, tetrahydronaphthyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl, and the like. In some embodiments, 1, 2, 3, or 4 hydrogen atoms of each ring can be substituted by a substituent.

"Acyl" refers to an alkyl-CO— group, wherein alkyl is as previously described. Exemplary acyl groups comprise alkyl of 1 to about 30 carbon atoms. Exemplary acyl groups also include acetyl, propanoyl, 2-methylpropanoyl, butanoyl and palmitoyl.

The term "hydrophobic acyl group" refers to a R—C (=O)— group, wherein R is an alkyl, aryl, heteroayl, cyclyl, heterocyclyl, aralkyl or other non-polar group.

"Acylamino" refers to an acyl-NH— group, wherein acyl is as previously described.

"Alkoxy" refers to an alkyl-O— group, wherein alkyl is as previously described. Exemplary alkoxy groups include methoxy, ethoxy, n-propoxy, i-propoxy, n-butoxy, and heptoxy.

As used herein, the term "amino" means —NH$_2$. The term "alkylamino" means a nitrogen moiety having one straight or branched unsaturated aliphatic, cyclyl, or heterocyclyl radicals attached to the nitrogen. The term "dialkylamino" means a nitrogen moiety having two straight or branched unsaturated aliphatic, cyclyl, or heterocyclyl radicals attached to the nitrogen. Exemplary dialkylamino groups include ethylmethylamino, dimethylamino, and diethylamino.

The term "aminoalkyl" means an alkyl, alkenyl, and alkynyl as defined above and substituted with one or more substituents independently selected from amino, alkylamino and dialkylamino.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy, n-propyloxy, iso-propyloxy, n-butyloxy, iso-butyloxy, and the like. An "ether" is two hydrocarbons covalently linked by an oxygen. Accordingly, the substituent of an alkyl that renders that alkyl an ether is or resembles an alkoxyl, such as can be represented by one of alkyl, —O-alkenyl, and —O-alkynyl. Aroxy can be represented by —O-aryl or O-heteroaryl, wherein aryl and heteroaryl are as defined below. The alkoxy and aroxy groups can be substituted as described above for alkyl.

As used herein, the term "halogen" or "halo" refers to an atom selected from fluorine, chlorine, bromine and iodine. The term "halogen radioisotope" or "halo isotope" refers to a radionuclide of an atom selected from fluorine, chlorine, bromine and iodine. A "halogen-substituted moiety" or "halo-substituted moiety", as an isolated group or part of a larger group, means an aliphatic, alicyclic, or aromatic moiety, as described herein, substituted by one or more "halo" atoms, as such terms are defined in this application. For example, halo-substituted alkyl includes haloalkyl, dihaloalkyl, trihaloalkyl, perhaloalkyl and the like (e.g. halosubstituted ($C_1$-$C_3$)alkyl includes chloromethyl, dichloromethyl, difluoromethyl, trifluoromethyl (—$CF_3$), 2,2,2-trifluoroethyl, perfluoroethyl, 2,2,2-trifluoro-1,1-dichloroethyl, and the like).

As used herein, the term "substituted" refers to independent replacement of one or more (typically 1, 2, 3, 4, or 5) of the hydrogen atoms on the substituted moiety with substituents independently selected from the group of substituents listed below in the definition for "substituents" or otherwise specified. In general, a non-hydrogen substituent can be any substituent that can be bound to an atom of the given moiety that is specified to be substituted. Examples of substituents include, but are not limited to, acyl, acylamino, acyloxy, aldehyde, alicyclic, aliphatic, alkanesulfonamido, alkanesulfonyl, alkaryl, alkenyl, alkoxy, alkoxycarbonyl, alkyl, alkylamino, alkylcarbanoyl, alkylene, alkylidene, alkylthios, alkynyl, amide, amido, amino, amino, aminoalkyl, aralkyl, aralkylsulfonamido, arenesulfonamido, arenesulfonyl, aromatic, aryl, arylamino, arylcarbanoyl, aryloxy, azido, carbamoyl, carbonyl, carbonyls (including ketones, carboxy, carboxylates, $CF_3$, cyano (CN), cycloalkyl, cycloalkylene, ester, ether, haloalkyl, halogen, halogen, heteroaryl, heterocyclyl, hydroxy, hydroxy, hydroxyalkyl, imino, iminoketone, ketone, mercapto, nitro, oxaalkyl, oxo, oxoalkyl, phosphoryl (including phosphonate and phosphinate), silyl groups, sulfonamido, sulfonyl (including sulfate, sulfamoyl and sulfonate), thiols, and ureido moieties, each of which may optionally also be substituted or unsubstituted. In some cases, two substituents, together with the carbon(s) to which they are attached to, can form a ring.

Unless otherwise stated, structures depicted herein are meant to include compounds which differ only in the presence of one or more isotopically enriched atoms. For example, compounds having the present structure except for the replacement of a hydrogen atom by a deuterium or tritium, or the replacement of a carbon atom by a $^{13}$C- or $^{14}$C-enriched carbon are within the scope of the invention.

As used here in the term "isomer" refers to compounds having the same molecular formula but differing in structure.

Isomers which differ only in configuration and/or conformation are referred to as "stereoisomers." The term "isomer" is also used to refer to an enantiomer.

The term "sample" or "test sample" as used herein can denote a sample taken or isolated from a biological organism, e.g., a blood or plasma sample from a subject. In some embodiments of any of the aspects, the present invention encompasses several examples of a biological sample. In some embodiments of any of the aspects, the biological sample is cells, or tissue, or peripheral blood, or bodily fluid. Exemplary biological samples include, but are not limited to, a fecal sample, a biopsy, a tumor sample, biofluid sample; blood; serum; plasma; urine; sperm; mucus; tissue biopsy; organ biopsy; synovial fluid; bile fluid; cerebrospinal fluid; mucosal secretion; effusion; sweat; saliva; and/or tissue sample etc. The term also includes a mixture of the above-mentioned samples. The term "test sample" also includes untreated or pretreated (or pre-processed) biological samples. In some embodiments of any of the aspects, a test sample can comprise cells from a subject.

The test sample can be obtained by removing a sample from a subject, but can also be accomplished by using a previously isolated sample (e.g. isolated at a prior timepoint and isolated by the same or another person).

In some embodiments of any of the aspects, the test sample can be an untreated test sample. As used herein, the phrase "untreated test sample" refers to a test sample that has not had any prior sample pre-treatment except for dilution and/or suspension in a solution. Exemplary methods for treating a test sample include, but are not limited to, centrifugation, filtration, sonication, homogenization, heating, freezing and thawing, and combinations thereof. In some embodiments of any of the aspects, the test sample can be a frozen test sample, e.g., a frozen tissue. The frozen sample can be thawed before employing methods, assays and systems described herein. After thawing, a frozen sample can be centrifuged before being subjected to methods, assays and systems described herein. In some embodiments of any of the aspects, the test sample is a clarified test sample, for example, by centrifugation and collection of a supernatant comprising the clarified test sample. In some embodiments of any of the aspects, a test sample can be a pre-processed test sample, for example, supernatant or filtrate resulting from a treatment selected from the group consisting of centrifugation, filtration, thawing, purification, and any combinations thereof. In some embodiments of any of the aspects, the test sample can be treated with a chemical and/or biological reagent. Chemical and/or biological reagents can be employed to protect and/or maintain the stability of the sample, including biomolecules (e.g., nucleic acid and protein) therein, during processing. One exemplary reagent is a protease inhibitor, which is generally used to protect or maintain the stability of protein during processing. The skilled artisan is well aware of methods and processes appropriate for pre-processing of biological samples required for determination of the level of an expression product as described herein.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g. the absence of a given treatment or agent) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, a "increase" is a statistically significant increase in such level.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of, e.g., colorectal cancer. A subject can be male or female.

A subject can be one who has been previously diagnosed with or identified as suffering from or having a condition in need of treatment (e.g. colorectal cancer) or one or more complications related to such a condition, and optionally, have already undergone treatment for the condition or the one or more complications related to the condition. Alternatively, a subject can also be one who has not been previously diagnosed as having the condition or one or more complications related to the condition. For example, a subject can be one who exhibits one or more risk factors for the condition or one or more complications related to the condition or a subject who does not exhibit risk factors.

A "subject in need" of treatment for a particular condition can be a subject having that condition, diagnosed as having that condition, or at risk of developing that condition.

In some embodiments, the methods described herein relate to measuring, detecting, or determining the level of at least one marker. As used herein, the term "detecting" or "measuring" refers to observing a signal from, e.g. a probe, label, or target molecule to indicate the presence of an analyte in a sample. Any method known in the art for detecting a particular label moiety can be used for detection. Exemplary detection methods include, but are not limited to, spectroscopic, fluorescent, photochemical, biochemical, immunochemical, electrical, optical or chemical methods. In some embodiments of any of the aspects, measuring can be a quantitative observation.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder, e.g. colorectal cancer. The term "treating" includes reducing or alleviating at least one adverse effect or symptom of a condition, disease or disorder. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

In some embodiments of any of the aspects, described herein is a prophylactic method of treatment. As used herein "prophylactic" refers to the timing and intent of a treatment relative to a disease or symptom, that is, the treatment is administered prior to clinical detection or diagnosis of that particular disease or symptom in order to protect the patient from the disease or symptom. Prophylactic treatment can encompass a reduction in the severity or speed of onset of the disease or symptom, or contribute to faster recovery from the disease or symptom. Accordingly, the methods described herein can be prophylactic relative to cancer when the subject has a pks+ bacterial infection. In some embodiments of any of the aspects, prophylactic treatment is not prevention of all symptoms or signs of a disease.

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. In some embodiments of any of the aspects, a pharmaceutically acceptable carrier can be a carrier other than water. In some embodiments of any of the aspects, a pharmaceutically acceptable carrier can be a cream, emulsion, gel, liposome, nanoparticle, and/or ointment. In some embodiments of any of the aspects, a pharmaceutically acceptable carrier can be an artificial or engineered carrier, e.g., a carrier that the active ingredient would not be found to occur in in nature.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject. In some embodiments, administration comprises physical human activity, e.g., an injection, act of ingestion, an act of application, and/or manipulation of a delivery device or machine. Such activity can be performed, e.g., by a medical professional and/or the subject being treated.

As used herein, "contacting" refers to any suitable means for delivering, or exposing, an agent to at least one cell. Exemplary delivery methods include, but are not limited to, direct delivery to cell culture medium, perfusion, injection, or other delivery method well known to one skilled in the art. In some embodiments, contacting comprises physical human activity, e.g., an injection; an act of dispensing, mixing, and/or decanting; and/or manipulation of a delivery device or machine.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the invention.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology and molecular biology can be found in The Merck Manual of Diagnosis and Therapy, 20th Edition, published by Merck Sharp & Dohme Corp., 2018 (ISBN 0911910190, 978-0911910421); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), W. W. Norton & Company, 2016 (ISBN 0815345054, 978-0815345053); Lewin's Genes XI, published by Jones & Bartlett Publishers, 2014 (ISBN-1449659055); Michael Richard Green and Joseph Sambrook, Molecular Cloning: A Laboratory Manual, 4th ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, A D A M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

One of skill in the art can readily identify a chemotherapeutic agent of use (e.g. see Physicians' Cancer Chemotherapy Drug Manual 2014, Edward Chu, Vincent T. DeVita Jr., Jones & Bartlett Learning; Principles of Cancer Therapy, Chapter 85 in Harrison's Principles of Internal Medicine, 18th edition; Therapeutic Targeting of Cancer Cells: Era of Molecularly Targeted Agents and Cancer Pharmacology, Chs. 28-29 in Abeloff's Clinical Oncology, 2013 Elsevier; and Fischer D S (ed): The Cancer Chemotherapy Handbook, 4th ed. St. Louis, Mosby-Year Book, 2003).

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

In some embodiments, the present technology may be defined in any of the following numbered paragraphs:

1. A method of inhibiting ClbP, the method comprising contacting ClbP with one or more ClbP inhibitors having the structure of:

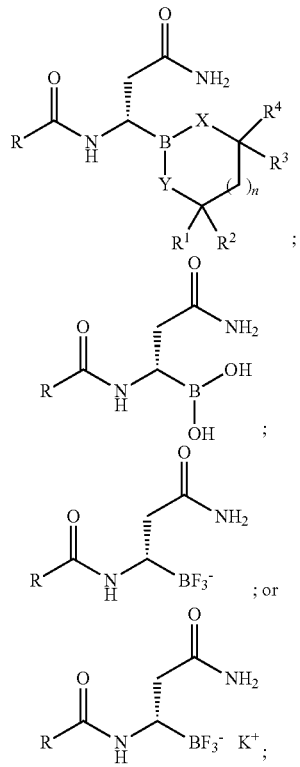

wherein R is selected from the group consisting of H, OH, alkyl, alkenyl, alkynyl, aryl, heteroaryl, cycloalkyl, or heterocycle;

$R^1$, $R^2$, $R^3$ and $R^4$ independently are H, alkyl, alkenyl, alkynyl, aryl, heteroaryl, cycloalkyl or heterocycle, or $R^2$ and $R^3$, together with the carbons they are attached to, form an aryl, heteroaryl, cycloalkyl or heterocycle;

X and Y independently are O, S or NH, and n is 0, or 1.

2. The method of paragraph 1, wherein three of $R^1$, $R^2$, $R^3$ and $R^4$ are H and the other is methyl.
3. The method of paragraph 1, wherein $R^2$ and $R^3$, together with the carbon atoms they are attached to, form 2,3,4-trihydroxytetrahydropyran.
4. The method of paragraph 1, wherein n is 0, $R^1$ is methyl, $R^4$ is H, and $R^2$ and $R^3$, together with the carbon atoms they are attached to, form a 6,6-dimethylbicycle [3.1.1]heptane.
5. The method of paragraph 1, wherein n is 0, $R^1$ and $R^4$ are H, and $R^2$ and $R^3$, together with the carbon atoms they are attached to, form a benzene ring.
6. The method of any of paragraphs 1-5, wherein the ClbP inhibitor has the structure of:

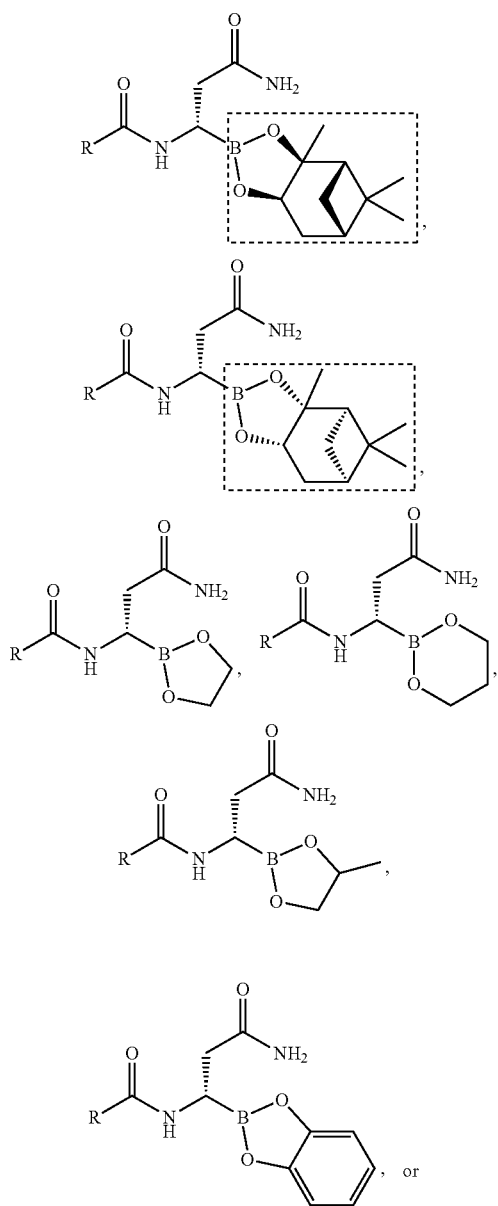

7. The method of any of paragraphs 1-6, wherein the ClbP inhibitor has the structure of:

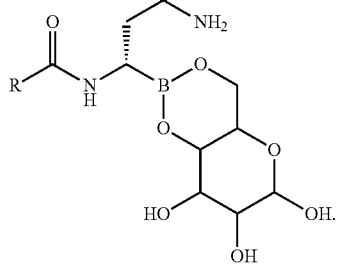

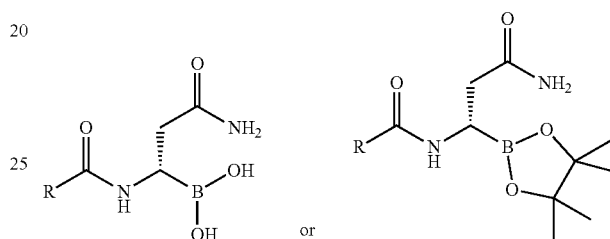

wherein R is, selected from the group consisting of H, OH, alkyl, alkenyl, alkynyl, aryl, heteroaryl, cycloalkyl, or heterocycle;

wherein the alkyl, alkenyl, alkynyl, or cycloalkyl, whether alone or as part of a substituent group, is optionally substituted with one or more substituents independently selected from the group consisting of halogen, —OH, alkyl, O-alkyl, —NR$^A$R$^B$, —S-alkyl, —SO-alkyl, —SO$_2$— alkyl, alkenyl, alkynyl, aryl, heteroaryl, cycloalkyl or heterocycle; and the alkenyl, alkynyl, or optionally includes —O—, —S—, —SO$_2$—, —N(R$^C$)— substituting one or more carbons in the carbon chain, wherein the aryl or heteroaryl, whether alone or as part of a substituent group, is optionally substituted with one or more substituents independently selected from the group consisting of halogen, OH, alkyl, O-alkyl, —NR$^D$R$^E$, —S-alkyl, —SO-alkyl and —SO$_2$-alkyl, alkenyl, alkynyl, aryl, heteroaryl, cycloalkyl or heterocycle;

wherein $R^A$, $R^B$, $R^C$, $R^D$, and $R^E$, are each independently selected from hydrogen and $C_{1-4}$ alkyl.

8. The method of any of paragraphs 1-7, wherein R is alkyl or aryl.
9. The method of any of paragraphs 1-8, wherein R is not a phenyl group.
10. The method of any of paragraphs 1-9, wherein R is selected from the group consisting of:

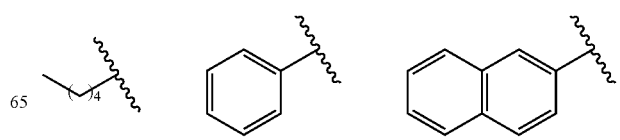

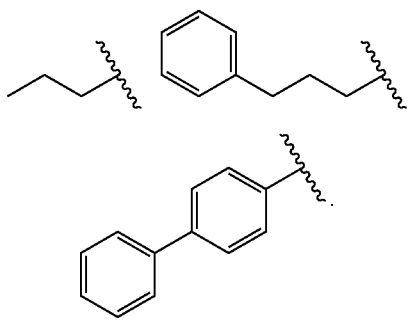

11. The method of any of paragraphs 1-10, wherein the ClbP inhibitor does not have the following structure:

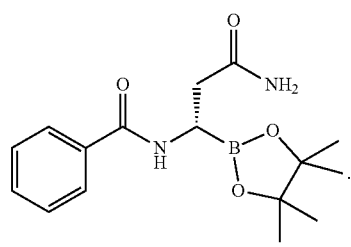 [SMILES: CC1(C)OB([C@@H](CC(N)=O)NC(=O)c2ccccc2)OC1(C)C]

12. The method of any of the preceding paragraphs, wherein the ClbP inhibitor comprises a D-asparagine group and not an L-asparagine group.
13. The method of any of the preceding paragraphs, wherein R is hydrophobic.
14. The method of any of the preceding paragraphs, wherein the ClbP inhibitor has a structure selected from the following:

Formula IV

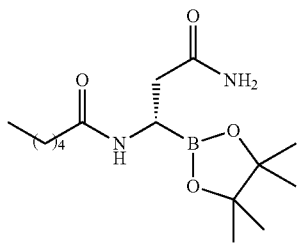

Hexanoyl-pinacolboro-Asn
(MRV03-037)

Formula V

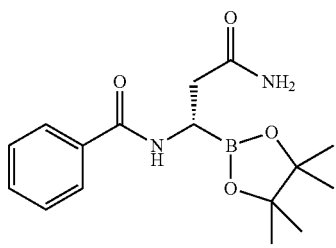

Formula VI

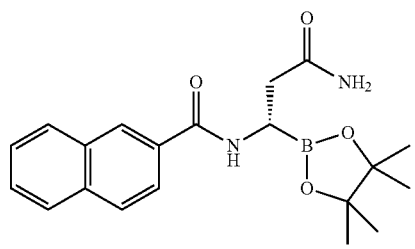

Formula VII

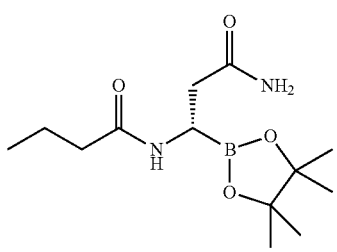

Formula VIII

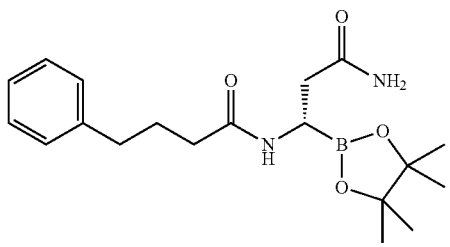

Formula IX

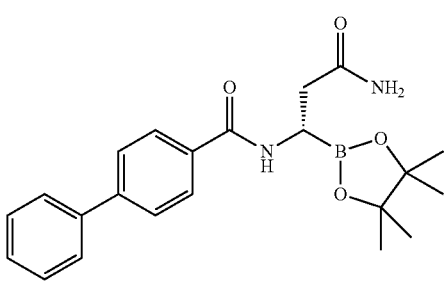

Formula X

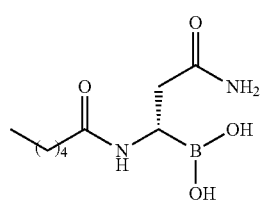

Formula XI

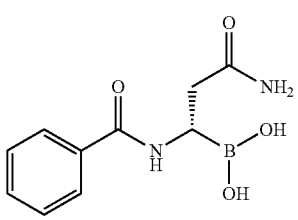

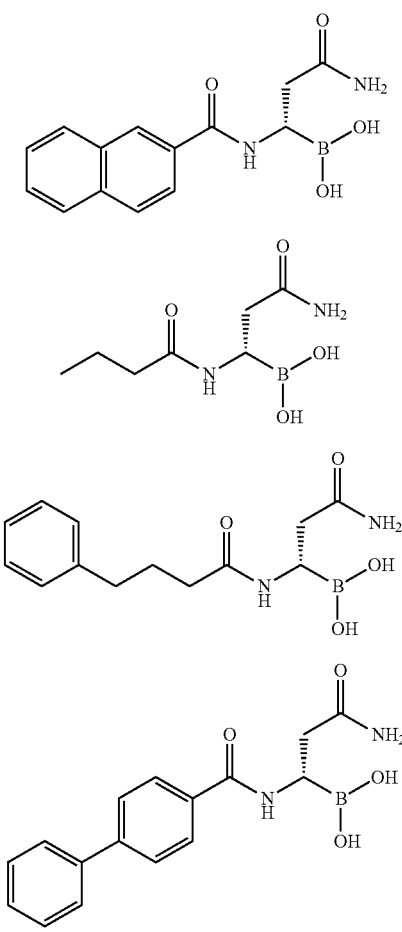
Formula XII
Formula XIII
Formula XIV
Formula XV
15. The method of any of the preceding paragraphs, wherein the ClbP inhibitor has a structure selected from the following:
Formula IV
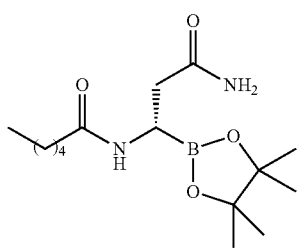
Hexanoyl-pinacolboro-Asn
(MRV03-037)
Formula VI
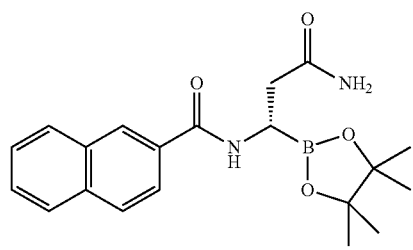
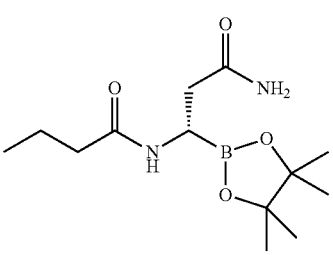
Formula VII
Formula VIII
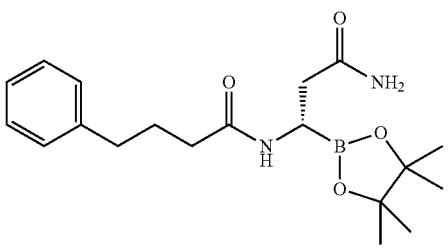
Formula IX
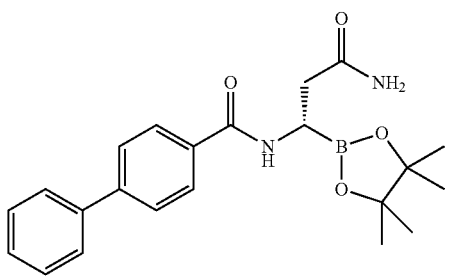
Formula X
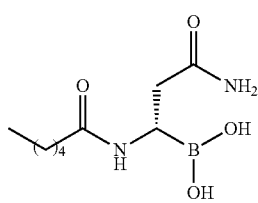
Formula XII
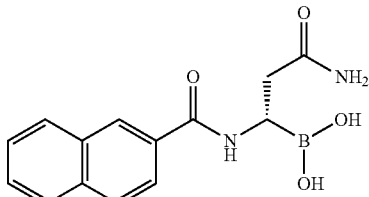
Formula XIII
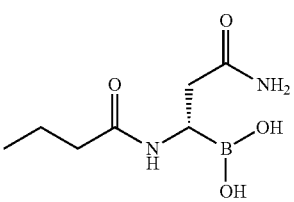
Formula XIV
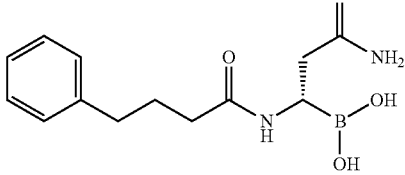

-continued

Formula XV

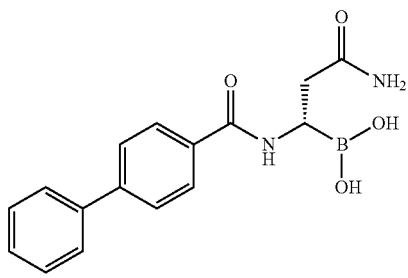

16. The method of any of the preceding paragraphs, wherein contacting comprises administering the ClbP inhibitor to a subject.
17. The method of paragraph 16, wherein the subject has a population and/or infection of pks+ bacteria.
18. The method of paragraph 17, wherein the bacteria is E. coli.
19. The method of any of the preceding paragraphs, whereby the level of genotoxin in a sample or subject is reduced and/or the production of genotoxin in a sample or subject is inhibited.
20. The method of paragraph 19, wherein the genotoxin is colibactin.
21. The method of any of the preceding paragraphs, whereby the risk and/or progression of cancer in subject is reduced or inhibited.
22. The method of paragraph 21, wherein the cancer is colorectal cancer.
23. A method of treating a pks+ bacterial infection or treating cancer in a subject in need thereof, the method comprising administering to the subject one or more ClbP inhibitors having the structure of:

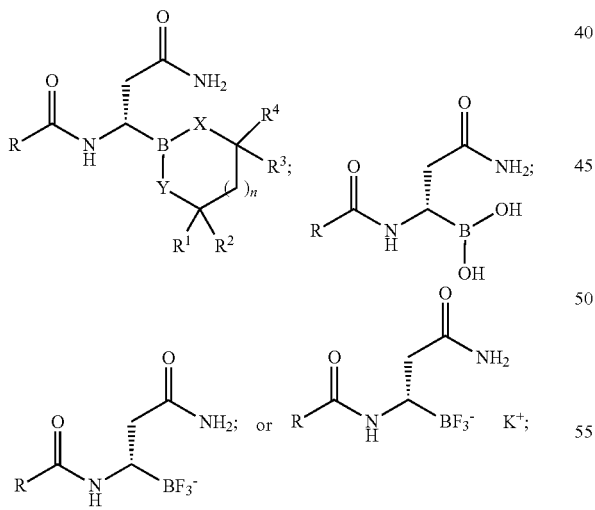

wherein R is selected from the group consisting of H, OH, alkyl, alkenyl, alkynyl, aryl, heteroaryl, cycloalkyl, or heterocycle;
$R^1$, $R^2$, $R^3$ and $R^4$ independently are H, alkyl, alkenyl, alkynyl, aryl, heteroaryl, cycloalkyl or heterocycle, or $R^2$ and $R^3$, together with the carbons they are attached to, form an aryl, heteroaryl, cycloalkyl or heterocycle;

X and Y independently are O, S or NH, and n is 0, or 1.

24. The method of paragraph 23, wherein three of $R^1$, $R^2$, $R^3$ and $R^4$ are H and the other is methyl.
25. The method of paragraph 23, wherein $R^2$ and $R^3$, together with the carbon atoms they are attached to, form 2,3,4-trihydroxytetrahydropyran.
26. The method of paragraph 23, wherein n is 0, $R^1$ is methyl, $R^4$ is H, and $R^2$ and $R^3$, together with the carbon atoms they are attached to, form a 6,6-dimethylbicycle[3.1.1]heptane.
27. The method of paragraph 23, wherein n is 0, $R^1$ and $R^4$ are H, and $R^2$ and $R^3$, together with the carbon atoms they are attached to, form a benzene ring.
28. The method of any of paragraphs 23-27, wherein the ClbP inhibitor has the structure of:

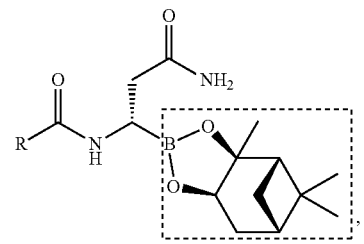

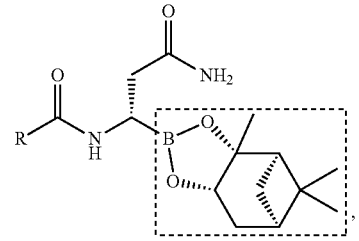

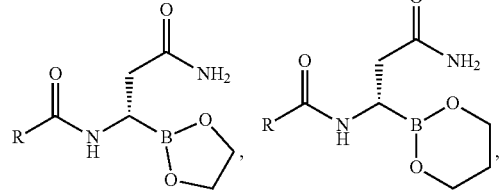

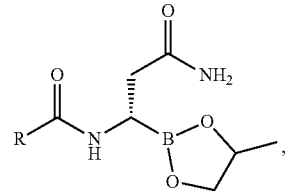

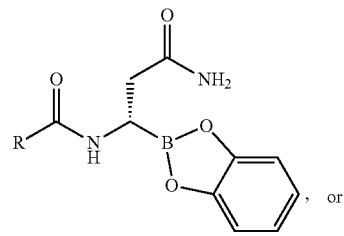, or

-continued

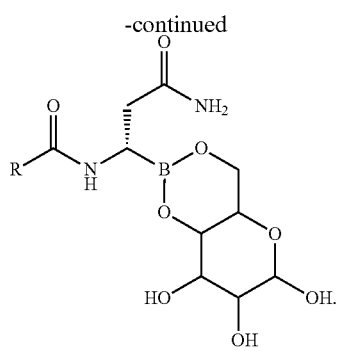

29. The method of any of paragraphs 23-28, wherein the ClbP inhibitor has the structure of:

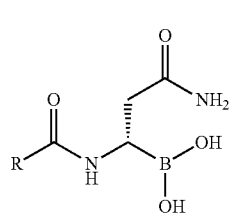 or 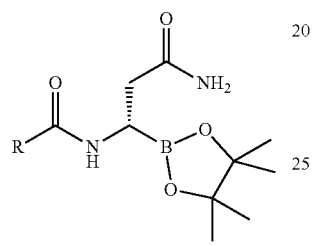

wherein R is, selected from the group consisting of H, OH, alkyl, alkenyl, alkynyl, aryl, heteroaryl, cycloalkyl, or heterocycle;

wherein the alkyl, alkenyl, alkynyl, or cycloalkyl, whether alone or as part of a substituent group, is optionally substituted with one or more substituents independently selected from the group consisting of halogen, —OH, alkyl, O-alkyl, —NR$^A$R$^B$, —S-alkyl, —SO-alkyl, —SO$_2$— alkyl, alkenyl, alkynyl, aryl, heteroaryl, cycloalkyl or heterocycle; and the alkenyl, alkynyl, or optionally includes —O—, —S—, —SO$_2$—, —N(R$^C$)— substituting one or more carbons in the carbon chain, wherein the aryl or heteroaryl, whether alone or as part of a substituent group, is optionally substituted with one or more substituents independently selected from the group consisting of halogen, OH, alkyl, O-alkyl, —NR$^D$R$^E$, —S-alkyl, —SO-alkyl and —SO$_2$-alkyl, alkenyl, alkynyl, aryl, heteroaryl, cycloalkyl or heterocycle;

wherein R$^A$, R$^B$, R$^C$, R$^D$, and R$^E$, are each independently selected from hydrogen and C$_{1-4}$ alkyl.

30. The method of any of paragraphs 23-29, wherein R is alkyl or aryl.

31. The method of any of paragraphs 23-30, wherein R is not a phenyl group.

32. The method of any of paragraphs 23-31, wherein R is selected from the group consisting of:

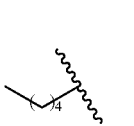 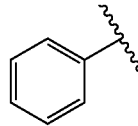 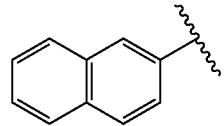

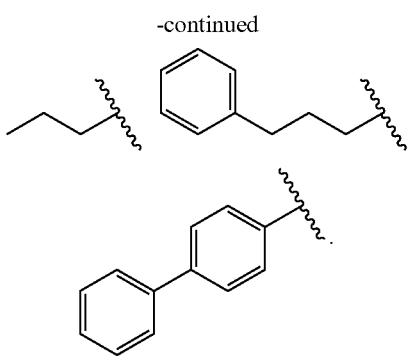

33. The method of any of paragraphs 23-32, wherein the ClbP inhibitor does not have the following structure:

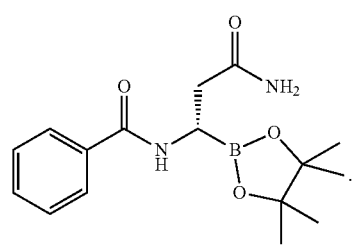 [SMILES: CC1(C)OB([C@@H](CC(N)=O)NC(=O)c2ccccc2)OC1(C)C]

34. The method of any of paragraphs 23-33, wherein the ClbP inhibitor comprises a D-asparagine group and not an L-asparagine group.

35. The method of any of paragraphs 23-34, wherein R is hydrophobic.

36. The method of any of paragraphs 23-35, wherein the ClbP inhibitor has a structure selected from the following:

Formula IV

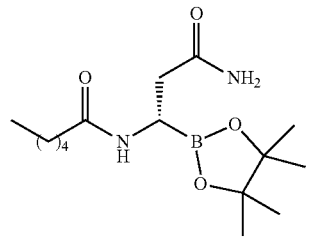

Hexanoyl-pinacolbora-Asn
(MRV03-037)

Formula V

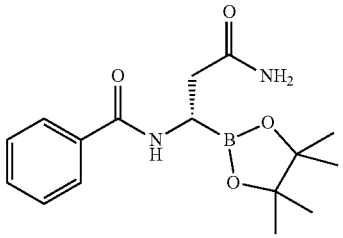

Formula VI
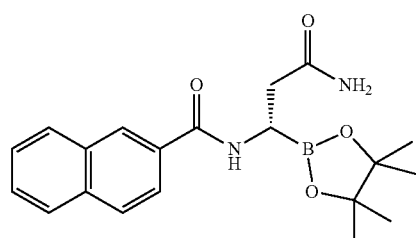
Formula VII
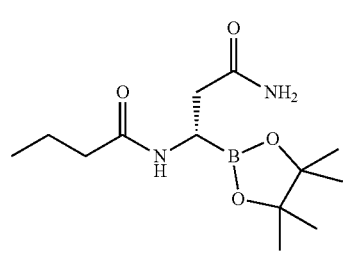
Formula VIII
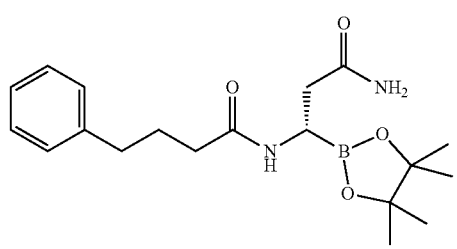
Formula IX
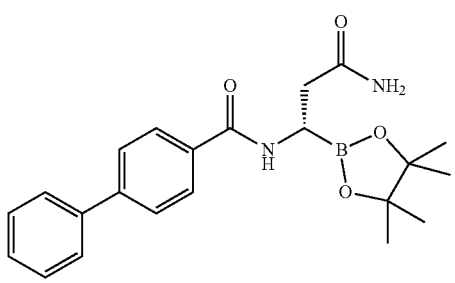
Formula X
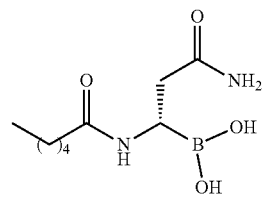
Formula XI
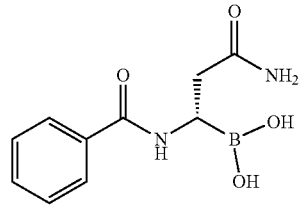
Formula XII
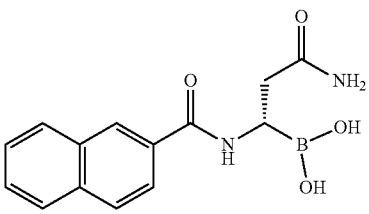
Formula XIII
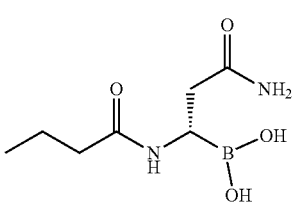
Formula XIV
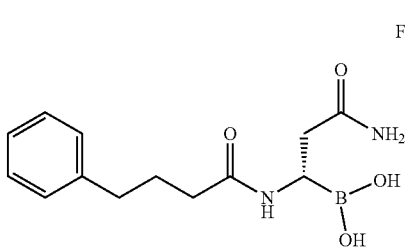
Formula XV
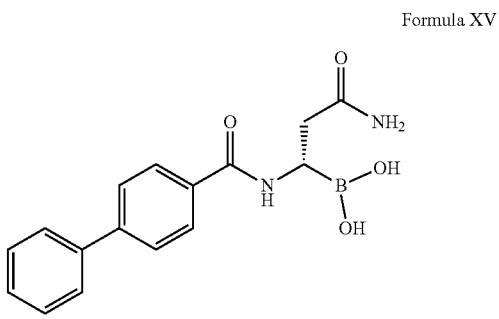
37. The method of any of paragraphs 23-36, wherein the ClbP inhibitor has a structure selected from the following:
Formula IV
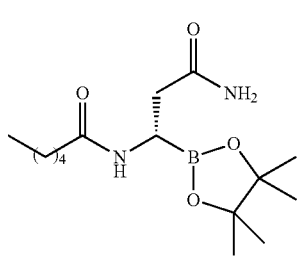
Hexanoyl-pinacolboro-Asn
(MRV03-037)

Formula VI
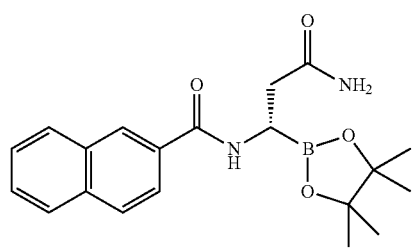

Formula VII
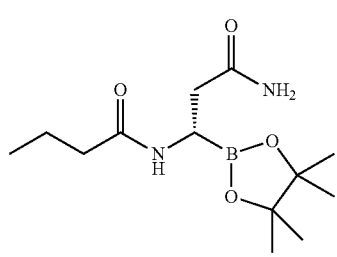

Formula VIII
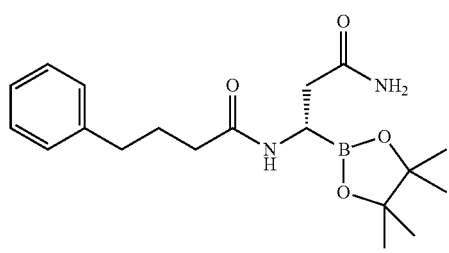

Formula IX
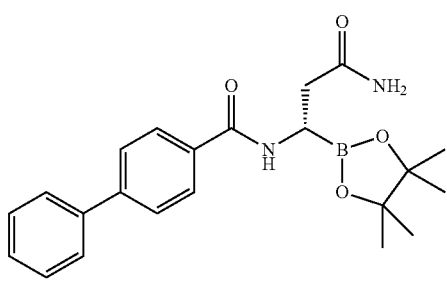

Formula X
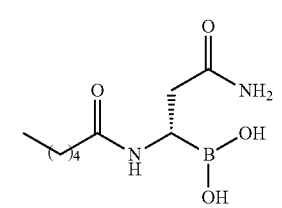

Formula XII
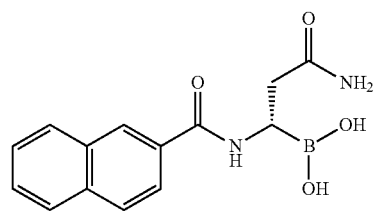

Formula XIII
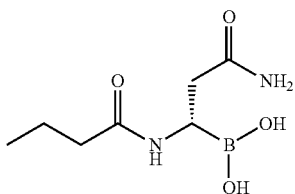

Formula XIV
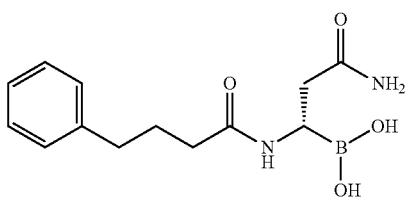

Formula XV
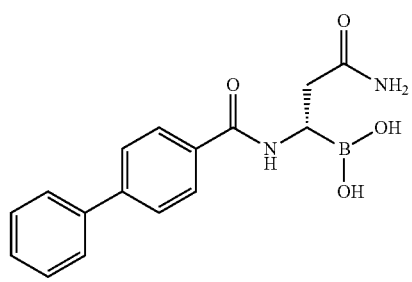

38. The method of any of paragraphs 23-37, wherein the subject has a population and/or infection of pks+ bacteria.

39. The method of paragraph 38, wherein the bacteria is *E. coli*.

40. The method of any of paragraphs 23-39, whereby the level of genotoxin in a sample or subject is reduced and/or the production of genotoxin in a sample or subject is inhibited.

41. The method of paragraph 40, wherein the genotoxin is colibactin.

42. The method of any of paragraphs 23-41, whereby the risk and/or progression of cancer in subject is reduced or inhibited.

43. The method of paragraph 42, wherein the cancer is colorectal cancer.

44. A ClbP inhibitor for use in a method of inhibiting ClbP or treating a pks+ bacterial infection or treating cancer in a subject in need thereof, the ClbP inhibitor having the structure of:

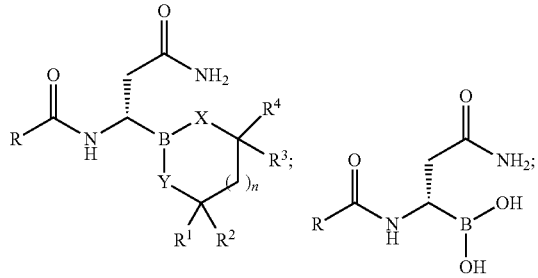

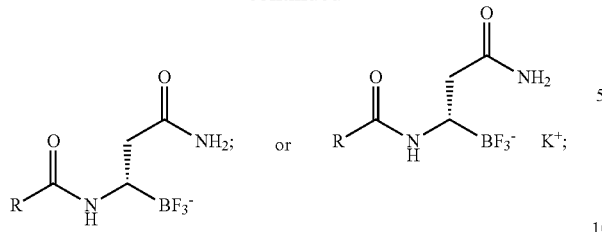

wherein R is selected from the group consisting of H, OH, alkyl, alkenyl, alkynyl, aryl, heteroaryl, cycloalkyl, or heterocycle;

$R^1$, $R^2$, $R^3$ and $R^4$ independently are H, alkyl, alkenyl, alkynyl, aryl, heteroaryl, cycloalkyl or heterocycle, or $R^2$ and $R^3$, together with the carbons they are attached to, form an aryl, heteroaryl, cycloalkyl or heterocycle;

X and Y independently are O, S or NH, and n is 0, or 1.

45. The ClbP inhibitor of paragraph 44, wherein three of $R^1$, $R^2$, $R^3$ and $R^4$ are H and the other is methyl.

46. The ClbP inhibitor of paragraph 44, wherein $R^2$ and $R^3$, together with the carbon atoms they are attached to, form 2,3,4-trihydroxytetrahydropyran.

47. The ClbP inhibitor of paragraph 44, wherein n is 0, $R^1$ is methyl, $R^4$ is H, and $R^2$ and $R^3$, together with the carbon atoms they are attached to, form a 6,6-dimethylbicycle[3.1.1]heptane.

48. The ClbP inhibitor of paragraph 44, wherein n is 0, $R^1$ and $R^4$ are H, and $R^2$ and $R^3$, together with the carbon atoms they are attached to, form a benzene ring.

49. The ClbP inhibitor of any of paragraphs 44-48, wherein the ClbP inhibitor has the structure of:

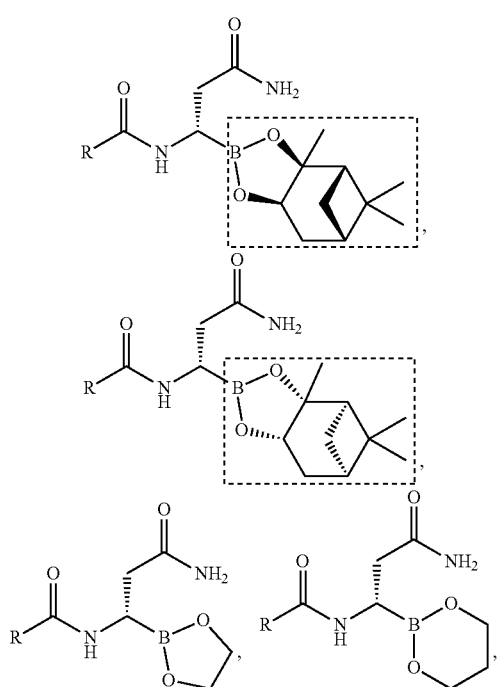

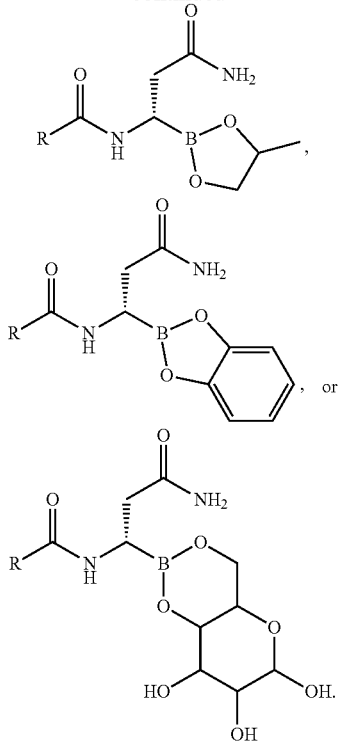

50. The ClbP inhibitor of any of paragraphs 44-49, wherein the ClbP inhibitor has the structure of:

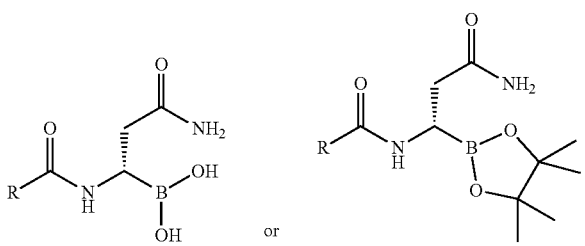

wherein R is, selected from the group consisting of H, OH, alkyl, alkenyl, alkynyl, aryl, heteroaryl, cycloalkyl, or heterocycle;

wherein the alkyl, alkenyl, alkynyl, or cycloalkyl, whether alone or as part of a substituent group, is optionally substituted with one or more substituents independently selected from the group consisting of halogen, —OH, alkyl, O-alkyl, —$NR^A R^B$, —S-alkyl, —SO-alkyl, —$SO_2$— alkyl, alkenyl, alkynyl, aryl, heteroaryl, cycloalkyl or heterocycle; and the alkenyl, alkynyl, or optionally includes —O—, —S—, —$SO_2$—, —$N(R^C)$— substituting one or more carbons in the carbon chain, wherein the aryl or heteroaryl, whether alone or as part of a substituent group, is optionally substituted with one or more substituents independently selected from the group consisting of halogen, OH, alkyl, O-alkyl, —$NR^D R^E$, —S-alkyl, —SO-alkyl and —$SO_2$-alkyl, alkenyl, alkynyl, aryl, heteroaryl, cycloalkyl or heterocycle;

wherein $R^A$, $R^B$, $R^C$, $R^D$, and $R^E$, are each independently selected from hydrogen and $C_{1-4}$ alkyl.

51. The ClbP inhibitor of any of paragraphs 44-50, wherein R is alkyl or aryl.

52. The ClbP inhibitor of any of paragraphs 44-51, wherein R is not a phenyl group.

53. The ClbP inhibitor of any of paragraphs 44-52, wherein R is selected from the group consisting of:

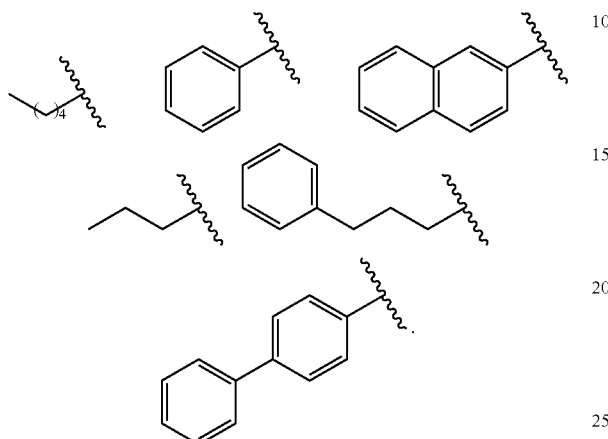

54. The ClbP inhibitor of any of paragraphs 44-53, wherein the ClbP inhibitor does not have the following structure:

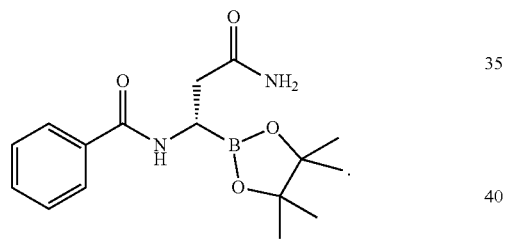

55. The ClbP inhibitor of any of paragraphs 44-54, wherein the ClbP inhibitor comprises a D-asparagine group and not an L-asparagine group.

56. The ClbP inhibitor of any of paragraphs 44-55, wherein R is hydrophobic.

57. The ClbP inhibitor of any of paragraphs 44-56, wherein the ClbP inhibitor has a structure selected from the following:

Formula IV

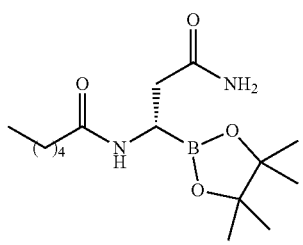

Hexanoyl-pinacolboro-Asn
(MRV03-037)

Formula V

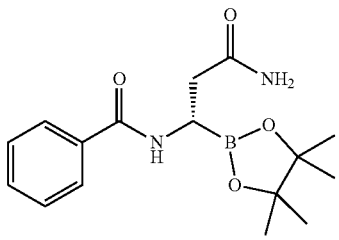

Formula VI

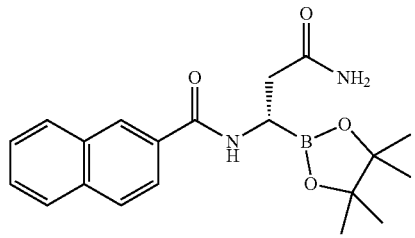

Formula VII

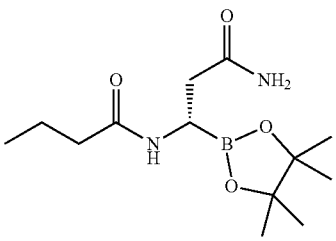

Formula VIII

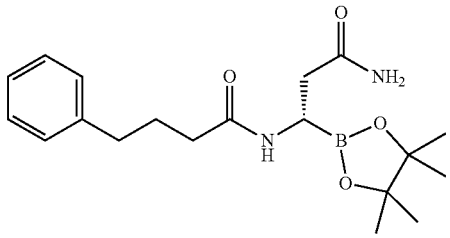

Formula IX

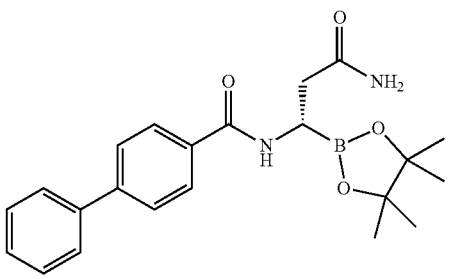

Formula X

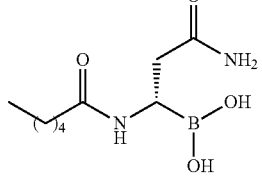

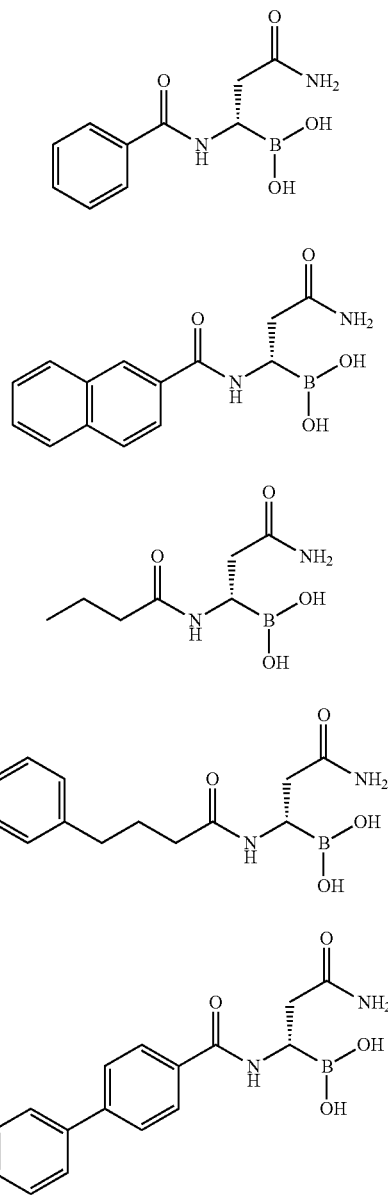
Formula XI
Formula XII
Formula XIII
Formula XIV
Formula XV
58. The ClbP inhibitor of any of paragraphs 44-57, wherein the ClbP inhibitor has a structure selected from the following:
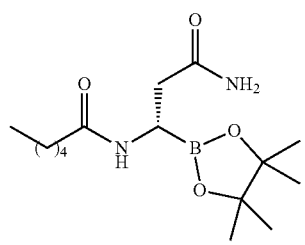
Formula IV
Hexanoyl-pinacolboro-Asn
(MRV03-037)
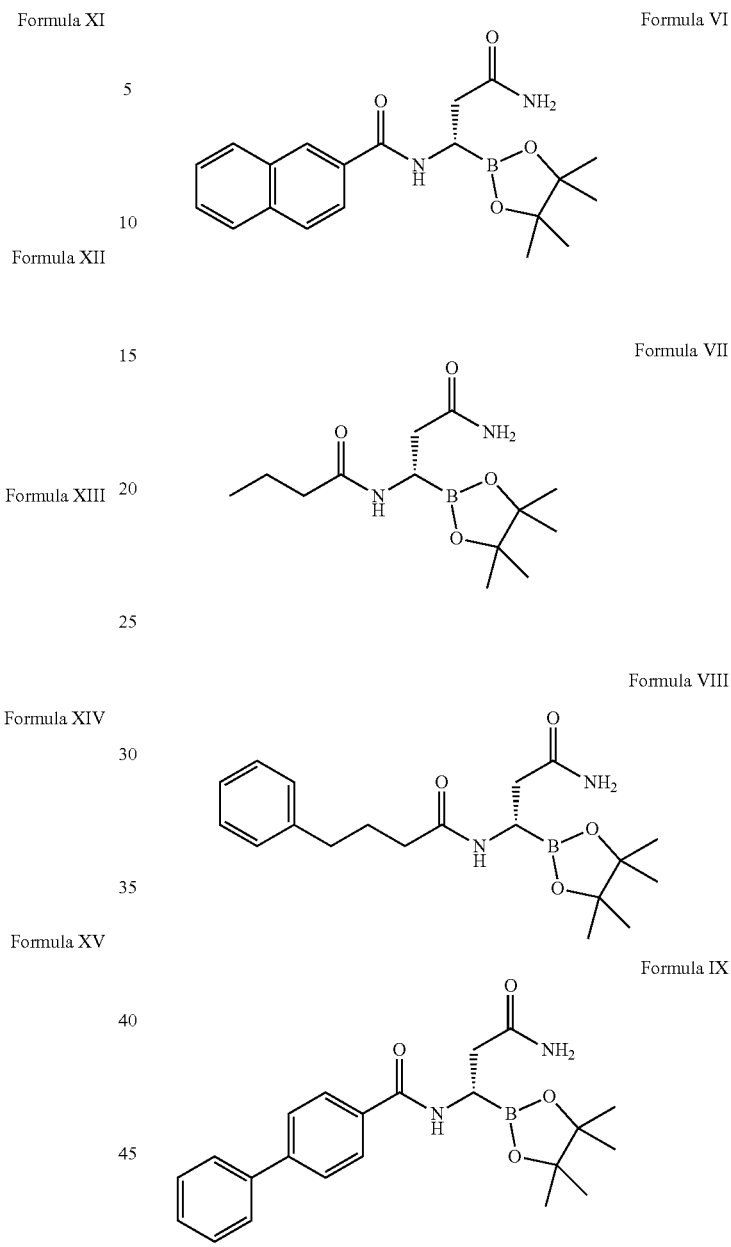
Formula VI
Formula VII
Formula VIII
Formula IX
Formula X
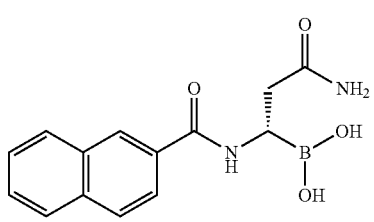
Formula XII -continued

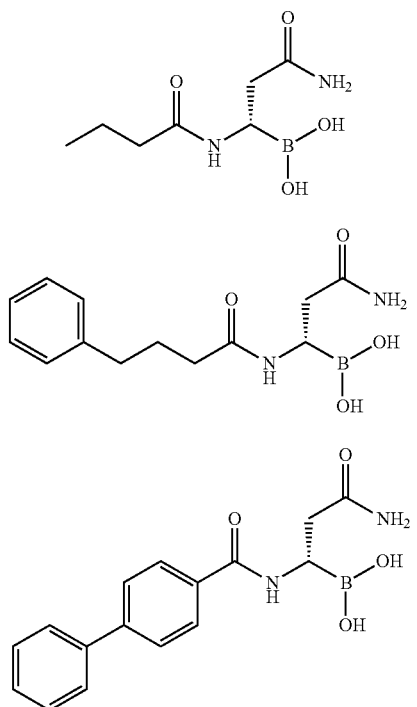

Formula XIII

Formula XIV

Formula XV

59. The ClbP inhibitor of any of paragraphs 44-58, wherein the subject has a population and/or infection of pks+ bacteria.

60. The ClbP inhibitor of paragraph 59, wherein the bacteria is *E. coli*.

61. The ClbP inhibitor of any of paragraphs 44-60, whereby the level of genotoxin in a sample or subject is reduced and/or the production of genotoxin in a sample or subject is inhibited.

62. The ClbP inhibitor of paragraph 61, wherein the genotoxin is colibactin.

63. The ClbP inhibitor of any of paragraphs 44-62, whereby the risk and/or progression of cancer in subject is reduced or inhibited.

64. The ClbP inhibitor of paragraph 63, wherein the cancer is colorectal cancer.

In some embodiments, the present technology may be defined in any of the following numbered paragraphs:

1. A method of inhibiting ClbP, the method comprising contacting ClbP with one or more ClbP inhibitors having the structure of:

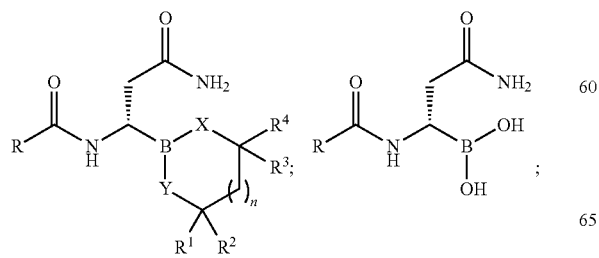

-continued

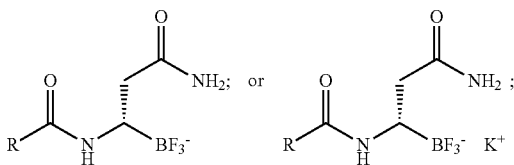

wherein R is selected from the group consisting of H, OH, alkyl, alkenyl, alkynyl, aryl, heteroaryl, cycloalkyl, or heterocycle;

$R^1$, $R^2$, $R^3$ and $R^4$ independently are H, alkyl, alkenyl, alkynyl, aryl, heteroaryl, cycloalkyl or heterocycle, or $R^2$ and $R^3$, together with the carbons they are attached to, form an aryl, heteroaryl, cycloalkyl or heterocycle;

X and Y independently are O, S or NH, and n is 0, or 1; or an R enantiomer of any of the foregoing.

2. The method of paragraph 1, wherein three of $R^1$, $R^2$, $R^3$ and $R^4$ are H and the other is methyl.

3. The method of paragraph 1, wherein $R^2$ and $R^3$, together with the carbon atoms they are attached to, form 2,3,4-trihydroxytetrahydropyran.

4. The method of paragraph 1, wherein n is 0, $R^1$ is methyl, $R^4$ is H, and $R^2$ and $R^3$, together with the carbon atoms they are attached to, form a 6,6-dimethylbicycle[3.1.1]heptane.

5. The method of paragraph 1, wherein n is 0, $R^1$ and $R^4$ are H, and $R^2$ and $R^3$, together with the carbon atoms they are attached to, form a benzene ring.

6. The method of any of paragraphs 1-5, wherein the ClbP inhibitor has the structure of:

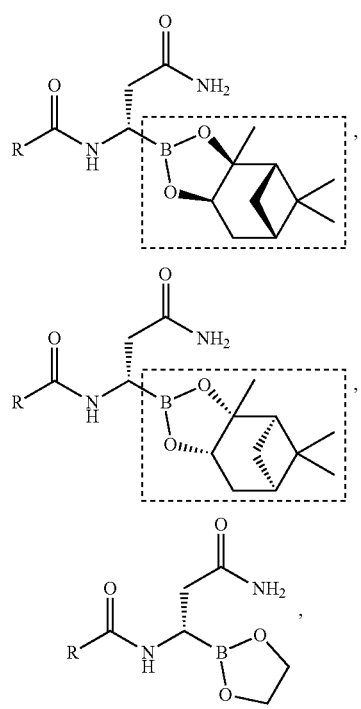

-continued

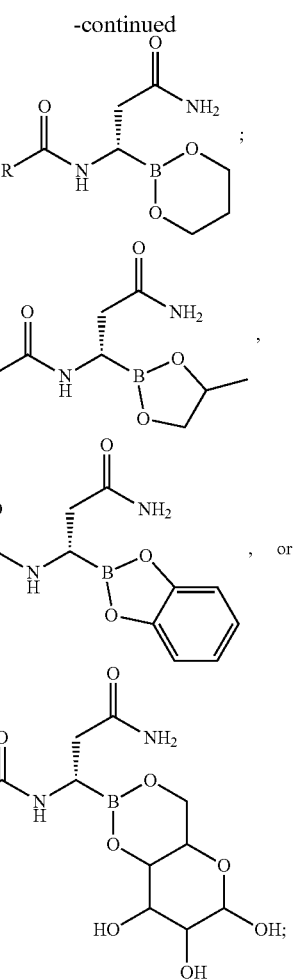

or an R enantiomer of any of the foregoing.

7. The method of any of paragraphs 1-6, wherein the ClbP inhibitor has the structure of:

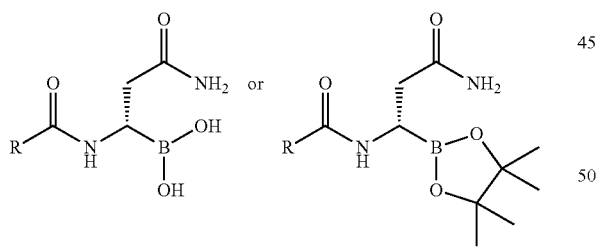

wherein R is, selected from the group consisting of H, OH, alkyl, alkenyl, alkynyl, aryl, heteroaryl, cycloalkyl, or heterocycle;

wherein the alkyl, alkenyl, alkynyl, or cycloalkyl, whether alone or as part of a substituent group, is optionally substituted with one or more substituents independently selected from the group consisting of halogen, —OH, alkyl, O-alkyl, —NR$^A$R$^B$, —S-alkyl, —SO-alkyl, —SO$_2$— alkyl, alkenyl, alkynyl, aryl, heteroaryl, cycloalkyl or heterocycle; and the alkenyl, alkynyl, or optionally includes —O—, —S—, —SO$_2$—, —N(R$^C$)— substituting one or more carbons in the carbon chain, wherein the aryl or heteroaryl, whether alone or as part of a substituent group, is optionally substituted with one or more substituents independently selected from the group consisting of halogen, OH, alkyl, O-alkyl, —NR$^D$R$^E$, —S-alkyl, —SO-alkyl and —SO$_2$-alkyl, alkenyl, alkynyl, aryl, heteroaryl, cycloalkyl or heterocycle;

wherein R$^A$, R$^B$, R$^C$, R$^D$, and R$^E$, are each independently selected from hydrogen and C$_{1-4}$ alkyl; or an R enantiomer of any of the foregoing.

8. The method of any of paragraphs 1-7, wherein R is alkyl or aryl.

9. The method of any of paragraphs 1-8, wherein R is not a phenyl group.

10. The method of any of paragraphs 1-9, wherein R is selected from the group consisting of:

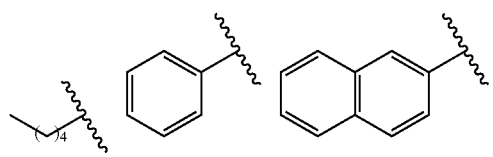

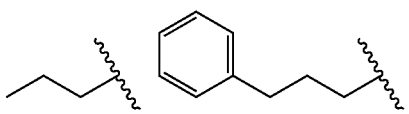

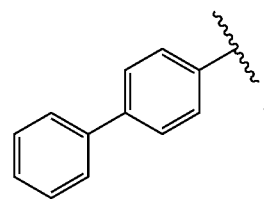

11. The method of any of paragraphs 1-10, wherein the ClbP inhibitor does not have the following structure:

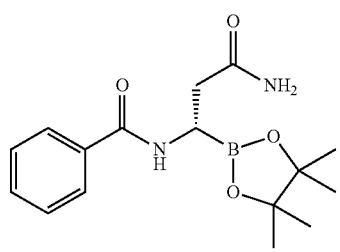

12. The method of any of the preceding paragraphs, wherein the ClbP inhibitor comprises a D-asparagine group and not an L-asparagine group.

13. The method of any of the preceding paragraphs, wherein R is hydrophobic.

14. The method of any of the preceding paragraphs, wherein the ClbP inhibitor has a structure selected from the following:

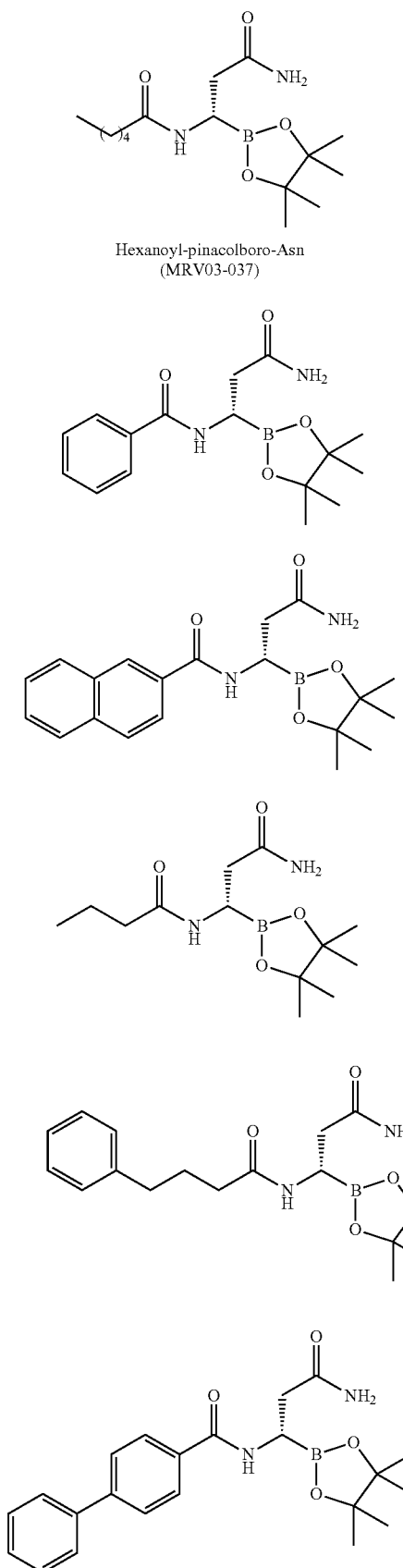
Hexanoyl-pinacolboro-Asn
(MRV03-037)
Formula IV
Formula V
Formula VI
Formula VII
Formula VIII
Formula IX
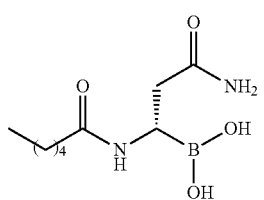
Formula X
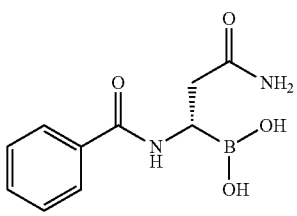
Formula XI
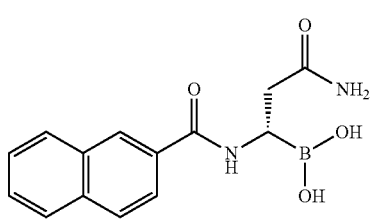
Formula XII
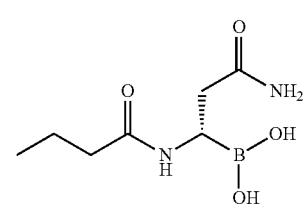
Formula XIII
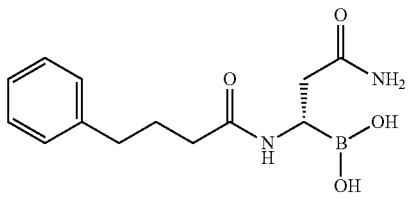
Formula XIV
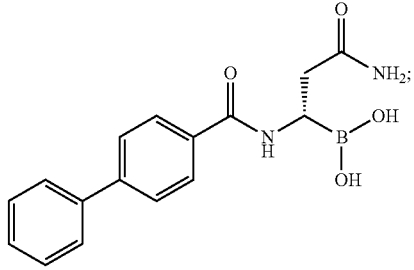
Formula XV
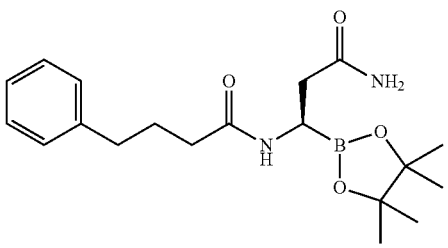
or an R enantiomer of any of the foregoing.

15. The method of any of the preceding paragraphs, wherein the ClbP inhibitor has a structure selected from the following:

Formula IV

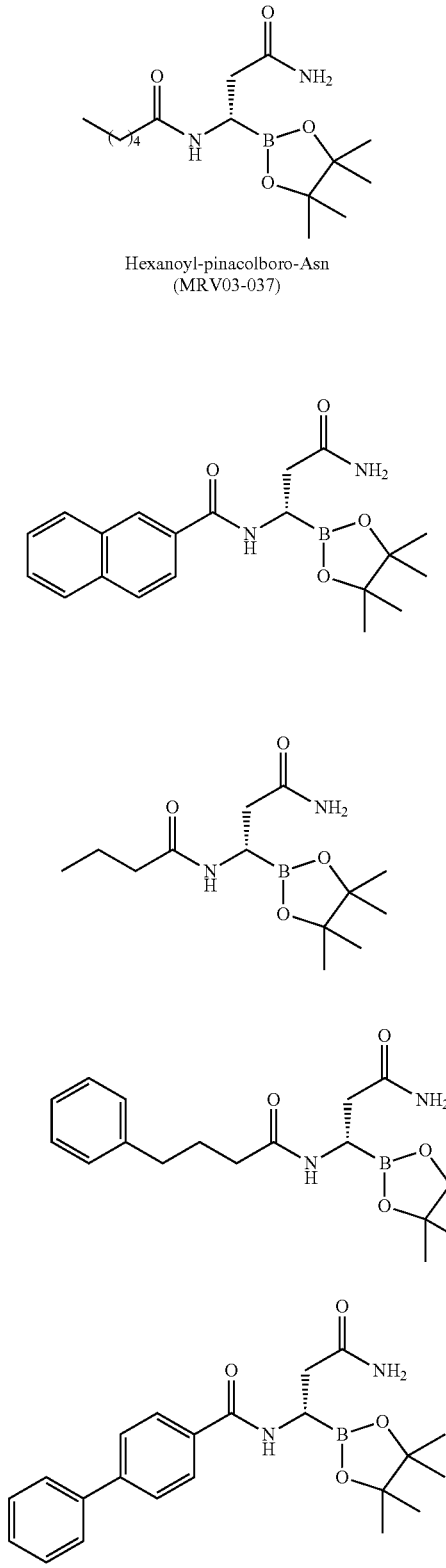

Hexanoyl-pinacolboro-Asn
(MRV03-037)

Formula VI

Formula VII

Formula VIII

Formula IX

Formula X

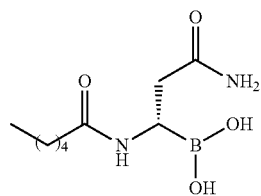

Formula XII

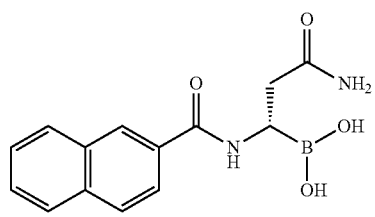

Formula XIII

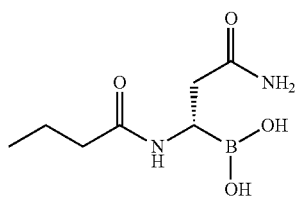

Formula XIV

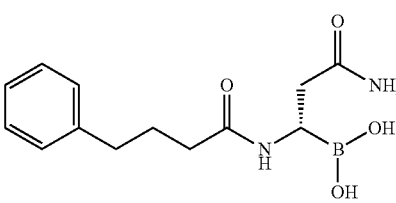

Formula XV

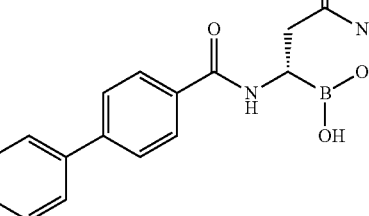

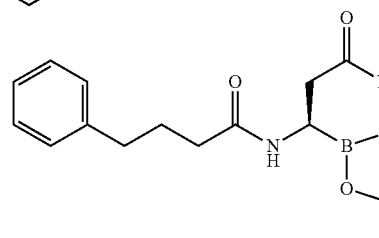;

or an R enantiomer of any of the foregoing.

16. The method of any of the preceding paragraphs, wherein contacting comprises administering the ClbP inhibitor to a subject.
17. The method of paragraph 16, wherein the subject has a population and/or infection of pks+ bacteria.
18. The method of paragraph 17, wherein the bacteria is *E. coli*.
19. The method of any of the preceding paragraphs, whereby the level of genotoxin in a sample or subject is reduced and/or the production of genotoxin in a sample or subject is inhibited.

20. The method of paragraph 19, wherein the genotoxin is colibactin.
21. The method of any of the preceding paragraphs, whereby the risk and/or progression of cancer in subject is reduced or inhibited.
22. The method of paragraph 21, wherein the cancer is colorectal cancer.
23. A method of treating a pks+ bacterial infection or treating cancer in a subject in need thereof, the method comprising administering to the subject one or more ClbP inhibitors having the structure of:

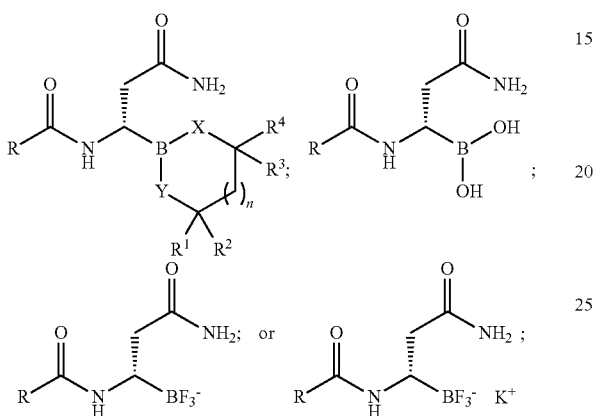

wherein R is selected from the group consisting of H, OH, alkyl, alkenyl, alkynyl, aryl, heteroaryl, cycloalkyl, or heterocycle;
R¹, R², R³ and R⁴ independently are H, alkyl, alkenyl, alkynyl, aryl, heteroaryl, cycloalkyl or heterocycle, or R² and R³, together with the carbons they are attached to, form an aryl, heteroaryl, cycloalkyl or heterocycle;
X and Y independently are O, S or NH, and n is 0, or 1; or an R enantiomer of any of the foregoing.
24. The method of paragraph 23, wherein three of R¹, R², R³ and R⁴ are H and the other is methyl.
25. The method of paragraph 23, wherein R² and R³, together with the carbon atoms they are attached to, form 2,3,4-trihydroxytetrahydropyran.
26. The method of paragraph 23, wherein n is 0, R¹ is methyl, R⁴ is H, and R² and R³, together with the carbon atoms they are attached to, form a 6,6-dimethylbicycle[3.1.1]heptane.
27. The method of paragraph 23, wherein n is 0, R¹ and R⁴ are H, and R² and R³, together with the carbon atoms they are attached to, form a benzene ring.
28. The method of any of paragraphs 23-27, wherein the ClbP inhibitor has the structure of:

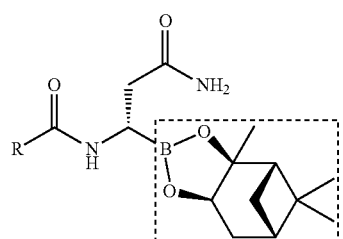

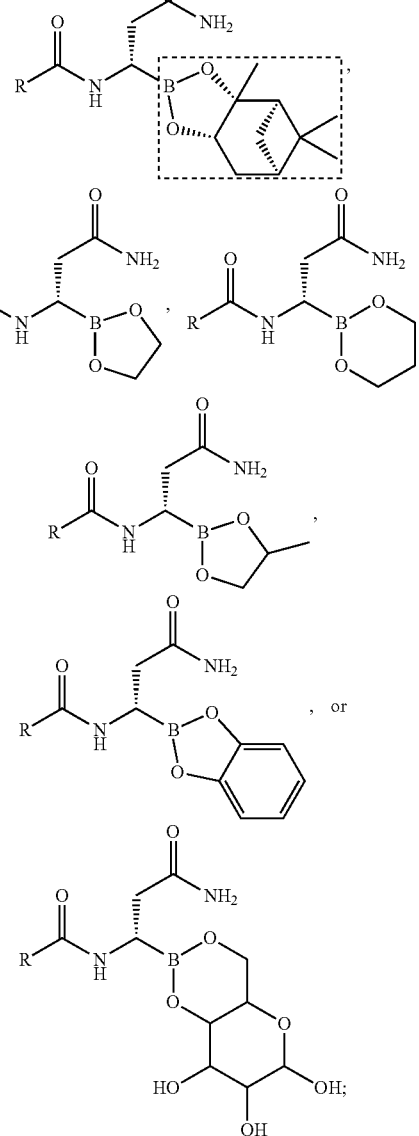

or an R enantiomer of any of the foregoing.
29. The method of any of paragraphs 23-28, wherein the ClbP inhibitor has the structure of:

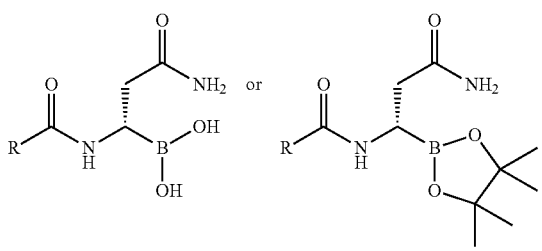

wherein R is, selected from the group consisting of H, OH, alkyl, alkenyl, alkynyl, aryl, heteroaryl, cycloalkyl, or heterocycle;

wherein the alkyl, alkenyl, alkynyl, or cycloalkyl, whether alone or as part of a substituent group, is optionally substituted with one or more substituents independently selected from the group consisting of halogen, —OH, alkyl, O-alkyl, —NR$^A$R$^B$, —S-alkyl, —SO-alkyl, —SO$_2$— alkyl, alkenyl, alkynyl, aryl, heteroaryl, cycloalkyl or heterocycle; and the alkenyl, alkynyl, or optionally includes —O—, —S—, —SO$_2$—, —N(R$^C$)— substituting one or more carbons in the carbon chain, wherein the aryl or heteroaryl, whether alone or as part of a substituent group, is optionally substituted with one or more substituents independently selected from the group consisting of halogen, OH, alkyl, O-alkyl, —NR$^D$R$^E$, —S-alkyl, —SO-alkyl and —SO$_2$-alkyl, alkenyl, alkynyl, aryl, heteroaryl, cycloalkyl or heterocycle;

wherein R$^A$, R$^B$, R$^C$, R$^D$, and R$^E$, are each independently selected from hydrogen and C$_{1-4}$ alkyl; or an R enantiomer of any of the foregoing.

30. The method of any of paragraphs 23-29, wherein R is alkyl or aryl.
31. The method of any of paragraphs 23-30, wherein R is not a phenyl group.
32. The method of any of paragraphs 23-31, wherein R is selected from the group consisting of:

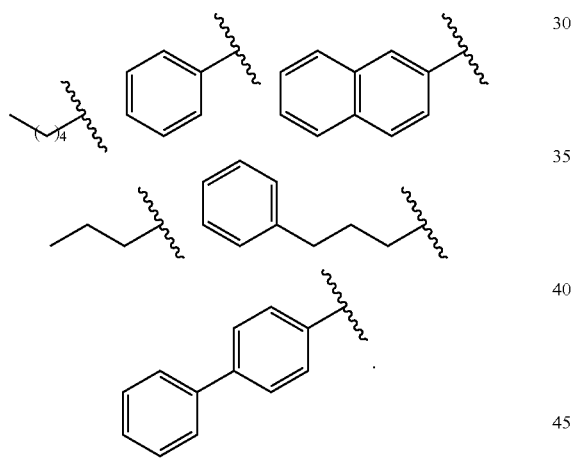

33. The method of any of paragraphs 23-32, wherein the ClbP inhibitor does not have the following structure:

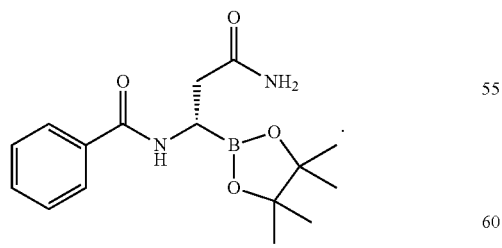

34. The method of any of paragraphs 23-33, wherein the ClbP inhibitor comprises a D-asparagine group and not an L-asparagine group.
35. The method of any of paragraphs 23-34, wherein R is hydrophobic.
36. The method of any of paragraphs 23-35, wherein the ClbP inhibitor has a structure selected from the following:

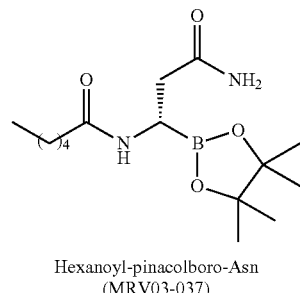

Hexanoyl-pinacolboro-Asn (MRV03-037)

Formula IV

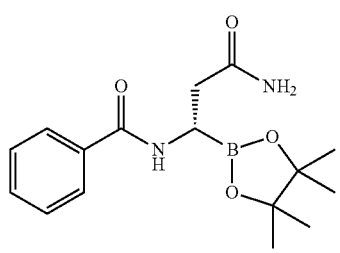

Formula V

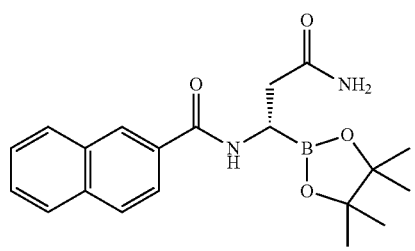

Formula VI

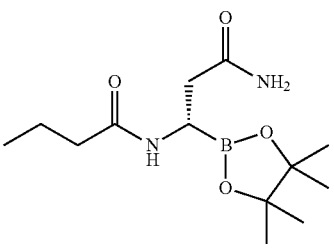

Formula VII

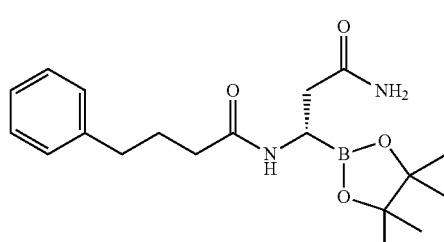

Formula VIII

Formula IX
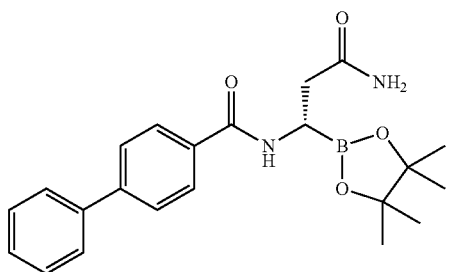
Formula X
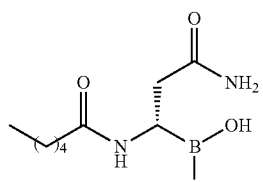
Formula XI
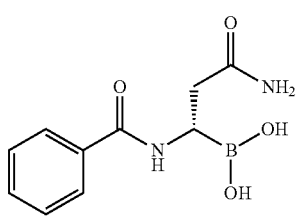
Formula XII
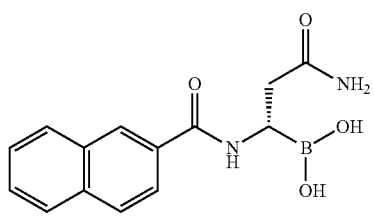
Formula XIII
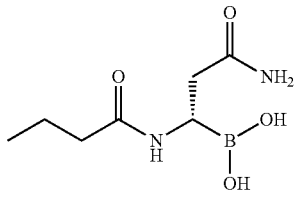
Formula XIV
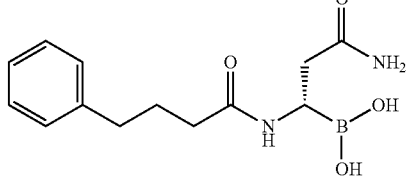
Formula XV
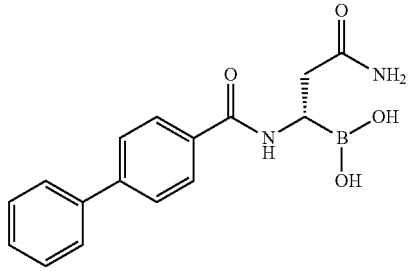
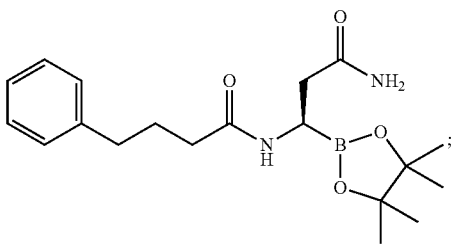
or an R enantiomer of any of the foregoing.
37. The method of any of paragraphs 23-36, wherein the ClbP inhibitor has a structure selected from the following:
Formula IV
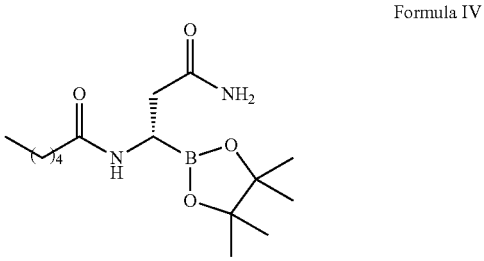
Hexanoyl-pinacolboro-Asn
(MRV03-037)
Formula VI
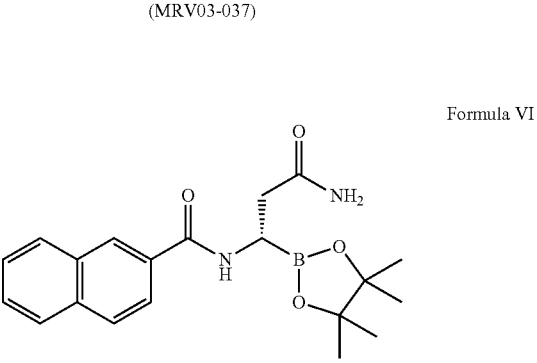
Formula VII
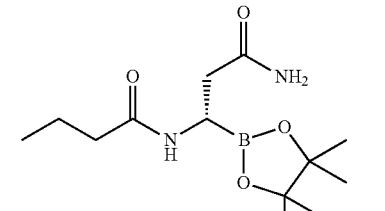
Formula VIII
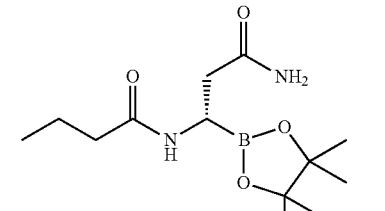

Formula IX
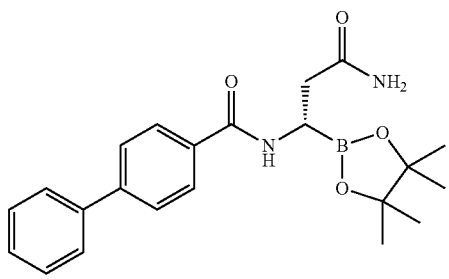

Formula X
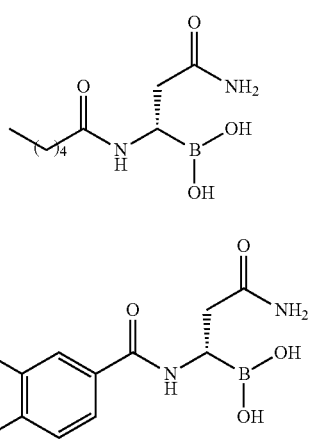

Formula XII
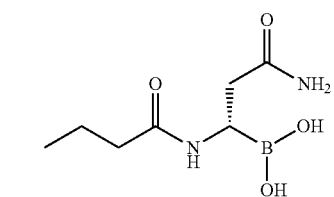

Formula XIII
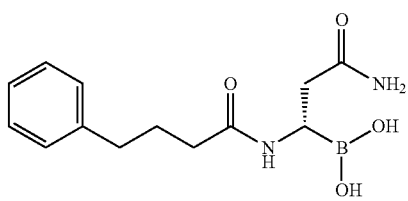

Formula XIV
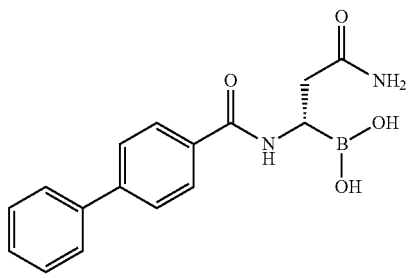

Formula XV
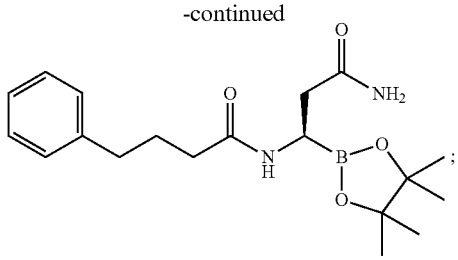

or an R enantiomer of any of the foregoing.

38. The method of any of paragraphs 23-37, wherein the subject has a population and/or infection of pks+ bacteria.
39. The method of paragraph 38, wherein the bacteria is *E. coli*.
40. The method of any of paragraphs 23-39, whereby the level of genotoxin in a sample or subject is reduced and/or the production of genotoxin in a sample or subject is inhibited.
41. The method of paragraph 40, wherein the genotoxin is colibactin.
42. The method of any of paragraphs 23-41, whereby the risk and/or progression of cancer in subject is reduced or inhibited.
43. The method of paragraph 42, wherein the cancer is colorectal cancer.
44. A ClbP inhibitor for use in a method of inhibiting ClbP or treating a pks+ bacterial infection or treating cancer in a subject in need thereof, the ClbP inhibitor having the structure of:

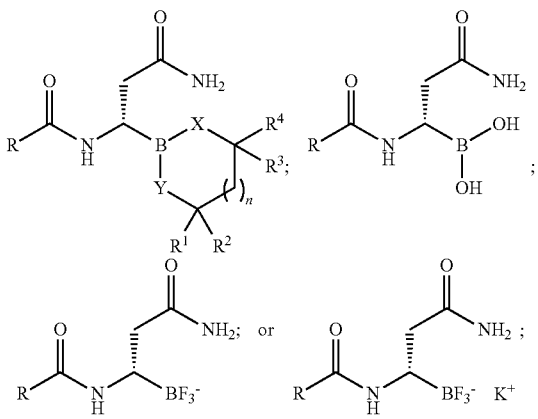

wherein R is selected from the group consisting of H, OH, alkyl, alkenyl, alkynyl, aryl, heteroaryl, cycloalkyl, or heterocycle;

$R^1$, $R^2$, $R^3$ and $R^4$ independently are H, alkyl, alkenyl, alkynyl, aryl, heteroaryl, cycloalkyl or heterocycle, or $R^2$ and $R^3$, together with the carbons they are attached to, form an aryl, heteroaryl, cycloalkyl or heterocycle;

X and Y independently are O, S or NH, and n is 0, or 1; or an R enantiomer of any of the foregoing.

45. The ClbP inhibitor of paragraph 44, wherein three of $R^1$, $R^2$, $R^3$ and $R^4$ are H and the other is methyl.
46. The ClbP inhibitor of paragraph 44, wherein $R^2$ and $R^3$, together with the carbon atoms they are attached to, form 2,3,4-trihydroxytetrahydropyran.

47. The ClbP inhibitor of paragraph 44, wherein n is 0, $R^1$ is methyl, $R^4$ is H, and $R^2$ and $R^3$, together with the carbon atoms they are attached to, form a 6,6-dimethylbicycle[3.1.1]heptane.

48. The ClbP inhibitor of paragraph 44, wherein n is 0, $R^1$ and $R^4$ are H, and $R^2$ and $R^3$, together with the carbon atoms they are attached to, form a benzene ring.

49. The ClbP inhibitor of any of paragraphs 44-48, wherein the ClbP inhibitor has the structure of:

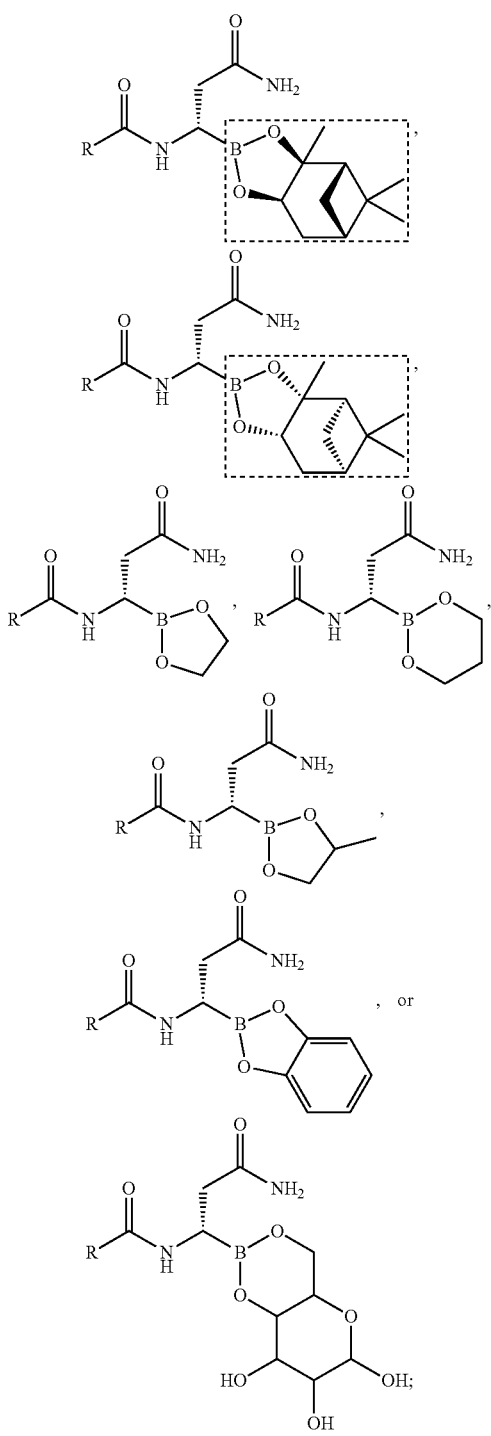

or an R enantiomer of any of the foregoing.

50. The ClbP inhibitor of any of paragraphs 44-49, wherein the ClbP inhibitor has the structure of:

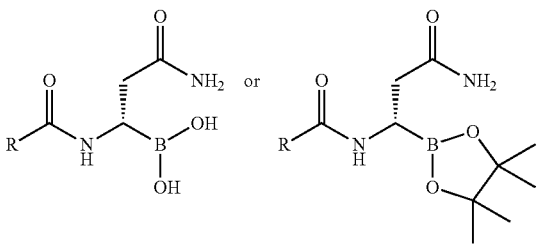

wherein R is, selected from the group consisting of H, OH, alkyl, alkenyl, alkynyl, aryl, heteroaryl, cycloalkyl, or heterocycle;

wherein the alkyl, alkenyl, alkynyl, or cycloalkyl, whether alone or as part of a substituent group, is optionally substituted with one or more substituents independently selected from the group consisting of halogen, —OH, alkyl, O-alkyl, —$NR^AR^B$, —S-alkyl, —SO-alkyl, —$SO_2$— alkyl, alkenyl, alkynyl, aryl, heteroaryl, cycloalkyl or heterocycle; and the alkenyl, alkynyl, or optionally includes —O—, —S—, —$SO_2$—, —$N(R^C)$— substituting one or more carbons in the carbon chain, wherein the aryl or heteroaryl, whether alone or as part of a substituent group, is optionally substituted with one or more substituents independently selected from the group consisting of halogen, OH, alkyl, O-alkyl, —$NR^DR^E$, —S-alkyl, —SO-alkyl and —$SO_2$-alkyl, alkenyl, alkynyl, aryl, heteroaryl, cycloalkyl or heterocycle;

wherein $R^A$, $R^B$, $R^C$, $R^D$, and $R^E$, are each independently selected from hydrogen and $C_{1-4}$ alkyl; or an R enantiomer of any of the foregoing.

51. The ClbP inhibitor of any of paragraphs 44-50, wherein R is alkyl or aryl.

52. The ClbP inhibitor of any of paragraphs 44-51, wherein R is not a phenyl group.

53. The ClbP inhibitor of any of paragraphs 44-52, wherein R is selected from the group consisting of:

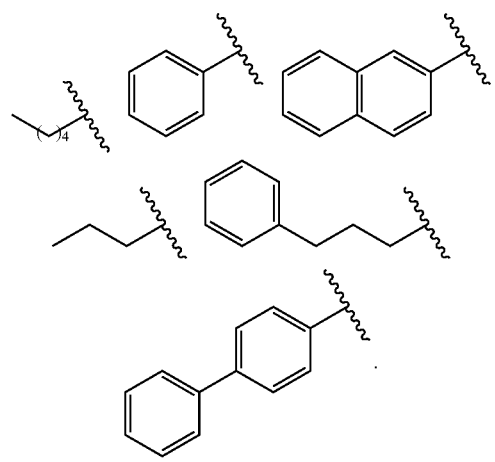

54. The ClbP inhibitor of any of paragraphs 44-53, wherein the ClbP inhibitor does not have the following structure:

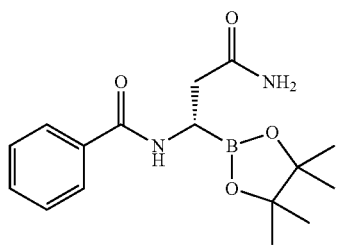

55. The ClbP inhibitor of any of paragraphs 44-54, wherein the ClbP inhibitor comprises a D-asparagine group and not an L-asparagine group.
56. The ClbP inhibitor of any of paragraphs 44-55, wherein R is hydrophobic.
57. The ClbP inhibitor of any of paragraphs 44-56, wherein the ClbP inhibitor has a structure selected from the following:

Formula IV

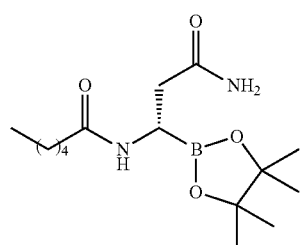

Hexanoyl-pinacolboro-Asn
(MRV03-037)

Formula V

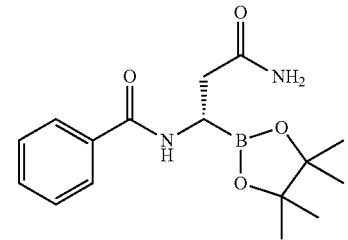

Formula VI

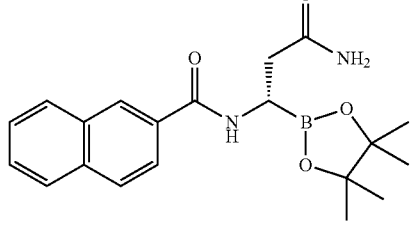

Formula VII

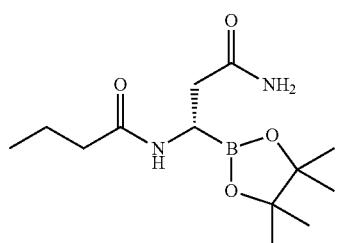

-continued

Formula VIII

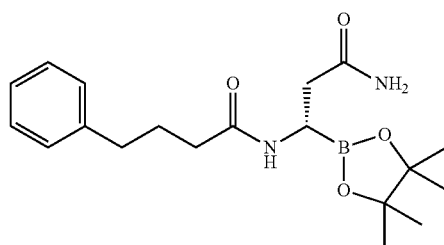

Formula IX

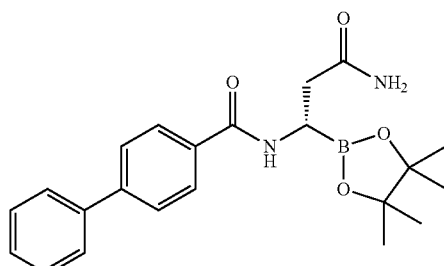

Formula X

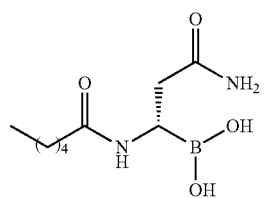

Formula XI

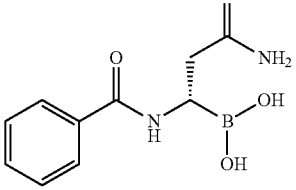

Formula XII

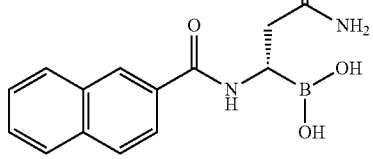

Formula XIII

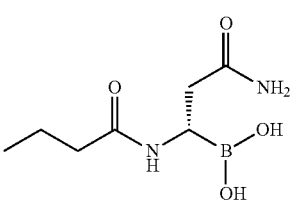

Formula XIV

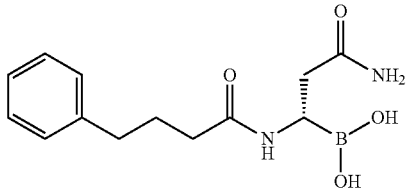

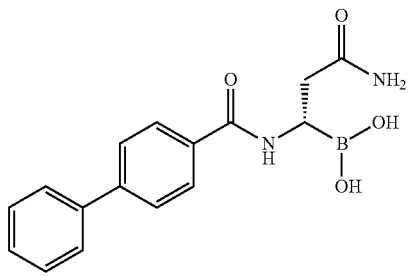
Formula XV
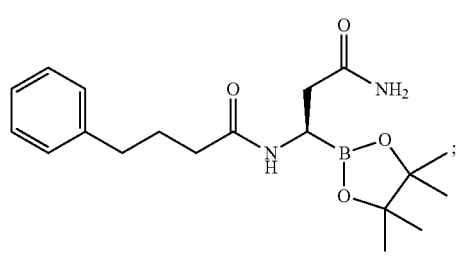
or an R enantiomer of any of the foregoing.
58. The ClbP inhibitor of any of paragraphs 44-57, wherein the ClbP inhibitor has a structure selected from the following:
Formula IV
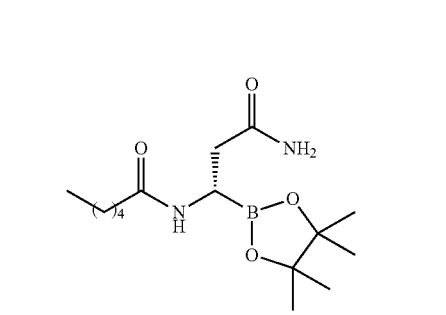
Hexanoyl-pinacolboro-Asn
(MRV03-037)
Formula VI
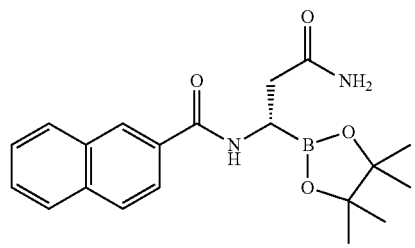
Formula VII
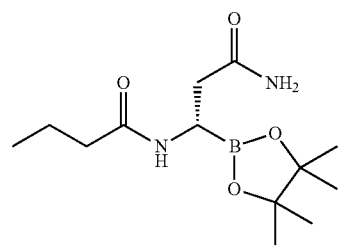
Formula VIII
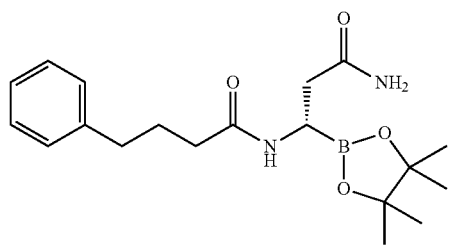
Formula IX
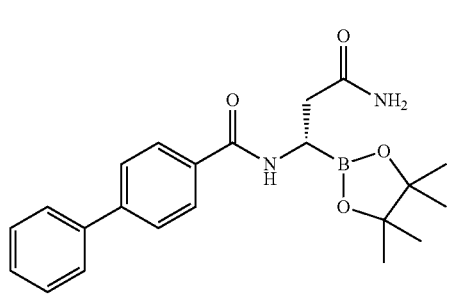
Formula X
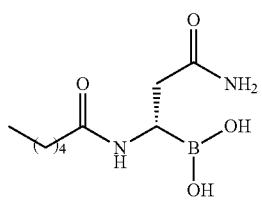
Formula XII
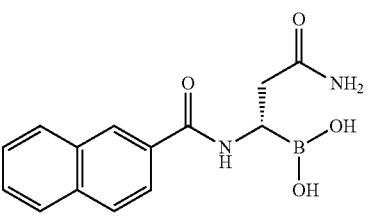
Formula XIII
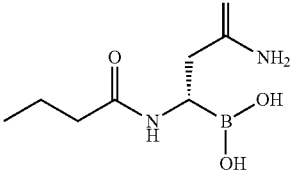
Formula XIV
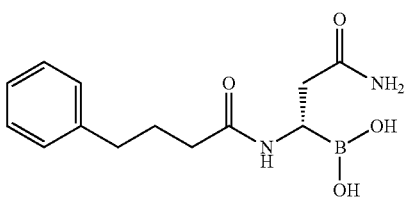

-continued

Formula XV

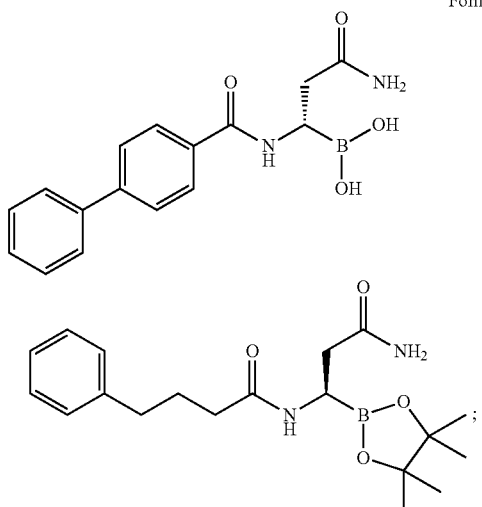

or an R enantiomer of any of the foregoing.

59. The ClbP inhibitor of any of paragraphs 44-58, wherein the subject has a population and/or infection of pks+ bacteria.
60. The ClbP inhibitor of paragraph 59, wherein the bacteria is *E. coli*.
61. The ClbP inhibitor of any of paragraphs 44-60, whereby the level of genotoxin in a sample or subject is reduced and/or the production of genotoxin in a sample or subject is inhibited.
62. The ClbP inhibitor of paragraph 61, wherein the genotoxin is colibactin.
63. The ClbP inhibitor of any of paragraphs 44-62, whereby the risk and/or progression of cancer in subject is reduced or inhibited.
64. The ClbP inhibitor of paragraph 63, wherein the cancer is colorectal cancer.

In some embodiments, the present technology may be defined in any of the following numbered paragraphs:

1. A composition comprising one or more ClbP inhibitors having a structure selected from the group consisting of:

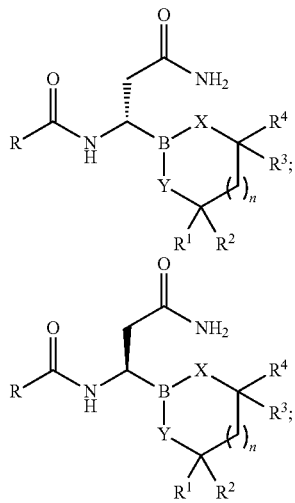

-continued

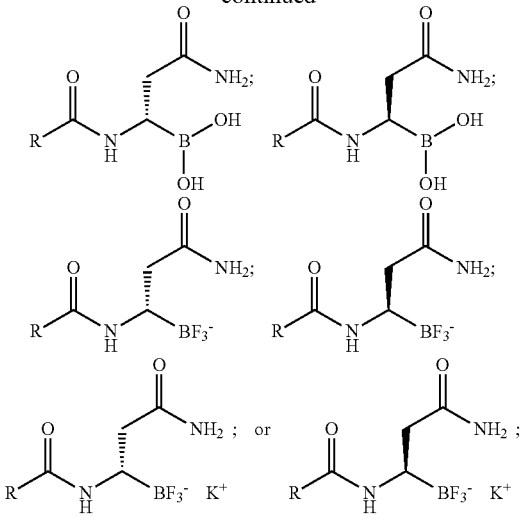

wherein R is selected from the group consisting of H, OH, alkyl, alkenyl, alkynyl, aryl, heteroaryl, cycloalkyl, or heterocycle;

$R^1$, $R^2$, $R^3$ and $R^4$ independently are H, alkyl, alkenyl, alkynyl, aryl, heteroaryl, cycloalkyl or heterocycle, or $R^2$ and $R^3$, together with the carbons they are attached to, form an aryl, heteroaryl, cycloalkyl or heterocycle;

X and Y independently are O, S or NH, and n is 0, or 1.

2. The composition of paragraph 1, wherein three of $R^1$, $R^2$, $R^3$ and $R^4$ are H and the other is methyl.
3. The composition of paragraph 1, wherein $R^2$ and $R^3$, together with the carbon atoms they are attached to, form 2,3,4-trihydroxytetrahydropyran.
4. The composition of paragraph 1, wherein n is 0, $R^1$ is methyl, $R^4$ is H, and $R^2$ and $R^3$, together with the carbon atoms they are attached to, form a 6,6-dimethylbicycle[3.1.1]heptane.
5. The composition of paragraph 1, wherein n is 0, $R^1$ and $R^4$ are H, and $R^2$ and $R^3$, together with the carbon atoms they are attached to, form a benzene ring.
6. The composition of any of paragraphs 1-5, wherein the ClbP inhibitor has the structure of:

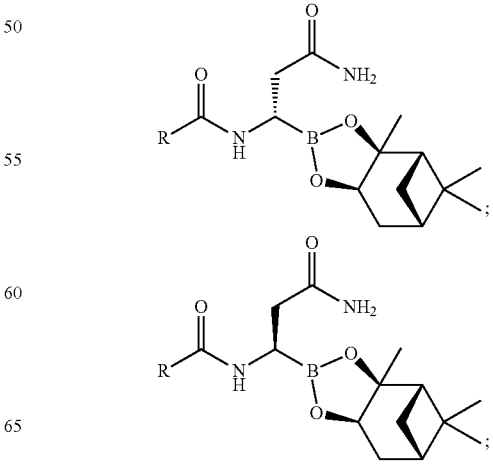

-continued

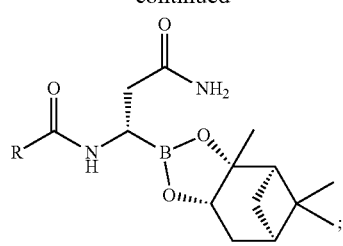

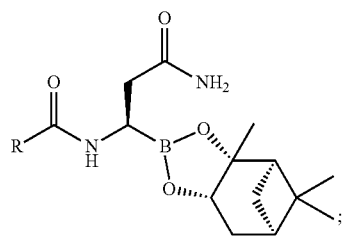

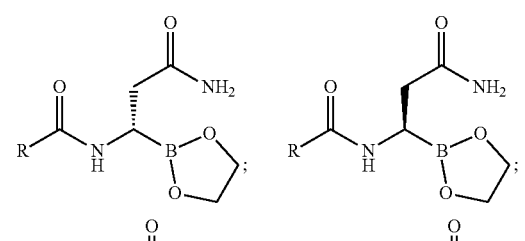

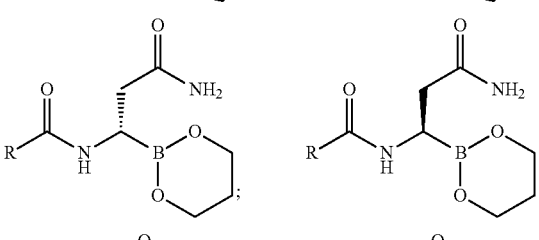

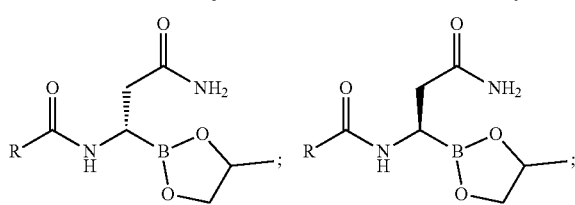

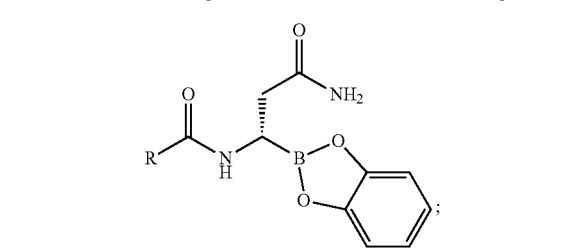

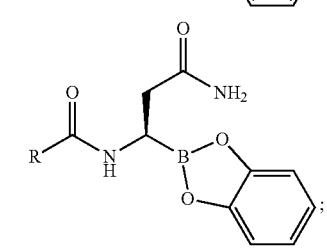

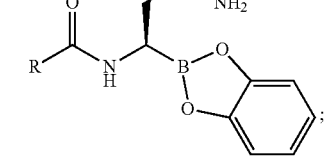

-continued

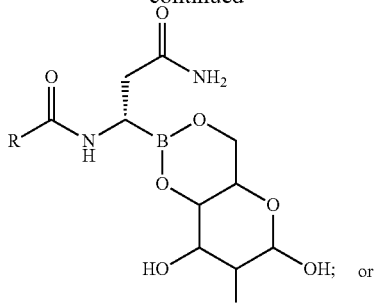

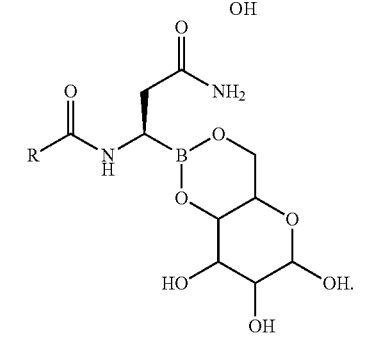

7. The composition of any of paragraphs 1-6, wherein the ClbP inhibitor has the structure of:

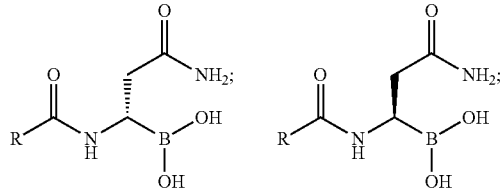

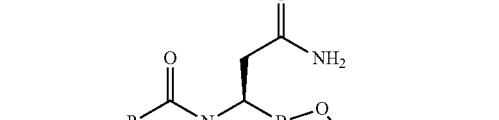

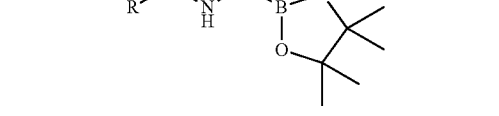

wherein R is, selected from the group consisting of H, OH, alkyl, alkenyl, alkynyl, aryl, heteroaryl, cycloalkyl, or heterocycle;

wherein the alkyl, alkenyl, alkynyl, or cycloalkyl, whether alone or as part of a substituent group, is optionally substituted with one or more substituents independently selected from the group consisting of halogen, —OH, alkyl, O-alkyl, —NR$^A$R$^B$, —S-alkyl, —SO-alkyl, —SO$_2$— alkyl, alkenyl, alkynyl, aryl, heteroaryl, cycloalkyl or heterocycle; and the alkenyl, alkynyl, or optionally includes —O—, —S—, —SO$_2$—, —N(R$^C$)— substituting one or more carbons in the carbon chain, wherein the aryl or heteroaryl, whether alone or as part of a substituent group, is optionally substituted with one or more substituents independently selected from the group consisting of halogen, OH, alkyl, O-alkyl, —NR$^D$R$^E$, —S-alkyl, —SO-alkyl and —SO$_2$-alkyl, alkenyl, alkynyl, aryl, heteroaryl, cycloalkyl or heterocycle;

wherein R$^A$, R$^B$, R$^C$, R$^D$, and R$^E$, are each independently selected from hydrogen and C$_{1-4}$ alkyl.

8. The composition of any of paragraphs 1-7, wherein R is alkyl or aryl.
9. The composition of any of paragraphs 1-8, wherein R is not a phenyl group.
10. The composition of any of paragraphs 1-9, wherein R is selected from the group consisting of:

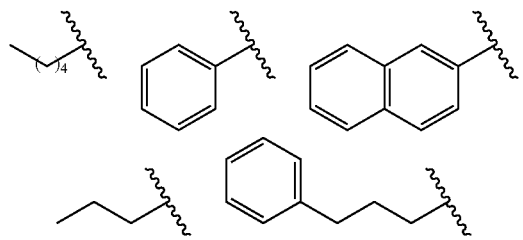

11. The composition of any of paragraphs 1-10, wherein the ClbP inhibitor does not have the following structure:

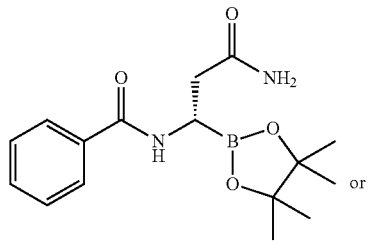

or

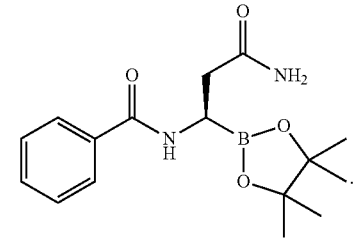 [SMILES: CC1(C)OB([C@@H](CC(N)=O)NC(=O)c2ccccc2)OC1(C)C]

12. The composition of any of the preceding paragraphs, wherein the ClbP inhibitor comprises a D-asparagine group and not an L-asparagine group.
13. The composition of any of the preceding paragraphs, wherein R is hydrophobic.
14. The composition of any of the preceding paragraphs, wherein the ClbP inhibitor has a structure selected from the following:

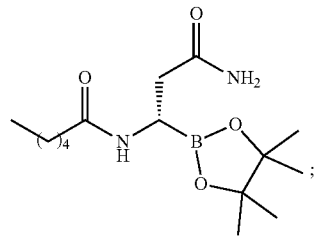

Hexanoyl-pinacolboro-Asn
(MRV03-037)

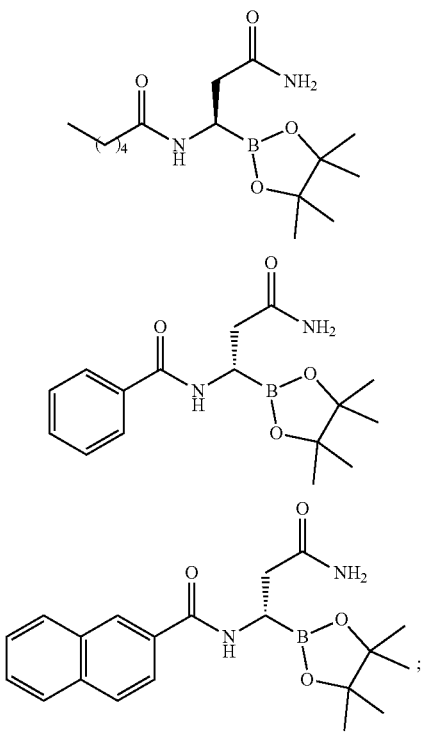

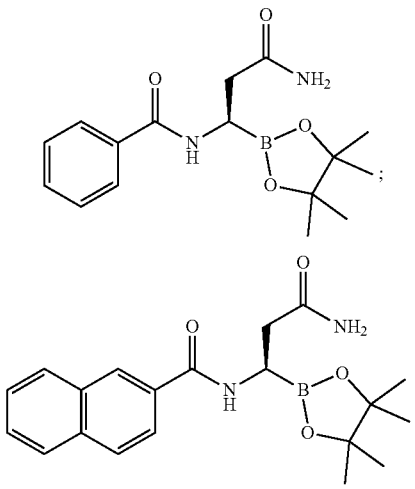

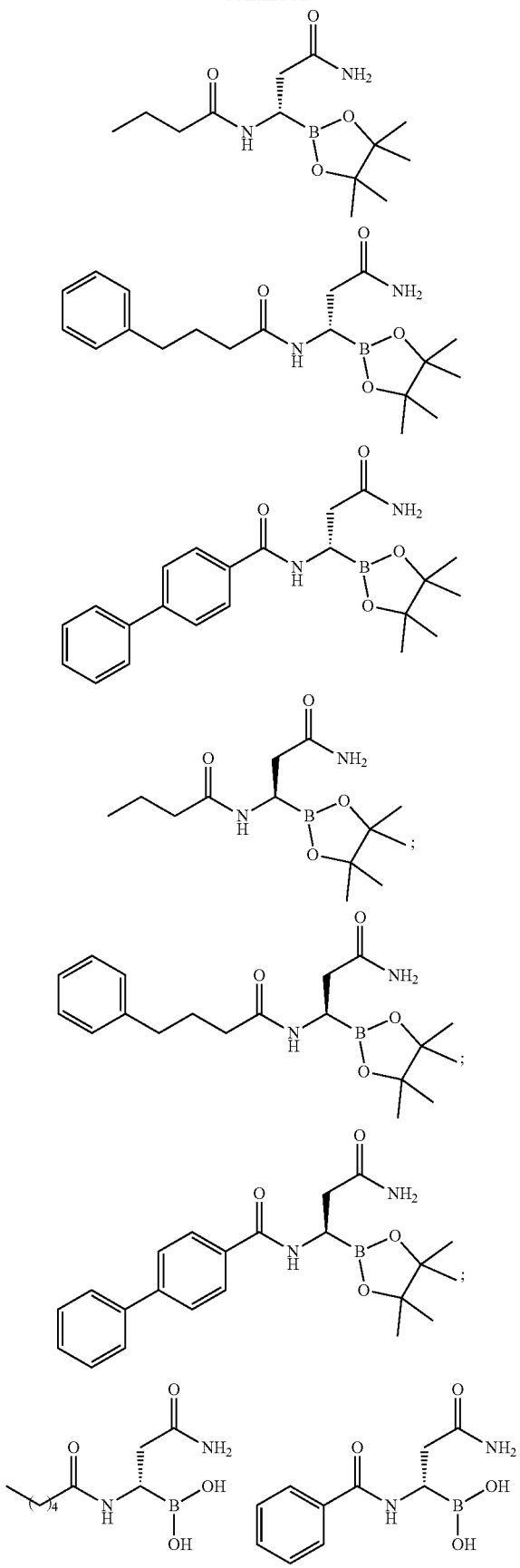
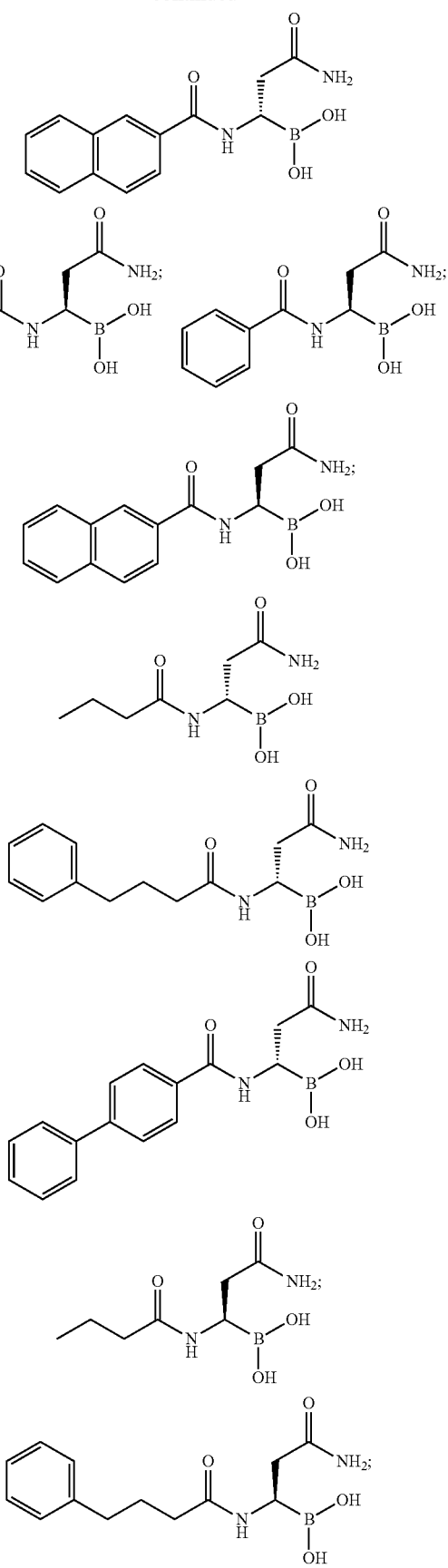

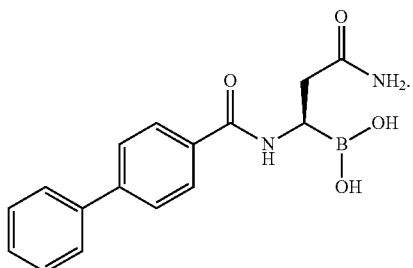
15. The composition of any of the preceding paragraphs, wherein the ClbP inhibitor has a structure selected from the following:
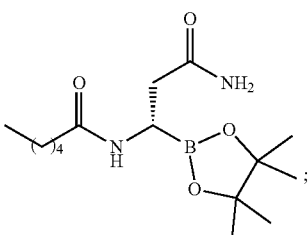
Hexanoyl-pinacolboro-Asn
(MRV03-037)
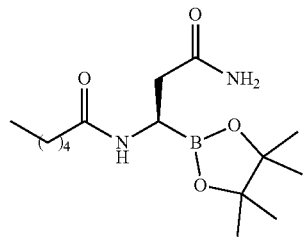
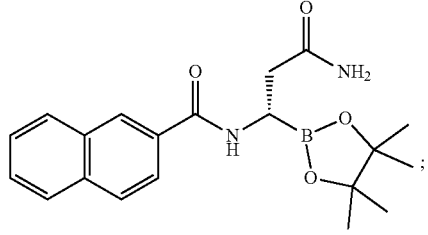
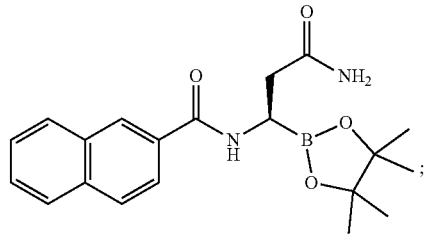
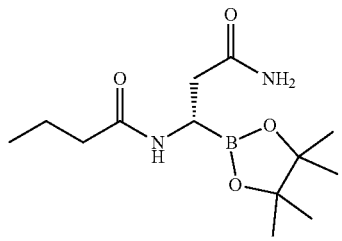
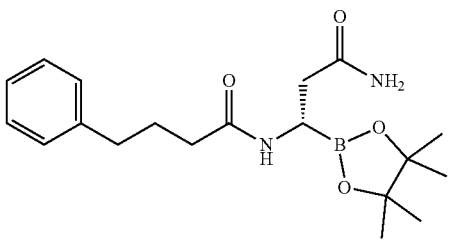
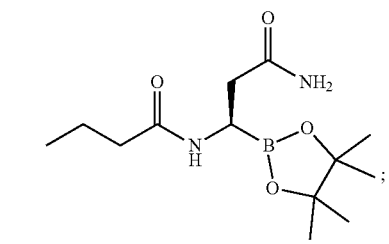
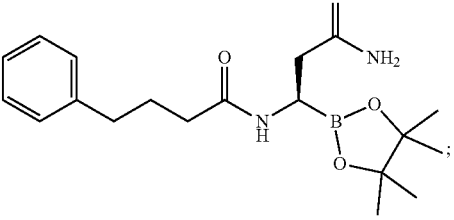
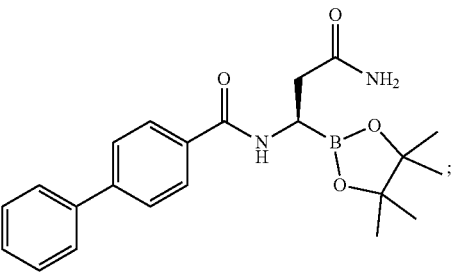
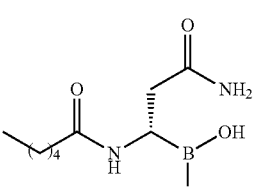
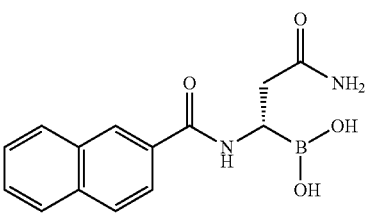

-continued

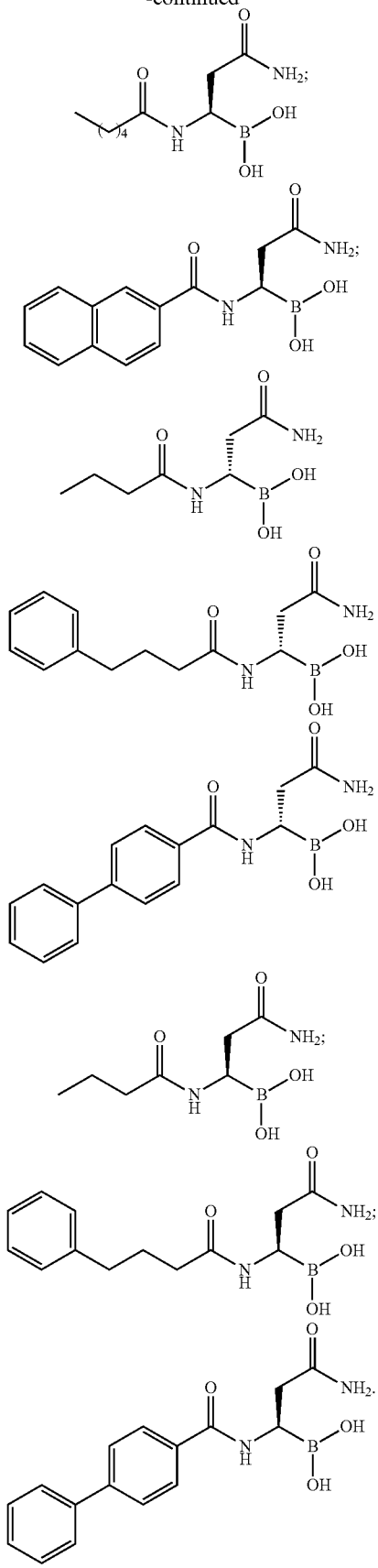

In some embodiments, the present technology may be defined in any of the following numbered paragraphs:

1. A method of inhibiting ClbP, the method comprising contacting ClbP with one or more ClbP inhibitors having the structure of:

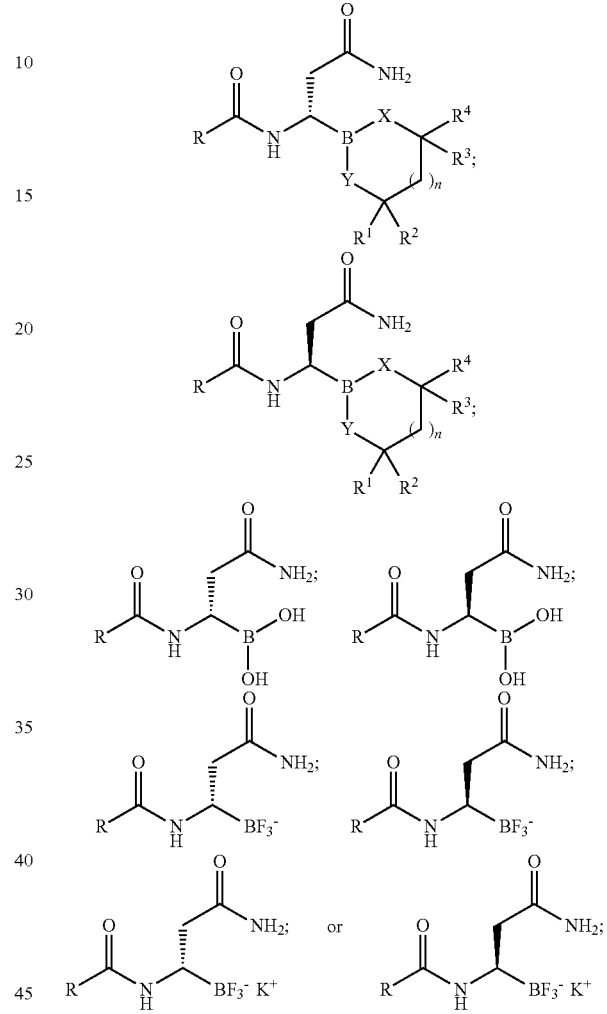

wherein R is selected from the group consisting of H, OH, alkyl, alkenyl, alkynyl, aryl, heteroaryl, cycloalkyl, or heterocycle;

$R^1$, $R^2$, $R^3$ and $R^4$ independently are H, alkyl, alkenyl, alkynyl, aryl, heteroaryl, cycloalkyl or heterocycle, or $R^2$ and $R^3$, together with the carbons they are attached to, form an aryl, heteroaryl, cycloalkyl or heterocycle;

X and Y independently are O, S or NH, and n is 0, or 1.

2. The method of paragraph 1, wherein three of $R^1$, $R^2$, $R^3$ and $R^4$ are H and the other is methyl.

3. The method of paragraph 1, wherein $R^2$ and $R^3$, together with the carbon atoms they are attached to, form 2,3,4-trihydroxytetrahydropyran.

4. The method of paragraph 1, wherein n is 0, $R^1$ is methyl, $R^4$ is H, and $R^2$ and $R^3$, together with the carbon atoms they are attached to, form a 6,6-dimethylbicycle[3.1.1]heptane.

5. The method of paragraph 1, wherein n is 0, $R^1$ and $R^4$ are H, and $R^2$ and $R^3$, together with the carbon atoms they are attached to, form a benzene ring.
6. The method of any of paragraphs 1-5, wherein the ClbP inhibitor has the structure of:
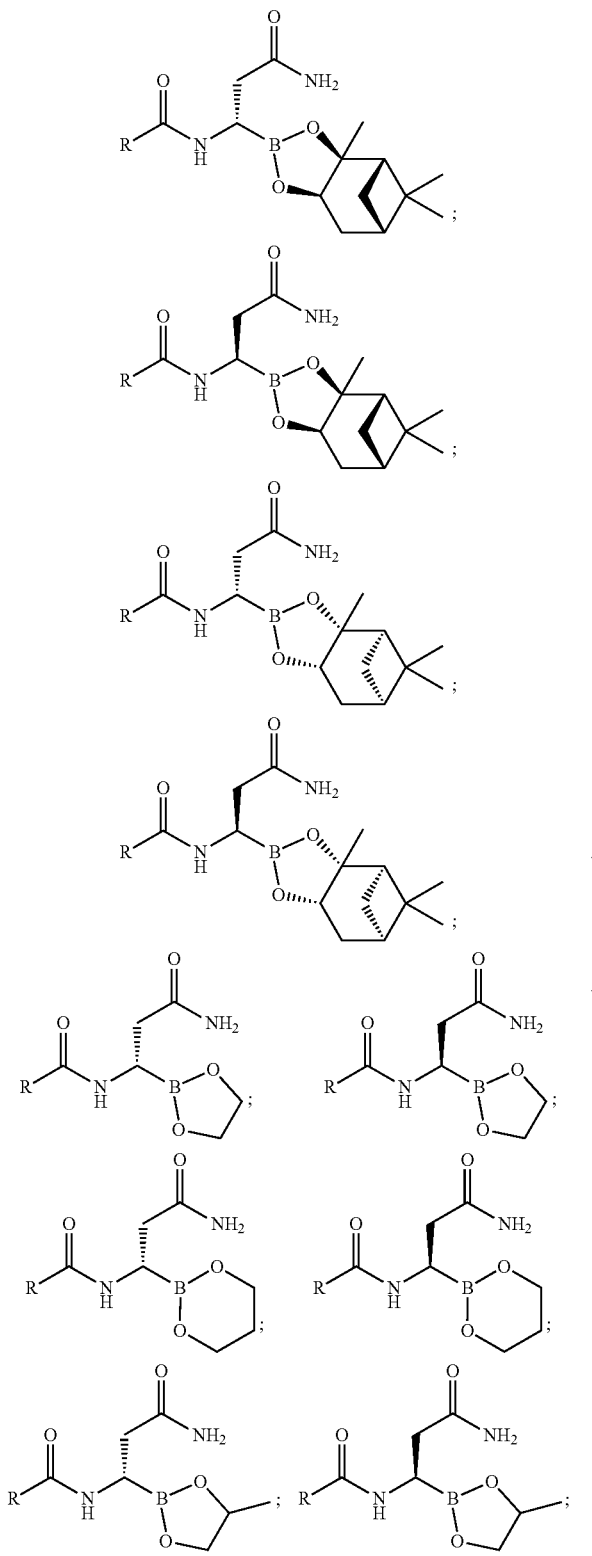
-continued
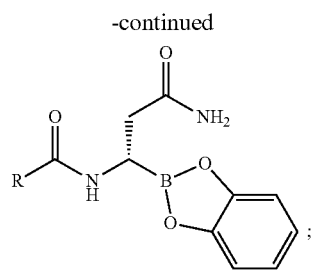
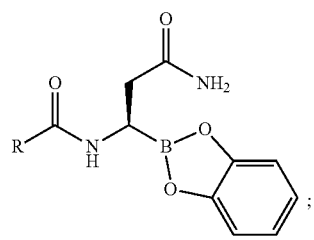
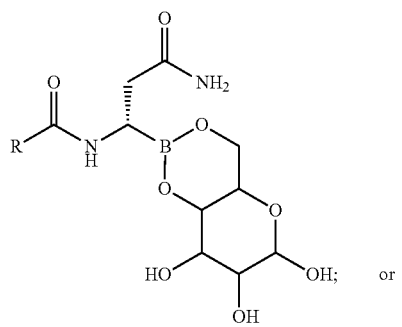
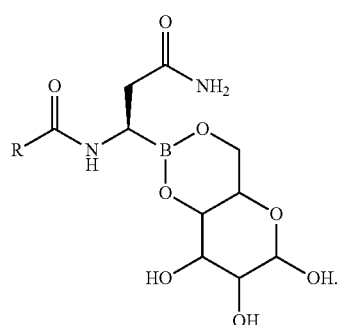
7. The method of any of paragraphs 1-6, wherein the ClbP inhibitor has the structure of:
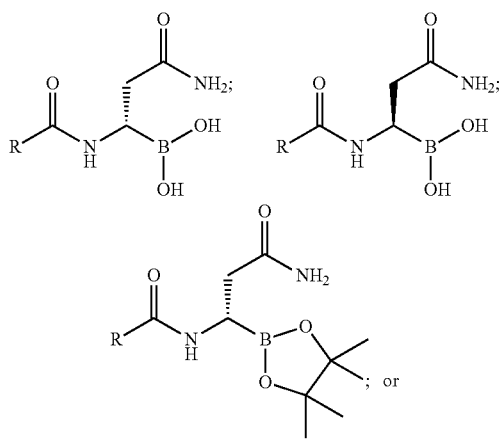

-continued

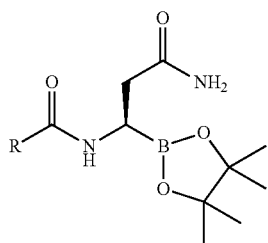

wherein R is, selected from the group consisting of H, OH, alkyl, alkenyl, alkynyl, aryl, heteroaryl, cycloalkyl, or heterocycle;

wherein the alkyl, alkenyl, alkynyl, or cycloalkyl, whether alone or as part of a substituent group, is optionally substituted with one or more substituents independently selected from the group consisting of halogen, —OH, alkyl, O-alkyl, —NR$^A$R$^B$, —S-alkyl, —SO-alkyl, —SO$_2$— alkyl, alkenyl, alkynyl, aryl, heteroaryl, cycloalkyl or heterocycle; and the alkenyl, alkynyl, or optionally includes —O—, —S—, —SO$_2$—, —N(R$^C$)— substituting one or more carbons in the carbon chain, wherein the aryl or heteroaryl, whether alone or as part of a substituent group, is optionally substituted with one or more substituents independently selected from the group consisting of halogen, OH, alkyl, O-alkyl, —NR$^D$R$^E$, —S-alkyl, —SO-alkyl and —SO$_2$-alkyl, alkenyl, alkynyl, aryl, heteroaryl, cycloalkyl or heterocycle;

wherein R$^A$, R$^B$, R$^C$, R$^D$, and R$^E$, are each independently selected from hydrogen and C$_{1-4}$ alkyl.

8. The method of any of paragraphs 1-7, wherein R is alkyl or aryl.
9. The method of any of paragraphs 1-8, wherein R is not a phenyl group.
10. The method of any of paragraphs 1-9, wherein R is selected from the group consisting of:

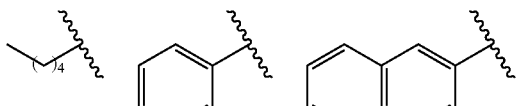

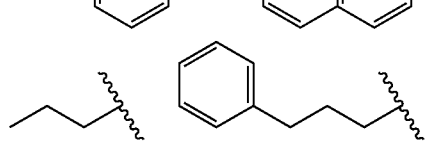

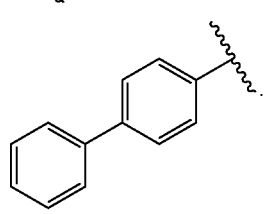

11. The method of any of paragraphs 1-10, wherein the ClbP inhibitor does not have the following structure:

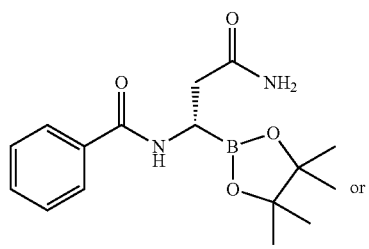

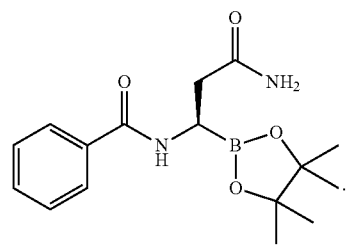 [SMILES: CC1(C)OB([C@@H](CC(N)=O)NC(=O)c2ccccc2)OC1(C)C]

12. The method of any of the preceding paragraphs, wherein the ClbP inhibitor comprises a D-asparagine group and not an L-asparagine group.
13. The method of any of the preceding paragraphs, wherein R is hydrophobic.
14. The method of any of the preceding paragraphs, wherein the ClbP inhibitor has a structure selected from the following:

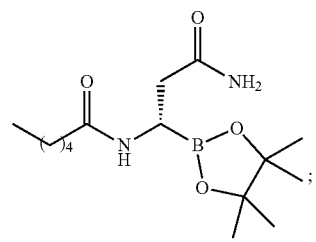

Hexanoyl-pinacolboro-Asn
(MRV03-037)

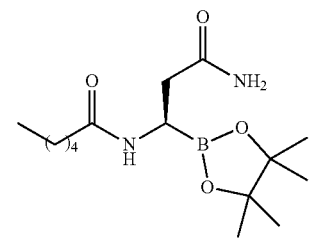

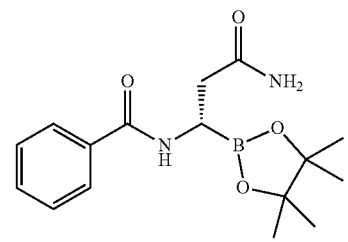

123
-continued
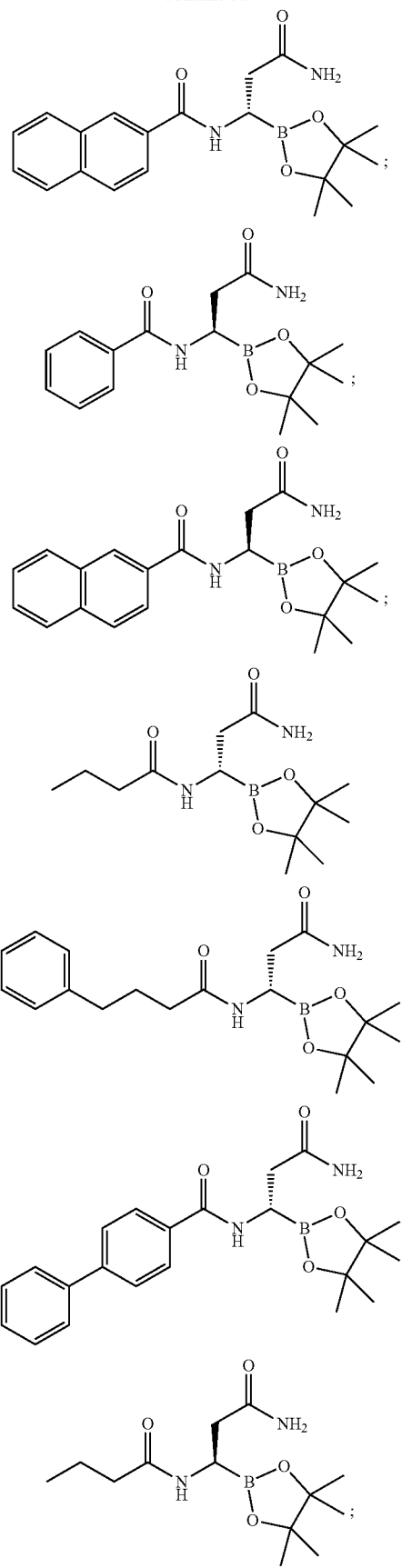
124
-continued
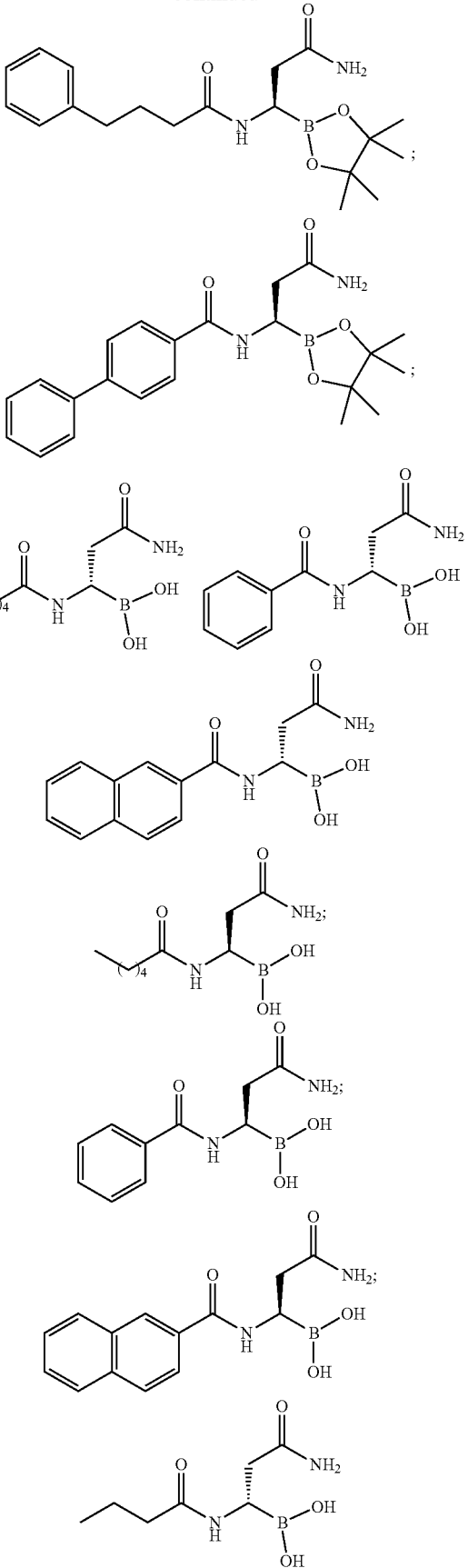

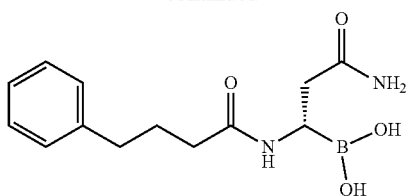
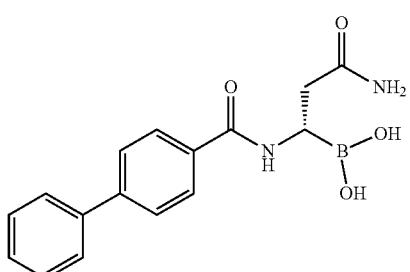
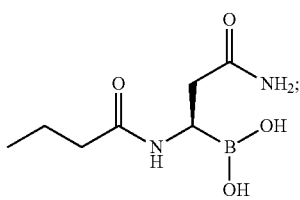
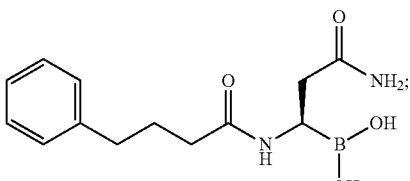
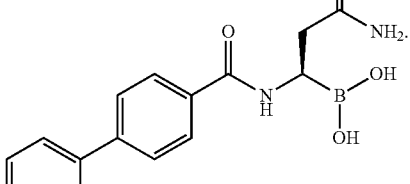
15. The method of any of the preceding paragraphs, wherein the ClbP inhibitor has a structure selected from the following:
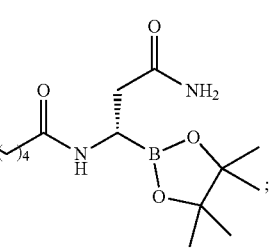
Hexanoyl-pinacolboro-Asn
(MRV03-037)
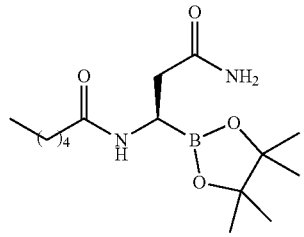
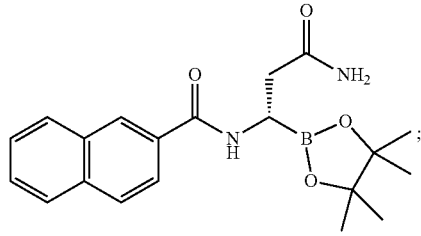
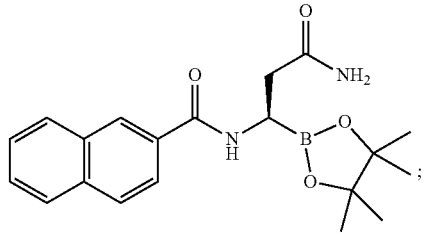
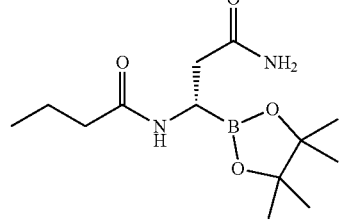
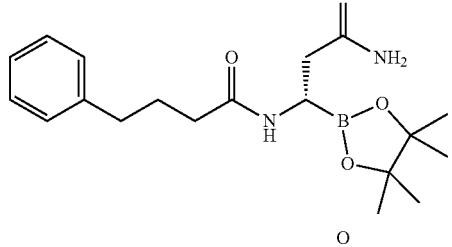
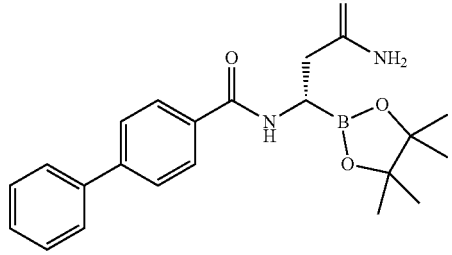
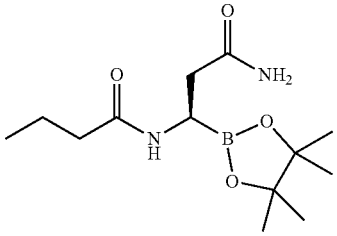

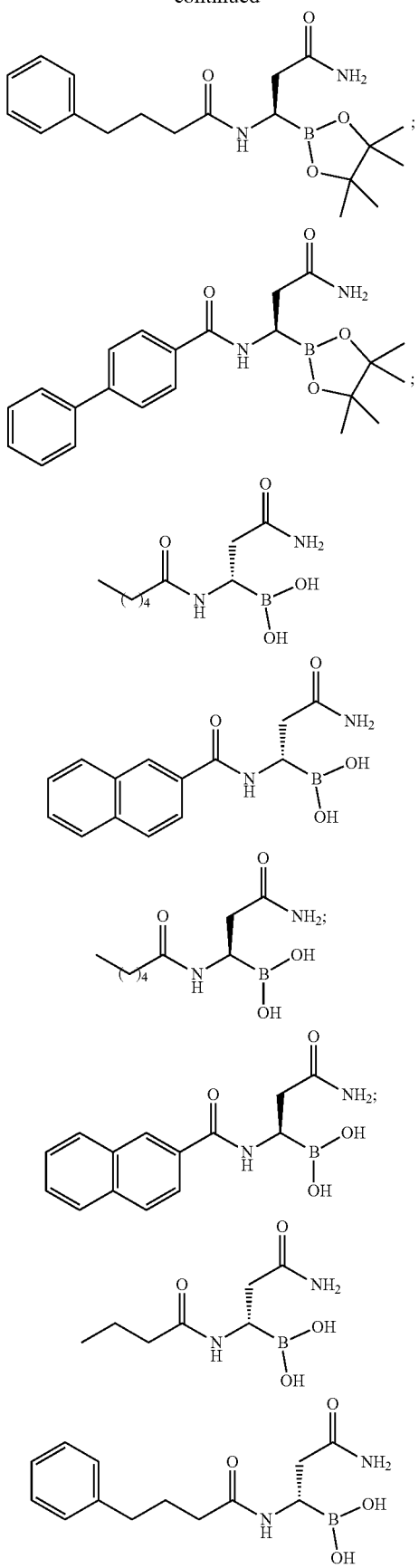

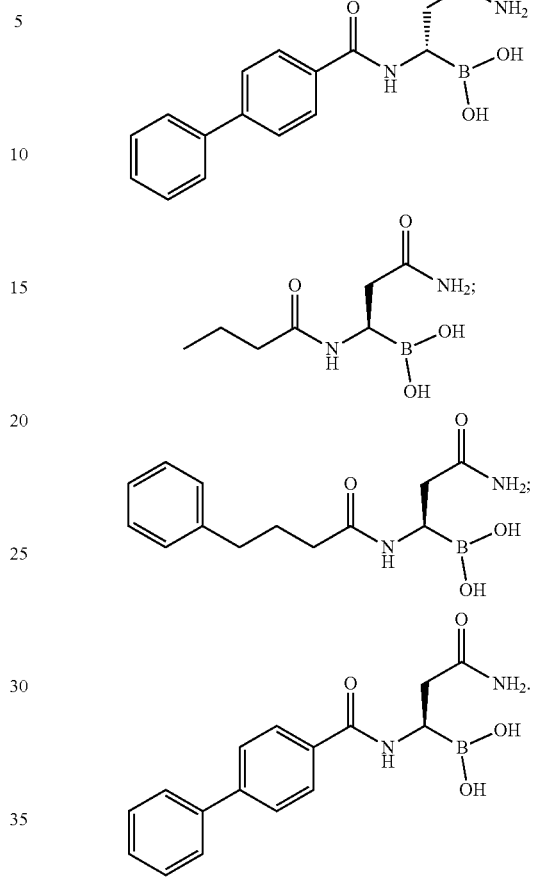

16. The method of any of the preceding paragraphs, wherein contacting comprises administering the ClbP inhibitor to a subject.

17. The method of paragraph 16, wherein the subject has a population and/or infection of pks+ bacteria.

18. The method of paragraph 17, wherein the bacteria is a Proteobacteria, e.g., *Citrobacter, Klebsiella, Eshcerichia*, or *E. coli*.

19. The method of any of the preceding paragraphs, whereby the level of genotoxin in a sample or subject is reduced and/or the production of genotoxin in a sample or subject is inhibited.

20. The method of paragraph 19, wherein the genotoxin is colibactin.

21. The method of any of the preceding paragraphs, whereby the risk and/or progression of cancer in subject is reduced or inhibited.

22. The method of paragraph 21, wherein the cancer is colorectal cancer, a urinary tract cancer, a squamous cell carcinoma, an oral squamous cell carcinoma, or a head-and-neck cancer.

23. A method of treating a pks+ bacterial infection or treating cancer in a subject in need thereof, the method comprising administering to the subject one or more ClbP inhibitors having the structure of:

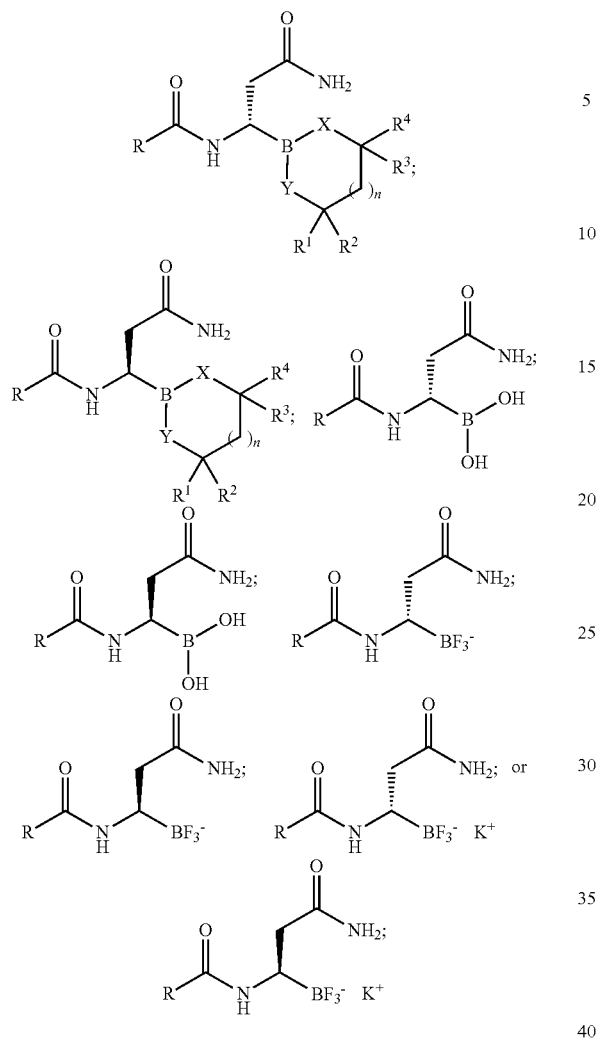

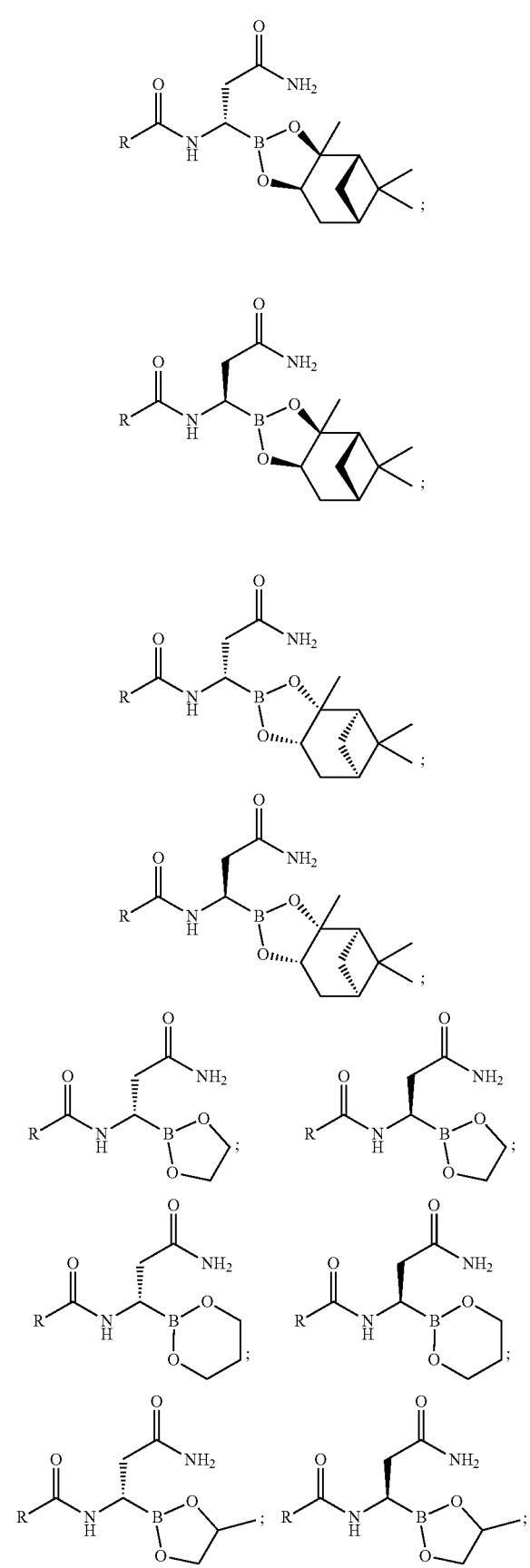

wherein R is selected from the group consisting of H, OH, alkyl, alkenyl, alkynyl, aryl, heteroaryl, cycloalkyl, or heterocycle;

$R^1$, $R^2$, $R^3$ and $R^4$ independently are H, alkyl, alkenyl, alkynyl, aryl, heteroaryl, cycloalkyl or heterocycle, or $R^2$ and $R^3$, together with the carbons they are attached to, form an aryl, heteroaryl, cycloalkyl or heterocycle;

X and Y independently are O, S or NH, and n is 0, or 1.

24. The method of paragraph 23, wherein three of $R^1$, $R^2$, $R^3$ and $R^4$ are H and the other is methyl.

25. The method of paragraph 23, wherein $R^2$ and $R^3$, together with the carbon atoms they are attached to, form 2,3,4-trihydroxytetrahydropyran.

26. The method of paragraph 23, wherein n is 0, $R^1$ is methyl, $R^4$ is H, and $R^2$ and $R^3$, together with the carbon atoms they are attached to, form a 6,6-dimethylbicycle[3.1.1]heptane.

27. The method of paragraph 23, wherein n is 0, $R^1$ and $R^4$ are H, and $R^2$ and $R^3$, together with the carbon atoms they are attached to, form a benzene ring.

28. The method of any of paragraphs 23-27, wherein the ClbP inhibitor has the structure of:

-continued

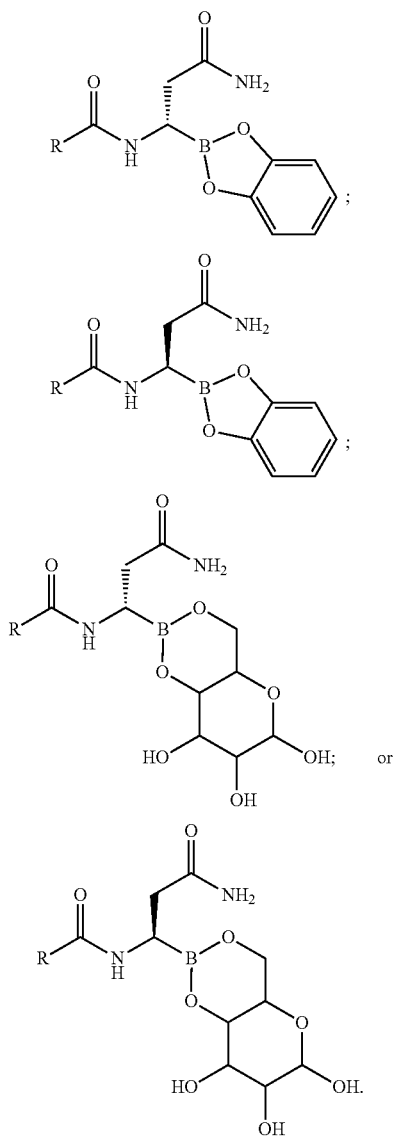

29. The method of any of paragraphs 23-28, wherein the ClbP inhibitor has the structure of:

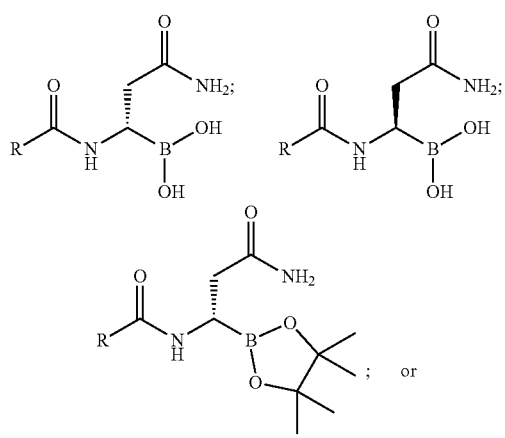

-continued

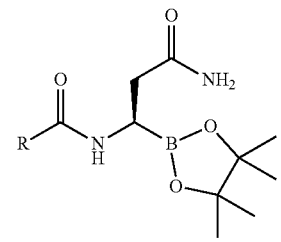

wherein R is, selected from the group consisting of H, OH, alkyl, alkenyl, alkynyl, aryl, heteroaryl, cycloalkyl, or heterocycle;

wherein the alkyl, alkenyl, alkynyl, or cycloalkyl, whether alone or as part of a substituent group, is optionally substituted with one or more substituents independently selected from the group consisting of halogen, —OH, alkyl, O-alkyl, —NR$^A$R$^B$, —S-alkyl, —SO-alkyl, —SO$_2$— alkyl, alkenyl, alkynyl, aryl, heteroaryl, cycloalkyl or heterocycle; and the alkenyl, alkynyl, or optionally includes —O—, —S—, —SO$_2$—, —N(R$^C$)— substituting one or more carbons in the carbon chain, wherein the aryl or heteroaryl, whether alone or as part of a substituent group, is optionally substituted with one or more substituents independently selected from the group consisting of halogen, OH, alkyl, O-alkyl, —NR$^D$R$^E$, —S-alkyl, —SO-alkyl and —SO$_2$-alkyl, alkenyl, alkynyl, aryl, heteroaryl, cycloalkyl or heterocycle;

wherein R$^A$, R$^B$, R$^C$, R$^D$, and R$^E$, are each independently selected from hydrogen and C$_{1-4}$ alkyl.

30. The method of any of paragraphs 23-29, wherein R is alkyl or aryl.

31. The method of any of paragraphs 23-30, wherein R is not a phenyl group.

32. The method of any of paragraphs 23-31, wherein R is selected from the group consisting of:

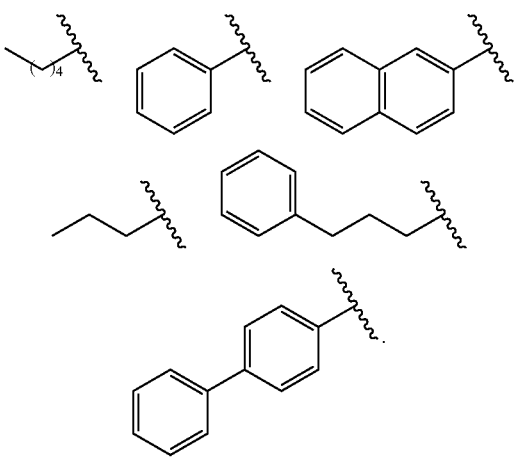

33. The method of any of paragraphs 23-32, wherein the ClbP inhibitor does not have the following structure:

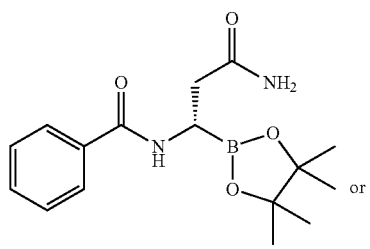
or
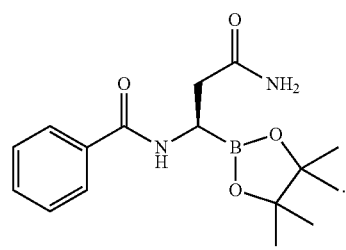
34. The method of any of paragraphs 23-33, wherein the ClbP inhibitor comprises a D-asparagine group and not an L-asparagine group.
35. The method of any of paragraphs 23-34, wherein R is hydrophobic.
36. The method of any of paragraphs 23-35, wherein the ClbP inhibitor has a structure selected from the following:
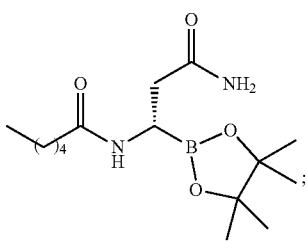
Hexanoyl-pinacolboro-Asn
(MRV03-037)
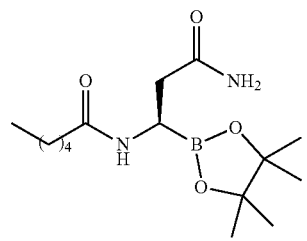
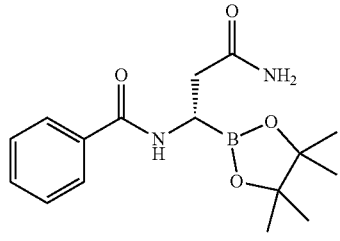
-continued
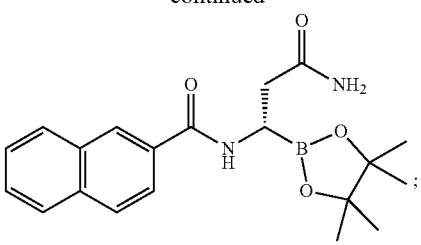
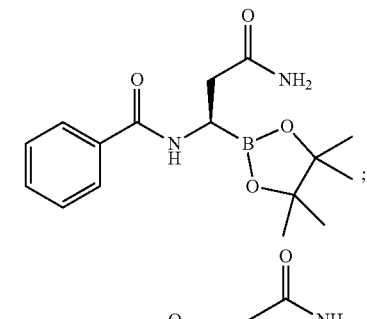
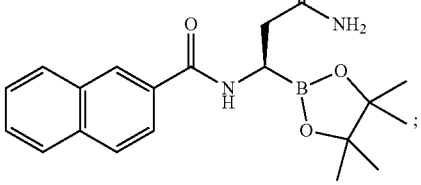
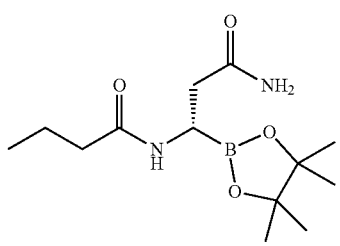
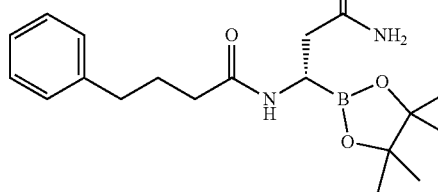
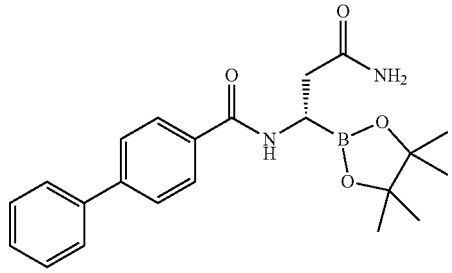
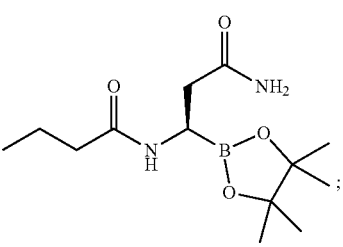

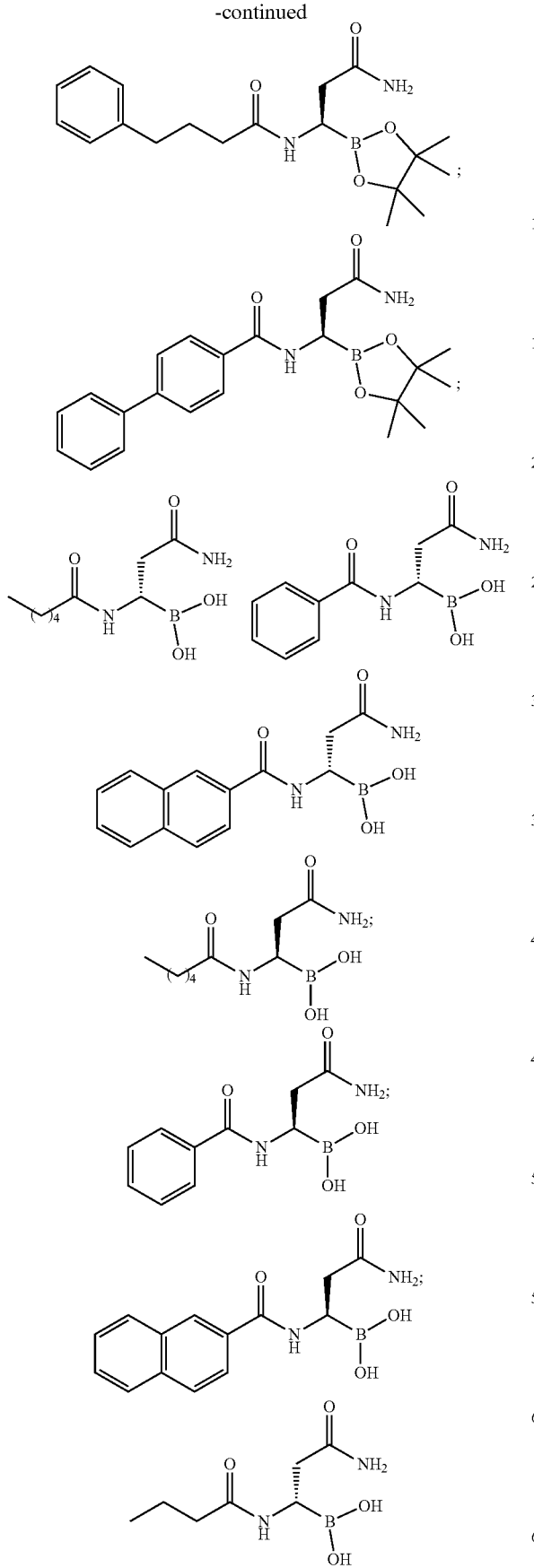
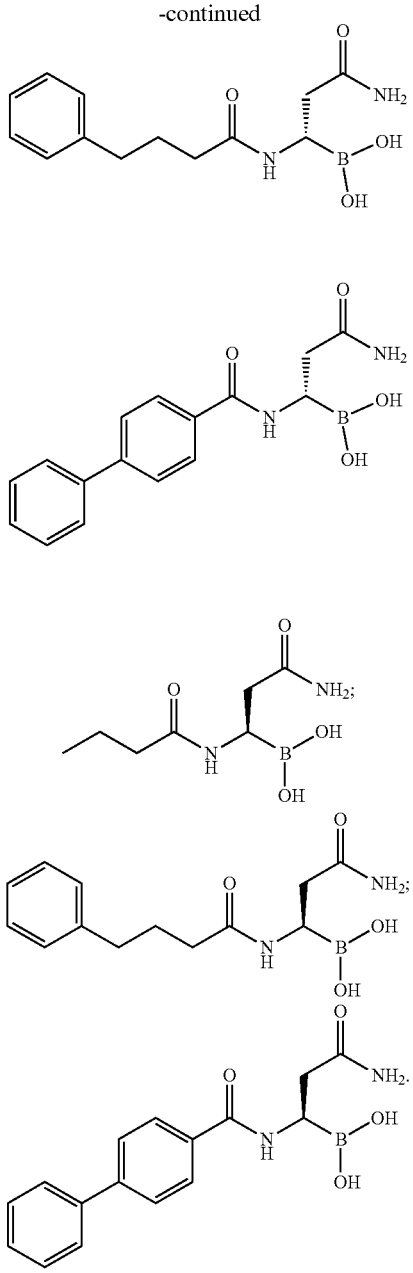
37. The method of any of paragraphs 23-36, wherein the ClbP inhibitor has a structure selected from the following:
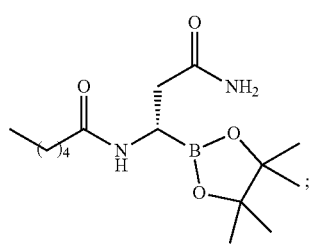
Hexanoyl-pinacolboro-Asn
(MRV03-037)

137
-continued
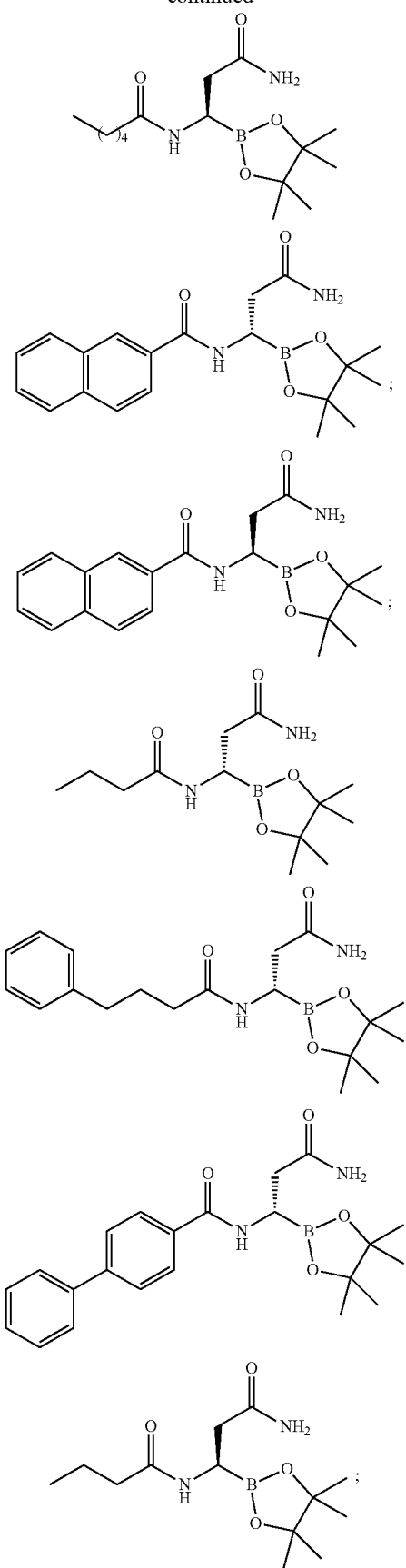
138
-continued
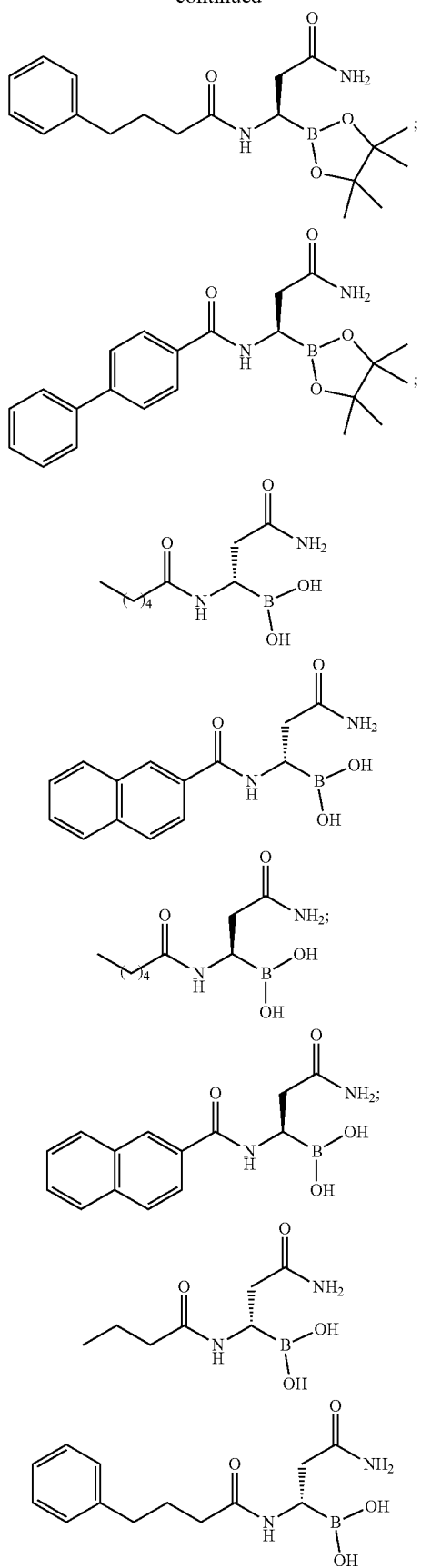

-continued

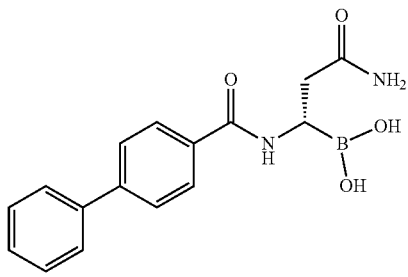

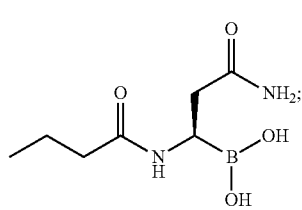

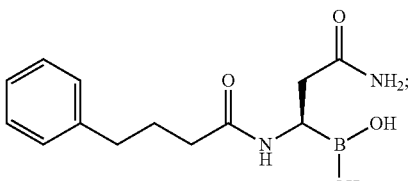

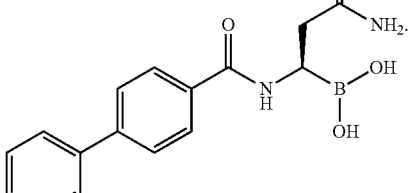

38. The method of any of paragraphs 23-37, wherein the subject has a population and/or infection of pks+ bacteria.

39. The method of paragraph 38, wherein the bacteria is a Proteobacteria, e.g., *Citrobacter, Klebsiella, Eshcerichia*, or *E. coli*.

40. The method of any of paragraphs 23-39, whereby the level of genotoxin in a sample or subject is reduced and/or the production of genotoxin in a sample or subject is inhibited.

41. The method of paragraph 40, wherein the genotoxin is colibactin.

42. The method of any of paragraphs 23-41, whereby the risk and/or progression of cancer in subject is reduced or inhibited.

43. The method of paragraph 42, wherein the cancer is colorectal cancer, a urinary tract cancer, a squamous cell carcinoma, an oral squamous cell carcinoma, or a head-and-neck cancer.

44. A ClbP inhibitor for use in a method of inhibiting ClbP or treating a pks+ bacterial infection or treating cancer in a subject in need thereof, the ClbP inhibitor having the structure of:

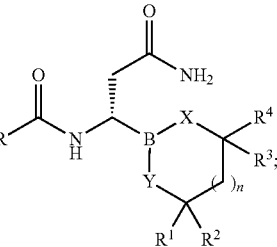

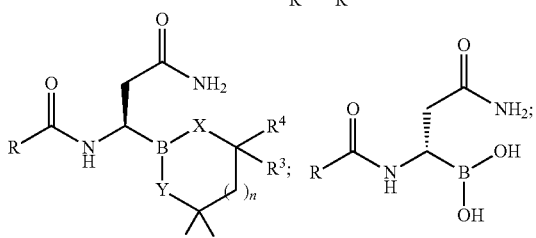

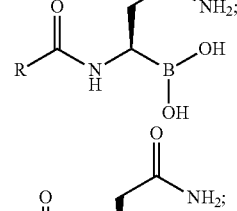

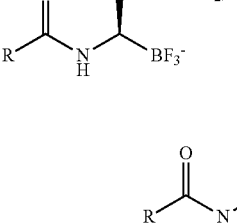

wherein R is selected from the group consisting of H, OH, alkyl, alkenyl, alkynyl, aryl, heteroaryl, cycloalkyl, or heterocycle;

$R^1$, $R^2$, $R^3$ and $R^4$ independently are H, alkyl, alkenyl, alkynyl, aryl, heteroaryl, cycloalkyl or heterocycle, or $R^2$ and $R^3$, together with the carbons they are attached to, form an aryl, heteroaryl, cycloalkyl or heterocycle;

X and Y independently are O, S or NH, and n is 0, or 1; or

45. The ClbP inhibitor of paragraph 44, wherein three of $R^1$, $R^2$, $R^3$ and $R^4$ are H and the other is methyl.

46. The ClbP inhibitor of paragraph 44, wherein $R^2$ and $R^3$, together with the carbon atoms they are attached to, form 2,3,4-trihydroxytetrahydropyran.

47. The ClbP inhibitor of paragraph 44, wherein n is 0, $R^1$ is methyl, $R^4$ is H, and $R^2$ and $R^3$, together with the carbon atoms they are attached to, form a 6,6-dimethylbicycle[3.1.1]heptane.

48. The ClbP inhibitor of paragraph 44, wherein n is 0, $R^1$ and $R^4$ are H, and $R^2$ and $R^3$, together with the carbon atoms they are attached to, form a benzene ring.

49. The ClbP inhibitor of any of paragraphs 44-48, wherein the ClbP inhibitor has the structure of:

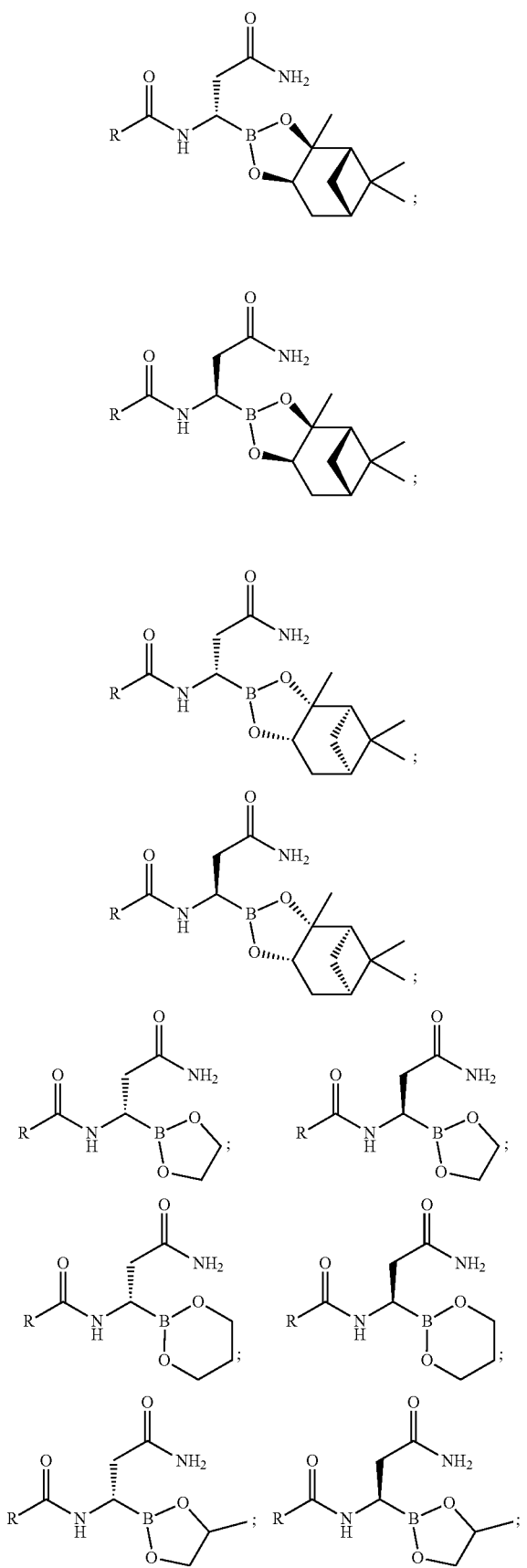
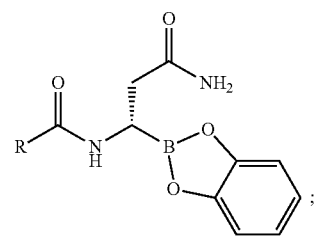
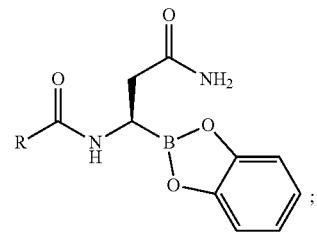
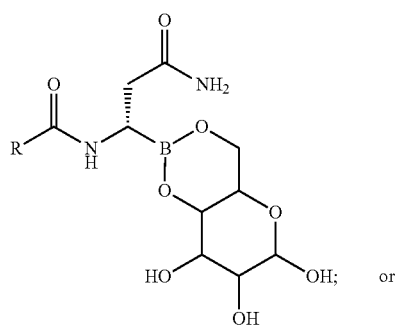
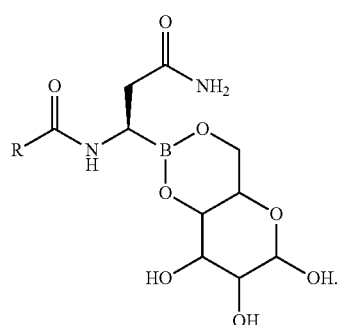
50. The ClbP inhibitor of any of paragraphs 44-49, wherein the ClbP inhibitor has the structure of:
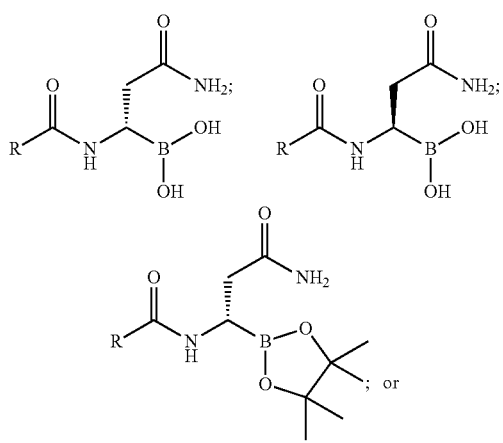

-continued

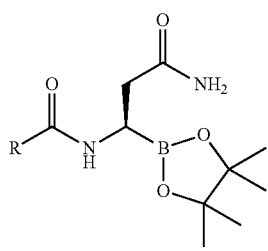

wherein R is, selected from the group consisting of H, OH, alkyl, alkenyl, alkynyl, aryl, heteroaryl, cycloalkyl, or heterocycle;

wherein the alkyl, alkenyl, alkynyl, or cycloalkyl, whether alone or as part of a substituent group, is optionally substituted with one or more substituents independently selected from the group consisting of halogen, —OH, alkyl, O-alkyl, —NR$^A$R$^B$, —S-alkyl, —SO-alkyl, —SO$_2$— alkyl, alkenyl, alkynyl, aryl, heteroaryl, cycloalkyl or heterocycle; and the alkenyl, alkynyl, or optionally includes —O—, —S—, —SO$_2$—, —N(R$^C$)— substituting one or more carbons in the carbon chain, wherein the aryl or heteroaryl, whether alone or as part of a substituent group, is optionally substituted with one or more substituents independently selected from the group consisting of halogen, OH, alkyl, O-alkyl, —NR$^D$R$^E$, —S-alkyl, —SO-alkyl and —SO$_2$-alkyl, alkenyl, alkynyl, aryl, heteroaryl, cycloalkyl or heterocycle;

wherein R$^A$, R$^B$, R$^C$, R$^D$, and R$^E$, are each independently selected from hydrogen and C$_{1-4}$ alkyl.

51. The ClbP inhibitor of any of paragraphs 44-50, wherein R is alkyl or aryl.

52. The ClbP inhibitor of any of paragraphs 44-51, wherein R is not a phenyl group.

53. The ClbP inhibitor of any of paragraphs 44-52, wherein R is selected from the group consisting of:

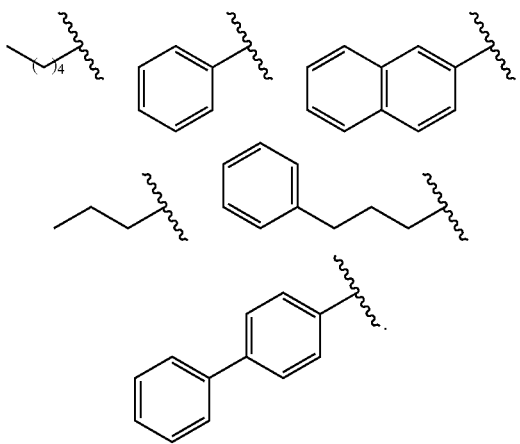

54. The ClbP inhibitor of any of paragraphs 44-53, wherein the ClbP inhibitor does not have the following structure:

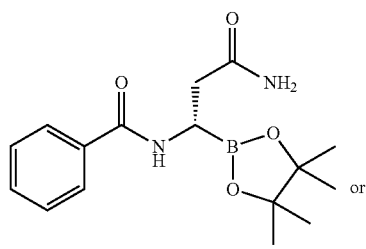

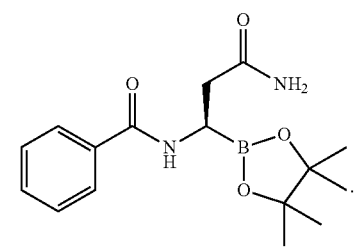 [SMILES: CC1(C)OB([C@@H](CC(N)=O)NC(=O)c2ccccc2)OC1(C)C]

55. The ClbP inhibitor of any of paragraphs 44-54, wherein the ClbP inhibitor comprises a D-asparagine group and not an L-asparagine group.

56. The ClbP inhibitor of any of paragraphs 44-55, wherein R is hydrophobic.

57. The ClbP inhibitor of any of paragraphs 44-56, wherein the ClbP inhibitor has a structure selected from the following:

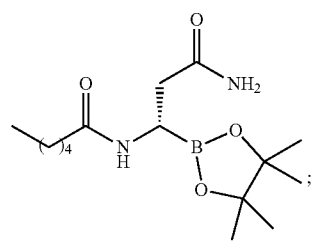

Hexanoyl-pinacolboro-Asn
(MRV03-037)

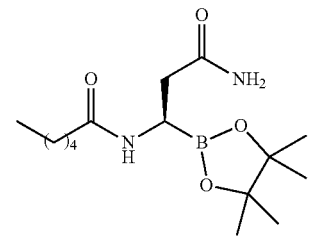

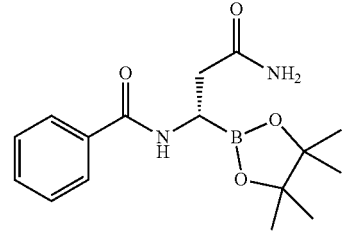

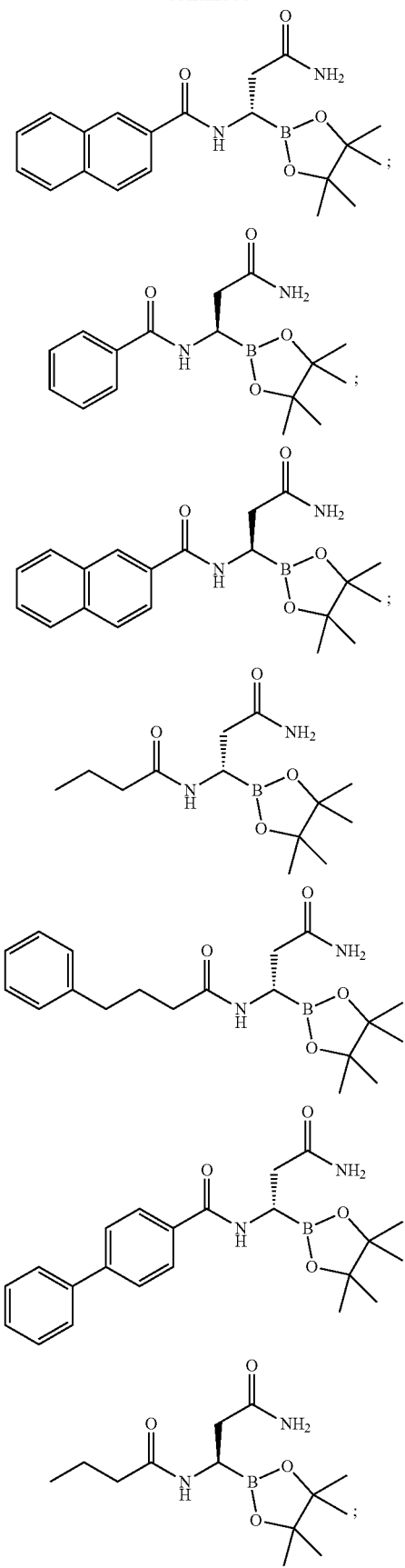
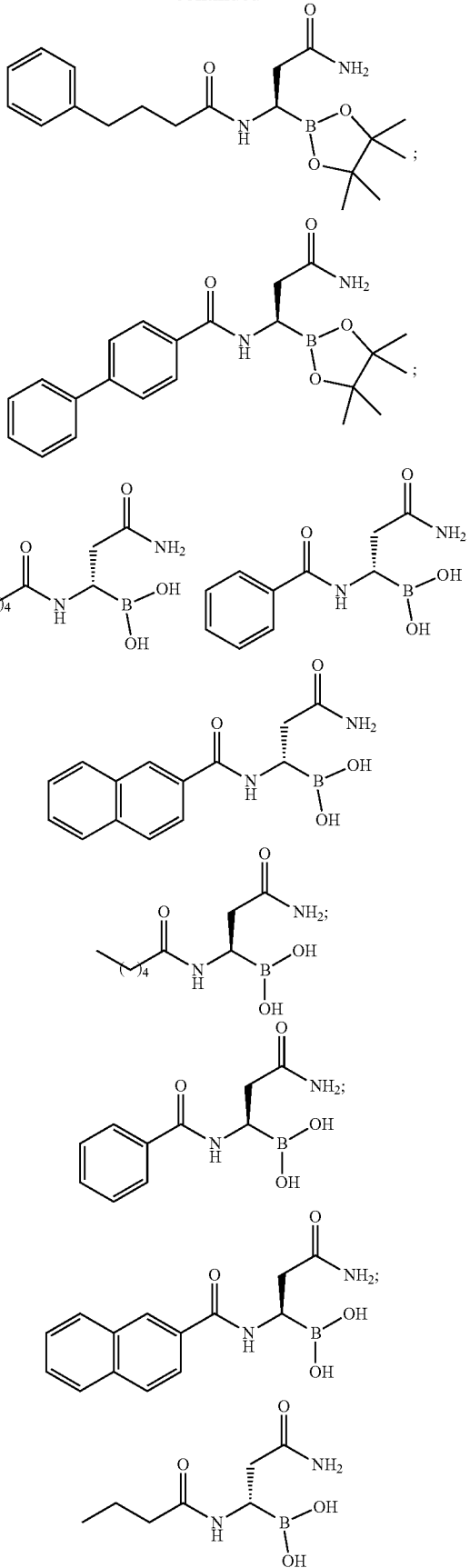

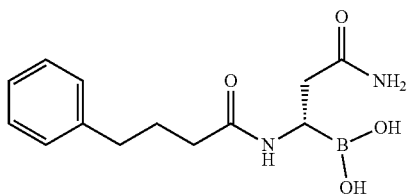
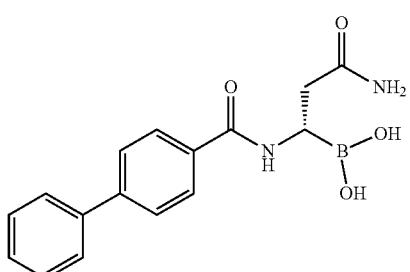
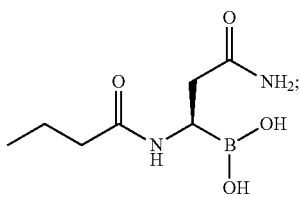
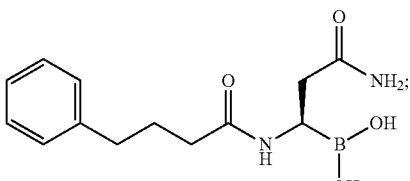
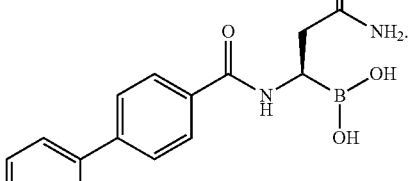
58. The ClbP inhibitor of any of paragraphs 44-57, wherein the ClbP inhibitor has a structure selected from the following:
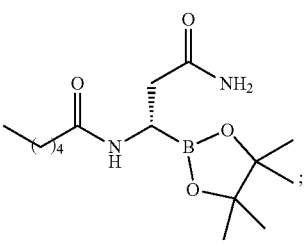
Hexanoyl-pinacolboro-Asn
(MRV03-037)
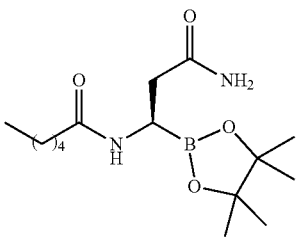
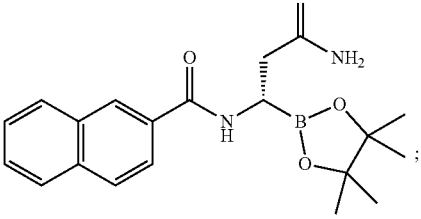
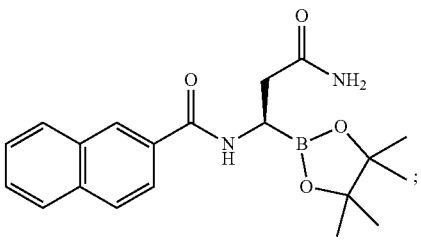
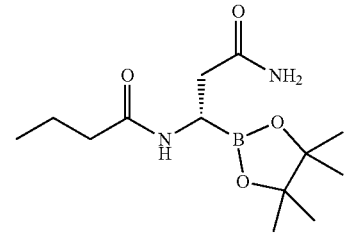
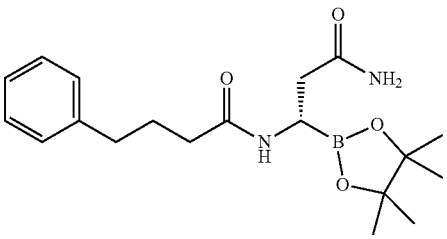
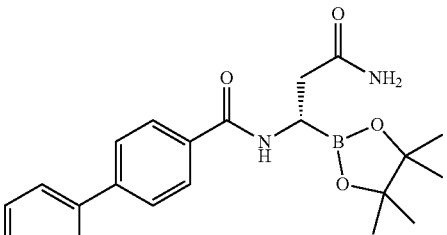
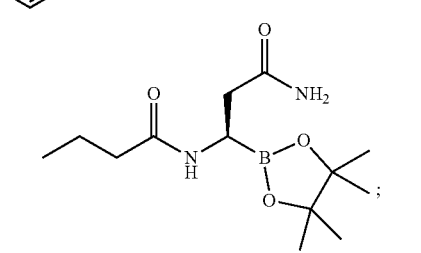

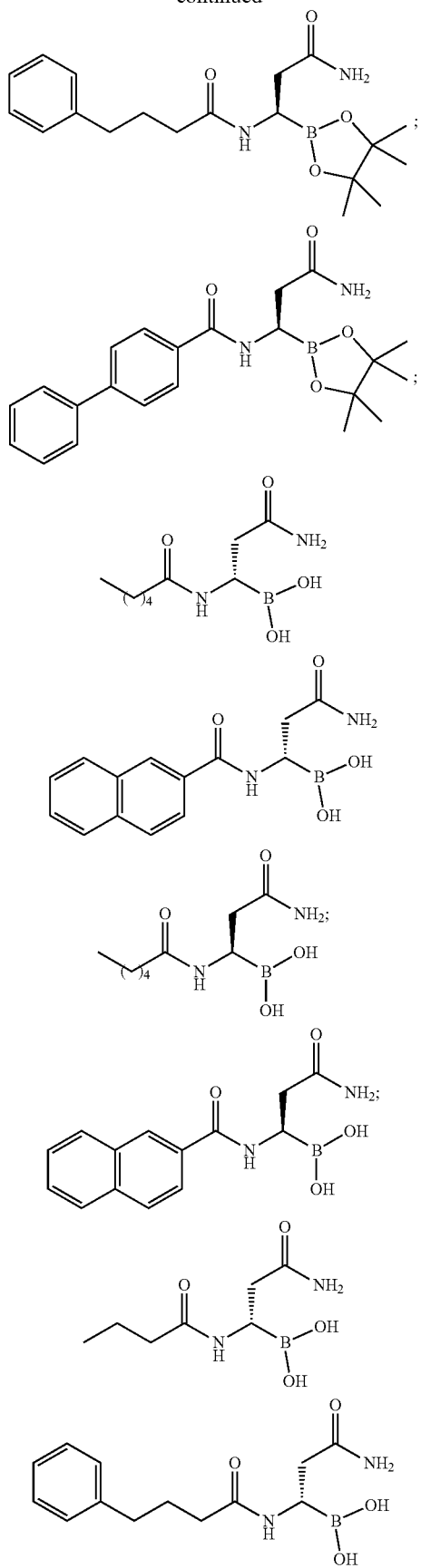

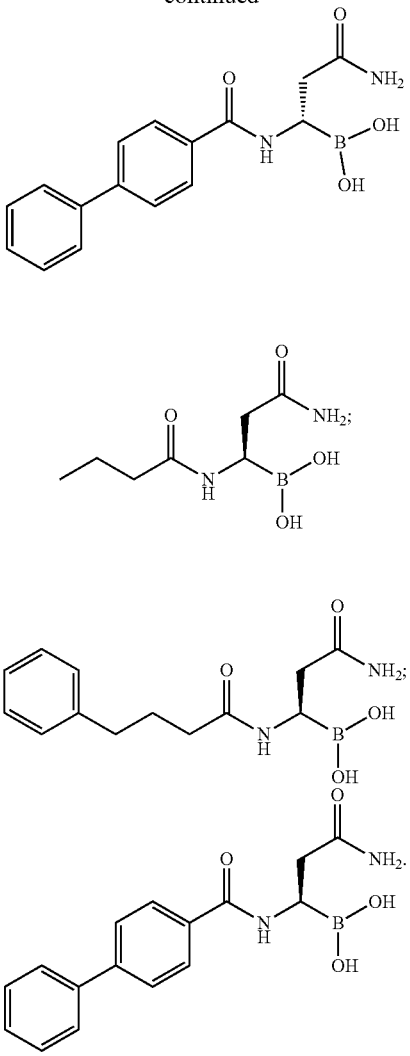

59. The ClbP inhibitor of any of paragraphs 44-58, wherein the subject has a population and/or infection of pks+ bacteria.

60. The ClbP inhibitor of paragraph 59, wherein the bacteria is a Proteobacteria, e.g., *Citrobacter, Klebsiella, Eshcerichia*, or *E. coli*.

61. The ClbP inhibitor of any of paragraphs 44-60, whereby the level of genotoxin in a sample or subject is reduced and/or the production of genotoxin in a sample or subject is inhibited.

62. The ClbP inhibitor of paragraph 61, wherein the genotoxin is colibactin.

63. The ClbP inhibitor of any of paragraphs 44-62, whereby the risk and/or progression of cancer in subject is reduced or inhibited.

64. The ClbP inhibitor of paragraph 63, wherein the cancer is colorectal cancer, a urinary tract cancer, a squamous cell carcinoma, an oral squamous cell carcinoma, or a head-and-neck cancer.

The technology described herein is further illustrated by the following examples which in no way should be construed as being further limiting.

EXAMPLES

Example 1—A Small Molecule Inhibitor Prevents Gut Bacterial Genotoxin Production Design of a Selective Inhibitor of Colibactin Biosynthesis The human gut bacterial genotoxin colibactin has emerged as a possible key driver of colorectal cancer (CRC) development. Understanding colibactin's biological effects remains difficult due to the remarkable instability of the proposed active species and the complexity of the gut microbial community. Described herein are small molecule boronic acid inhibitors of colibactin biosynthesis and genotoxicity. Designed to mimic the biosynthetic precursor precolibactin, these compounds potently inhibit the colibactin-activating peptidase ClbP. Using biochemical assays and crystallography, it is demonstrated that they tightly engage the ClbP binding pocket, forming a covalent bond with the catalytic serine. These highly selective inhibitors reproduce the phenotypes observed in a clbP deletion mutant. Finally, they block the genotoxic effects of colibactin on eukaryotic cells without toxicity to bacteria or human cell lines. The availability of potent, selective colibactin biosynthesis inhibitors permits precise, temporal control over this pathway, enabling the study of its role in CRC carcinogenesis.

The trillions of commensal and pathogenic microorganisms which colonize the human gut, collectively termed the gut microbiota, secrete a diverse milieu of small molecules with profound impacts on human health. In particular, several members of this community have been proposed to play roles in the development of colorectal cancer (CRC) through the production of toxic small molecules and proteins, or other unknown mechanisms. While possible microbial culprits have been identified and associated with CRC, we still have limited knowledge of the molecular mechanisms underlying the contributions of these organisms to carcinogenesis because of the inherent challenges of studying a complex and dynamic microbial community.

These challenges are exemplified by recent efforts to characterize the genotoxic gut bacterial natural product colibactin. Colibactin is produced by a non-ribosomal peptide synthetase-polyketide synthase (NRPS-PKS) assembly line encoded on the pks genomic island, which is carried by many strains of $E.\ coli$ (pks$^+$ $E.\ coli$) and other Proteobacteria. While it was initially observed over a decade ago that pks$^+$ $E.\ coli$ elicit a genotoxic phenotype and cause DNA double-strand breaks in cultured epithelial cells, the chemical species responsible for these effects could not be readily identified. Based on extensive metabolomics experiments, characterization of the biosynthetic enzymes, and total synthesis, potential structures of colibactin have been proposed, though it has not been isolated from a natural source. The proposed structure that is most consistent with colibactin's biological effects contains two highly electrophilic cyclopropane warheads linked by a 1,2-diketone; the sensitivity of this linkage to oxidative C—C bond cleavage may explain the difficulty of isolation. Formation of the warheads is accomplished in the final step of biosynthesis by the periplasmic peptidase ClbP, which hydrolyzes two units of the N-myristoyl-D-asparagine 'prodrug motif' from a larger precursor precolibactin. This reaction releases the active species, which alkylates two adenine residues on opposite strands of the target cell's DNA, resulting in highly toxic and mutagenic DNA interstrand crosslinks. These crosslinks are unstable and break down into mono-adducts which can be detected by mass spectrometry in both in vitro reaction conditions and DNA extracted from epithelial tissue of mice infected with pks$^+$ $E.\ coli$.

Multiple lines of evidence have indicated colibactin-mediated DNA damage plays a role in CRC development. Studies of human cohorts have found that pks$^+$ $E.\ coli$ are found more frequently in patients with CRC relative to healthy controls. In addition, colonization with pks$^+$ $E.\ coli$ increased tumor loads in multiple gnotobiotic mouse models of colitis-associated colorectal cancer. Perhaps most notably, recent work identified a pks-dependent mutational signature in a colonic epithelial cell-derived organoid model and detected the same signatures in sequenced human cancer genomes, indicating a possible genetic basis for colibactin's carcinogenic potential.

While these studies have illuminated a great deal about colibactin's possible carcinogenic activity, they have also revealed that this natural product and its biosynthetic enzymes are part of a complex network of interactions in the gut microbiota which cannot be untangled with current tools. In addition to genotoxin synthesis, the colibactin biosynthetic enzymes have been linked to siderophore biosynthesis and microcin production. The intermediates produced by these enzymes en route to colibactin, as well as a number of alternative products of the pathway have been shown to possess distinct bioactivities of their own, complicating the interpretation of experiments performed with deletion mutants. The observation that the genotoxic effects of colibactin are cell-contact and inflammation-dependent have made it especially challenging to distinguish the effects of this toxin from other changes in the gut microbiota and host metabolism. Moreover, while it has been suggested that colibactin could work cooperatively with other disease-associated microorganisms, little work has been done to investigate possible mechanisms. Finding answers to these questions requires examining colibactin's effects in the context of a complex gut community. The use of genetically modified organisms in this context is often limited by colonization resistance, imprecise control of the pathway of interest, and may result in changes to other bacterial cellular functions that rely on the same genes. Direct addition of colibactin could offer very precise control over exposure but is currently impossible due to its instability and unresolved identity. A tool compound which can specifically modulate the colibactin biosynthetic machinery can shed light on these questions by enabling studies of colibactin in complex pks$^+$ communities with far greater precision than is currently possible.

To address this need, the inventors designed and characterized of a series of boronic acid-based inhibitors of colibactin biosynthesis. These inhibitors directly engage the colibactin-activating peptidase ClbP and show a high degree of selectivity over other human and bacterial proteases. It is demonstrated that chemical inhibition of ClbP using these compounds modulates colibactin production in pks+$E.\ coli$ and pks$^+$ communities. Finally, it is confirmed that these inhibitors can completely block the genotoxic effects of colibactin on mammalian cells in culture. By establishing precise control over colibactin production, these inhibitors present a unique opportunity to study the effects of colibactin in complex microbial communities and explore the therapeutic strategy of blocking colibactin production.

Results

To design a specific inhibitor of colibactin biosynthesis, the inventors targeted the colibactin-activating enzyme ClbP. This membrane-anchored periplasmic serine peptidase is essential for the genotoxicity of pks$^+$ $E.\ coli$. Genetic deletion of ClbP results in an accumulation of biosynthetic intermediates and shunt metabolites from the NRPS-PKS assembly line, termed "candidate precolibactins," many of which have been structurally characterized. This enzyme is an attractive target for chemical inhibition as it is homologous to the AmpC β-lactamase (30% amino acid identity), which has already been successfully targeted with small molecule inhibitors. However, based on in vitro studies with ClbP, this enzyme is not inhibited by several known β-lactamase inhibitors or broad-spectrum serine hydrolase inhibitors. While one previous study reported a pair of boronic acid-based ClbP inhibitors identified using an in silico screening approach, the inventors found that these compounds have only minimal effect on ClbP's catalytic activity in vitro or in bacterial culture, even at millimolar concentrations. Thus, there are currently no potent and selective inhibitors of this enzyme available.

Synthesis and In Vitro Evaluation of Putative ClbP Inhibitors

Figure 1B:
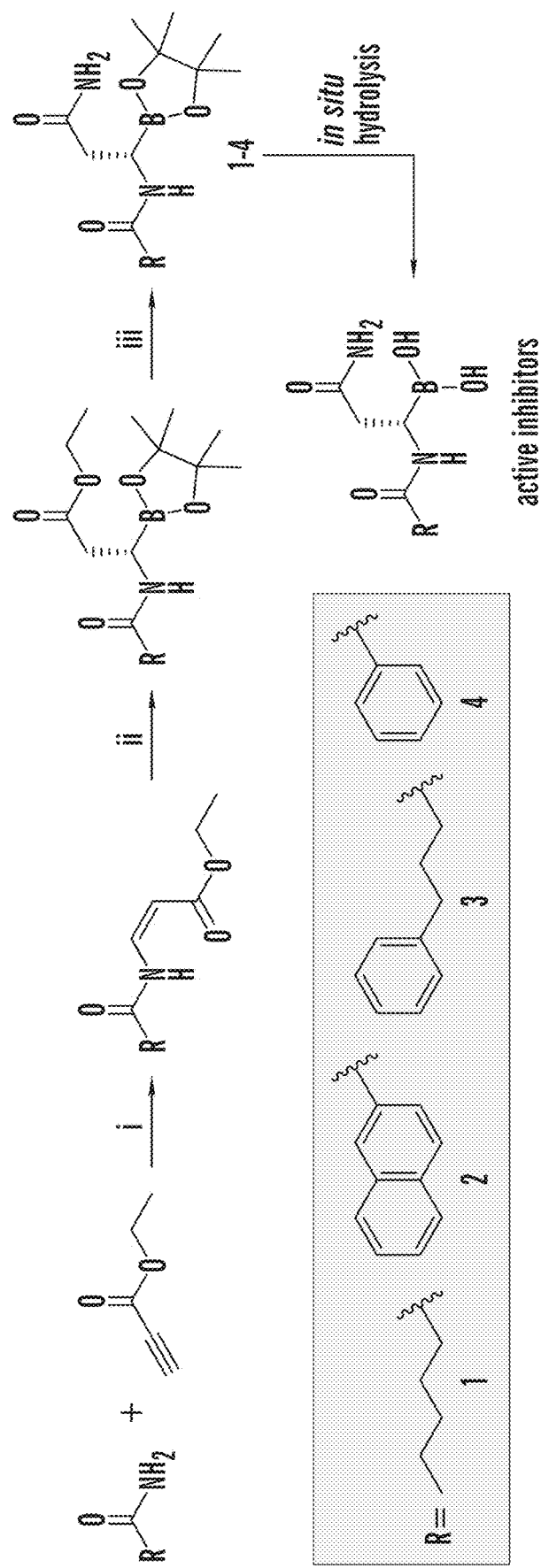
Figure 9A:
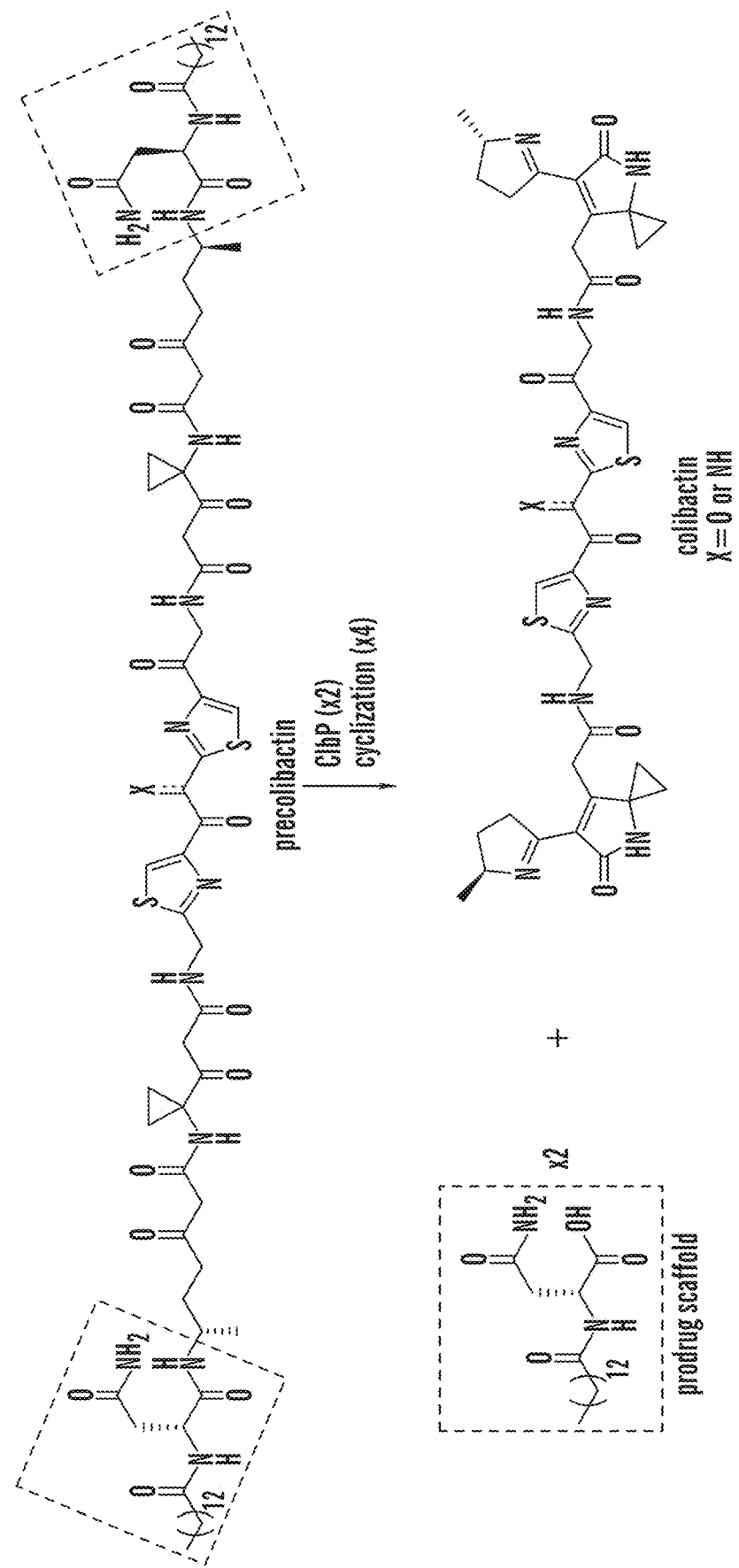
FIGS. 9A-9B demonstrate that the activity of ClbP guides rational design of a colibactin biosynthesis inhibitor.
Figure 9B:
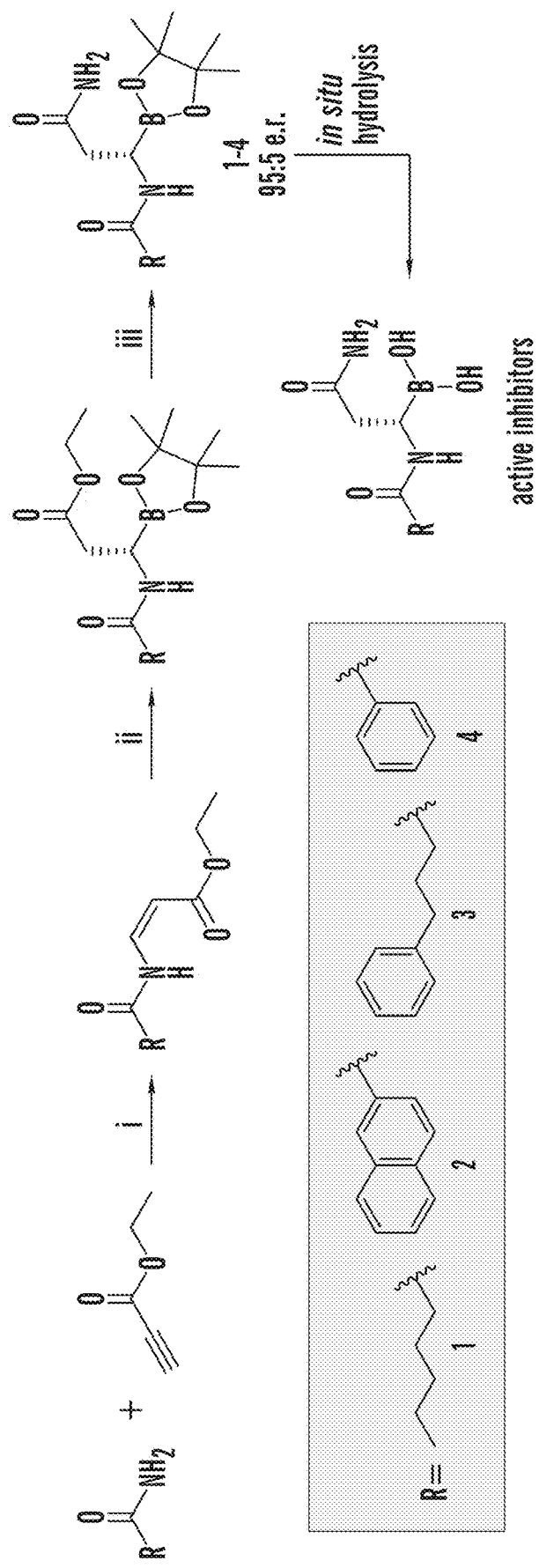

Previous work has shown that ClbP contains a catalytic triad typical of the S12 family of serine peptidases formed by the essential residues S95, K98 and Y186. The inventors targeted S95 by exploiting ClbP's essential and unusual acyl-D-Asn substrate-recognition motif (FIG. 1A, 9A). Installing a boron electrophile only a few atoms away from the heteroatom-rich asparagine side chain posed a synthetic challenge. A small panel of potential pinacol boronate esters (1-4), which are precursors of the corresponding boronic acids, using a stereoselective copper-catalyzed hydroboration reaction of an ester intermediate followed by ammonolysis to install the side chain amide was utilized (FIG. 1B, 9B).

Figure 2D:
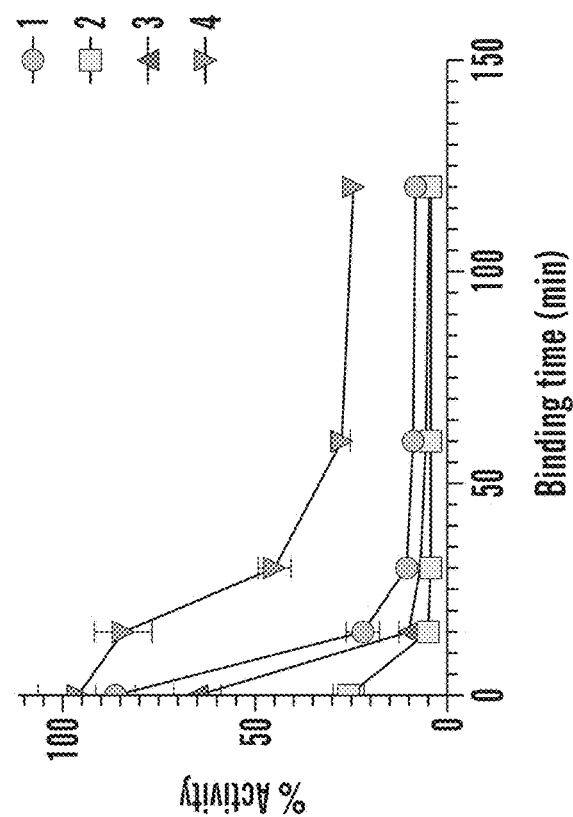
Figure 2C:
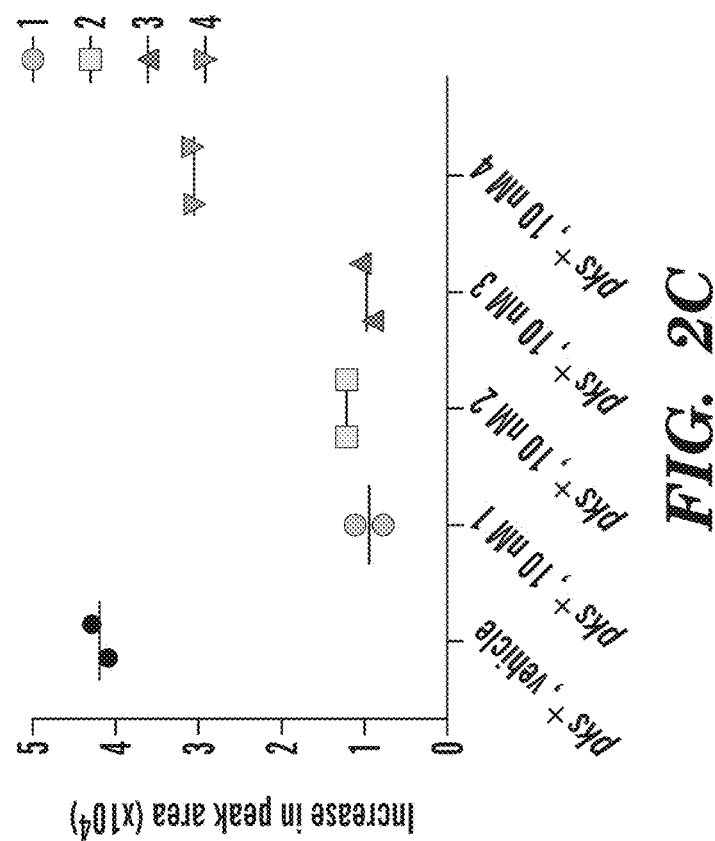
Figure 10B:
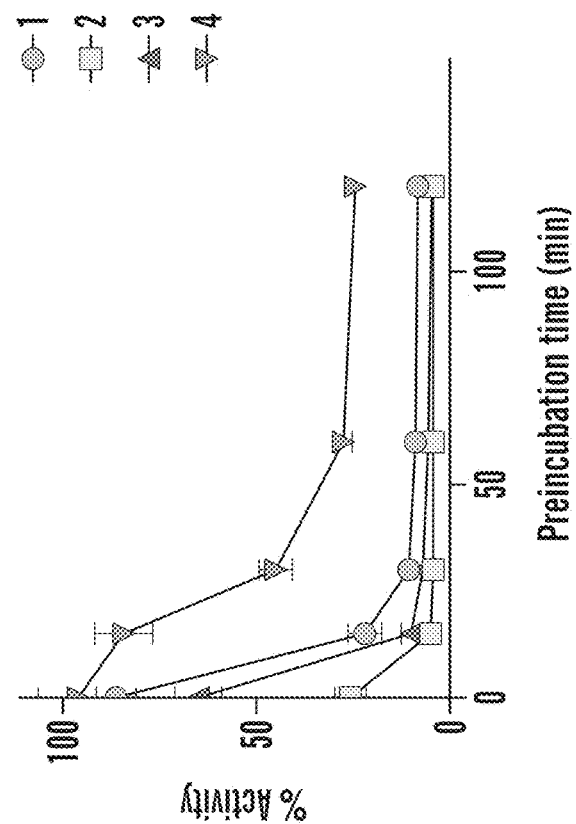
FIGS. 10A-10D demonstrate that compounds 1-4 inhibit ClbP activity.
Figure 10A:
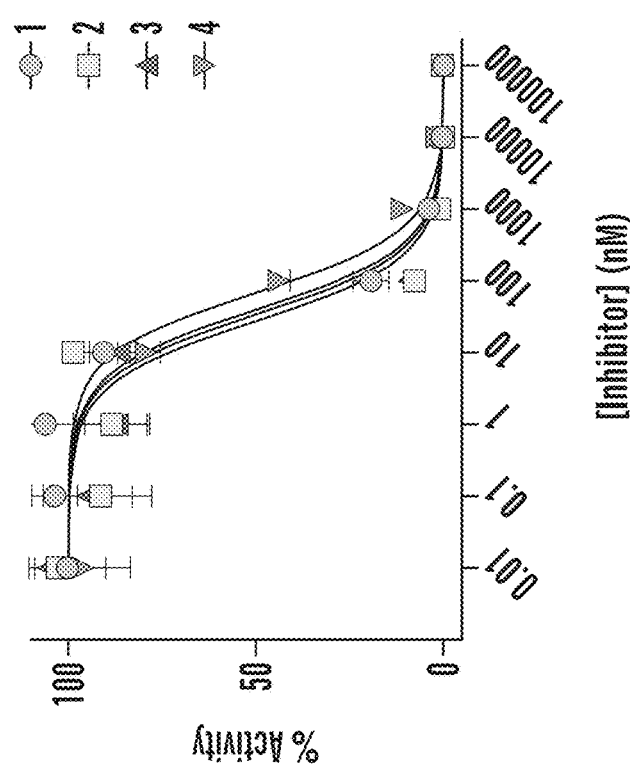
Figure 10D:
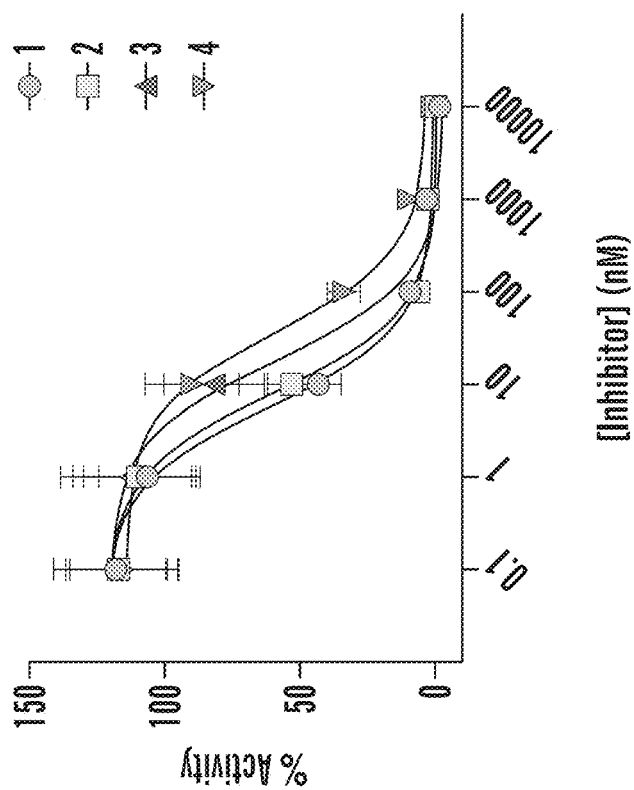
Figure 10C:
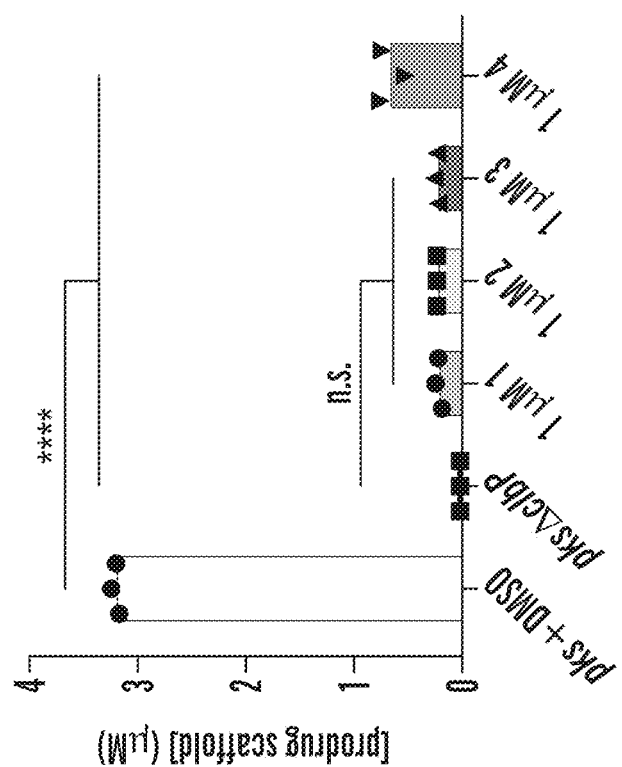

Initial tests of these compounds in a fluorescent activity assay with 25 nM purified ClbP showed promise, with $IC_{50}$ values for these compounds of 20-80 nM (FIG. 2A, 10A). Using E. coli overexpressing ClbP and the same fluorescent reporter as a readout yielded $IC_{50}$ values in the range of 4-40 nM, indicating that the E. coli outer membrane is not a significant barrier for these compounds (FIG. 2B, 10B). To confirm that these inhibitors block the cleavage of precolibactin, pks$^+$ E. coli were treated with 1-4 or a DMSO control and quantified the amount of the myristoyl-D-Asn prodrug motif using mass spectrometry (FIG. 2C, 10C). All compounds decreased the quantity of prodrug released, but compound 4 showed slightly lower potency than the others in this format. Previous work showed that ClbP prefers substrates with larger hydrophobic acyl groups, so the relatively smaller phenyl ring at this position in 4 may explain this difference. It was also confirmed that the inhibitory activity of these compounds is not due to an antibiotic effect on E. coli.

Establishing the Mechanism of ClbP Inhibition

It was hypothesized that these compounds inhibit ClbP by forming a covalent linkage to the critical active site serine residue. This phenomenon was examined using biochemical assays. Typically, boronic acid-based inhibitors exhibit two-step binding kinetics, where the free inhibitor is initially in equilibrium with the non-covalently bound inhibitor-enzyme complex, and subsequent covalent bond formation with the active site serine is slower and rate-limiting. This results in an apparent increase in potency of the inhibitors when incubated with the target for longer periods of time. Pre-incubating compounds 1-4 at 100 nM with ClbP for varying amounts of time confirmed that longer preincubation leads to increased potency (FIG. 2D, 10D). Further control experiments ruled out boronate ester hydrolysis as a possible limiting step in this phenomenon.

Figure 3C:
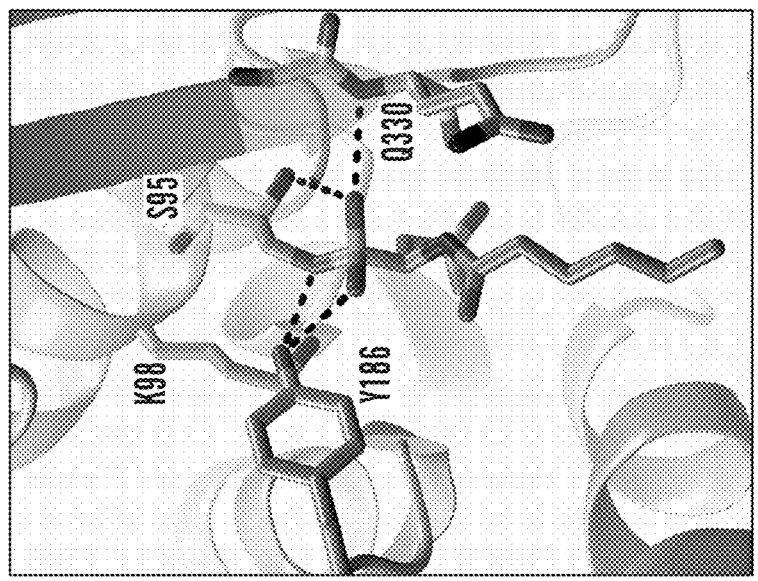
FIGS. 3A-3C depict the crystal structure of 1 bound to ClbP, demonstrating that Compound 1 binds the catalytic serine of ClbP directly.

To examine the interaction between inhibitor and enzyme directly, a crystal structure of ClbP bound to 1 to 2.8 Å resolution was obtained. The D-Asn side chain of the inhibitor projects into a tight-fitting pocket and forms hydrogen bonds with the sidechains of residues S188, H257, and N331 (FIG. 3A). N331 is also engaged in an additional hydrogen bond to E92, enforcing its orientation and helping to explain ClbP's selectivity for D-Asn-over D-Asp-containing substrates. These interactions and the steric occlusions in this pocket help account for ClbP's extremely strong preference for this amino acid side chain and stereochemical configuration. The acyl group of the inhibitor extends along the surface of the protein toward the membrane, suggesting that the longer myristoyl chain of precolibactin may interact directly with ClbP's transmembrane domain. A short helical linker between transmembrane helices 2 and 3 likely plays a key role in these interactions, with W466 projecting toward the periplasmic domain active site. Other studies have shown that this residue, which directly contacts the acyl group of larger substrates, is well conserved across ClbP homologs and that mutations to it cause a defect in catalytic activity.

Figure 3B:
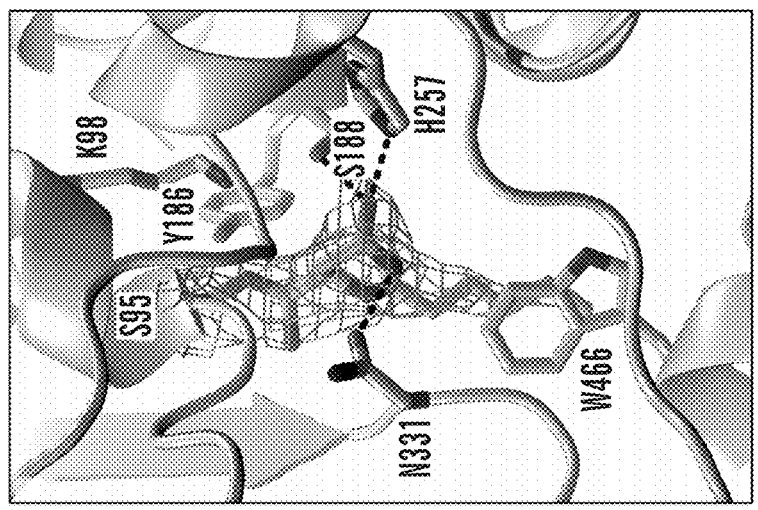
Figure 3A:
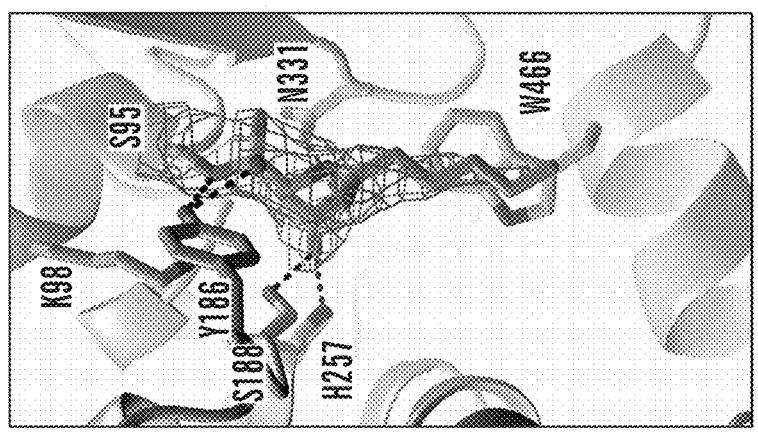

The other key observation from this structure is the continuous electron density from the S95 sidechain to the bound ligand which is clearly evident in 2Fo-Fc composite omit maps contoured to high a levels, indicating a strong covalent bond to the boron atom (FIG. 3B). This structure also supports the hypothesis that the free boronic acid is the active inhibitory species, as opposed to the pinacol ester. The build-up of negative charge on the boron center appears to be stabilized by a hydrogen bond from the backbone amide on Q330. In addition, Y186 is positioned such that it could stabilize either the attacking serine nucleophile or the tetrahedral intermediate via hydrogen bonding from its sidechain (FIG. 3C). These same interactions likely stabilize the native tetrahedral intermediate in the hydrolysis of precolibactin.

Selectivity of ClbP Inhibitors

Having established that this group of compounds can bind ClbP with high potency, their selectivity for ClbP over other enzymes was established other potential off-target effects examined. An activity-based protein profiling (ABPP) approach was used to search broadly for other serine hydrolases inhibited by compounds 1-4. In this gel-based assay, proteins which are bound by the inhibitors can be detected by observing decreased binding to the non-specific fluorophosphonate probe (FP) compound which covalently inhibits a wide variety of serine hydrolases. Applying this assay to both E. coli and HEK293T cell lysates showed no visible changes in protein labeling by FP, even at concentrations of 100 μM 1-4. Thus, none of the proteins which are labeled by FP are effectively bound by these ClbP inhibitors.

To search for core bacterial metabolic functions that might be inhibited by these compounds and further confirm ClbP as their main cellular target, metabolomics was used. An ideal chemical probe should be able to block colibactin biosynthesis while causing minimal disruptions to core metabolic functions of the producing organism, leading to an accumulation of the same biosynthetic intermediates and shunt metabolites that have previously been observed in pks$^+$ΔclbP mutant strains. The metabolites produced by a natural producer of colibactin isolated from laboratory mice, E. coli NC101, treated with 3 were compared to the metabolites produced by an isogenic ΔclbP mutant and analyzed the results using XCMS. The same experiment was also performed using a laboratory strain carrying the pks island on a bacterial artificial chromosome (E. coli BW25113 BACpks). In both cases, treatment of the wild-type strain with 3 resulted in the same changes in metabolites as genetic deletion of clbP—a decrease in the levels of the prodrug scaffold released from these strains, an accumulation of known upstream shunt metabolites from pathway, and minimal perturbation of levels of other metabolites.

Effects of Colibactin on the Gut Community and Mammalian Cells

Figure 4:
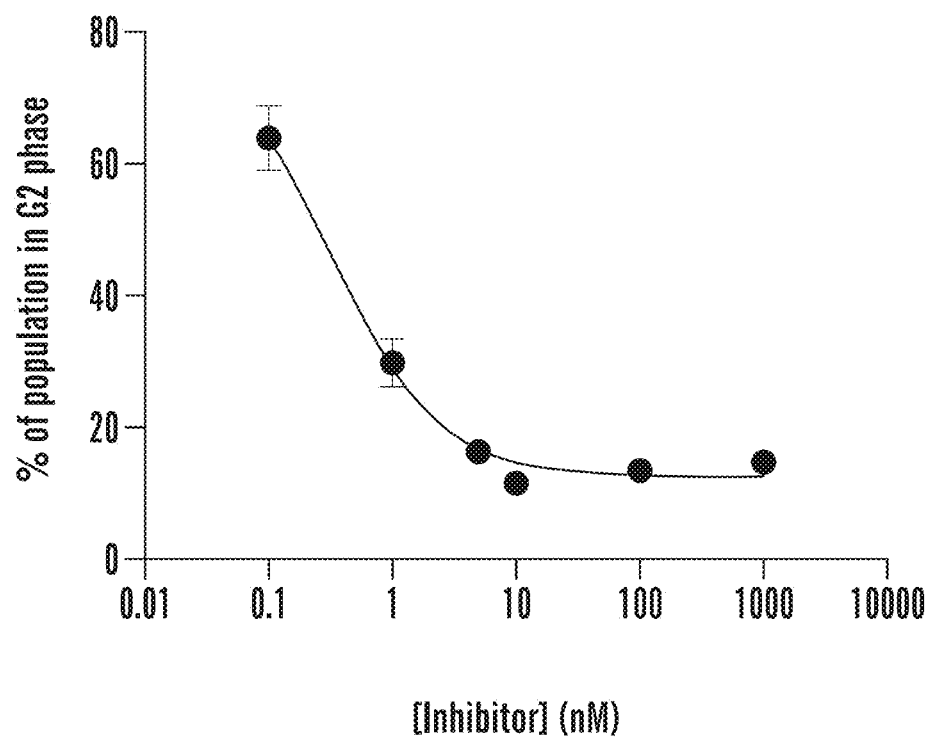
FIG. 4 demonstrates prevention of colibactin-induced genotoxicity. 3 inhibits the G2/M-phase arrest phenotype of HeLa cells infected with pks$^+$ E. coli with an apparent IC$_{50}$ of approximately 10 nM.

In addition to blocking the metabolic indicators of colibactin biosynthesis, it was also assessed whether 3 could inhibit the genotoxic effects of colibactin on human cells at physiologically accessible concentrations. A previously described infection assay with HeLa cells and pks+*E. coli* which was modified to include a 1-hour preincubation of the inhibitor with the *E. coli* as well as inclusion of the inhibitor in the infection medium was used. Cells exposed to colibactin generally exhibit G2/M phase cell cycle arrest which can be quantified by DNA staining and flow cytometry. Treatment with 3 was able to completely block this effect at concentrations as low as 5 nM (FIG. 4). It was also confirmed that 3 is not cytotoxic to human cell lines at concentrations up to 10 µM. Other common biomarkers for activation of the DNA damage response known to be induced by colibactin, including γH2AX staining, and ubiquitination of FANCD2 showed similar inhibition. In order to directly assess the impacts of 3 on colibactin's DNA crosslinking activity, purified plasmid DNA was incubated with pks⁺ *E. coli*, then subjected to gel electrophoresis under denaturing conditions. The results of this assay indicate that 3 can suppress DNA crosslinking activity at concentrations similar to those observed for preventing genotoxicity in mammalian cells.

Figure 7B:
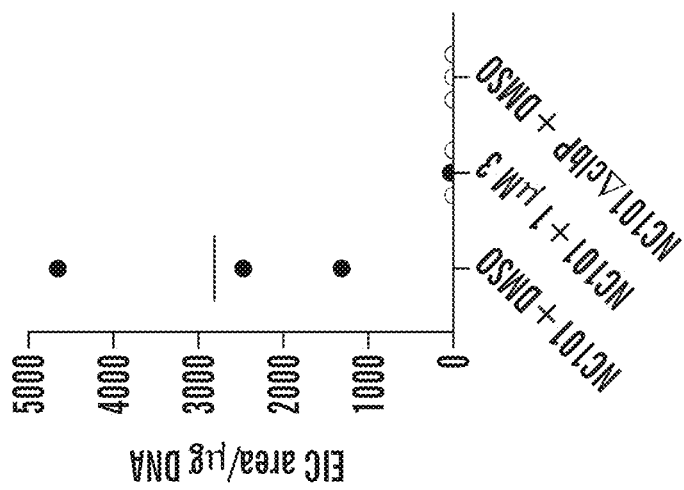
FIGS. 7A-7C.
Figure 7A:
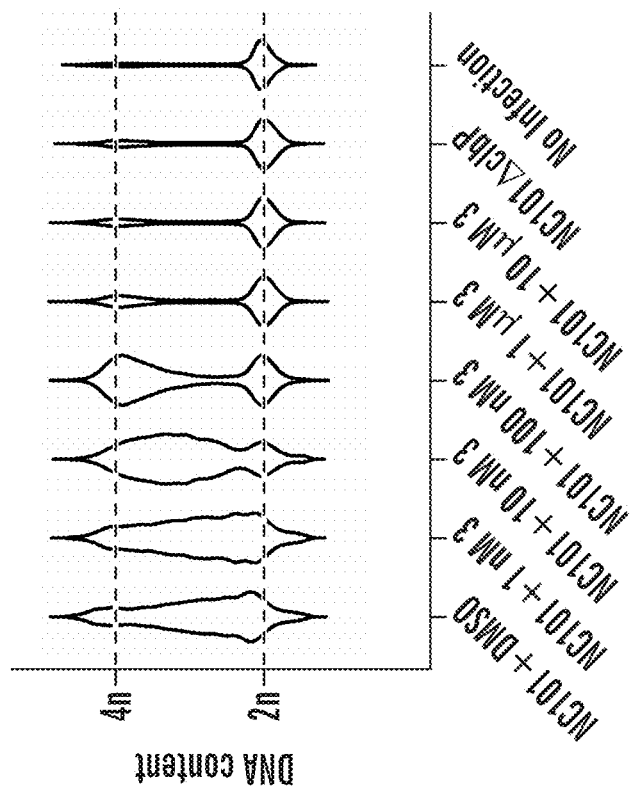
Figure 7C:
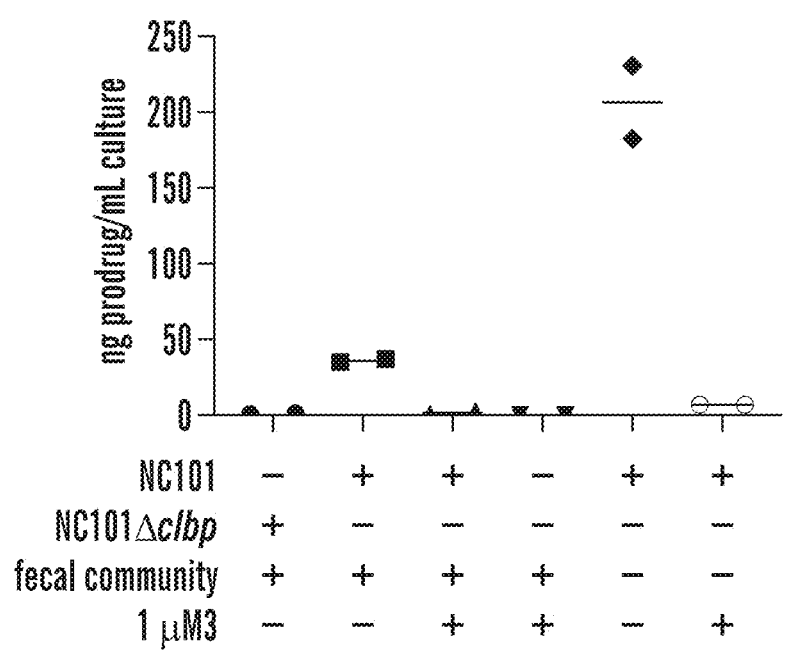

Finally, it was also confirmed that treatment with 3 could effectively suppress formation of a colibactin-derived DNA adduct in HeLa cells. HeLa cells infected with NC101 (a pks+*E. coli* strain) with or without inhibitor present (FIG. 7A, 12A) were analyzed by flow cytometry. ClbP inhibitor 3 can block the cell cycle arrest phenotype typical of colibactin's genotoxicity. The HeLa cells were also subjected to LCMS analysis, which revealed that ClbP inhibitor 3 can block DNA adduct formation (FIG. 7B, 12B) and reduce the release of N-myristoyl-Asn (prodrug motif) from NC101 in a complex microbial community from a mouse fecal sample (FIG. 7C). Thus, compound 3 is not only an inhibitor of ClbP, but a potent and specific inhibitor of colibactin biosynthesis and its associated genotoxicity. Furthermore, this inhibition is effective even in the presence of a complex microbial community.

Figure 8:
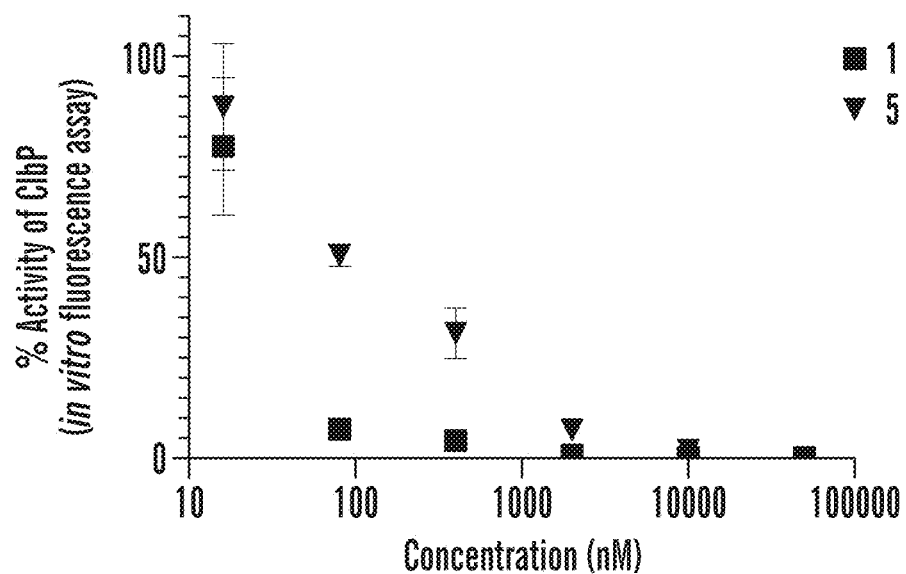
FIG. 8 depicts a graph demonstrating in vitro inhibitor characterization and that inhibition is insensitive to the boronate ester group.
Figure 8:
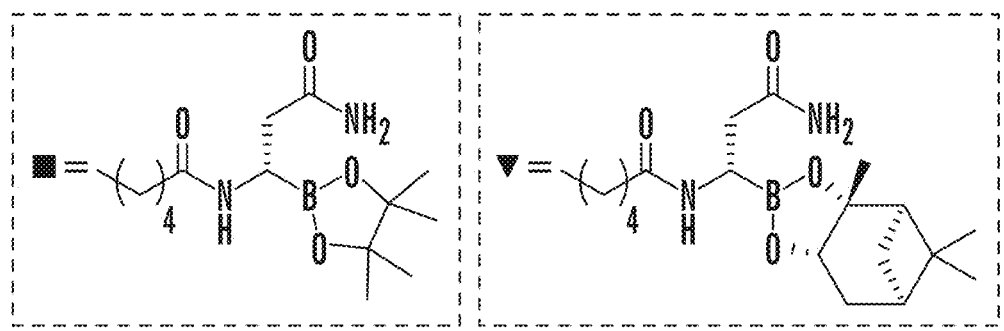

Additionally, the inhibition activity is insensitive to the boronate ester group, as a pinanediol compound was demonstrated to have activity (FIG. 8).

DISCUSSION

Chemical modulation of gut microbial functions is a promising avenue for therapeutic intervention in a wide variety of conditions. Several other efforts to develop small molecule inhibitors of gut microbial metabolic functions have demonstrated the utility of this strategy in the context of bacterial metabolism of xenobiotics and host-derived compounds. However, this approach has not been widely applied to biosynthetic pathway until now.

Building off past biochemical studies on the biosynthesis of colibactin, we prepared a panel of compounds which can potently and specifically inhibit the colibactin-activating peptidase ClbP. Past observations that ClbP recognizes a structural motif not commonly found in other metabolites made it uniquely well-suited for a substrate-guided design of a mechanism-based inhibitor. It is perhaps surprising that none of the inhibitors tested here show significant differences in inhibitory effect in vitro, despite bearing different N-acyl structures. One possible explanation for this is that the acyl group serves only a weak role in initial substrate recognition, while potency is driven the formation of a reversible covalent bond with a key active site serine residue via the boronic acid electrophile. This hypothesis is further supported by observations from the slow-binding inhibition assay, in which compounds with larger acyl groups such as 2 and 3 achieved their maximum potency faster than compound 4.

In addition to their high potency, these compounds are extremely selective for ClbP over other proteases and serine hydrolases. A broad range of potential off-targets were surveyed for inhibitory activity, and the assays used here examine direct binding of inhibitors to enzyme active sites. The fact that these compounds show limited toxicity to a variety of organisms, including bacteria and mammalian cells, and minimal metabolic perturbation outside of the colibactin pathway are strong evidence that their off-target effects are low.

It was also shown that small molecules like 3 can effectively block both colibactin biosynthesis and its associated genotoxic effects. One potential challenge in pursuing a chemical inhibition strategy is that if ClbP were not a rate-limiting step of colibactin biosynthesis, or if only a small fraction of the colibactin normally produced were sufficient to cause major DNA damage, even strong inhibitors of ClbP in vitro might not appear biologically efficacious. Compound 3, however, is able to block genotoxicity even at nanomolar concentrations. In addition, past studies have attempted to vary the dosage of colibactin by changing the number of bacteria used in a given assay, which affords only a coarse and inconsistent level of control. It was shown herein that 3 can be used to tightly and reproducibly tune colibactin production across a range of concentrations.

With these tool compounds in hand, a wide range of new experimental questions that have been inaccessible using classic genetic tools becomes possible. Though colibactin has widely been studied as a possible carcinogen, its remarkable instability and the complexity of the gut environment have posed a formidable challenge in understanding its biological effects. These inhibitors provide a method for precisely controlling colibactin exposure to mammalian cells. Using inhibitors like 3, we can begin to understand how the duration and timing of colibactin exposure influences cancer development. These tools will also be essential in understanding the connection between colibactin and inflammation, which can be intermittent in the gut, but is essential for colibactin-related CRC in mouse models. In addition, since 3 is non-toxic to all of the bacterial species tested and effective in a community setting in culture, this inhibitor can be utilized therapeutically and to study how colibactin exposure modulates the surrounding community, and what effect this altered community could have on the host.

Example 2

The human gut bacterial genotoxin colibactin has emerged as a possible key driver of colorectal cancer (CRC) development. Understanding colibactin's biological effects remains difficult due to the instability of the proposed active species and the complexity of the gut microbial community. Described herein are small molecule boronic acid inhibitors of colibactin biosynthesis and genotoxicity. Designed to mimic the biosynthetic precursor precolibactin, these compounds potently inhibit the colibactin-activating peptidase ClbP. Using biochemical assays and crystallography, it is shawn that they tightly engage the ClbP binding pocket, forming a covalent bond with the catalytic serine. These highly selective inhibitors reproduce the phenotypes observed in a clbP deletion mutant. Finally, they block the genotoxic effects of colibactin on eukaryotic cells without toxicity to bacteria or human cell lines. The availability of potent, selective colibactin biosynthesis inhibitors permits precise, temporal control over this pathway, and further permtis the study of its role in CRC carcinogenesis.

INTRODUCTION

The trillions of commensal and pathogenic microorganisms which colonize the human gut, collectively termed the gut microbiota, secrete a diverse milieu of small molecules with profound impacts on human health.[1] In particular, several members of this community have been proposed to play roles in the development of colorectal cancer (CRC), e.g., through the production of small molecule natural products or the expression of toxic proteins.[2-4] While possible microbial culprits have been identified and associated with CRC, knowledge of the molecular mechanisms underlying the contributions of these organisms to carcinogenesis remains limited because of the inherent challenges of studying a complex and dynamic microbial community.

These challenges are exemplified by recent efforts to characterize the genotoxic gut bacterial natural product colibactin. Colibactin is produced by a non-ribosomal peptide synthetase-polyketide synthase (NRPS-PKS) assembly line encoded by the pks genomic island, which is carried by many strains of E. coli (pks$^+$ E. coli) and other Proteobacteria.[5-7] While it was initially observed over a decade ago that pks$^+$ E. coli elicit a genotoxic phenotype and cause DNA double-strand breaks in cultured epithelial cells, the chemical species responsible for these effects could not be readily identified.[5,8-10] Based on extensive metabolomics, characterization of biosynthetic enzymes, and total synthesis, potential structures of colibactin have been proposed, though it has not been isolated from a natural source. The proposed structure that is most consistent with colibactin's biological effects contains two highly electrophilic cyclopropane warheads linked by a 1,2-diketone; the sensitivity of this linkage to oxidative C—C bond cleavage may explain the difficulty of isolation.[11,12] Formation of the warheads is accomplished in the final step of biosynthesis by the periplasmic peptidase ClbP, which hydrolyzes two units of the N-myristoyl-D-asparagine 'prodrug scaffold' from a larger pseudodimeric precursor, precolibactin.[13,14] This reaction releases the active species, colibactin, which alkylates two adenine residues on opposite strands of the target cell's DNA, resulting in highly toxic and mutagenic DNA interstrand crosslinks.[10,12] These crosslinks are unstable and break down into mono-adducts which can be detected in genomic DNA extracted from either cultured cells or epithelial tissue of mice infected with pks$^+$ E. coli using mass spectrometry.[15]

Multiple lines of evidence indicate colibactin-mediated DNA damage plays a role in CRC development. Studies have reported that pks E. coli were found more frequently in patient cohorts with CRC relative to healthy controls.[16,17] In addition, colonization with pks E. coli increased tumor loads in multiple gnotobiotic mouse models of colitis-associated colorectal cancer.[16,18,19] Recently, several studies identified pks-dependent mutational signatures in both colonic epithelial cell-derived organoid models and in sequenced human cancer genomes. These signatures are found in AT-rich regions of DNA and show a strand bias consistent with an interstrand crosslinking agent, supporting the mechanism proposed in prior studies and indicating that colibactin could directly cause CRC driver mutations.[20-22] However, such alterations in the genome are not limited to tumors. One of the pks-dependent mutational signatures was identified in biopsies of morphologically normal colon crypts and shown to accumulate primarily before the individual reached 10 years of age.[23] Even short-term exposure to pks$^+$ E. coli in culture can cause enough mutations to lead to changes in growth factor dependence and differentiation in murine colon cells.[24] Thus, while colibactin has been strongly correlated with CRC, the timing and duration of the colibactin insult is likely an important variable in determining CRC risk.

While studies have illuminated a great deal about colibactin's possible carcinogenic activity, they have also revealed that this natural product and its biosynthetic enzymes are part of a complex network of interactions in the gut microbiota which cannot be untangled with current tools. While deletion of any of the biosynthetically essential pks island genes abolishes production of colibactin, different deletion mutants in the same strain background have shown different phenotypes in vivo, suggesting other roles for these enzymes.[25,26] To date, genes in the pks island have been linked to a number of seemingly disparate functions including siderophore biosynthesis, microcin production, and the probiotic effects of the pks$^+$ strain Nissle 1917.[27,28] The observation that the genotoxic effects of colibactin are cell-contact- and inflammation-dependent have made it especially challenging to distinguish the effects of this toxin from other changes in the gut microbiota and host metabolism that occur during periods of inflammation.[29,30] Moreover, while it has been suggested that colibactin could work cooperatively with other disease-associated microorganisms, potential mechanisms for such cooperativity have not been identified.[19] Finding answers to these questions requires examining colibactin's effects in the context of a complex gut community, but adding genetically modified organisms into these communities requires overcoming colonization resistance. In addition, whole gene deletions may result in changes to other pathways where the gene product plays a structural role, and there is evidence that ClbP performs additional, noncatalytic functions in other biosynthetic pathways.[28] Finally, genetic knock-outs cannot offer temporal control over colibactin exposure, making it impossible to investigate questions about the importance of timing in colibactin exposure. Direct addition of colibactin could offer precise control over exposure but is currently impossible due to its instability and unresolved identity. A tool compound which can specifically modulate the colibactin biosynthetic machinery could shed light on these questions by enabling studies of colibactin in complex pks$^+$ communities with greater precision than is currently possible.

To address this need, the inventors designed and characterized a series of boronic acid-based inhibitors of colibactin biosynthesis. These inhibitors directly engage the colibactin-activating peptidase ClbP and show a high degree of selectivity over other human and bacterial proteases. It is demonstrated herein that chemical inhibition of ClbP using these compounds abrogates colibactin production in pks$^+$ E. coli and pks$^+$ communities. Finally, it is confirmed herein that these inhibitors can completely block the genotoxic effects of colibactin on mammalian cells in culture. By establishing precise control over colibactin production, these inhibitors present a unique opportunity to study the effects of colibactin in complex microbial communities and provide a therapeutic strategy by blocking colibactin production.

Results

Synthesis and in vitro evaluation of putative ClbP inhibitors. To design a specific inhibitor of colibactin biosynthesis, the colibactin-activating enzyme ClbP was targeted. This membrane-anchored periplasmic senile peptidase is essential for the genotoxicity of pks+ E. coli. Genetic deletion of ClbP results in an accumulation of biosynthetic intermediates and shunt metabolites from the NRPS-PKS assembly line, termed "candidate precolibactins," many of which have been structurally characterized.[31,32] This enzyme is an attractive target for chemical inhibition as it belongs to the same enzyme family as β-lactamases like AmpC, which have already been successfully targeted with small molecule inhibitors.[13,33] However, in vitro experiments have shown that ClbP is not inhibited by several known β-lactamase inhibitors or broad-spectrum serine hydrolase inhibitors.[34] While one previous study reported a pair of boronic acid-based ClbP inhibitors identified using an in silico screening approach,[35] it was found that these compounds have minimal impact on ClbP's catalytic activity in vitro or in bacterial culture, even at millimolar concentrations.[34] Thus, there are currently no potent and selective inhibitors of this enzyme available.

ClbP contains a catalytic triad typical of the S12 family of serine peptidases formed by the essential residues S95, K98 and Y186. S95 was targeted by exploiting ClbP's essential and unusual acyl-D-Asn substrate-recognition motif (FIG. 9A). Boron-based electrophiles have frequently been employed in inhibitors of serine and threonine peptidases,[36] but posed a synthetic challenge here due to the proximity of the potentially nucleophilic asparagine sidechain. A panel of pinacol boronate esters (1-4), which are precursors of the corresponding boronic acids, using a stereoselective copper-catalyzed hydroboration reaction of an ester intermediate followed by ammonolysis to install the sidechain amide, were used herein (FIG. 9B).[37]

Figure 5:
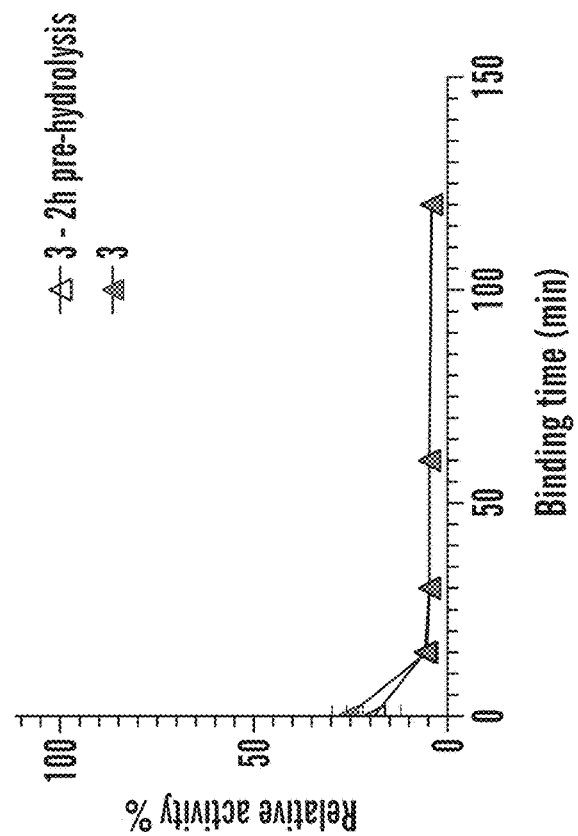
FIG. 5 demonstrates that compounds 1-4 show a typical "slow binding kinetics" profiles, with potency increasing with longer incubation times and reaching a maximum at approximately 1 hour. When the inhibitors were pre-soaked in aqueous buffer, no change to this slow binding behavior is observed, indicating that this behavior is not a result of slow hydrolysis of the pinacol ester, but of interaction with ClbP. Each condition was tested in n=3 biological replicates. Error bars represent 1 standard deviation (s.d.).
Figure 5:
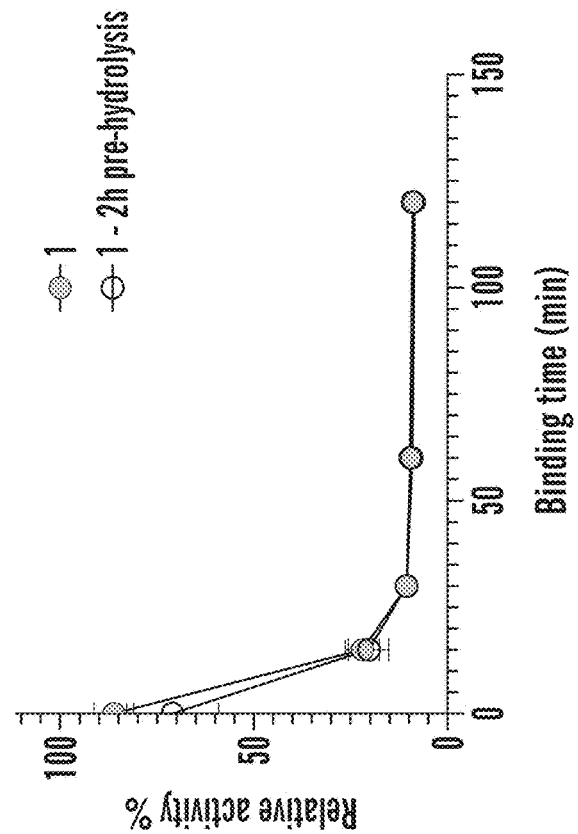
Figure 5:
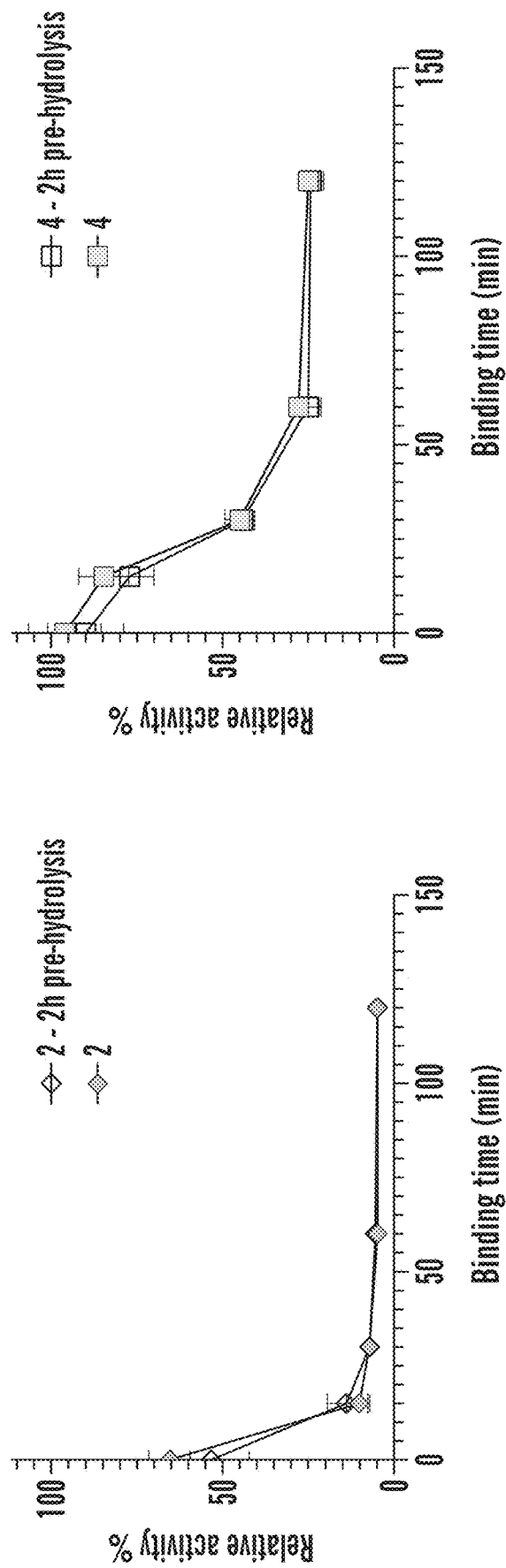

This panel of compounds was initially evaluated using a previously reported fluorogenic ClbP substrate in vitro. In this context, with 25 nM purified ClbP, all compounds had IC50 values between 20 and 80 nM after 1-hour preincubation, indicating that all are similarly potent inhibitors despite their structural differences (FIG. 10A, Table 1). Because these compounds were designed to inhibit ClbP by forming a covalent linkage to the critical active site serine residue, the kinetics of inhibition were examined using this fluorogenic assay format. Highly potent boronic acid-based inhibitors often exhibit slow-binding kinetics, where the free inhibitor is initially in equilibrium with the non-covalently bound inhibitor-enzyme complex, and subsequent covalent bond formation with the active site serine is slower and rate-limiting.[38,39] This behavior often results in an increase in potency of the inhibitors when incubated with the target for longer periods of time. Pre-incubating compounds 1-4 at 100 nM with ClbP for varying amounts of time confirmed that longer preincubation leads to increased potency for all of the compounds (FIG. 10B). While 1-3 all reached maximum potency within 30 minutes, 4 showed a significant lag, suggesting that the initial non-covalent complex of 4 with ClbP is weaker than those of the other inhibitors. Previous work showed that ClbP substrates with smaller acyl groups exhibit higher $K_M$ values, so the relatively smaller phenyl ring at this position in 4 may explain this difference.[34] Further control experiments ruled out boronate ester hydrolysis as a possible limiting step in this phenomenon (FIG. 5).

Using E. coli overexpressing ClbP and the same fluorescent reporter yielded IC50 values in the range of 4-40 nM for compounds 1-4, indicating that the E. coli outer membrane is not a significant barrier for these compounds (FIG. 10C, Table 1). To confirm that these inhibitors are effective against the cleavage of precolibactin by ClbP, a laboratory strain carrying the pks island on a bacterial artificial chromosome (E. coli BW25113 BACpks, "BW pks") was treated with 1-4 or a DMSO control and the amount of N-myristoyl-D-Asn released quantified by liquid chromatography-mass spectrometry (LC-MS, FIG. 10D). All compounds decreased the quantity of prodrug released, but compound 4 showed slightly lower potency than the others in this format.

Establishing the mechanism of ClbP inhibition. To examine the interaction between an inhibitor and ClbP directly, a crystal structure of full-length ClbP bound to 1, which bears the same type of aliphatic linear hydrocarbon tail as the native prodrug scaffold, but shortened in order to minimize solubility issues was obtained (PDB 7MDC, Table 2). There are several features in this structure which help explain ClbP's unique substrate specificity. The D-Asn sidechain of the inhibitor projects into a tight-fitting pocket and hydrogen-bonds with the sidechains of residues S188, H257, and N331 (FIG. 3A). N331 also hydrogen-bonds to E92, setting its orientation and helping to enforce ClbP's selectivity for D-Asn-over D-Asp-containing substrates.

Another key observation from the inhibitor-bound ClbP structure is the continuous electron density from the S95 sidechain to the ligand, which is evident in the electron density map (FIG. 3A), indicating essentially complete conversion to a covalent protein-inhibitor complex in these crystals. The electron density in the active site also shows that the free boronic acid is the active inhibitory species, as opposed to the pinacol ester, as no density is observed which would correspond to the pinacol group. This boronate complex is a structural analog of the tetrahedral intermediates formed during amide bond hydrolysis and shows a number of stabilizing interactions which are likely to play a role in the activation of precolibactin. The negative charge which accumulates upon formation of the covalent bond with S95 appears to be stabilized by hydrogen bonds from the backbone amides of Q330 and S95 to one of the boronate oxygen atoms. In addition, Y186, which is part of the catalytic triad that defines this enzyme family, is positioned to stabilize this complex by donating a hydrogen bond to either the other boronate oxygen atom or the oxygen nucleophile on the serine sidechain (FIG. 3C). Thus, the potency of these inhibitors arises both from their ability to mimic the hydrogen-bonding interactions of intermediates in the hydrolysis of precolibactin and the formation of a covalent bond with the catalytic serine residue.

Figure 13:
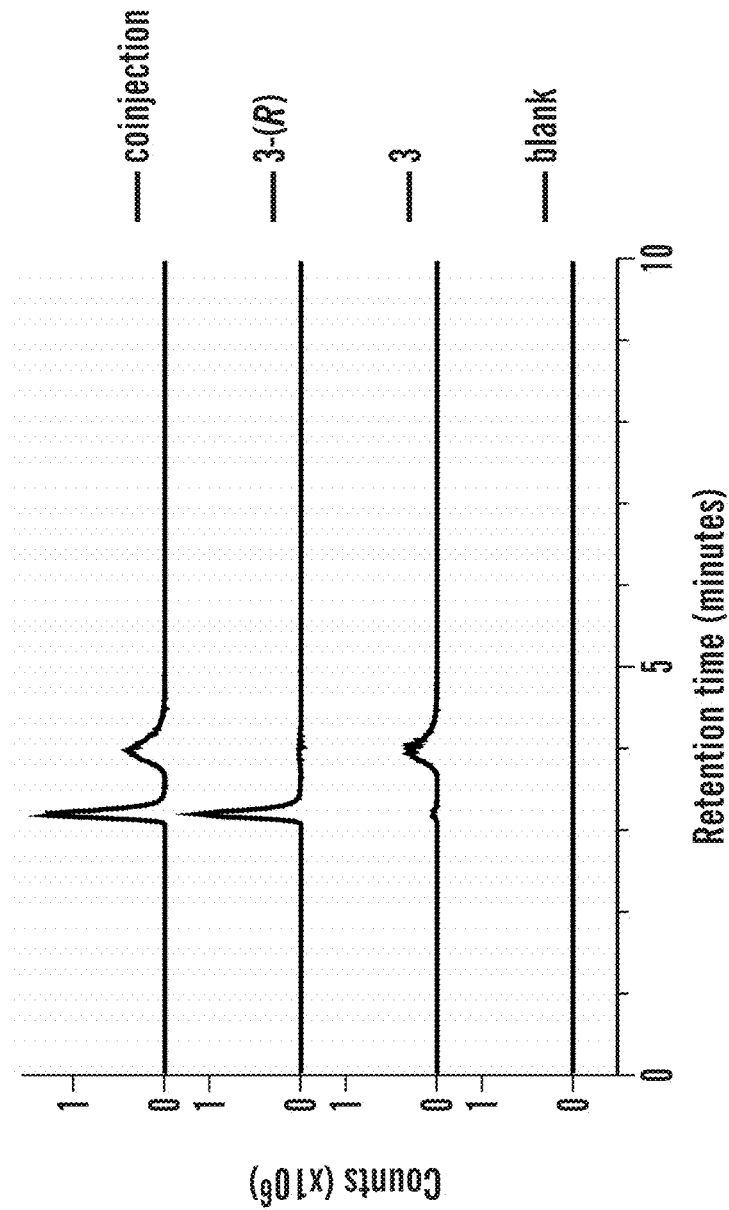
FIG. 13 depicts Chiral LC-MS for 3 and 3-(R). Curves shown are extracted ion chromatograms (EICs) for m/z 361.2308 (+1-5 ppm) corresponding to the [M+H]$^+$ ion of 3 and 3-(R). The area under the curves (AUCs) for the peaks corresponding to each enantiomer indicate that each compound is a 95:5 molar ratio of major vs. minor enantiomer.

Selectivity of ClbP inhibitors. Having established that this group of compounds can bind and inhibit ClbP with high potency, the next focus was establishing the selectivity of these interactions. Since the structural studies support the hypothesis that ClbP can only accept inhibitors of this class with the S stereochemical configuration, one of the highest-potency compounds, 3, was selected and the opposite enantiomer, 3-(R) synthesized. It was hypothesized that this compound should be a much less potent inhibitor given that N-acyl-L-Asn containing substrates are not accepted by the enzyme.[14,34] When tested side-by-side for their ability to inhibit the release of the prodrug from BW pks, 3-(R) is 40-fold less potent than 3. The weak inhibitory effect of 3-(R) likely results from the presence of a small amount of 3, which is an expected minor product of the synthetic route (see Methods). Both compounds were prepared in an enantiomeric ratio of 95:5 (determined by chiral LC-MS, FIG. 13) for the desired versus undesired enantiomer, so 3-(R) is expected to be at least 20-fold less potent if the residual 3 present is responsible for the inhibition observed.

Figure 11A:
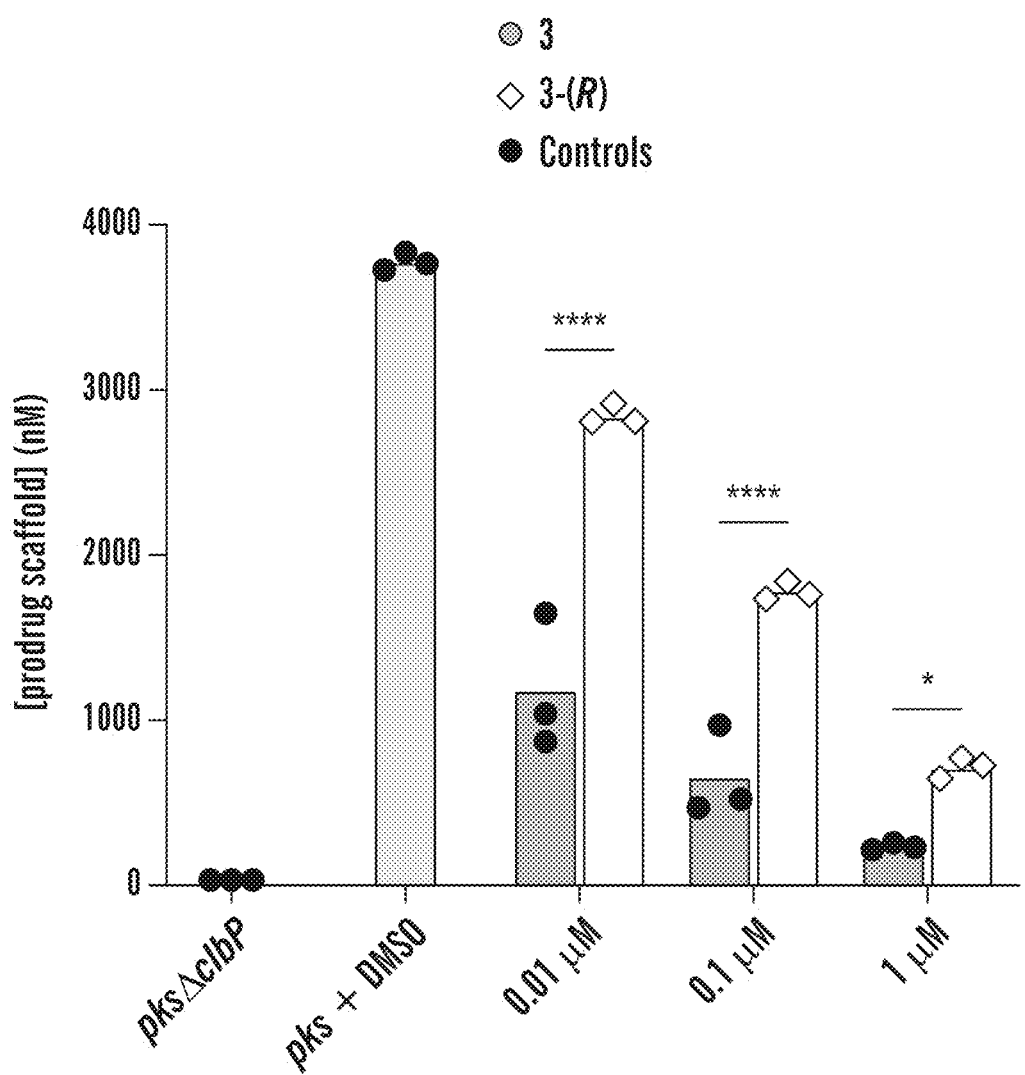
FIGS. 11A-11D demonstrate that Compound 3 is selective for ClbP inhibition and active in a microbial community setting.
Figure 11B:
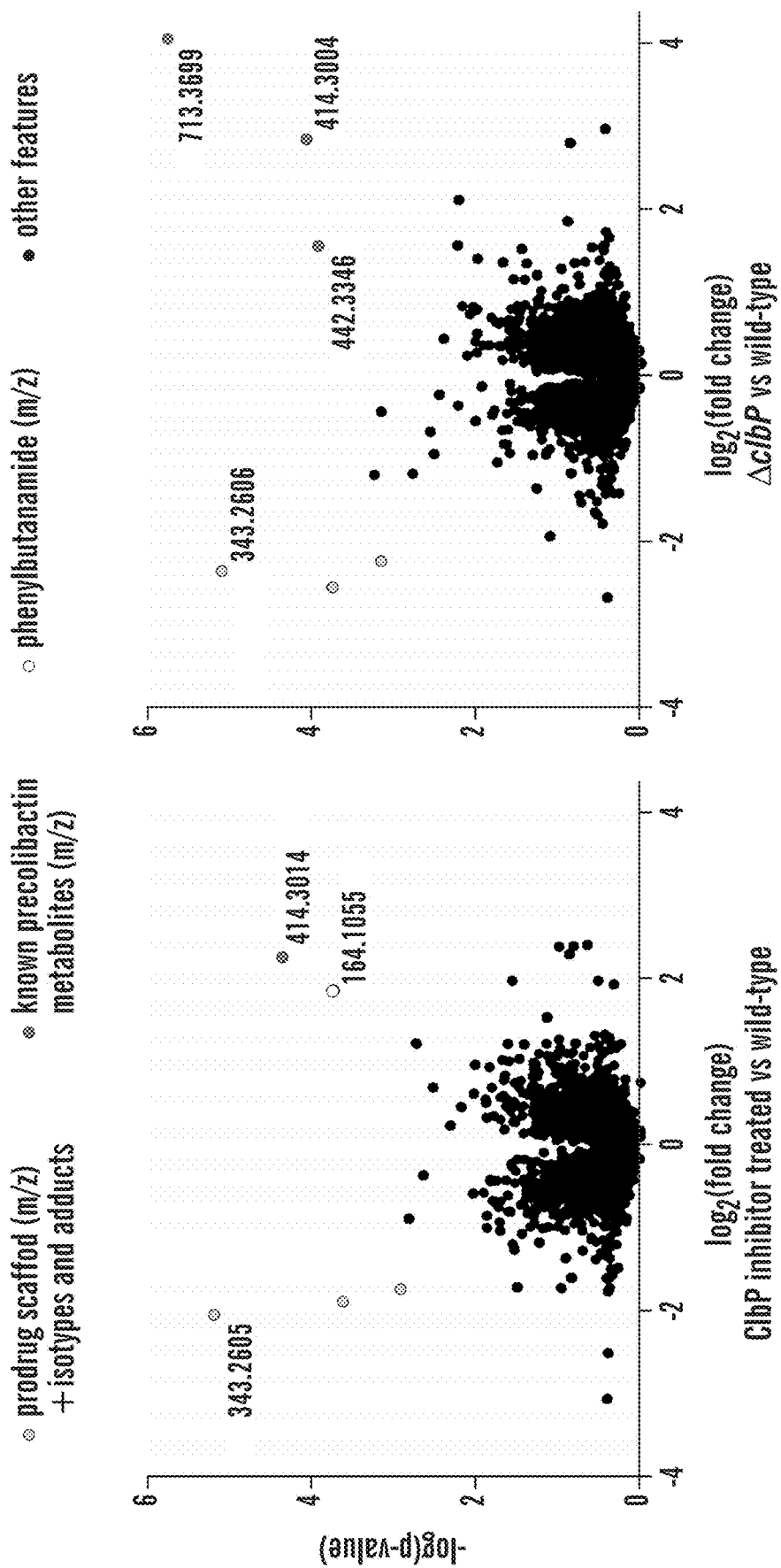

Metabolomics were used to investigate whether treatment with 3 could elicit the same metabolic changes in E. coli as a clbP genetic knockout. An ideal chemical probe should block colibactin biosynthesis while causing minimal disruptions to core metabolic functions of the producing organism, leading to an accumulation of the same biosynthetic intermediates and shunt metabolites that have previously been observed in pks+ΔclbP mutant strains. The metabolites produced by BW pks were compared to the metabolites produced by an isogenic ΔclbP mutant (E. coli BW25113 BACpksΔclbP, "BW ΔP") using LC-MS and analyzed the results using the XCMS software platform (FIG. 11B). The same experiment was also conducted comparing BW pks treated with 1 µM 3 vs the DMSO-treated culture (FIG. 11B). The results show that treatment of the wild-type strain with 3 resulted in similar changes in metabolite abundance as did genetic deletion of clbP. The primary features identified in both cases were decreased levels of the prodrug scaffold (M+H+=m/z 343.2605) relative to the DMSO-treated wild-type, and an accumulation of known upstream shunt metabolites from pathway (precolibactins m/z 414.3014, m/z 442.3346, and m/z 713.3699).[8,9,41] One other significant feature, an increase of a metabolite at m/z 164.1055, was observed only in the case of inhibitor treatment and is consistent with the mass and retention time of phenylbutanamide, a likely degradation product of 3. Based on these observations, 3 appears to be sufficiently potent and specific to serve as a tool for precise control of ClbP activity in living organisms.

Figure 6:
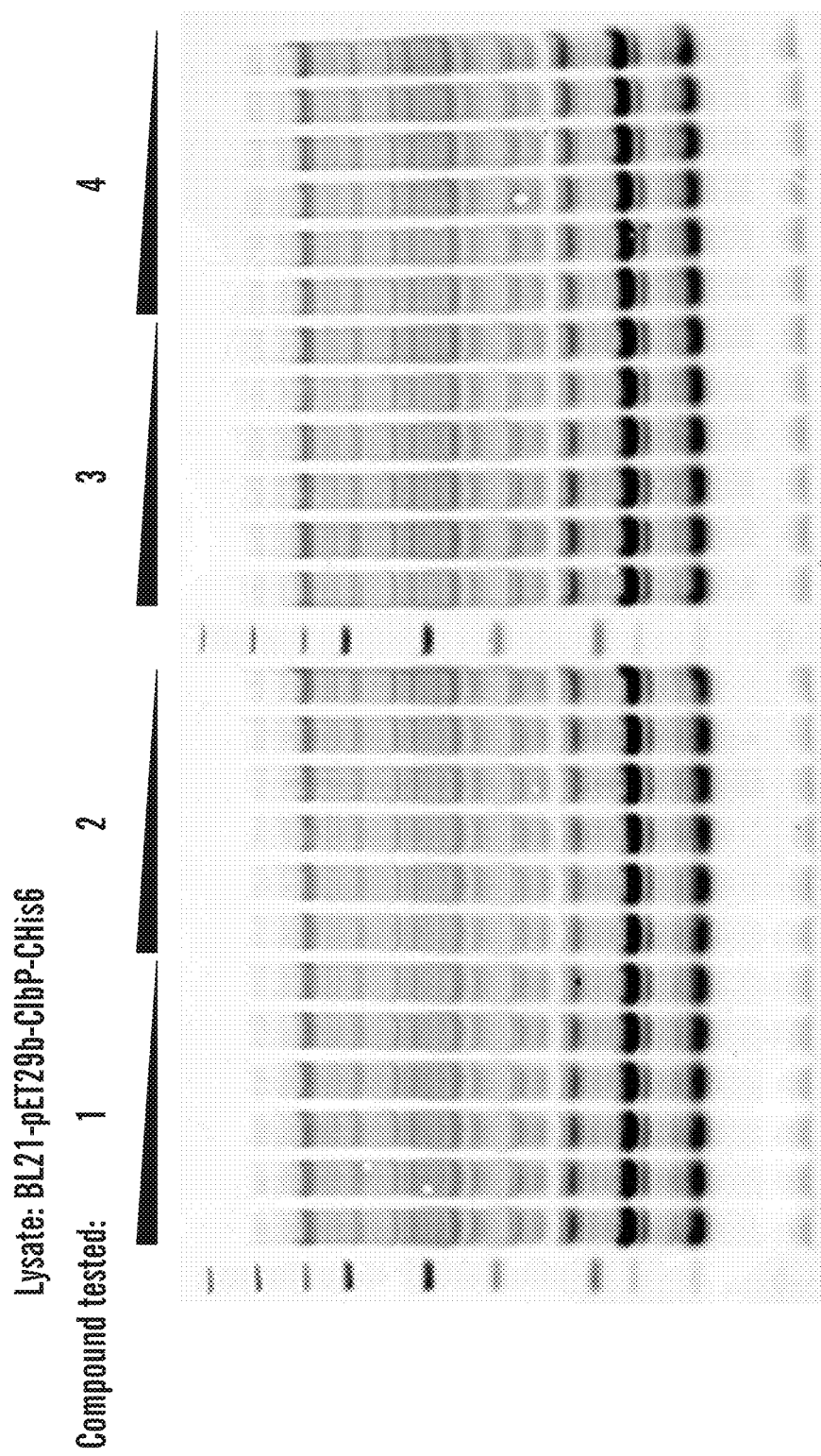
FIG. 6 demonstrates that gel-based ABPP assay shows no inhibition of other serine hydrolases by 1-4.
Figure 6:
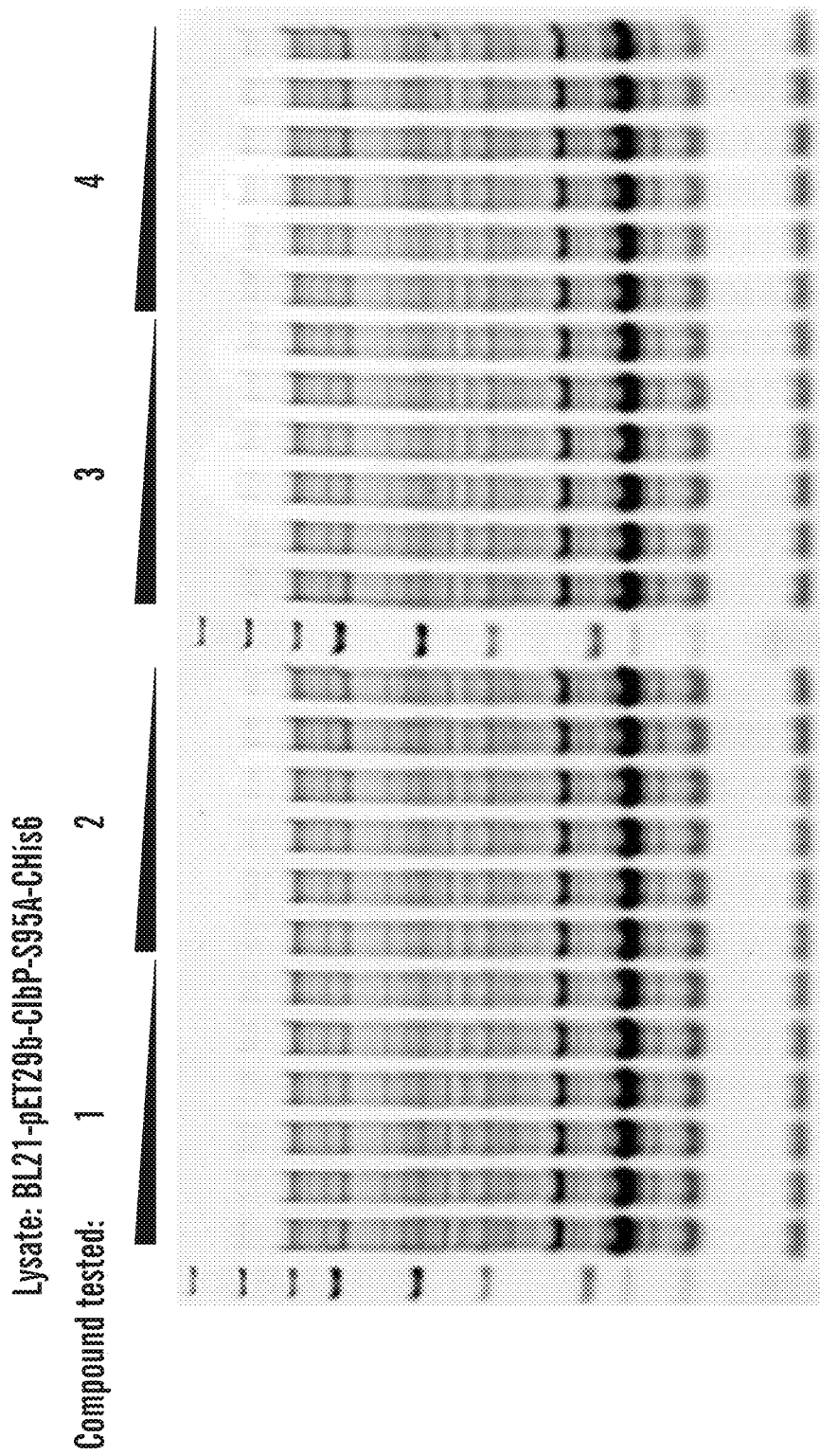
Figure 6:
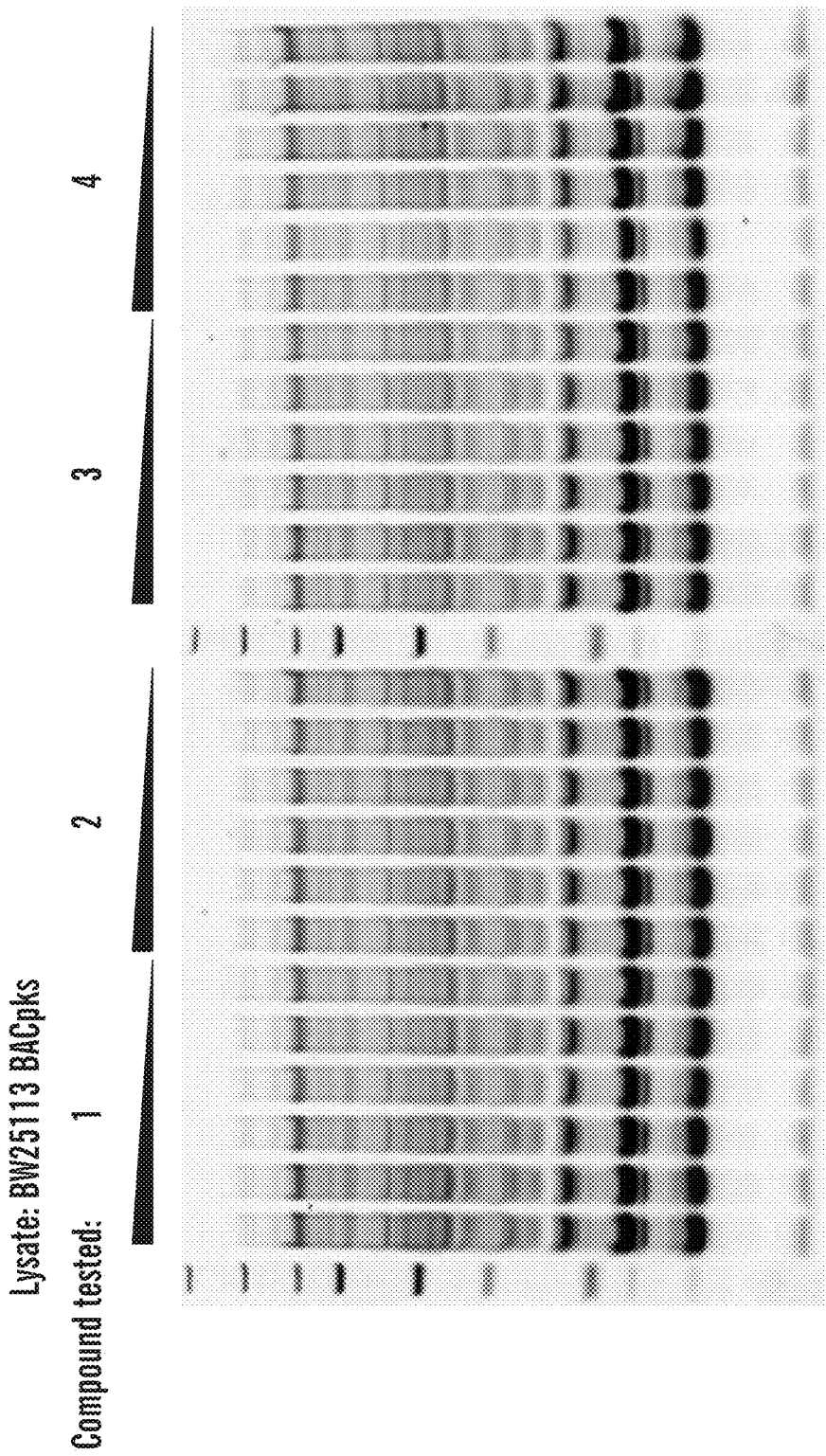
Figure 6:
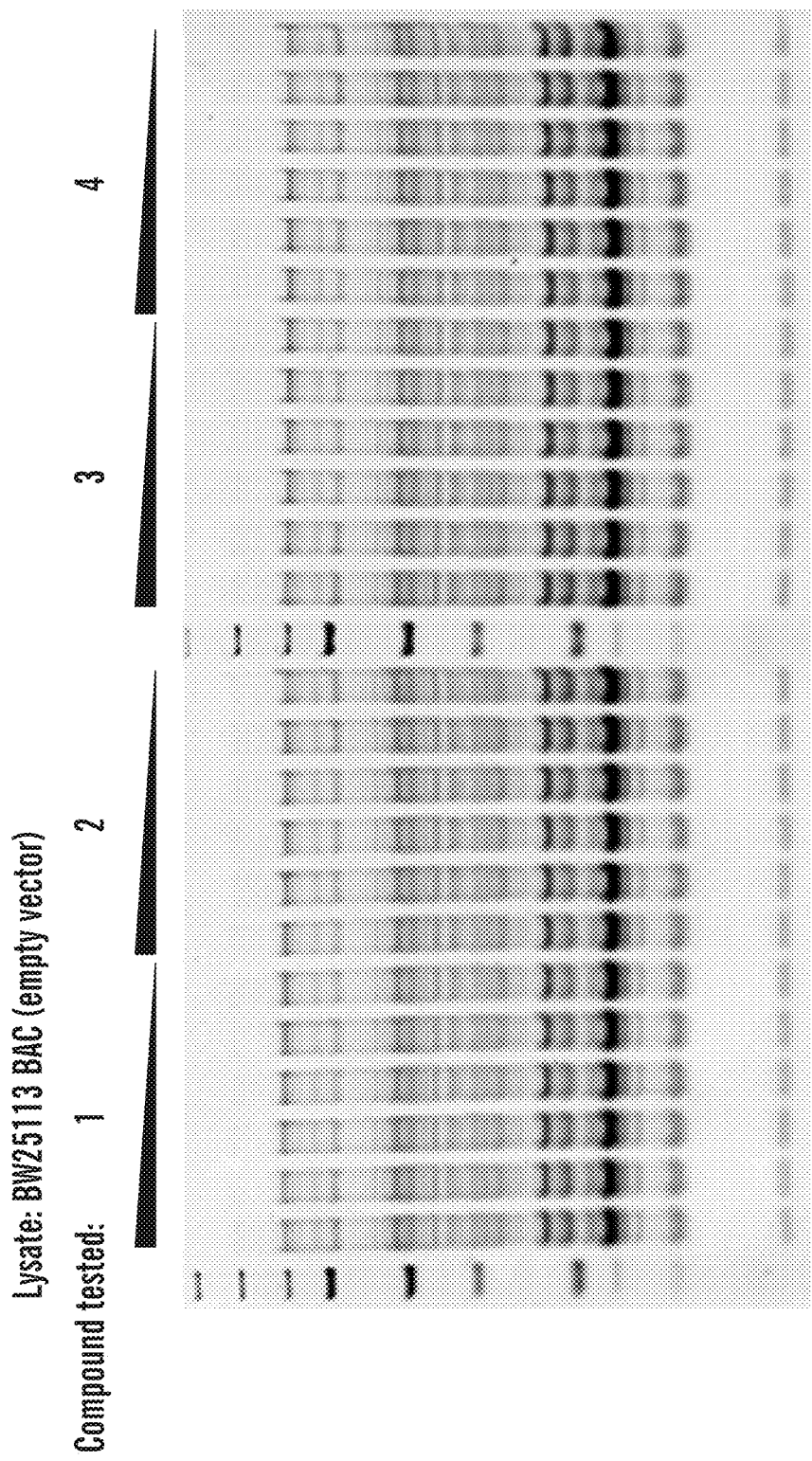
Figure 6:
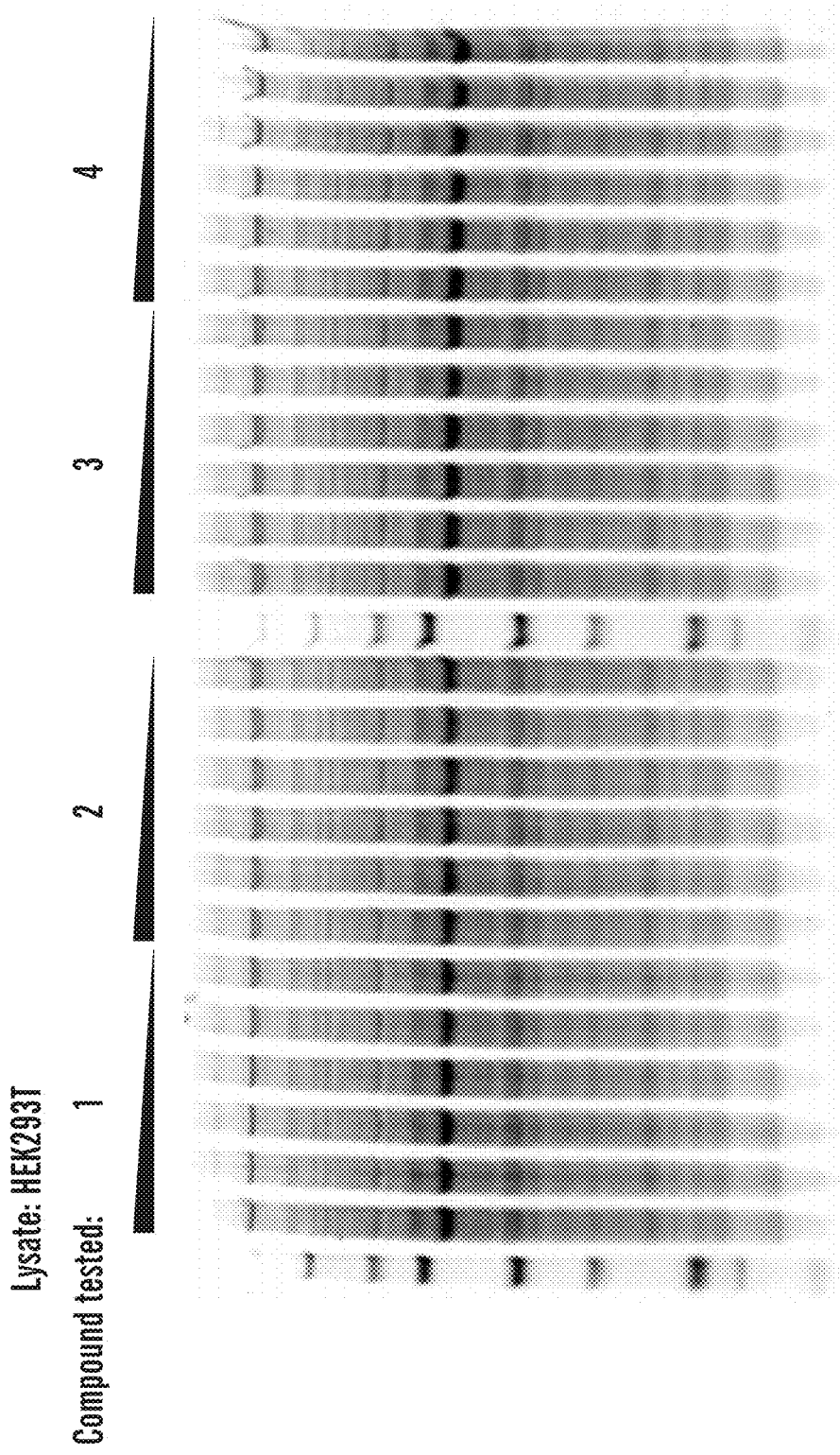
Figure 6:
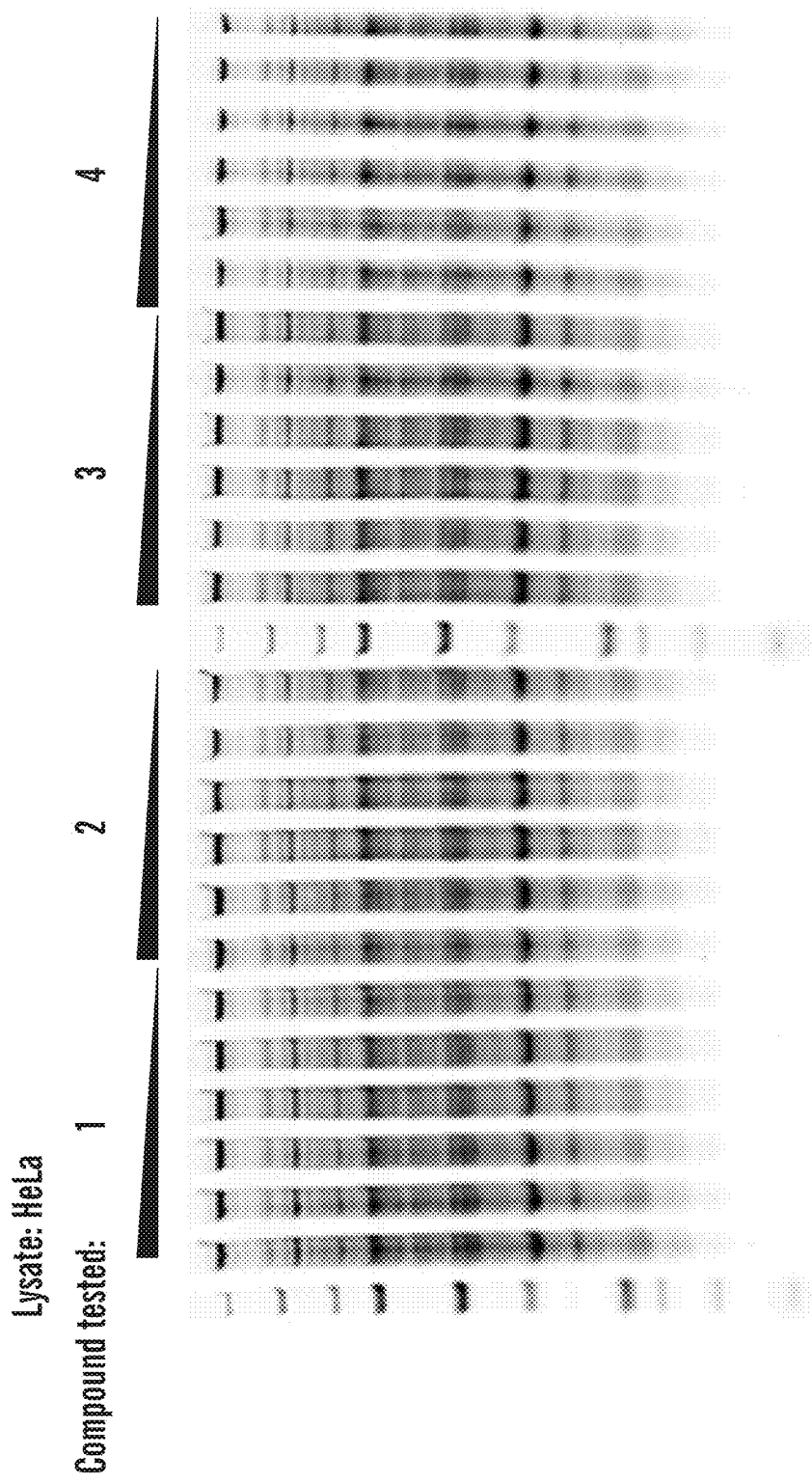
Figure 11C:
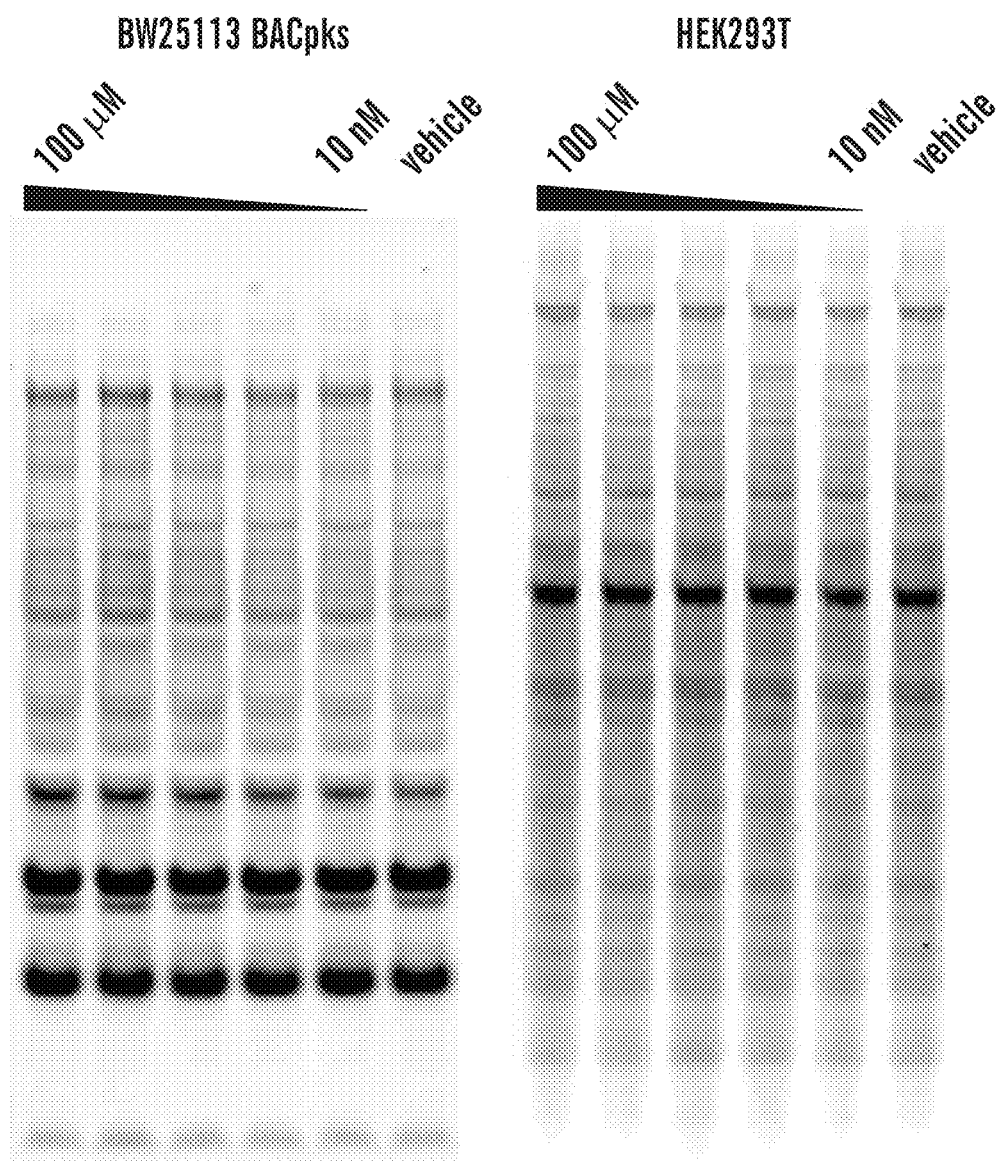

To further explore other possible targets of inhibitors 1-4, an activity-based protein profiling (ABPP) approach was used to assay their activity against a wide variety of serine hydrolases in bacterial and mammalian proteomes. In this gel-based assay, the binding of a small molecule to a target protein is detected as a decrease in that protein's ability to bind a non-specific fluorophosphonate probe (FP) compound which irreversibly inhibits a wide variety of serine hydrolases.[42] Applying this assay to both E. coli and HEK293T cell lysates showed no visible changes in protein labeling by FP at inhibitor concentrations of up to 100 µM (FIG. 11C and FIG. 6). One limitation of this assay is that ClbP is not labeled by the FP probe, so it cannot be observed as a reference for binding. Any other proteins which evade labeling by FP would also not be detected in this assay. However, this type of assay has been widely used to study the specificity of small molecule-protein binding interactions and provides strong evidence that the majority of serine hydrolases, which would be expected to be ideal secondary targets, do not interact significantly with these inhibitors.[43]

Figure 14:
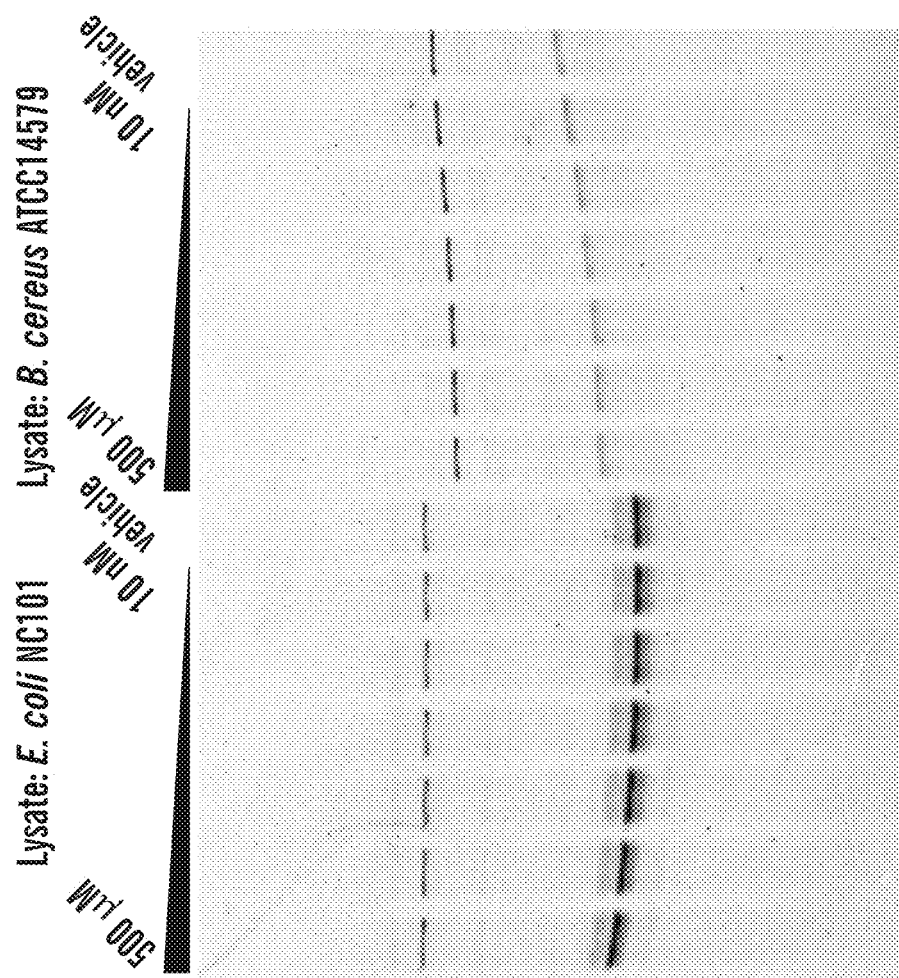
FIG. 14 depicts gel-based ABPP with the BOCILLIN-FL probe labels known Penicillin Binding Proteins (PBPs) in (left) *E. coli* NC101 and (right) *B. cereus* ATCC14579, but labeled proteins show no competitive binding to inhibitor 3.

To further explore the specificity of our inhibitors, another ABPP assay was used in which the broad-spectrum FP probe was replaced with a specific probe, BOCILLIN-FL, which targets penicillin binding proteins (PBPs) using a β-lactam warhead. This probe was chosen because of ClbP's homology to AmpC β-lactamases. Since PBPs are targeted by β-lactams, it was reasoned that the similarity of their binding pockets would mean a greater chance of identifying a secondary target among this family of enzymes. While this labeling strategy was able to identify several known PBPs in various bacterial lysates, none of these PBPs showed any binding to inhibitor 3 (FIG. 14). This observation also indicated that the recognition motif which guided our rational design strategy is highly specific to ClbP and its closest homologs.

Figure 11D:
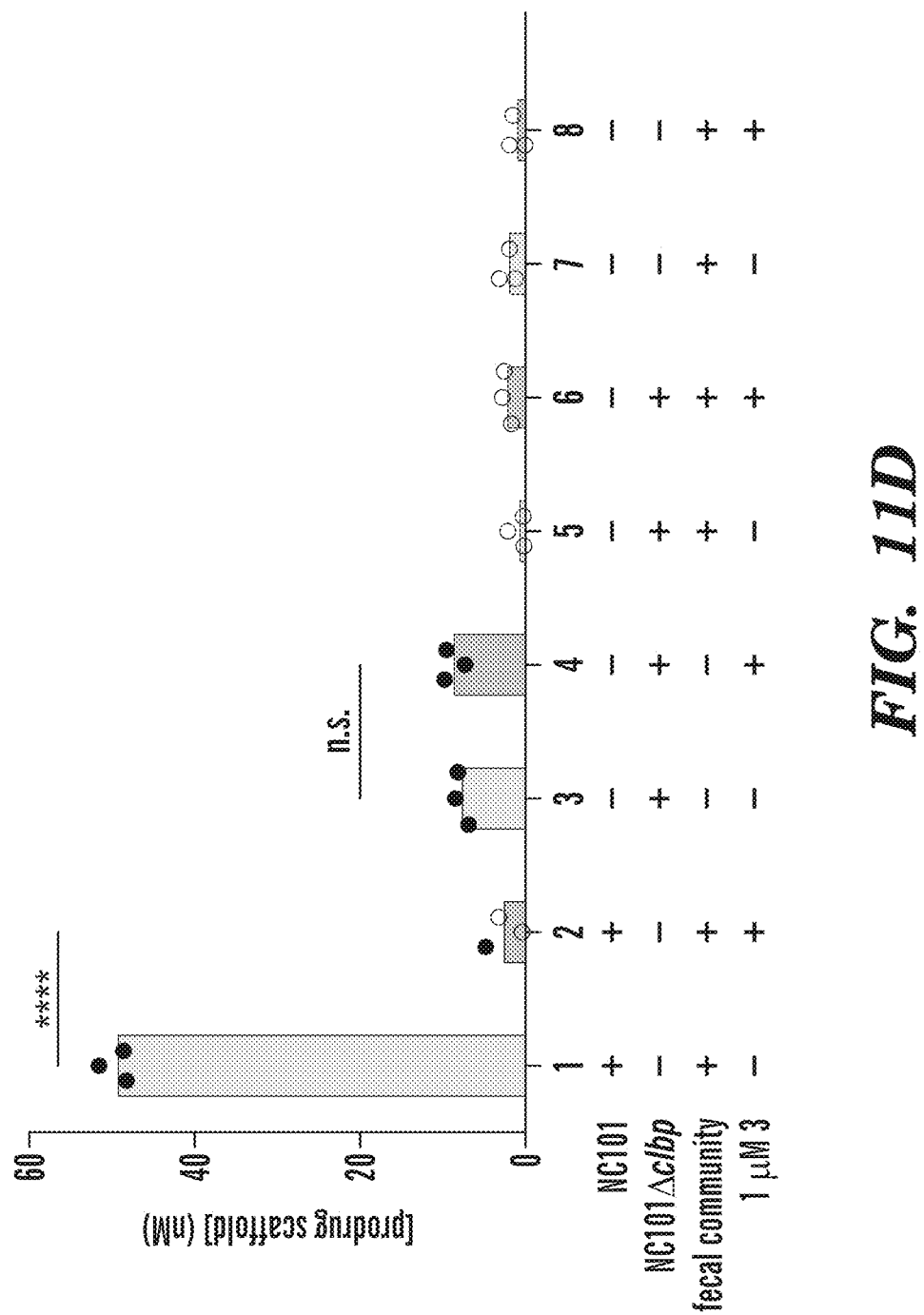
Figure 15:
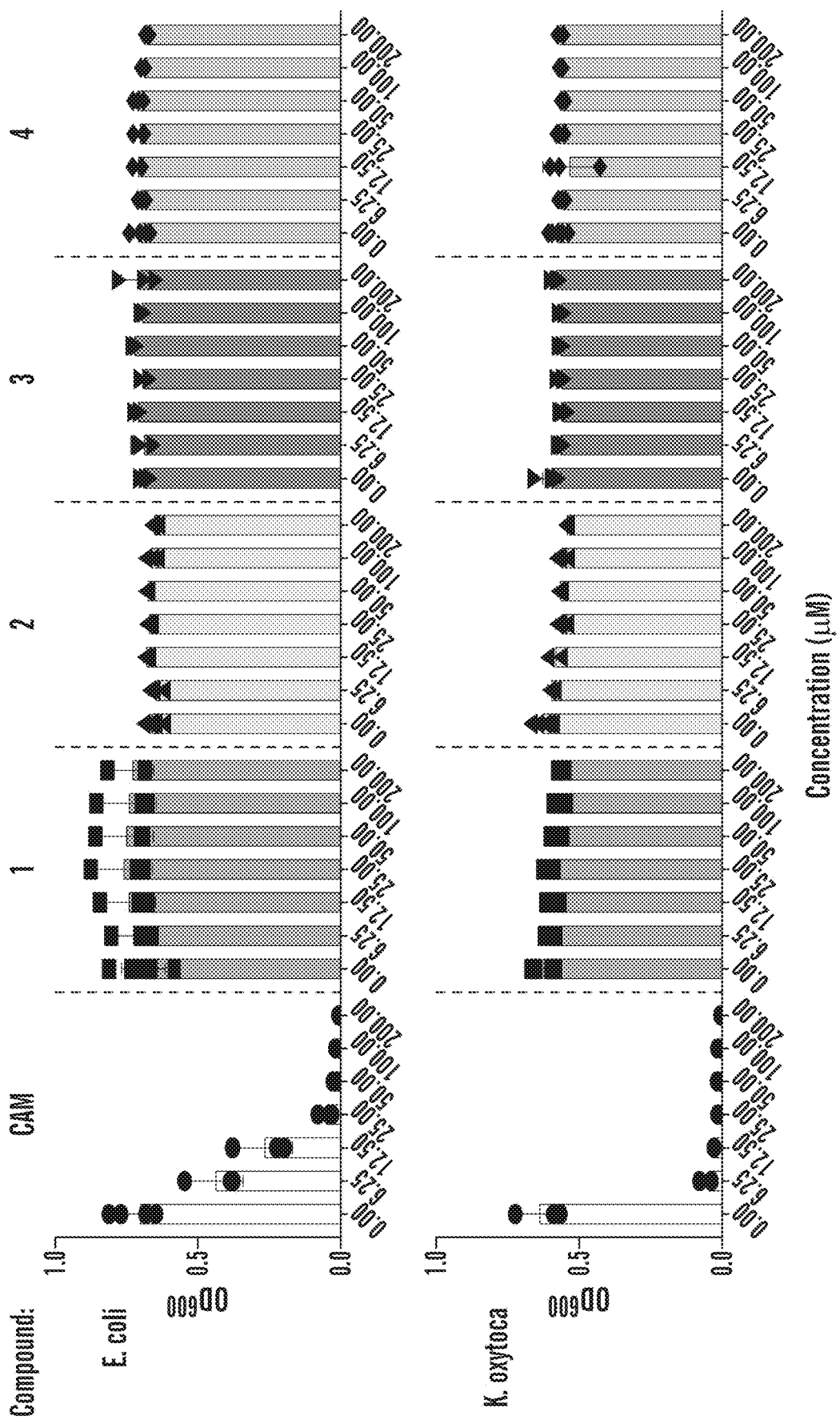
FIG. 15 depicts raw OD$_{600}$ measurements after 15 hours of anaerobic growth for strains tested in MIC assays with compounds 1-4 and chloramphenicol (CAM). Values shown are after subtraction of a media-only blank. Each combination of strain, compound, and concentration was tested in n=3 biological replicates, with individual replicates shown. Bars show the mean for each condition.
Figure 15:
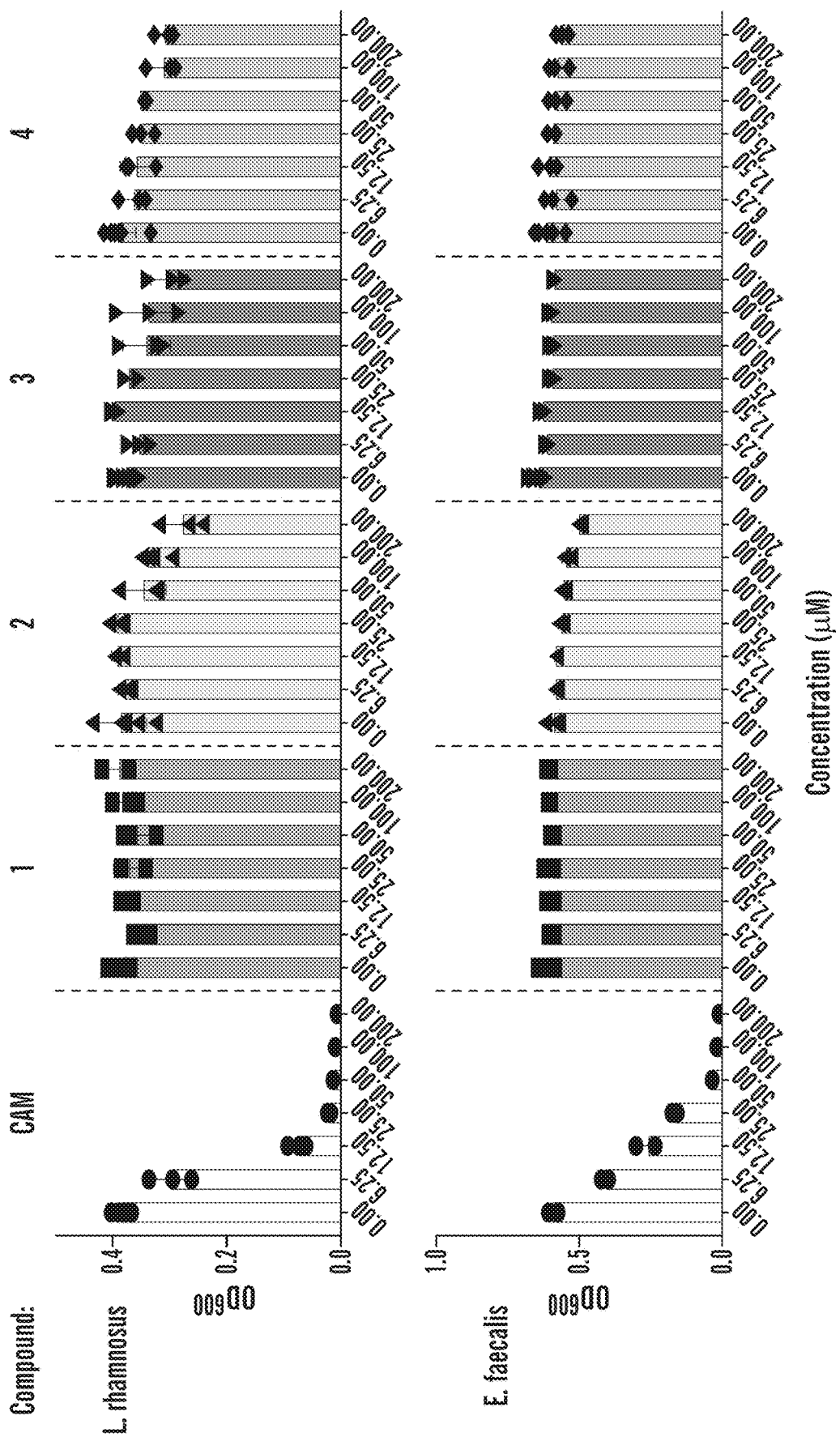
Figure 15:
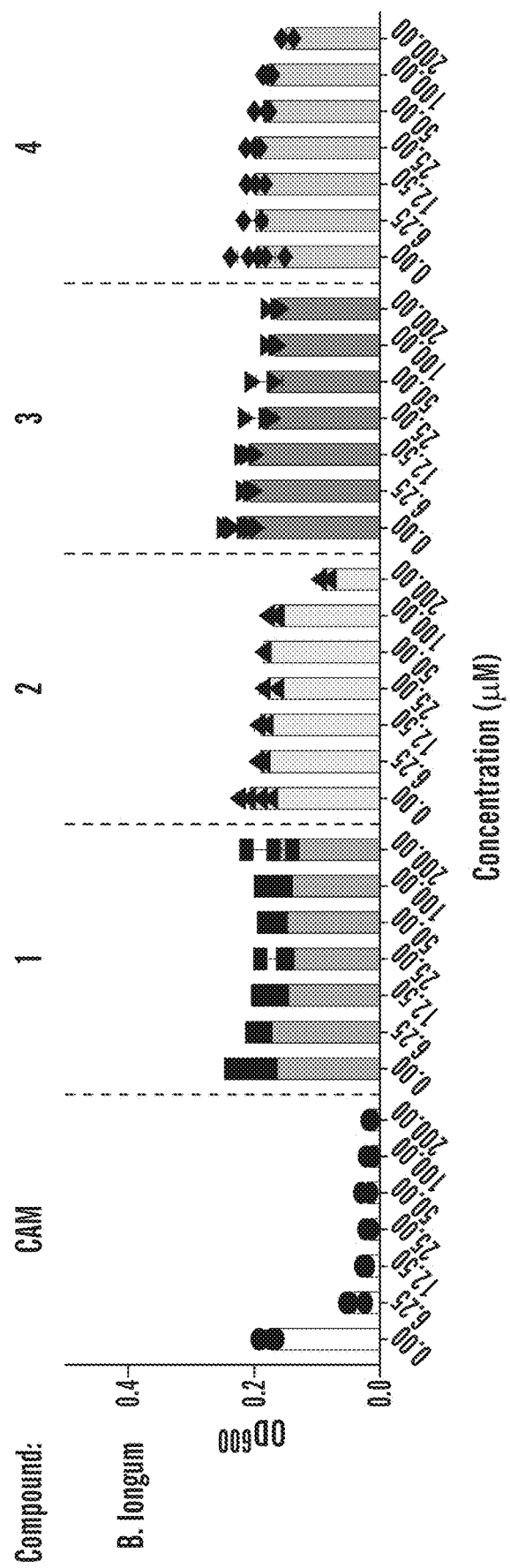

Compound 3 is an inhibitor of colibactin-associated genotoxicity. Since colibactin is produced in the context of the gut microbiota, it is essential to understand how 3 can affect other members of this community and whether it remains an effective inhibitor under these conditions. To assess what impact a community would have on the efficacy of 3, a complex pks+ community was simulated by inoculating anaerobic liquid cultures with fecal pellets from C57BL/6J mice, which do not contain colibactin-producing organisms, and adding E. coli NC101 to this community.[30] This strain was chosen because it is a known colibactin-producer which was originally isolated from a mouse gut, and because of the availability of an isogenic E. coli NC101ΔclbP knockout to use as a control.[44] Both the simulated pks+ and pksΔclbP gut communities were treated with 3 or with DMSO and monitored the production of the colibactin prodrug scaffold in these cultures by LC-MS. Under these conditions, treatment with 3 fully suppressed production of the prodrug scaffold in the pks+ community to the same level as that observed in the pksΔclbP gut community (FIG. 11D). A turbidity assay was used to determine minimum inhibitory concentrations (MICs) in liquid culture of 1-4 against a variety of bacterial strains from common gut phyla, including E. coli (Table 3). In all cases, MICs were above the upper limit tested in this assay (200 µM), though some species showed partial growth inhibition at 200 µM (FIG. 15). Since the maximum concentration tested here is more than 100-fold greater than the previously determined $IC_{50}$ value for inhibition of prodrug release, this indicates that 1-4 can be used at concentrations that effectively inhibit ClbP without damage to other members of the gut microbiota.

Figure 12A:
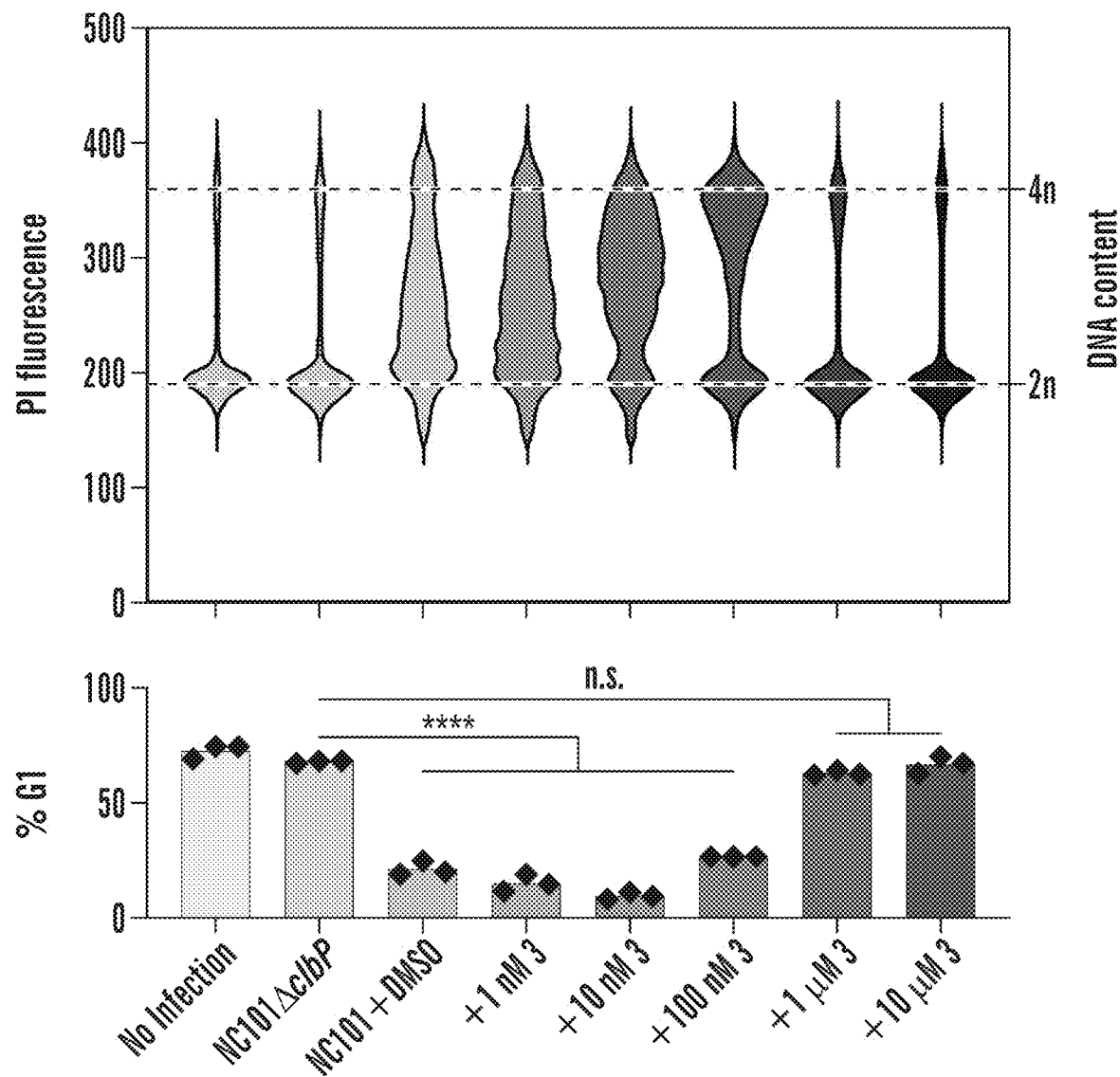
FIGS. 12A-12C demonstrate that Compound 3 prevents colibactin-induced genotoxicity in human cells.
Figure 12B:
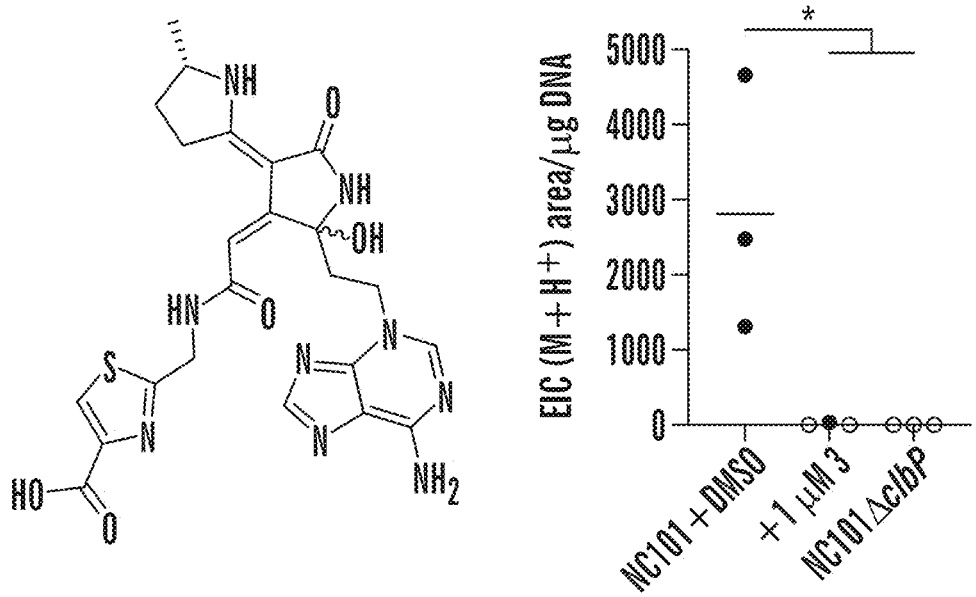
Figure 16:
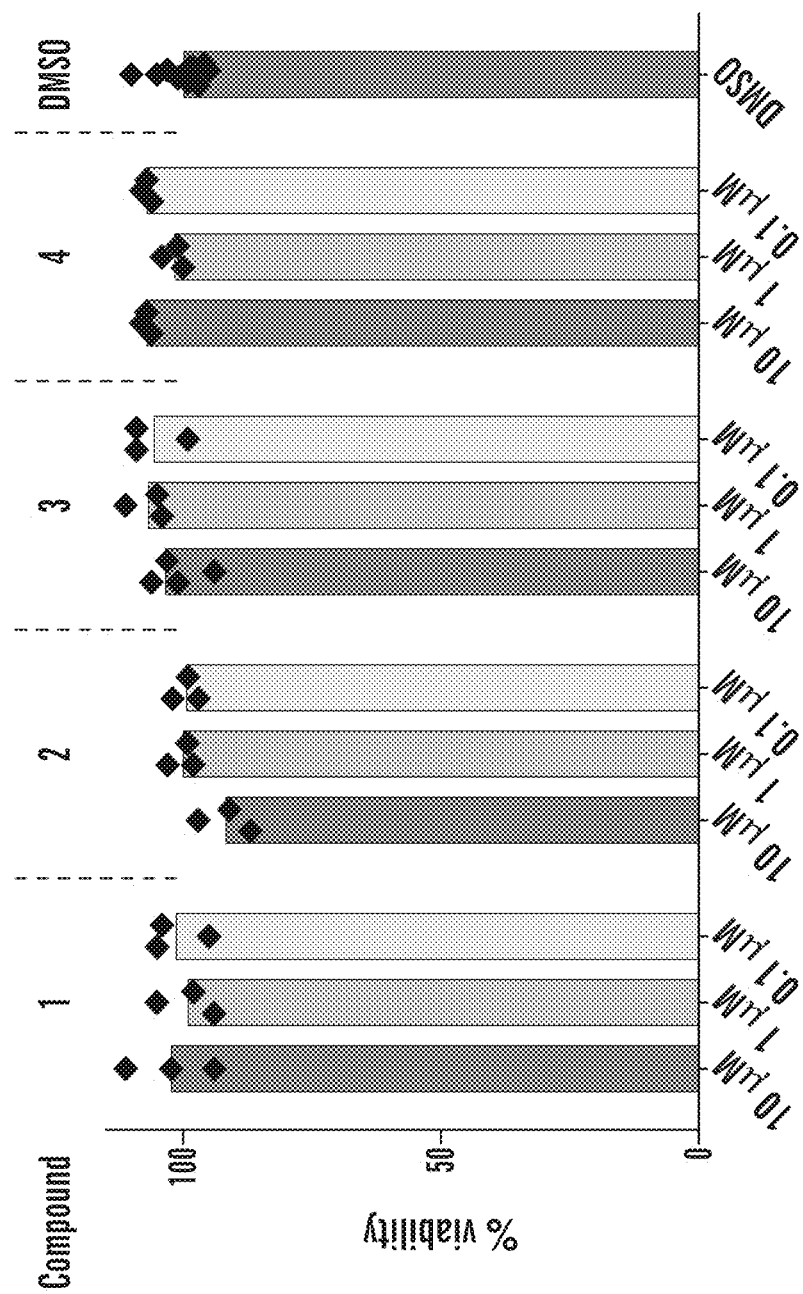
FIG. 16 demonstrates that 1-4 do not show cytotoxic activity toward mammalian cell lines up to 10 mM after 20 hours of exposure. No statistically significant difference was observed between any of the conditions tested (n=3 biological replicates for each) and the DMSO control (n=12) using an ordinary one-way ANOVA and Dunnett's multiple comparison test (P>0.05 in all comparisons to DMSO control).

In addition to blocking the metabolic indicators of colibactin biosynthesis, it was also aimed to assess whether 3 could inhibit the genotoxic effects of colibactin on human cells at physiologically accessible concentrations. A previously described infection assay with HeLa cells and NC101 was used with the addition of 3 at varying concentrations in the infection medium. Cells exposed to colibactin generally exhibit G2/M phase cell cycle arrest which can be quantified by DNA staining and flow cytometry. Treatment with 3 completely blocked this effect at concentrations as low as 100 nM (FIG. 12A). It was also confirmed that 3 is not cytotoxic to human cell lines at all concentrations tested (up to 10 µM, FIG. 16).

Figure 12C:
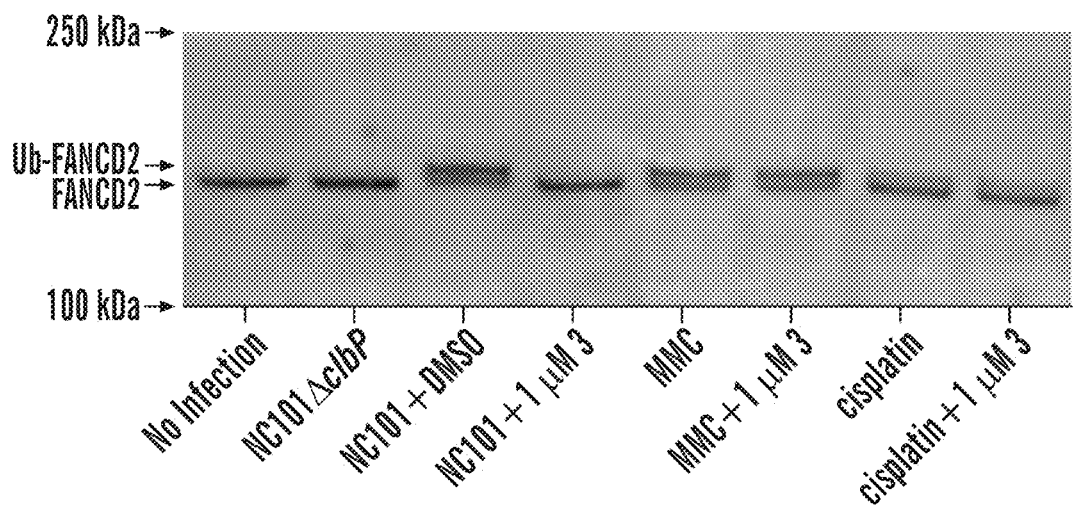

To directly assess the impacts of 3 on colibactin's DNA alkylating activity, HeLa cells with NC101 were also infected with and without 3 added and their genomic DNA isolated. This DNA was hydrolyzed and analyzed by LC-MS to detect two previously described diastereomeric colibactin-derived DNA adducts (FIG. 12B).[15] Treatment with 1 µM 3 was sufficient to suppress adduct formation to a degree similar to genetic deletion of clbP. Finally, the impact of 3 on the response to colibactin-mediated DNA damage in HeLa cells was assessed. In response to stalled replication forks, which can be caused by DNA crosslinking agents, the protein FANCD2 is monoubiquitinated (FANCD2-Ub) and subsequently activates homology-directed DNA repair.[45] FANCD2 is known to be important for response to the damage inflicted by colibactin, as cell lines missing this gene show increased sensitivity to colibactin exposure.[10] Using a western blot, an increase in abundance of FANCD2-Ub in HeLa cells was detected in response to exposure to NC101, as well as in response the DNA crosslinking agents mitomycin C (MMC) and cisplatin (FIG. 12C). Treatment of cells with 1 µM 3 prevented this response in colibactin-exposed cells but had no impact on the response to MMC or cisplatin, indicating that 3 is specific to the colibactin biosynthetic pathway and not inhibiting the DNA damage response. Thus, compound 3 is not only an inhibitor of ClbP, but a potent and specific inhibitor of colibactin biosynthesis and its associated genotoxicity.

DISCUSSION

The inventors have prepared a panel of compounds which can potently and specifically inhibit the colibactin-activating peptidase ClbP. Notably, none of the inhibitors tested here show significant differences in inhibitory effect in vitro, despite bearing different N-acyl structures. One possible explanation for this is that the acyl group serves only a weak role in initial substrate recognition, while potency is driven by the formation of a reversible covalent bond with a key active site serine residue via the boronic acid electrophile. This hypothesis is further supported by observations from the slow-binding inhibition assay, in which compounds with larger acyl groups such as 2 and 3 achieved their maximum potency faster than compound 4.

In addition to their high potency, these compounds are extremely selective for ClbP over other proteases and serine hydrolases. One of the potential risks of using electrophilic inhibitors is that their high potency and slow off-rates will lead to inhibition of a large number of cellular targets. Herein, a broad range of potential secondary targets were surveyed by using ABPP assays that directly examine binding of these inhibitors, as well as metabolomics. Examining additional aspects of inhibitor selectivity would be aided by the preparation of chemical tools based on 1-4 which can form irreversible covalent bonds with ClbP and other potential targets. However, the fact that these compounds show limited toxicity to a variety of organisms, including bacteria and mammalian cells, and minimal metabolic perturbation outside of the colibactin pathway are strong evidence that their off-target effects are low.

One of the most promising aspects of these inhibitors is the opportunity to study colibactin's effects in the context of a complex pks+ community. It is demonstrated wherein that 3 can selectively block colibactin biosynthesis in E. coli NC101 in the presence of complex gut community without antibiotic activity against any of the representatives of major gut bacterial phyla tested. These experiments also showed that baseline production of the prodrug scaffold is more than 10-fold lower in a community setting versus in monoculture. This dramatic difference is a reminder that studies in which germ-free mice are monocolonized with pks+ bacteria cannot offer a complete picture of colibactin's impacts in a community context. Small molecules tools like 3 will enable studies to determine whether observations from monocolonization studies can be reproduced in conventional hosts with pks+ communities.

Finally, it was confirmed that, in addition to blocking the formation of key metabolites like the prodrug scaffold, 3 can also prevent the genotoxic effects of colibactin on human cells. Treatment with 3 prevents cell cycle arrest, DNA adduct formation, and FANCD2 ubiquitination, biomarkers which have been widely used to monitor colibactin's carcinogenic effect.[10,15,16] One of the major challenges to studying colibactin has been the inability to establish precise control over colibactin exposure, limiting our ability to establish clear, causal connections between this unique toxin and the changes in the host which have been attributed to it. The present inhibitors can address this problem and permit dissection of colibactin's role in cancer in a new level of detail.

Chemical modulation of gut microbial functions is a promising avenue both for therapeutic intervention and for enabling basic research into the mechanisms of host-microbiota interactions.[46-48] Applying this strategy to colibactin biosynthesis offers a new way to interrogate the relationships between this enigmatic natural product, the surrounding microbiota, their host, and cancer.

Methods

Constructs and protein purification for in vitro assays. ClbP constructs described in this publication were derived from a previously described plasmid containing the Escherichia coli CFT073 ClbP sequence (GenBank ID: NP_754344.1) inserted between the NdeI and XhoI restriction sites of pET29b (Addgene plasmid #48244).[14] All in vitro experiments used a construct bearing a C-terminal 10×His tag. This longer polyhistidine-tag was obtained by extension of the previously described 6×His tag through site-directed mutagenesis. All site-directed mutations were introduced using the Quikchange mutagenesis protocol (Stratagene) and confirmed by Sanger DNA sequencing of the whole open reading frame. Plasmids were transformed into chemically competent C41(DE3) (Lucigen) cells and proteins were isolated as previously described.[34]

ClbP fluorescence activity assay (in vitro). Assays were performed in a buffer containing 50 mM Tris, 200 mM NaCl, 0.02% w/v DDM at pH 8.0 with 25 nM purified ClbP and 25 µM fluorogenic substrate in a total volume of 20 µL.[34] Purified ClbP was defrosted on ice from stocks stored at −80° C. Stocks were diluted to 50 nM enzyme in assay buffer in the wells of a black, flat-bottom 384-well plate and the appropriate inhibitor in DMSO or DMSO was added to a final concentration of 1%. For experiments testing different inhibitor concentrations, reactions were allowed to sit for 1 hour at room temperature. For experiments testing different preincubation times, the inhibitor in DMSO was added to each reaction X minutes before initiating the reaction, where X is the time indicated on the x-axis for that sample. For experiments to test whether hydrolysis of the boronic ester was rate-limiting, the inhibitor was added to buffer with no enzyme present and allowed to sit at room temperature for the time indicated before adding the enzyme. In all cases, reactions were initiated by the addition of 10 µL, of buffer containing the 50 µM fluorogenic substrate to achieve a final concentration of 25 µM and pipetting once with a multichannel pipette to mix. Reaction progress was monitored in a plate reader (Bio-Tek Synergy HTX multimode plate reader) with an excitation filter of 360/40 nm and an emission filter of 440/20 nm. "% activity" was determined based on the measured relative fluorescence units (RFU) of each condition after 1 hour using the following formula:

$$\% \text{ activity} = \frac{RFU_{sample} - RFU_{ClbP-S95A}}{RFU_{vehicle} - RFU_{ClbP-S95A}} \times 100$$

ClbP fluorescence activity assay (live cells). One 5 mL starter culture each E. coli BL21 pET-29b-ClbP and pET-29b-ClbP-S95A were inoculated from frozen stocks and grown overnight at 37° C. in LB medium supplemented with 50 µg/ml kanamycin (LB+kan). Overnight cultures were diluted 1:100 in fresh LB+kan and incubated at 37° C. to an $OD_{600}$ of 0.3, at which point protein expression was induced by the addition of 500 µM isopropyl β-D-1-thiogalactopyranoside (IPTG) and cultures were moved to 15° C. for 4 hours. Cultures were then aliquoted in a black 384-well plate and the appropriate concentration of inhibitor was added as a DMSO stocks to a final concentration of 1% DMSO in a volume of 30 µL. Reactions were initiated by the addition of 10 µL of LB+kan+IPTG containing the fluorogenic substrate (final concentration=100 µM). Plastes were incubated at 25° C. with intermittent shaking while taking regular fluorescence measurements in a Bio-Tek Synergy HTX multimode plate reader with an excitation filter of 360/40 nm and an emission filter of 440/20 nm. "% activity" was determined based on the formula above using RFU measurements after 7 hours.

LC-MS quantitation of N-myristoyl-D-Asn produced by pks+ E. coli. One 5 mL starter culture each of E. coli BW25113 BACpks and E. coli BW25113 BACpksΔclbP was inoculated from frozen stocks and grown overnight at 37° C. in LB medium supplemented with 35 µg/ml chloramphenicol (LB+cam). Overnights were diluted 1:100 in fresh LB+cam+1% DMSO with the appropriate concentration of inhibitor and grown for 20 hours at 37° C. in a deep well plate in a shaking incubator. A 500 µL aliquot was taken from each sample, flash frozen in liquid nitrogen and lyophilized to dryness. Lyophilized pellets were extracted with 500 µL LC-MS grade methanol which contained 100 nM $d_{27}$-N-myristoyl-D-asparagine as an internal standard, prepared as previously described, and vortexed for 30 seconds. After centrifugation at 16,500×g for 10 minutes in a tabletop microcentrifuge, supernatants were transferred to fresh 1.5 mL tubes and stored at −20° C. overnight. Samples were centrifuged again, and the supernatants analyzed by LC-MS/MS on a Waters Xevo TQ-S UPLC-triple quadrupole mass spectrometer using an Agilent Poroshell 120 EC-C18 column (2.7 µm, 4.6 mm×50 mm). The conditions were as follows: 0.6 mL/minute flow rate, 5 µL, injection, 10% solvent B in solvent A for 1 min, a linear gradient increasing to 90% solvent B in solvent A over 2 min, 90% solvent B in solvent A for 1.5 min, followed by a linear gradient to 2% solvent B in solvent A over 30 seconds, and re-equilibration in at 2% s solvent B for 1 minute. (solvent A=95:5 water/methanol+0.03% ammonium hydroxide; solvent B=80:15:5 isopropanol/methanol/water; flow rate 0.6 mL/min, 5 µL injection). The mass spectrometer was run in negative mode MRM with a Cone voltage of 2V, monitoring transitions of m/z 341→m/z 114 (retention time (rt)=3.3 minutes, Collision Energy (CE)=20 V) for the prodrug scaffold and m/z 368→m/z 114 (rt=3.3 minutes, CE=22 V) for the deuterated internal standard. Data analysis was conducted using the TargetLynx software platform (Waters) and Microsoft Excel. For all samples, peak areas for the m/z 341→m/z 114 were normalized to the m/z 368→m/z 114 transition for the same sample, and then normalized values compared to a standard curve of unlabeled N-myristoyl-D-asparagine containing 100 nM $d_{27}$-N-myristoyl-D-asparagine, which was run in triplicate.

ClbP expression and purification for crystallography. ClbP-6×His was expressed and purified as described.[40] C41(DE3) cells transformed with the construct were grown in terrific broth supplemented with 50 µg/mL kanamycin until they reached an optical density at 600 nm of 0.6. Cells were induced with 0.5 mM IPTG and grown for 20 hours at 15° C. Cells were harvested through centrifugation at 4000 rpm (Beckman JS4.2 rotor) for 15 minutes and flash frozen. To isolate the membrane fraction, cells were thawed and resuspended in load buffer (20 mM sodium phosphate pH 8.0, 20 mM imidazole, 500 mM NaCl, 10% glycerol) supplemented with 1 mM phenylmethylsulfonyl fluoride and 1 mM benzamidine. Cells were disrupted by sonication on ice (six cycles of 45 seconds each in a Branson Sonifier 450 under duty cycle of 65% and output control of 10) and cell debris was cleared from the lysate by centrifugation at 20,000 rpm (Beckman JA-20) for 20 minutes. Membranes were pelleted by ultracentrifugation at 45,000 rpm (Beckman type 45Ti) for 70 minutes, homogenized in load buffer using a glass Potter-Elvehjem grinder, and solubilized by incubation with 1% (w/v) n-dodecyl-β-D-maltoside (DDM; Anatrace) for 2 hours under constant mixing at 4° C. Detergent-insoluble materials were removed by ultracentrifugation at 35,000 rpm (Beckman type 45Ti) for 35 minutes and the supernatant was incubated with Ni-sepharose resin (Qiagen) for 2 hours under constant mixing. The resin was washed with 12 column volumes (CV) of load buffer containing 0.03% DDM, 10 CV of load buffer containing 0.5% lauryl maltose neopentyl glycol (LMNG; Anatrace), and 12 CV of load buffer containing 0.1% LMNG. ClbP was eluted in two fractions of 6 CV and 3 CV of load buffer containing 450 mM imidazole and 0.01% LMNG. Both elutions were combined, concentrated, and injected onto an S200 10/300 size exclusion column (GE Healthcare) equilibrated with SEC buffer (10 mM Tris pH 8.1, 150 mM NaCl, 0.003% LMNG). Column fractions enriched with ClbP were pooled, concentrated to 7 mg/mL in a volume of 450 µL and incubated with a ~10-fold molar excess of 1 (addition of 11 µL of a 50 mM DMSO stock) on ice for 3 hours to allow complete binding. Protein was finally concentrated to 24 mg/mL and flash frozen.

Inhibitor-bound ClbP crystallization. Inhibitor-bound wildtype ClbP was crystallized as described.[40] In short, frozen stocks of wildtype ClbP incubated with 1 were thawed and reconstituted in a monopalmitolein mesophase (1:1 protein to monopalmitolein ratio) using the syringe reconstitution method. The mesophase bolus was dispensed onto custom-made 96-well glass sandwich plates using an NT8 drop setter (Formulatrix) in 75 nL drops and overlaid with 900 nL of precipitant (mixture of 200 nL of 0.1 M imidazole pH 7.8, 10% (v/v) PEG400, 150 mM Li$_2$SO$_4$ containing 11 mM of 1 and 700 nL of 0.1 M Tris pH 7.2, 25% (v/v) PEG400, 200 mM Li$_2$SO$_4$). Crystals appeared after 12 hours and were harvested after 7 days by using mesh loops (MiTeGen) and plunge freezing in liquid nitrogen.

Diffraction data collection and processing. Diffraction data were collected at beamline 23ID-B of the Advanced Photon Source at a wavelength of 0.98 Å. Data from a single crystal were indexed using DIALS[49], scaled in CCP4 AIMLESS[50,51], and phased by molecular replacement in PHENIX[52] using the model of full-length ClbP reported in an accompanying paper[40] (PDB: 7MDE) as search model. Data statistics are listed in Table 1.

Structure refinement and model building. Model building was done in COOT[53] and refinement was done in Phenix.refine by series of 5 macrocycles including reciprocal space refinement, TLS parameters, and individual B-factors and optimizing the X-ray/ADP weights. The final model of inhibitor-bound ClbP contained residues 36-409 and 430-491, with 96.3% of backbone atoms in Ramachandran favored regions, 3.7% in allowed regions, and no outliers. Model statistics are listed in Table 1. Structural biology applications used in this project were compiled and configured by SBGrid[54].

Metabolomics. One 5 mL starter culture each of E. coli BW25113 BACpks and E. coli BW25113 BACpksΔclbP was inoculated from frozen stocks and grown overnight at 37° C. in LB medium supplemented with 35 µg/ml chloramphenicol (LB+cam). Overnights were diluted 1:1000 in fresh LB+cam+1% DMSO with or without 1 µM inhibitor 3 in 5 replicates for each condition and grown for 20 hours at 37° C. A 500 µL aliquot was taken from each replicate, flash frozen in liquid nitrogen and lyophilized to dryness. Lyophilized pellets were extracted with 500 µL LC-MS grade methanol and prepared in the same manner as described above for metabolomics. Samples were analyzed by LC-MS on an Agilent Technologies 1200 series LC with a Phenomenex Luna C18 column (5 µm, 100 Å, 250×4.6 mm) coupled to an Agilent 6530 Quadrupole-Time of Flight mass spectrometer. The following chromatography conditions were used: 99% Solvent A in Solvent B for 1.5 minutes, linear gradient to 0% Solvent A in Solvent B over 43.5 minutes, 0% Solvent A for 8 minutes, linear gradient back to 99% Solvent A over 1 minute, equilibration in 99% solvent A for 9 minutes at flow rate of 0.4 mL/min and a 10 uL injection volume. Solvent A is water with 0.1% formic acid, solvent B is acetonitrile with 0.1% formic acid. Mass spectrometry was conducted in ESI+ mode, with a source gas flow of 8 L/min at 275° C., capillary voltage of 3500 V, fragmentor at 175 V, skimmer at 65 V, Oct1 RF at 750 V. Data analysis was conducted on the XCMS online platform using the standard "Q-TOF" parameter set in pairwise comparison mode.[55]

Activity-Based Protein Profiling. Bacterial or mammalian cell lysates were normalized to 1 mg/mL protein concentrations in PBS using the DC protein assay (Bio-Rad). 50 µL aliquots of lysates were incubated with compounds at the indicated concentrations (1 µL of a 50X stock in DMSO) for 30 minutes at room temperature and subsequently labeled with 5 µM of fluorophosphonate-PEG(4)-biotin probe (1 µL of a 50X stock in DMSO, synthesized as previously reported)[56] for 1 hour at room temperature. The reactions were mixed with 50 µL of 2X SDS protein loading buffer, boiled for 10 minutes at 95° C., and separated by SDS-PAGE. The labeled proteins were detected by IRdye-conjugated streptavidin (Li-Cor) and visualized using the GellOdyssey™ Imaging System (Li-Cor).[56]

ClbP inhibition in a microbial community. Mouse pellets were aseptically collected from cages and immediately stored at −80° C. until use. One 5 mL starter culture each of E. coli NC101 and E. coli NC101ΔclbP was started from frozen stocks in deoxygenated Brain-Heart Infusion media (BHI) inside an anaerobic chamber under a 95% N2/5% H2 atmosphere and incubated at 37° C. overnight. Mouse fecal pellets were defrosted in the anaerobic chamber and resuspended in BHI with 10 mL media/100 mg pellet mass. The fecal slurry was then centrifuged at 1000×g for 5 minutes to separate solids and the resulting supernatant was used as the media for all "+ community" conditions. Cultures were incubated in 500 µL volumes in triplicate in a deep-well plate under anaerobic conditions, with a 1:100 inoculum of the appropriate E. coli overnight for the "+E. coli" conditions. All samples contained a final concentration of 1% DMSO, with or without 1 µM inhibitor 3. After 20 hours at 37° C., samples were processed, and the concentration of N-myristoyl-D-asparagine quantified via LC-MS/MS as described above.

General tissue culture methods. HeLa cells (ATCC CCL-2) were maintained at 37° C. in a humidified 5% $CO_2$ incubator using Gibco Dulbecco's Modified Eagle Medium (DMEM, Themo Fisher Scientific) supplemented with 10% Fetal Bovine Serum (FBS, Thermo Fisher Scientific) and penicillin/streptomycin/amphotericin B cocktail (Thermo Fisher Scientific). Cell stocks were passaged every 3 days at a 1:4 split ratio.

Infection with pks+ E. coli. Assays for cell-cycle arrest and FANCD2 ubiquitination were performed by seeding 24-well plates with 125,000 HeLa cells per well and incubating those plates under standard conditions for 24 hours. At the same time, cultures of NC101 and NC101ΔclbP were started from frozen stocks in LB broth and grown at 37° C. with shaking overnight. The next day, bacterial overnights were diluted 1:50 into fresh tissue culture media which did not contain antibiotics (DMEM+FBS). Cultures were monitored until an $OD_{600}$ of 0.3-0.5 was reached. At that point, samples of the cultures were removed and DMSO stock solutions of the inhibitor of interest were added to each sample to a final concentration of 1% DMSO and the concentration of inhibitor indicated.

Media in the 24-well plate was aspirated, HeLa cells were washed with sterile DPBS (Thermo Fisher Scientific), and fresh DMEM+FBS+1% DMSO with the indicated concentration of inhibitor was added. A volume of E. coli equivalent to $2.5 \times 10^7$ bacteria based on OD in DMEM+FBS+1% DMSO with the indicated concentration of inhibitor was then added directly to wells (Multiplicity of Infection, MOI 1:100). Infections were carried out for 4 hours at 37° C. in a humidified 5% $CO_2$ incubator. Media was then aspirated and cells were washed with DPBS twice to remove bacteria, and fresh DMEM+FBS+PSF supplemented with 50 µg/mL gentamicin was added.

Cell Cycle Analysis. Between 20 and 24 hours after infection, HeLa cells were trypsinized (0.25% Trypsin-EDTA, Gibco), washed with DPBS, and fixed in cold 70% ethanol and stored at 4° C. until flow cytometry analysis (24-48 hours). Cells were centrifuged at 800×g for 10 minutes and 70% ethanol was aspirated. Cells were resuspended in DPBS for 15 minutes, then centrifuged and supernatant aspirated again. Cells were then resuspended in DPBS with 0.2 mg/mL RNAse A (Invitrogen) and 0.02 mg/mL propidium iodide (Millipore Sigma). After 30 minutes, cells were analyzed on a BD LSR II Analyzer at the Harvard University Bauer Core Flow Cytometry Facility. For each replicate, 10,000 events were collected and results were gated for single cells and plotted using the FloJo™ software package.

DNA adduct detection. Infections for DNA adduct detection were carried out using the protocol described above in 6-well plates where all volumes and cell numbers were increased by a factor of 4 accordingly. After trypsinization, cell pellets were frozen at −80° C. until analysis. DNA was isolated from cells as previously reported.[15] DNA samples (100 µL, 31-48 µg) in silanized glass vials were incubated at 80° C. for 1 hour. After the incubation, samples were allowed to cool to room temperature, and volumes were increased to 200 µL by adding LC-MS grade water. Samples were filtered using a Centrifree Ultrafiltration Device (30K molecular weight, Millipore Sigma) at 2000× g for 15 minutes. Samples were dried under vacuum and stored at −20° C. Mass spectrometric data was acquired with the following conditions. The dried samples were reconstituted in 10 µL of $H_2O$ and 4 µL of the resulting solution were injected onto an UltiMate 3000 RSLCnano UPLC (Thermo Fisher Scientific) system equipped with a 5 µL injection loop. Separation was performed with a capillary column (75 µm ID, 20 cm length, 10 µm orifice) created by hand packing a commercially available fused-silica emitter (New Objective, Woburn, MA) with 5 µm Luna C18 bonded separation media (Phenomenex, Torrance, CA). The flow rate was 1000 nL/min for 5.5 min at 0% $CH_3CN$, then decreased to 300 nL/min followed by a linear gradient of 0.05% formic acid aqueous solution of 3.57%/min over 7 min. The column was washed at 95% $CH_3CN$ for 2 min and re-equilibrated at 0% $CH_3CN$ with a flow rate of 1000 nL/min over 2 min. The injection valve was switched at 5.5 min to remove the sample loop from the flow path during the gradient. Mass spectrometric data was acquired with an Orbitrap Lumos mass spectrometer (Thermo Fisher Scientific). Positive mode electrospray ionization was used under nanospray conditions (300 nL/min) using a Thermo Scientific Nanoflex ion source with a source voltage of 2.2 kV. The instrument was operated with a capillary temperature of 300° C. and an S-Lens RF level setting of 40%. Targeted MS/MS spectra of the m/z 540.1772 analyte were acquired with a quadrupole isolation window of m/z 1.5 centered on m/z 540.2 with an HCD fragmentation setting of 25%, resolution setting of 120000, normalized AGC target of 2000%, and maximum injection times of 1000 ms. All spectra were acquired with the EASY-IC lock mass (m/z 202.0777) enabled.

Western Blot for FANCD2. Infections were carried out as described above. For conditions which involved other small molecules, no bacteria were introduced during the infection and cells were treated with either 0.5 µg/mL mitomycin C (MMC) or 7.5 µg/mL cisplatin under the same conditions for 4 hours. 20 hours after infection, cells were lysed directly in the culture wells (Lysis buffer: 50 mM Tris, (pH 8.0), 150 mM NaCl, 1% Triton X-100, 0.5% Sodium deoxycholate, 0.05% sodium dodecylsulfate, 1 mM $MgSO_4$, SIGMAFAST Protease inhibitor mix, 100 U/mL benzonase (Millipore-Sigma). Lysates were then spun down at 16,000×g to remove particulates and the supernatant was mixed 1:1 with 2X Laemmli sample buffer (Bio-Rad) containing 50 mg/mL dithiothreitol (DTT). Samples were then heated at 70° C. for 10 minutes and run on an SDS-PAGE gel (3-8% Tris-Acetate Novex gel, Invitrogen) at 150 V for 1.5 hours at 4° C. Bands were then transferred to PVDF membranes (100 V, 1 hour at 4° C.) and blocked with 10% skim milk powder in TBST buffer at 4° C. overnight. Blots were probed sequentially with either mouse anti-actin (1.5 µg/mL) or mouse anti-FANCD2 (0.1 µg/mL) primary antibodies (Thermo Fisher Scientific, Catalog #MA511869 and MA123347), followed by a peroxidase-conjugated goat anti-mouse secondary antibody (Jackson ImmunoResearch product 115-035-003, 0.08 µg/mL). Each probing step was conducted for 90 minutes at room temperature n 2.5% skim milk powder in TBST. Before imaging, blots were washed 3×15 minutes each in TBST for 10 minutes. Blots were imaged using the SuperSignal™ West Pico PLUS Chemiluminescent Substrate (Thermo Fisher Scientific) kit following the manufacturer's instructions and imaged using an Azure Biosystems c300 imager.

Data availability. Atomic coordinates and structure factors for the reported crystal structures in this work have been deposited to the Protein Data Bank under accession number 7MDC. Corresponding X-ray diffraction images have been deposited to the SBGrid Data Bank under accession number 832 (doi:10.15785/SBGRID/832).

REFERENCES

1. Milshteyn, A., Colosimo, D. A. & Brady, S. F. Accessing Bioactive Natural Products from the Human Microbiome. *Cell Host and Microbe* vol. 23 725-736 (2018).
2. Wong, S. H. & Yu, J. Gut microbiota in colorectal cancer: mechanisms of action and clinical applications. *Nature Reviews Gastroenterology & Hepatology* 2019 16: 11 16, 690-704 (2019).
3. Ternes, D. et al. Microbiome in Colorectal Cancer: How to Get from Meta-omics to Mechanism? *Trends in Microbiology* vol. 28 401-423 (2020).
4. Janney, A., Powrie, F. & Mann, E H. Host-microbiota maladaptation in colorectal cancer. *Nature* vol. 585 509-517 (2020).
5. Nougayrede, J.-P. et al. *Escherichia coli* Induces DNA Double-Strand Breaks in Eukaryotic Cells. *Science* 313, 848-851 (2006).
6. Putze, J. et al. Genetic Structure and Distribution of the Colibactin Genomic Island among Members of the Family Enterobacteriaceae. *Infection and Immunity* 77, 4696-4703 (2009).
7. Sarshar, M. et al. Genetic diversity, phylogroup distribution and virulence gene profile of pks positive *Escherichia coli* colonizing human intestinal polyps. *Microbial Pathogenesis* 112, 274-278 (2017).
8. Brotherton, C. A., Wilson, M., Byrd, G. & Balskus, E. P. Isolation of a metabolite from the pks island provides insights into colibactin biosynthesis and activity. *Organic Letters* 17, 1545-1548 (2015).
9. Vizcaino, M. I., Engel, P., Trautman, E. & Crawford, J. M. Comparative metabolomics and structural characterizations illuminate colibactin pathway-dependent small molecules. *Journal of the American Chemical Society* 136, 9244-9247 (2014).
10. Bossuet-Greif, N. et al. The Colibactin Genotoxin Generates DNA Interstrand Cross-Links in Infected Cells. *mBio* 9, 1-15 (2018).
11. Jiang, Y. et al. Reactivity of an Unusual Amidase May Explain Colibactin's DNA Cross-Linking Activity. *Journal of the American Chemical Society* 141, (2019).
12. Xue, M. et al. Structure elucidation of colibactin and its DNA cross-links. *Science* 365, (2019).
13. Dubois, D. et al. ClbP Is a Prototype of a Peptidase Subgroup Involved in Biosynthesis of Nonribosomal Peptides. *Journal of Biological Chemistry* 286, 35562-35570 (2011).
14. Brotherton, C. A. & Balskus, E. P. A Prodrug Resistance Mechanism Is Involved in Colibactin Biosynthesis and Cytotoxicity. *Journal of the American Chemical Society* 135, 3359-3362 (2013).
15. Wilson, M. R. et al. The human gut bacterial genotoxin colibactin alkylates DNA. *Science* 363, eaar7785 (2019).
16. Arthur, J. C. et al. Intestinal Inflammation Targets Cancer-Inducing Activity of the Microbiota. *Science* 338, 120-123 (2012).
17. Buc, E. et al. High Prevalence of Mucosa-Associated *E. coli* Producing Cyclomodulin and Genotoxin in Colon Cancer. *PLoS ONE* 8, e56964 (2013).
18. Cougnoux, A. et al. Bacterial genotoxin colibactin promotes colon tumour growth by inducing a senescence-associated secretory phenotype. *Gut* 1-11 (2014) doi:10.1136/gutjnl-2013-305257.
19. Dejea, C. M. et al. Patients with familial adenomatous polyposis harbor colonic biofilms containing tumorigenic bacteria. *Science* 359, 592-597 (2018).
20. Dziubanska-Kusibab, P. J. et al. Colibactin DNA-damage signature indicates mutational impact in colorectal cancer. *Nature Medicine* 26, 1063-1069 (2020).
21. Pleguezuelos-Manzano, C. et al. Mutational signature in colorectal cancer caused by genotoxic pks+*E. coli*. *Nature* (2020) doi:10.1038/s41586-020-2080-8.
22. Boot, A. et al. Characterization of colibactin-associated mutational signature in an Asian oral squamous cell carcinoma and in other mucosal tumor types. *Genome Research* 30, 803-813 (2020).
23. Lee-Six, H. et al. The landscape of somatic mutation in normal colorectal epithelial cells. *Nature* 574, 532-537 (2019).

24. Iftekhar, A. et al. Genomic aberrations after short-term exposure to colibactin-producing *E. coli* transform primary colon epithelial cells. *Nature Communications* 12, 1003 (2021).
25. Massip, C. et al. Deciphering the interplay between the genotoxic and probiotic activities of *Escherichia coli* Nissle 1917. *PLOS Pathogens* 15, e1008029 (2019).
26. Olier, M. et al. Genotoxicity of *Escherichia coli* nissle 1917 strain cannot be dissociated from its probiotic activity. *Gut Microbes* 3, 501-509 (2012).
27. Tronnet, S. et al. Iron homeostasis regulates the genotoxicity of *Escherichia coli* producing colibactin. *Infection and immunity* IAI.00659-16 (2016) doi:10.1128/IAI.00659-16.
28. Massip, C., Chagneau, C. v., Boury, M. & Oswald, E. The synergistic triad between microcin, colibactin, and salmochelin gene clusters in uropathogenic *Escherichia coli*. *Microbes and Infection* 22, 144-147 (2020).
29. Arthur, J. C. et al. Microbial genomic analysis reveals the essential role of inflammation in bacteria-induced colorectal cancer. *Nature Communications* 5, 4724 (2014).
30. Yang, Y., Gharaibeh, R. Z., Newsome, R. C. & Jobin, C. Amending microbiota by targeting intestinal inflammation with TNF blockade attenuates development of colorectal cancer. *Nature Cancer* 1, 723-734 (2020).
31. Balskus, E. P. Colibactin: understanding an elusive gut bacterial genotoxin. *Natural product reports* 32, 1534-40 (2015).
32. Healy, A. R. & Herzon, S. B. Molecular basis of gut microbiome-associated colorectal cancer: A synthetic perspective. *Journal of the American Chemical Society* jacs.7b07807 (2017) doi:10.1021/jacs.7b07807.
33. Jacoby, G. A. AmpC B-Lactamases. *Clinical Microbiology Reviews* 22, 161-182 (2009).
34. Volpe, M. R. et al. In Vitro Characterization of the Colibactin-Activating Peptidase ClbP Enables Development of a Fluorogenic Activity Probe. *ACS Chemical Biology* acschembio.9b00069 (2019) doi:10.1021/acschembio.9b00069.
35. Cougnoux, A. et al. Small-molecule inhibitors prevent the genotoxic and protumoural effects induced by colibactin-producing bacteria. *Gut* 65, 278-285 (2016).
36. Diaz, D. B. & Yudin, A. K. The versatility of boron in biological target engagement. *Nature chemistry* 9, 731-742 (2017).
37. López, A., Clark, T. B., Parra, A. & Tortosa, M. Copper-Catalyzed Enantioselective Synthesis of β-Boron β-Amino Esters. *Organic Letters* 19, 6272-6275 (2017).
38. Smoum, R., Rubinstein, A., Dembitsky, V. M. & Srebnik, M. Boron containing compounds as protease inhibitors. *Chemical Reviews* vol. 112 4156-4220 (2012).
39. Stein, R. L., DeCicco, C., Nelson, D. & Thomas, B. Slow-binding inhibition of γ-glutamyl transpeptidase by γ-boroglu. *Biochemistry* 40, 5804-5811 (2001).
40. Velilla, J. A., Volpe, M. R., Kenney, G. E., Balskus, E. P. & Gaudet, R. Structural basis of colibactin activation by the ClbP Peptidase. *Submitted Manuscript* (2021).
41. Li, Z. R. et al. Critical Intermediates Reveal New Biosynthetic Events in the Enigmatic Colibactin Pathway. *ChemBioChem* 16, 1715-1719 (2015).
42. Liu, Y., Patricelli, M. P. & Cravatt, B. F. Activity-based protein profiling: The serine hydrolases. *Proceedings of the National Academy of Sciences of the United States of America* 96, 14694-14699 (1999).
43. Bachovchin, D. A. et al. A high-throughput, multiplexed assay for superfamily-wide profiling of enzyme activity. *Nature Chemical Biology* 10, 656-663 (2014).
44. Tomkovich, S. et al. Locoregional Effects of Microbiota in a Preclinical Model of Colon Carcinogenesis. *Cancer Research* 77, 2620-2632 (2017).
45. Wang, X., Andreassen, P. R. & D'Andrea, A. D. Functional Interaction of Monoubiquitinated FANCD2 and BRCA2/FANCD1 in Chromatin. *Molecular and Cellular Biology* 24, 5850-5862 (2004).
46. Adhikari, A. A. et al. Development of a covalent inhibitor of gut bacterial bile salt hydrolases. *Nature Chemical Biology* 16, 318-326 (2020).
47. Wallace, B. D. et al. Alleviating Cancer Drug Toxicity by Inhibiting a Bacterial Enzyme. *Science* 330, 831-835 (2010).
48. Rekdal, V. M., Bess, E. N., Bisanz, J. E., Turnbaugh, P. J. & Balskus, E. P. Discovery and inhibition of an interspecies gut bacterial pathway for Levodopa metabolism. *Science* 364, 1055 (2019).
49. Winter, G. et al. DIALS: Implementation and evaluation of a new integration package. *Acta Crystallographica Section D: Structural Biology* 74, 85-97 (2018).
50. Winn, M. D. et al. Overview of the CCP4 suite and current developments. *Acta Crystallographica Section D: Biological Crystallography* vol. 67 235-242 (2011).
51. Evans, P. R. & Murshudov, G. N. How good are my data and what is the resolution? *Acta Crystallographica Section D: Biological Crystallography* 69, 1204-1214 (2013).
52. Liebschner, D. et al. Macromolecular structure determination using X-rays, neutrons and electrons: Recent developments in Phenix. *Acta Crystallographica Section D: Structural Biology* 75, 861-877 (2019).
53. Emsley, P., Lohkamp, B., Scott, W. G. & Cowtan, K. Features and development of Coot. *Acta Crystallographica Section D: Biological Crystallography* 66, 486-501 (2010).
54. Morin, A. et al. Collaboration gets the most out of software. *eLife* 2013, (2013).
55. Tautenhahn, R., Patti, G. J., Rinehart, D. & Siuzdak, G. XCMS online: A web-based platform to process untargeted metabolomic data. *Analytical Chemistry* 84, 5035-5039 (2012).
56. Griswold, A. R. et al. DPP9's Enzymatic Activity and Not Its Binding to CARD8 Inhibits Inflammasome Activation. *ACS Chemical Biology* 14, 2424-2429 (2019).

TABLE 1

$IC_{50}$ values of 1-4 measured both in vitro and in *E. coli* using a fluorogenic assay, with 95% confidence interval values given in parentheses.

| Compound | $IC_{50}$ measured in vitro (95% confidence interval) | $IC_{50}$ measured in *E. coli* BL21 overexpressing ClbP (95% confidence interval) |
| --- | --- | --- |
| 1 | 40 nM (30-54 nM) | 5.6 nM (4.0-7.9 nM) |
| 2 | 34 nM (22-54 nM) | 7.2 nM (5.2-10.0 nM) |
| 3 | 28 nM (19-40 nM) | 18.3 nM (12-28 nM) |
| 4 | 69 nM (52-92 nM) | 27 nM (18-38 nM) |

All assays were conducted with n = 4 biological replicates and normalized dose-response data was fit to a non-linear three parameter model.

TABLE 2

Data collection and refinement statistics (molecular replacement)

|  | WT ClbP bound to 1 |
|---|---|
| Data collection | |
| Space group | $P\,4_2\,2_1\,2$ |
| Cell dimensions | |
| a, b, c (Å) | 96.72, 96.72, 183.38 |
| α, β, γ (°) | 90, 90, 90 |
| Resolution (Å) | 45.58-2.47 (2.56-2.47) |
| $R_{sym}$ or $R_{merge}$ | 0.3284 (3.224) |
| I/σI | 6.46 (0.92) |
| Completeness (%) | 99.83 (99.36) |
| Redundancy | 11.0 (10.9) |
| Refinement | |
| Resolution (Å) | 45.58-2.47 (2.56-2.47) |
| No. reflections | 31990 (3118) |
| $R_{work}/R_{free}$ | 0.2026/0.2440 |
| No. atoms | 3630 |
| Protein | 3305 |
| Ligand/ion | 108 |
| Water | 217 |
| B-factors | |
| Protein | 56.26 |
| Ligand/ion | 75.36 |
| Water | 51.72 |
| R.m.s. deviations | |
| Bond lengths (Å) | 0.007 |
| Bond angles (°) | 0.87 |

*Values in parentheses are for highest-resolution shell.

TABLE 3

Minimum inhibitory concentrations (MICs) of compounds against other gut bacteria.

| | MICs by compound (μM) | | | | |
|---|---|---|---|---|---|
| Species | CAM | 1 | 2 | 3 | 4 |
| *Escherichia coli* NC101 | 25 | >200 | >200 | >200 | >200 |
| *Klebsiella oxytoca* | 6.25 | >200 | >200 | >200 | >200 |
| *Lactobacillus rhamnosus* | 25 | >200 | >200 | >200 | >200 |
| *Enterococcus faecalis* | 50 | >200 | >200 | >200 | >200 |
| *Bifidobacterium longum* | 12.5 | >200 | >200 | >200 | >200 |

Chloramphenicol (CAM) was included as a control for antibiotic activity. MICs were determined in using a broth dilution assay (see Supplemental Methods) and measuring $OD_{600}$ values after 15 hours of growth compared to DMSO control. Values reported here are the lowest concentration of compound at which a statistically significant (P < 0.05, one-way ANOVA and Dunnett's multiple comparison test, n = 3 biological replicates). "≤6.25" indicates that significant growth inhibition was observed even at the lowest concentration tested; ">200" indicates that no significant growth inhibition was observed at any concentration tested.

Supplemental Methods
Bacterial Strains

*Klebsiella oxytoca* (ATCC 8724) was obtained from the American Type Culture Collection. *Lactobacillus rhamnosus* strain LMS2-1, *Enterococcus faecalis* strain TX0104, and *Bifidobacterium longum* strain 44B were obtained from the Biodefense and Emerging Infections Research Resources Repository.

Chiral LC-MS

Relative chirality of 3 and 3-(R) were determined using an Agilent Technologies 1200 series LC equipped with a Phenomenex Lux 5 mm Amylose-1 column (100×4.6 mm). Compounds were eluted in an isocratic mobile phase of 5% water with 0.1% formic acid/95% acetonitrile with 0.1% formic acid (flow rate=0.5 mL/min; injection volume=2 mL). Compounds were detected using an Agilent 6530 Q-TOF Mass Spectrometer fitted with a dual-spray electrospray ionization (ESI) source. The capillary voltage was set to 3.5 kV, the fragmentor voltage to 175 V, the skimmer voltage to 65 V, and the Oct 1 RF to 750 V. The drying gas temperature was maintained at 275° C. with a flow rate of 8 L/min and a nebulizer pressure of 35 psi. A standard calibrant mix was introduced continuously during all experiments via the dual-spray ESI source in positive mode. Masses corresponding to the $[M+H]^+$ ions (+/−5 ppm) of 3 and 3-(R) were extracted using the Qualitative Analysis software platform and integrated to determine the area under the curve (AUC) for each analyte. Retention times were confirmed by co-injection of the two compounds mixed 1:1, and a dilution series of both compounds was run to ensure that the AUC for these compounds was linear with respect to concentration of compound.

Bacterial Minimum Inhibitory Concentration (MIC) Assay

MICs of compounds against different bacterial species were determined using a modified version of a broth microdilution protocol which has been previously reported.[1] Briefly, cultures of each species indicated were inoculated from frozen stocks in deoxygenated Wilkins-Chalgren Anaerobic Medium (WCAM) inside of an anerobic chamber with an 92.5% $N_2$/5% $CO_2$/2.5% $H_2$ atmosphere. Cultures were grown for 24-48 hours in a 37° C. incubator at which point an $OD_{600}$-measurement was taken for each culture and was accordingly diluted in fresh WCAM to an equivalent of $OD_{600}$=0.01. Diluted cultures were then distributed into the wells of a clear, flat-bottom 384-well plate and the compound of interest was added to a final DMSO concentration of 2% (or DMSO only for positive controls). 10 mL mineral oil (Millipore Sigma) was deposited on top of the cultures and plates were covered with a clear adhesive plate seal. Plates were incubated at 37° C. for 16 hours, at which point the $OD_{600}$ of all wells was recorded on a SpectraMax M2 plate reader (Molecular Devices). All conditions were tested in triplicate, and the MIC was determined as the minimum concentration of inhibitor at which the culture showed a statistically significant decrease (p<0.05, one way ANOVA followed by Dunnett's multiple comparison test) in $OD_{600}$ compared to the DMSO-only control of the same species at the same time point.

HeLa Cell Survival Assay

HeLa cells were maintained as described in the General Tissue Culture Methods section. After trypsinization and counting, cells were distributed in to the wells of a 96-well plate with media containing the indicated concentration of the synthetic compound and 1% DMSO (or DMSO alone) at 5000 cells per well. After 20 hours, cell viability was determined using the CellTiter-Glo® 3D Cell Viability Assay kit (Promega) following the manufacturer's instructions and measuring luminescence on a Bio-Tek Synergy HTX™ multimode plate reader.

Synthetic Procedures

All solvents for synthesis were obtained from Millipore-Sigma unless otherwise noted. All NMR solvents were purchased from Cambridge Isotope Laboratories (Tewksbury, MA). NMR chemical shifts are reported in parts per million downfield from tetramethylsilane using the solvent resonance as internal standard for $^1H$ ($CDCl_3$=7.26 ppm, DMSO-$d_6$=2.50 ppm, $CD_2Cl_2$=5.32 ppm) and $^{13}C$ ($CDCl_3$=77.25 ppm, DMSO-$d_6$=39.52 ppm, $CD_2Cl_2$=54 ppm). Data are reported as follows: chemical shift, integration multiplicity (s=singlet, d=doublet, t=triplet, q=quartet, quint=quintet, m=multiplet), coupling constant, integration, and assignment. NMR spectra were visualized and processed using MestreNova™, version 11.0.2-18153 (Mestrelab Research S.L., Escondido, CA) High-resolution LC-MS (HRMS) analyses of synthetic compounds were performed on an Agilent 6530™ Q-TOF Mass Spectrometer fitted with a dual-spray electrospray ionization (ESI) source. The capillary voltage was set to 3.5 kV, the fragmentor voltage to 175 V, the skimmer voltage to 65 V, and the Oct 1 RF to 750 V. The drying gas temperature was maintained at 275° C. with a flow rate of 8 L/min and a nebulizer pressure of 35 psi. A standard calibrant mix was introduced continuously during all experiments via the dual-spray ESI source. Low-resolution mass spectrometry analysis (LRMS) was conducted by direct infusion on an Advion CMS single-quadrupole mass spectrometer in ESI+ mode.

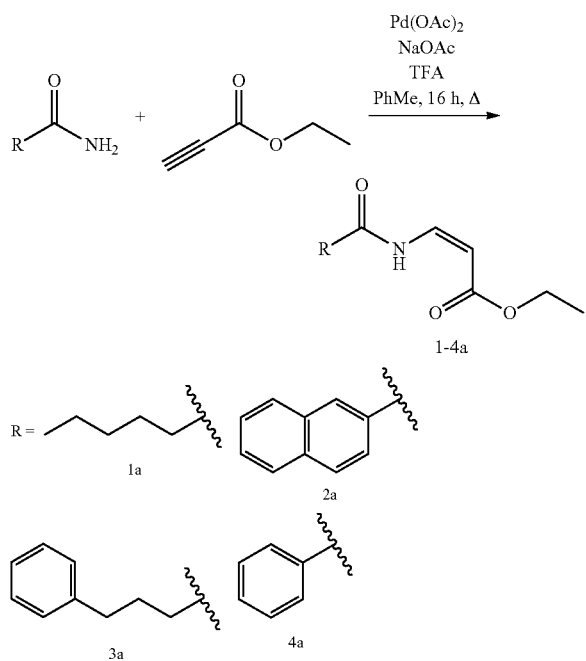

General Procedure A

Intermediates 1a, 2a, 3a, and 4a were prepared using the procedure described by Lopez and coworkers.[2] Briefly, an oven-dried glass microwave vial was charged with palladium (II) acetate (3.3 mg, 0.015 mmol, 0.01 equiv), sodium acetate (246 mg, 3 mmol, 2.0 equiv), the corresponding amide (1.5 mmol, 1.0 equiv), and anhydrous toluene (3.75 mL, 0.4 M). Trifluoroacetic acid (574 µL, 7.5 mmol, 5.0 equiv) was added and the reaction mixture was stirred for 5 minutes under nitrogen atmosphere at room temperature, and then ethyl propiolate (228 µL, 2.25 mmol, 1.5 equiv) was added dropwise. The reaction mixture was then stirred for 5 min and then heated at 80° C. overnight. The reaction mixture was diluted with EtOAc and water was added. The organic layer was separated, and the aqueous layer was extracted with EtOAc three times. The combined organic layers were washed with brine, dried over $Na_2SO_4$, and concentrated in vacuo. The residue was dissolved in EtOAc and purified by flash chromatography on silica (0-100% EtOAc in hexanes). In some cases, when left in solution for extended periods of time, these compounds were observed to equilibrate between the cis and trans isomers. In cases where this was observed, the chromatography was repeated under the same conditions to separate the isomers and use only the cis isomer as shown above in the subsequent step. Yields below refer to the final isolated amount of the cis isomer.

1a: Yield: 137 mg (81%, reaction performed on 1 equiv=0.4 mmol scale). $^1$H NMR (400 MHz DMSO-$d_6$): δ (ppm)=10.62 (d, J=11.2 Hz, 1H), 7.81 (dd, J=14.2, 11.2 Hz, 1H), 5.42 (d, J=14.1 Hz, 1H), 4.08 (q, J=7.1 Hz, 2H), 2.26 (t, J=7.4 Hz, 2H), 1.54 (quint, J=7.4 Hz, 2H), 1.34-1.16 (m, 7H), 0.90-0.81 (m, 3H). $^{13}$C NMR (101 MHz, DMSO-$d_6$) δ=171.9, 168.4, 138.5, 95.9, 60.2, 35.9, 31.2, 24.6, 22.8, 14.7, 14.3. LRMS (ESI): calcd for $C_{11}H_{20}NO_3[M+H]^+$, m/z 214.14; found, m/z 214.15.

2a: Yield: 165 mg (41%). $^1$H NMR (400 MHz DMSO-$d_6$): δ (ppm)=11.46 (d, J=11.1 Hz, 1H), 8.54 (s, 1H), 8.20-8.10 (m, 2H), 8.05 (d, J=8.0 Hz, 1H), 7.91 (d, J=8.6 Hz, 1H), 7.78 (t, J=10.6 Hz, 1H), 7.73-7.63 (m, 2H), 5.36 (d, J=8.9 Hz, 1H), 4.22 (q, J=7.1 Hz, 2H), 1.28 (t, J=7.1 Hz, 3H). $^{13}$C NMR (101 MHz, DMSO-$d_6$) δ=168.7, 163.8, 138.8, 134.9, 132.1, 129.3, 129.1, 129.0, 128.7, 128.5, 127.8, 127.3, 123.2, 97.2, 60.1, 14.1. LRMS (ESI): calcd for $C_{16}H_{16}NO_3$ $[M+H]^+$, m/z 270.11; found, m/z 270.11.

3a: Yield: 121 mg (31%). $^1$H NMR (400 MHz DMSO-$d_6$): δ (ppm)=6 10.34 (d, J=11.6 Hz, 1H), 7.45 (dd, J=11.6, 9.0 Hz, 1H), 7.32-7.24 (m, 2H), 7.22-7.14 (m, 3H), 5.11 (d, J=9.0 Hz, 1H), 4.13 (q, J=7.1 Hz, 2H), 2.59 (dd, J=8.7, 6.7 Hz, 2H), 2.45 (t, J=7.4 Hz, 2H), 1.85 (quint, J=7.5 Hz, 2H), 1.21 (t, J=7.1 Hz, 3H). $^{13}$C NMR (101 MHz, DMSO-$d_6$) δ=171.1, 167.8, 141.4, 128.4, 128.3, 126.1, 125.9, 95.4, 84.2, 59.6, 34.4, 26.2, 14.1. LRMS (ESI): calcd for $C_{15}H_{20}NO_3$ $[M+H]^+$, m/z 262.14; found, m/z 262.12.

4a: Yield: 110 mg (33%). $^1$H NMR (400 MHz DMSO-$d_6$): δ (ppm)=11.37 (d, J=11.1 Hz, 1H), 7.89 (dd, J=7.5, 1.7 Hz, 2H), 7.77-7.67 (m, 2H), 7.61 (dd, J=8.3, 6.8 Hz, 2H), 5.34 (d, J=8.8 Hz, 1H), 4.20 (q, J=7.1 Hz, 2H), 1.26 (t, J=7.1 Hz, 3H). $^{13}$C NMR (101 MHz, DMSO-$d_6$) δ=168.8, 163.6, 138.8, 133.2, 131.8, 129.2, 127.3, 97.1, 60.1, 14.1. LRMS (ESI): calcd for $C_{12}H_{14}NO_3$ $[M+H]^+$, m/z 220.10; found, m/z 220.12.

General Procedure B

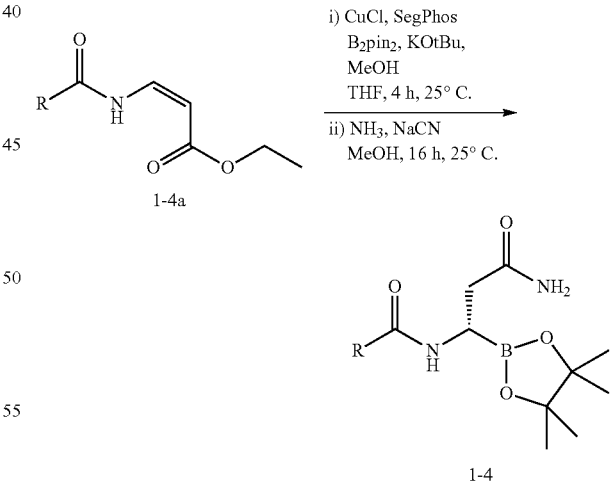

An oven-dried glass microwave vial or round bottom flask was charged with CuCl (2 mg, 0.02 mmol, 0.1 equiv), $B_2pin_2$ (56 mg, 0.22 mmol, 1.1 equiv), and SegPhos (13 mg, 0.022 mmol, 0.11 equiv, (S)-SegPhos was used for the preparation of 1, 2, 3, and 4, (R)-SegPhos was used for the preparation of 3-(R)). The vial was evacuated and backfilled with argon three times. Anhydrous THF (0.5 mL) was added followed by KOtBu (650 µL, 1 M solution in THF) and the mixture was stirred for 30 minutes at room temperature. A solution of the corresponding intermediate (1-4a) in THF was added (1 mL of a 0.2 M solution, 0.2 mmol, 1 equiv), followed by MeOH (32 μL, 0.8 mmol, 4 equiv), and the reaction was stirred for 4 hours at room temperature. The reaction was then concentrated in vacuo. The residue was taken up in 3:1 hexanes:EtOAc and filtered over a short plug of deactivated (35 wt % $H_2O$) silica. The filtrate was concentrated in vacuo in a round bottom flask with a stir bar. NaCN (2 mg, 0.04 mmol, 0.2 equiv) was added, followed by a solution of $NH_3$ in MeOH (7 M, 6 mL). The mixture was stirred at room temperature for 16 hours and then concentrated in vacuo and purified by flash chromatography using deactivated silica (35 wt % $H_2O$) and eluting with 0-20% MeOH in EtOAc.

1: Yield: 31.2 mg (50% over two steps) $^1$H NMR (400 MHz $CD_2Cl_2$): δ (ppm)=9.02 (s, 1H), 7.53 (s, 1H), 5.78 (s, 1H), 2.76 (t, J=6.3 Hz, 1H), 2.49-2.36 (m, 2H), 2.32 (d, J=7.6 Hz, 2H), 1.58 (q, J=7.5 Hz, 2H), 1.35-1.22 (m, 4H), 1.19-1.09 (m, 12H), 0.92-0.81 (m, 3H).j $^{13}$C NMR (101 MHz, $CD_2Cl_2$) δ (ppm)=179.5, 176.7, 80.7, 42.7 (br)*, 37.5, 31.7, 31.6, 25.6, 25.4, 25.3, 22.7, 14.2. $^{11}$B NMR (128 MHz, $CD_2Cl_2$) δ (ppm)=14.9 (br s). HRMS (ESI): calcd for $C_{15}H_{30}BN_2O_4$ [M+H]$^+$, m/z 313.2299; found, m/z 313.2230.

*the broad peak at 42.7 ppm in the $^{13}$C NMR spectrum of 1 corresponds to the carbon which is bound directly to the boron atom. Due to the line broadening effect of the quadrupolar boron nucleus, this signal is only visible after a very large number of scans and is not visible is the $^{13}$C NMR spectra of the other compounds reported here.

2: Yield: 11 mg (15% over two steps) $^1$H NMR (400 MHz $CDCl_3$): δ (ppm)=9.15 (s, 1H), 8.44 (s, 1H), 7.92-7.77 (m, 4H), 7.62-7.46 (m, 2H), 6.91 (s, 1H), 5.55 (s, 1H), 3.20-3.13 (m, 1H), 2.75-2.57 (m, 2H), 1.28 (m, 12H). $^{13}$C NMR (101 MHz, $CDCl_3$) δ (ppm)=176.5, 171.9, 135.8, 132.3, 130.4, 129.4, 128.9, 128.8, 127.9, 127.2, 123.6, 123.4, 80.6, 36.7, 25.5, 25.2. $^{11}$B NMR (128 MHz, $CDCl_3$) δ (ppm)=14.0 (br s). HRMS (ESI): calcd for $C_{20}H_{26}BN_2O_4$[M+H]$^+$, m/z 369.1986; found, m/z 369.1987.

3: Yield: 9.5 mg (13% over two steps) $^1$H NMR (400 MHz $CD_2Cl_2$): δ (ppm)=8.57 (s, 1H), 7.32-7.23 (m, 2H), 7.23-7.13 (m, 4H), 5.54 (s, 1H), 2.81 (t, J=6.4 Hz, 1H), 2.68-2.61 (m, 2H), 2.53-2.39 (m, 2H), 2.34 (t, J=7.6 Hz, 2H), 1.97-1.82 (m, 2H), 1.20-1.11 (m, 12H). $^{13}$C NMR (101 MHz, $CD_2Cl_2$) δ (ppm)=178.5, 176.2, 141.1, 128.6, 128.5, 126.2, 80.4, 36.8, 34.9, 30.6, 26.7, 25.1, 24.9. $^{11}$B NMR (128 MHz, $CD_2Cl_2$) δ (ppm)=15.4 (br s). HRMS (ESI): calcd for $C_{19}H_{30}BN_2O_4$ [M+H]$^+$, m/z 361.2299; found, m/z 361.2296.

3-(R): Yield: 12.3 mg (17% over two steps) $^1$H NMR (400 MHz $CD_2Cl_2$): δ (ppm)=8.48 (s, 1H), 7.36-7.23 (m, 2H), 7.23-7.13 (m, 3H), 7.02 (s, 1H), 5.48 (s, 1H), 2.81 (t, J=6.2 Hz, 1H), 2.67-2.61 (m, 3H), 2.52-2.38 (m, 2H), 2.38-2.27 (m, 2H), 2.00-1.88 (m, 2H), 1.22-1.12 (m, 12H). $^{13}$C NMR (101 MHz, $CD_2Cl_2$) δ (ppm)=178.5, 176.1, 141.2, 128.7, 128.6, 126.2, 80.4, 36.8, 34.9, 30.8, 26.8, 25.2, 24.9. $^{11}$B NMR (128 MHz, $CD_2Cl_2$) δ (ppm)=15.6 (br s). HRMS (ESI): calcd for $C_{19}H_{30}BN_2O_4$ [M+H]$^+$, m/z 361.2299; found, 361.2298 m/z.

4: Yield: 10 mg (16% over two steps) $^1$H NMR (400 MHz $CDCl_3$): δ (ppm)=6 8.84 (s, 1H), 7.89-7.82 (m, 2H), 7.61-7.52 (m, 1H), 7.48-7.38 (m, 2H), 6.67 (s, 1H), 5.46 (s, 1H), 3.14-3.06 (m, 1H), 2.70-2.51 (m, 2H), 1.24 (m, 12H). $^{13}$C NMR (101 MHz, $CDCl_3$) δ (ppm)=176.4, 171.8, 133.9, 128.9, 128.4, 126.7, 80.6, 36.5, 25.4, 25.1. $^{11}$B NMR (128 MHz, $CDCl_3$) δ (ppm)=16.2 (br s). HRMS (ESI): calcd for $C_{16}H_{24}BN_2O_4$ [M+H]$^+$, m/z 319.1829; found, m/z 319.1832.

SUPPLEMENTAL REFERENCES

1. Wiegand, I., Hilpert, K. & Hancock, R. E. W. Agar and broth dilution methods to determine the minimal inhibitory concentration (MIC) of antimicrobial substances. *Nature Protocols* 3, 163-175 (2008).
2. López, A., Clark, T. B., Parra, A. & Tortosa, M. Copper-Catalyzed Enantioselective Synthesis of β-Boron β-Amino Esters. Organic Letters 19, 6272-6275 (2017).

What is claimed herein is:

1. A method of inhibiting ClbP, the method comprising contacting ClbP in a sample or subject with one or more ClbP inhibitors having the structure of:

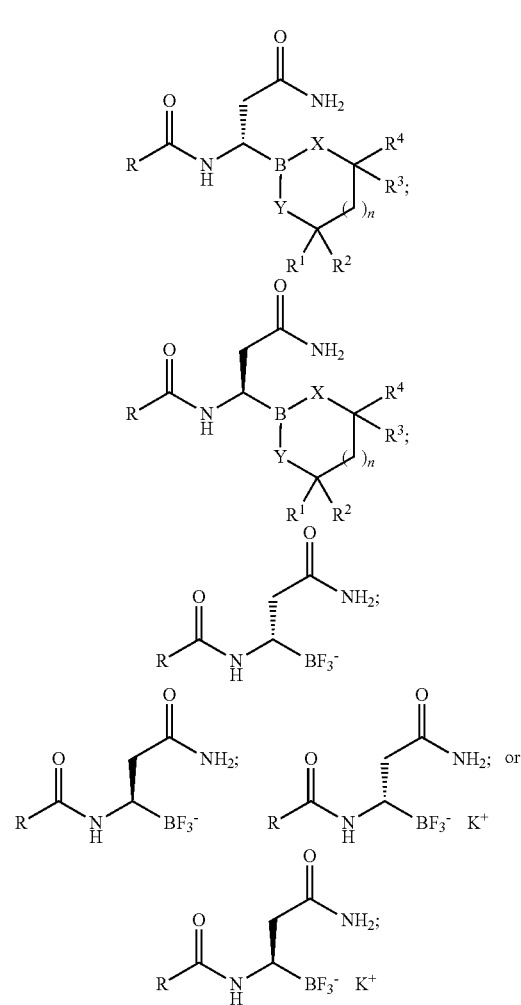

wherein R is selected from the group consisting of:

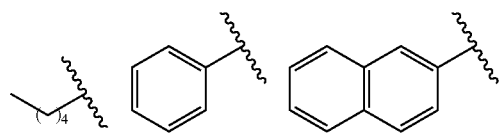

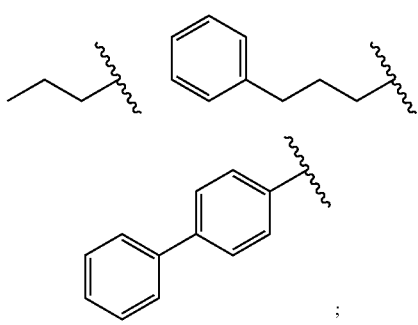

$R^1$, $R^2$, $R^3$ and $R^4$ independently are H, alkyl, alkenyl, alkynyl, aryl, heteroaryl, cycloalkyl or heterocycle, or $R^2$ and $R^3$, together with the carbons they are attached to, form an aryl, heteroaryl, cycloalkyl or heterocycle;

X and Y independently are O, S or NH; and n is 0, or 1; or

B)

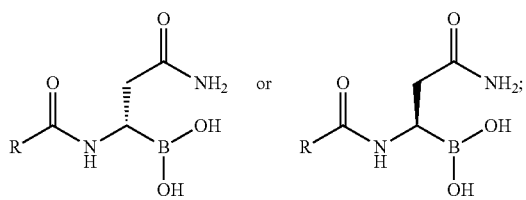

wherein R is selected from the group consisting of:

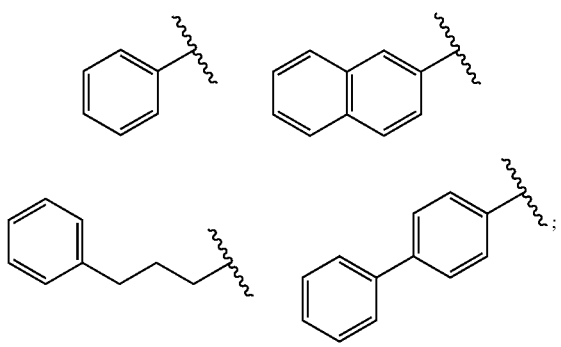

2. The method of claim 1, wherein the ClbP inhibitor has a structure selected from the following:

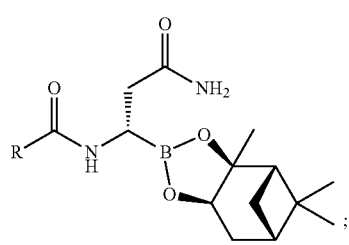

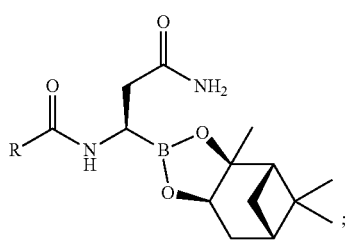

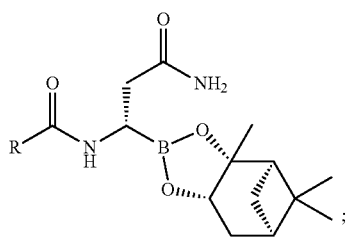

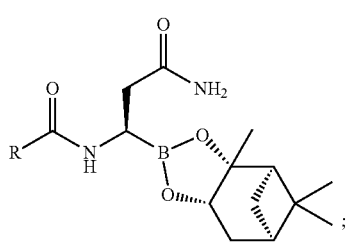

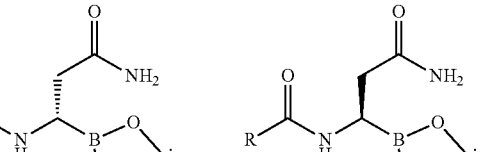

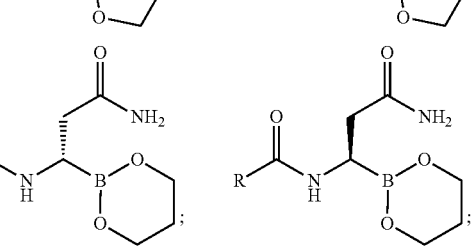

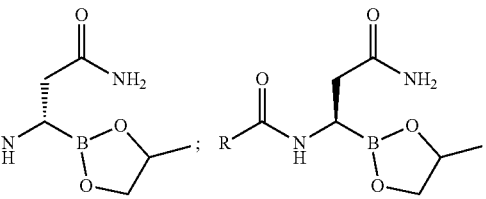

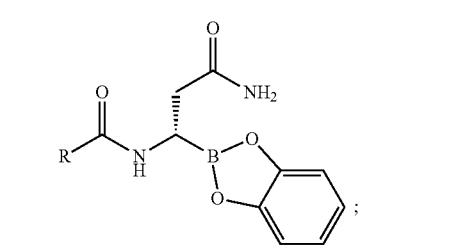

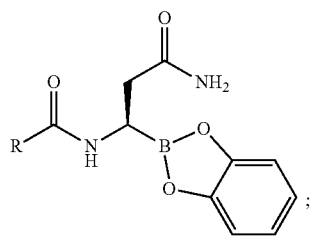
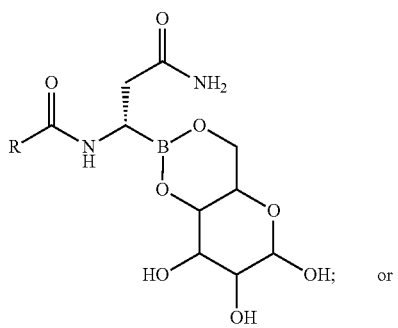
or
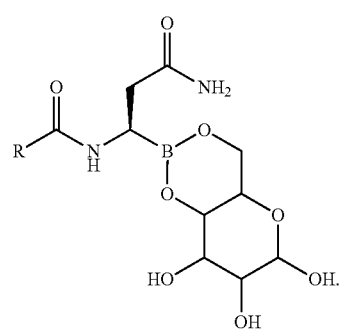
3. The method of claim 1, wherein the ClbP inhibitor has a structure selected from the following:
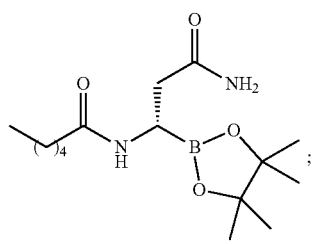
Hexanoyl-pinacolboro-Asn
(MRV03-037)
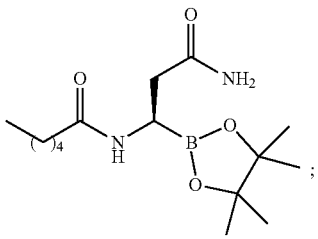
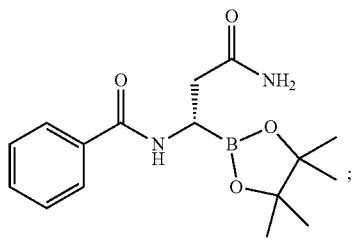
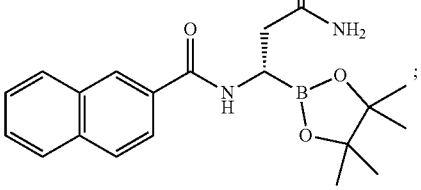
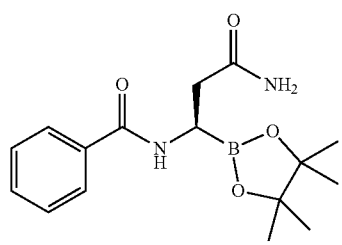
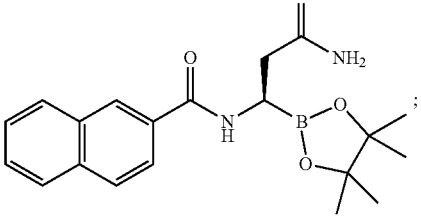
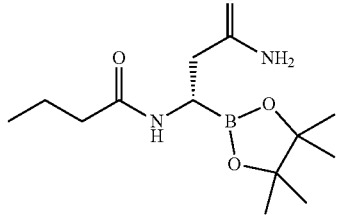
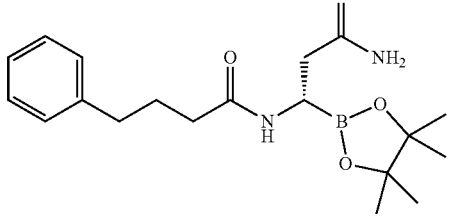
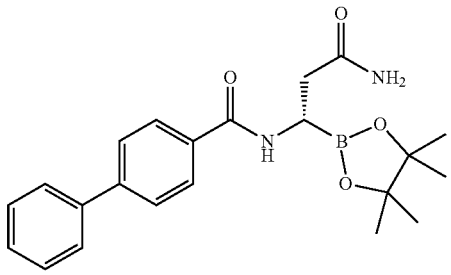

-continued
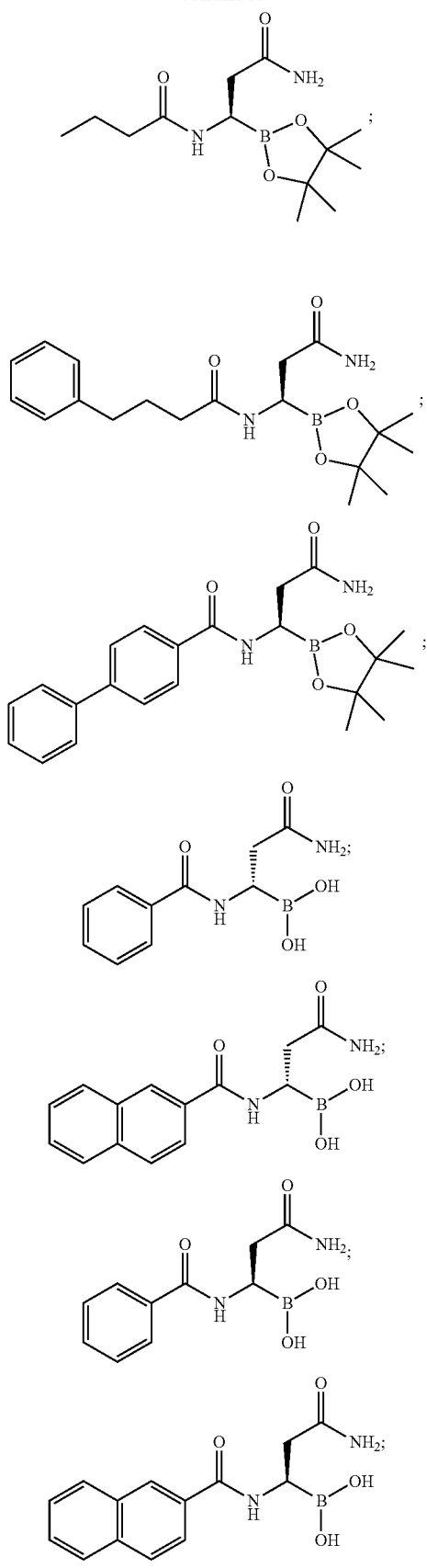
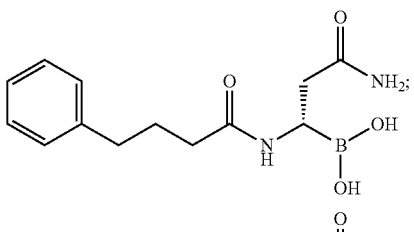
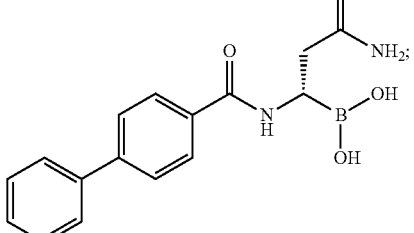
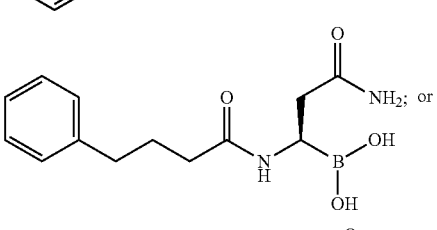
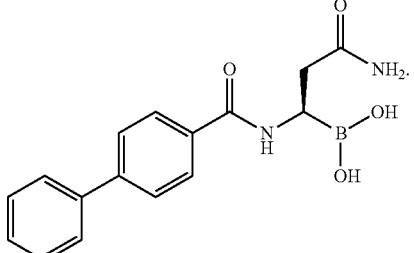
4. The method of claim 1, wherein the ClbP inhibitor has a structure selected from the following:
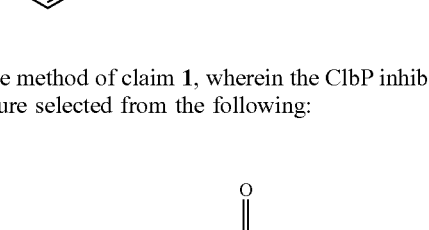
Hexanoyl-pinacolboro-Asn
(MRV03-037)
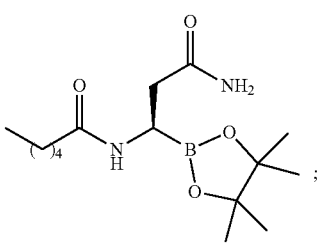

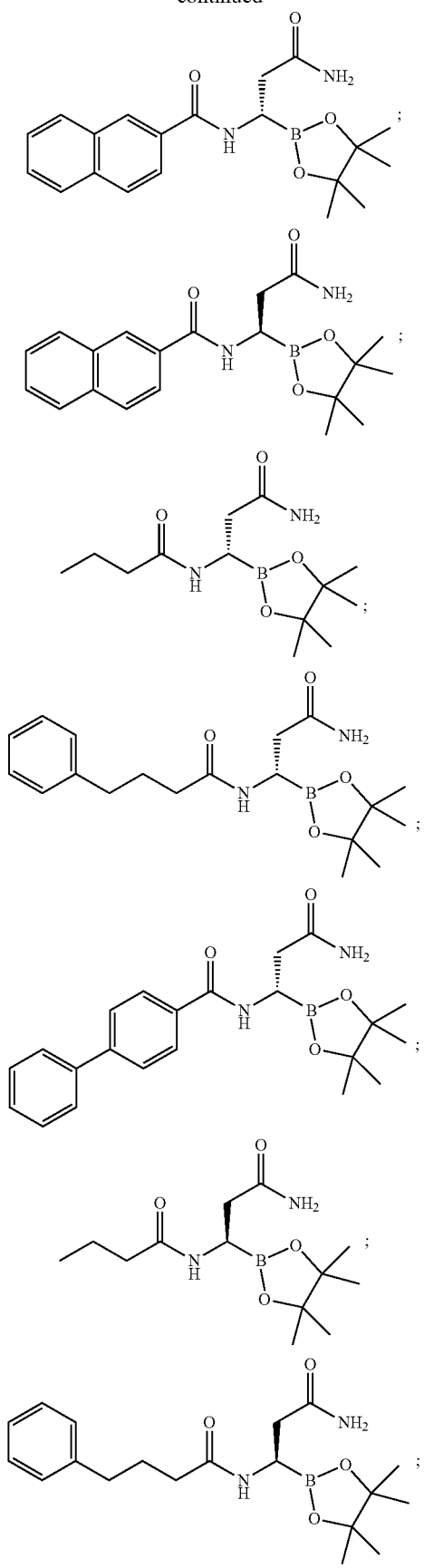
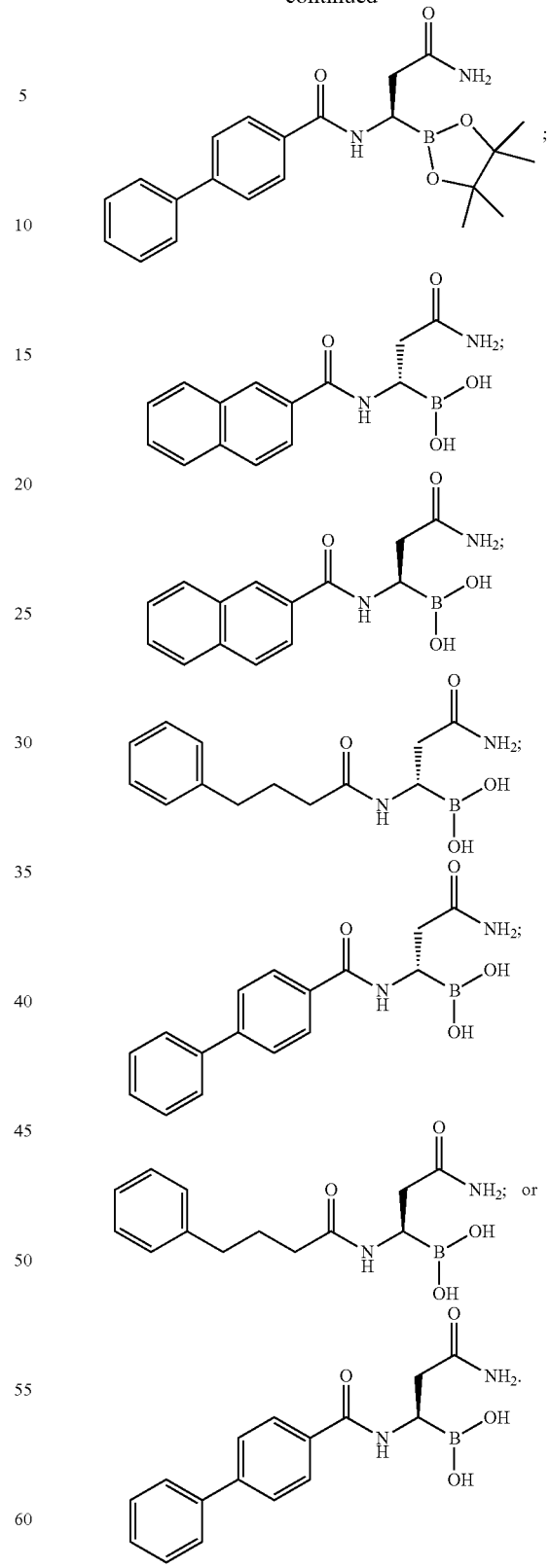
5. The method of claim 1, wherein contacting comprises administering the ClbP inhibitor to a subject.
6. The method of claim 5, wherein the subject has a population and/or infection of pks+bacteria.

7. The method of claim 6, wherein the bacteria is a Proteobacteria.

8. The method of claim 1, whereby the level of genotoxin in the sample or subject is reduced and/or the production of genotoxin in a sample or subject is inhibited.

9. The method of claim 8, wherein the genotoxin is colibactin.

10. The method of claim 1, whereby the risk and/or progression of cancer in the subject is reduced or inhibited.

11. The method of claim 10, wherein the cancer is colorectal cancer, a urinary tract cancer, a squamous cell carcinoma, an oral squamous cell carcinoma, or a head-and-neck cancer.

12. A method of treating a pks+bacterial infection or treating cancer in a subject in need thereof, the method comprising administering to the subject one or more ClbP inhibitors having the structure of:

A)

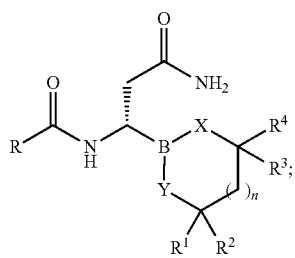

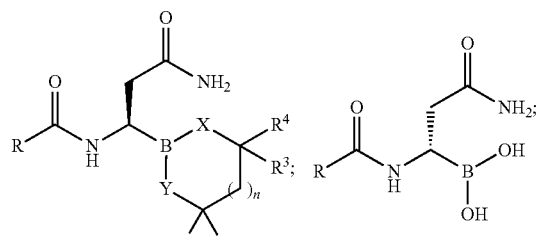

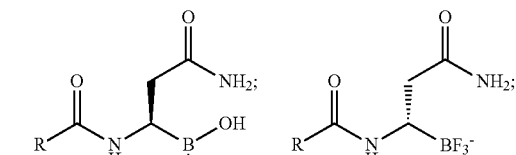

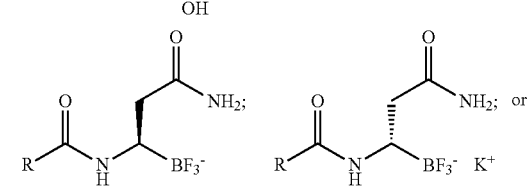

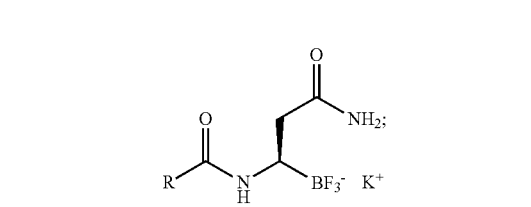

wherein R is selected from the group consisting of:

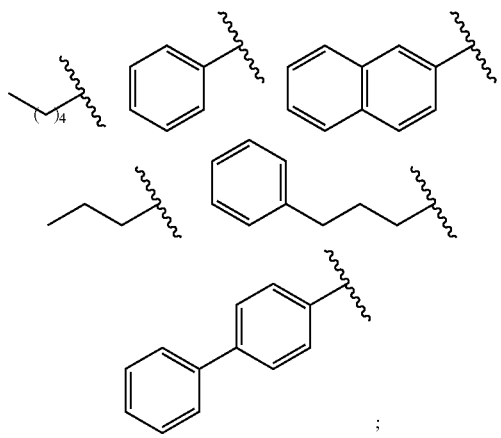

$R^1$, $R^2$, $R^3$ and $R^4$ independently are H, alkyl, alkenyl, alkynyl, aryl, heteroaryl, cycloalkyl or heterocycle, or $R^2$ and $R^3$, together with the carbons they are attached to, form an aryl, heteroaryl, cycloalkyl or heterocycle;

X and Y independently are O, S or NH; and n is 0, or 1; or

B)

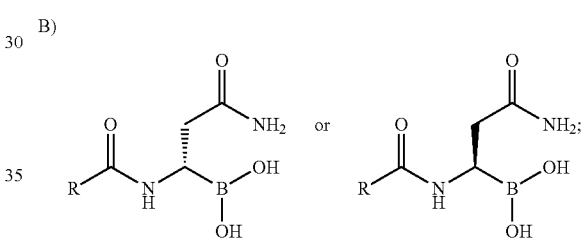

wherein R is selected from the group consisting of:

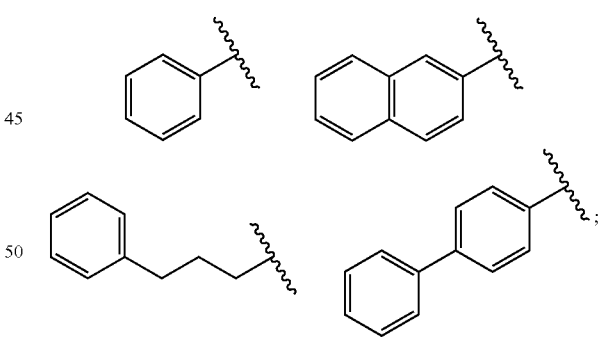

13. The method of claim 12, wherein the ClbP inhibitor has a structure selected from the following:

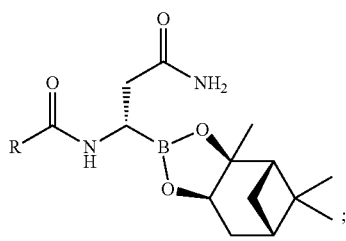

189
-continued
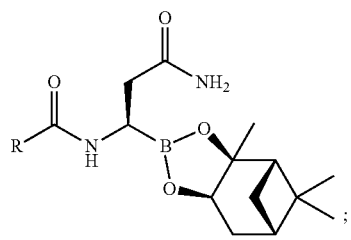
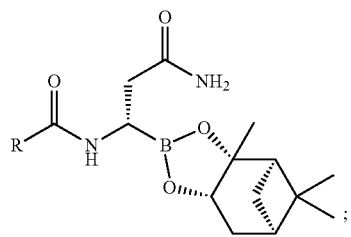
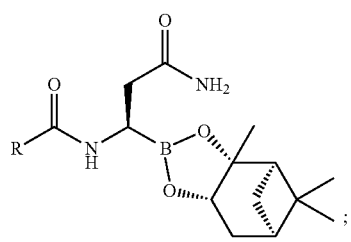
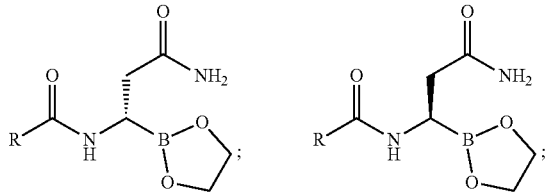
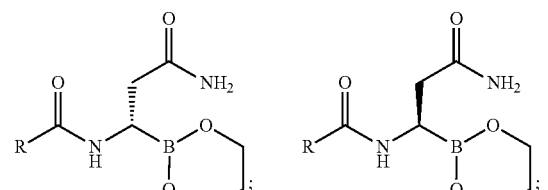
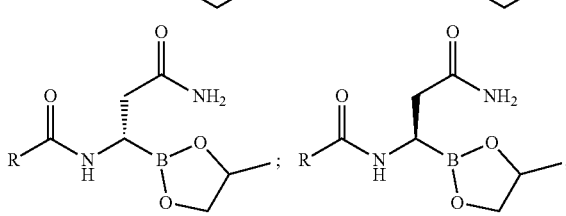
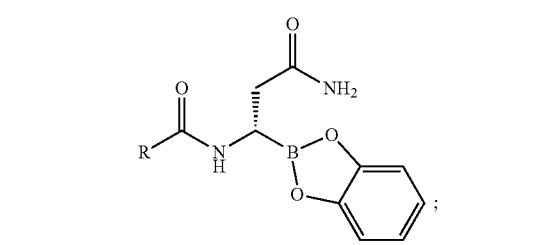
190
-continued
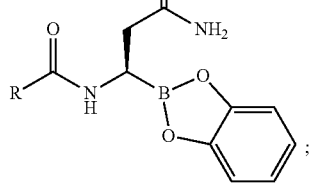
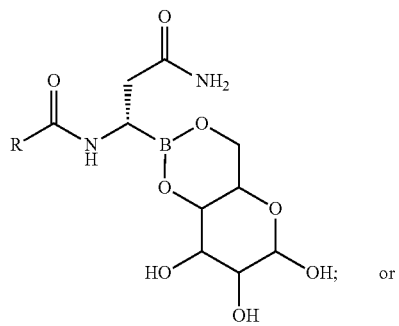
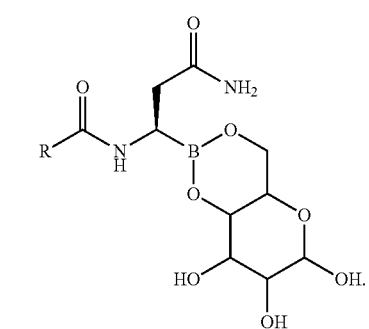
14. The method of claim 12, wherein the ClbP inhibitor has a structure selected from the following:
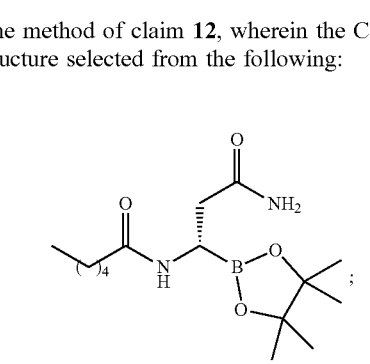
Hexanoyl-pinacolboro-Asn
(MRV03-037)
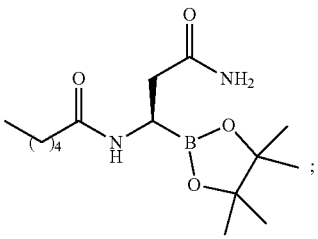

191
-continued
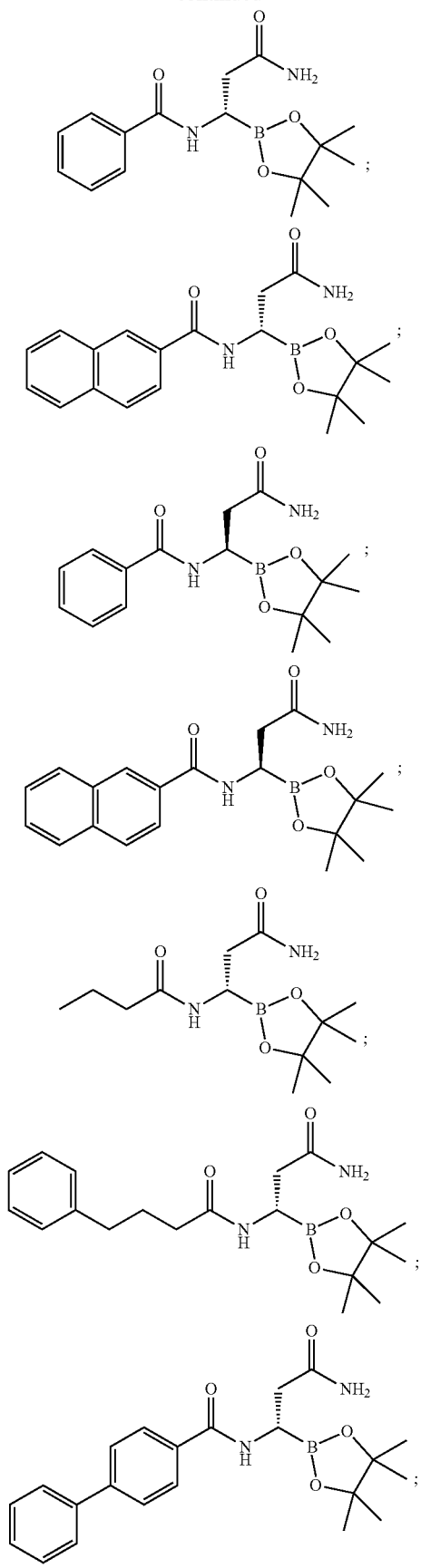
192
-continued
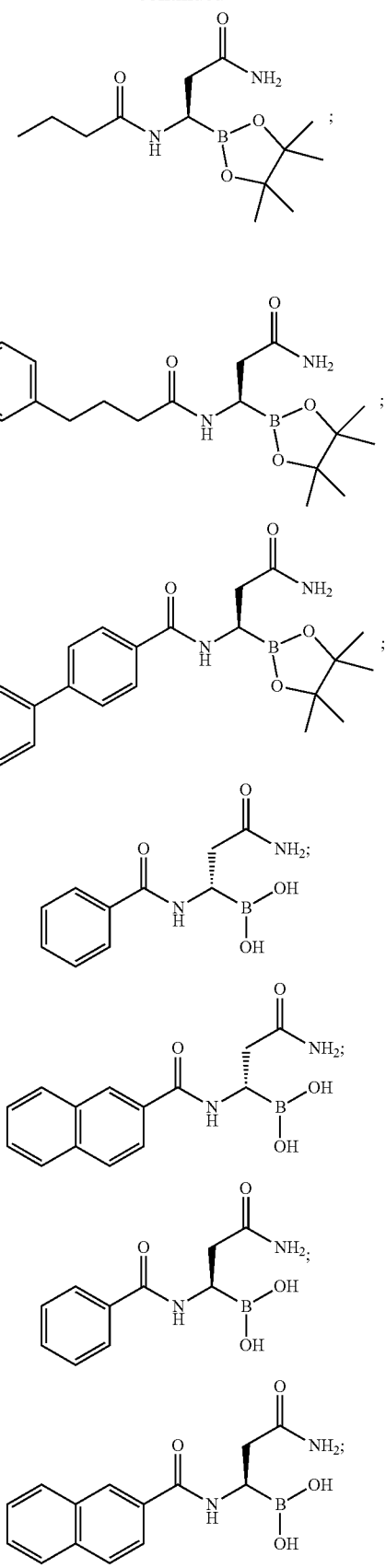

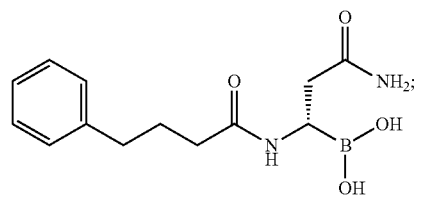
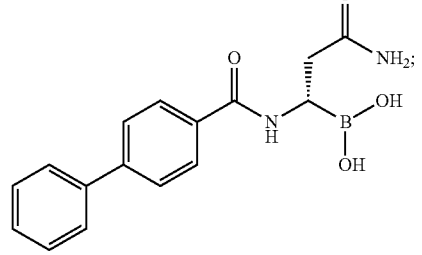
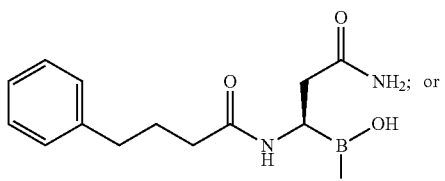
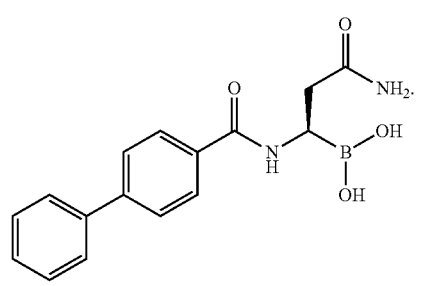
15. The method of claim 12, wherein the ClbP inhibitor has a structure selected from the following:
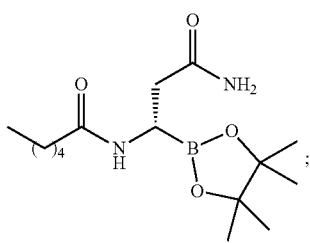
Hexanoyl-pinacolboro-Asn
(MRV03-037)
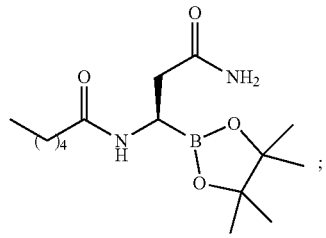
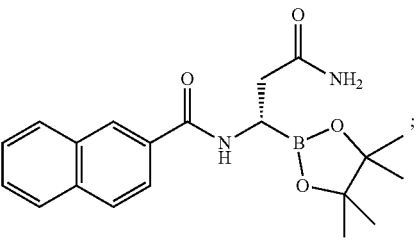
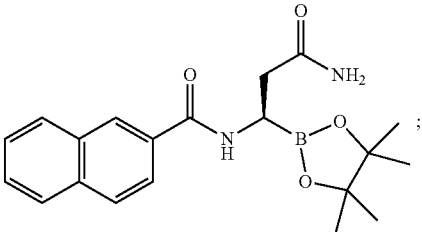
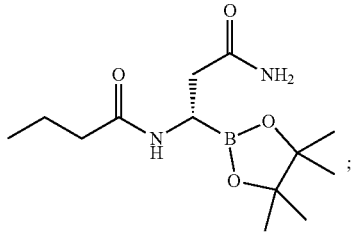
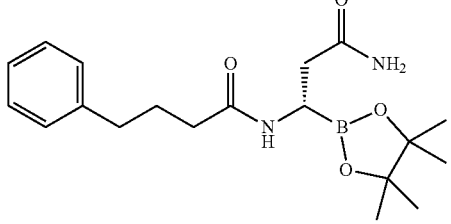
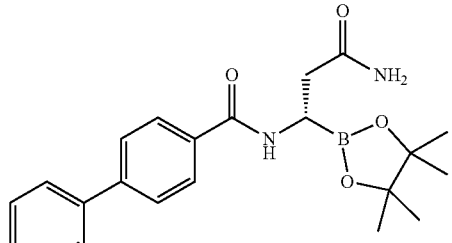
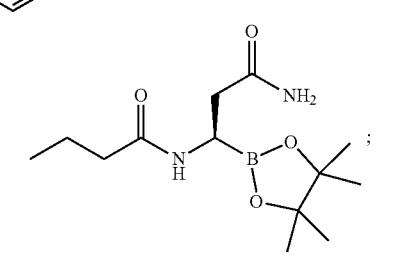
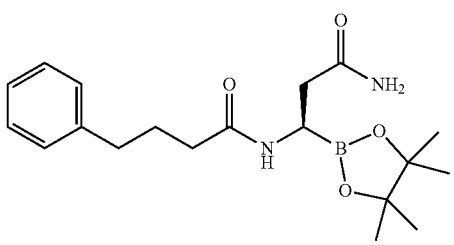

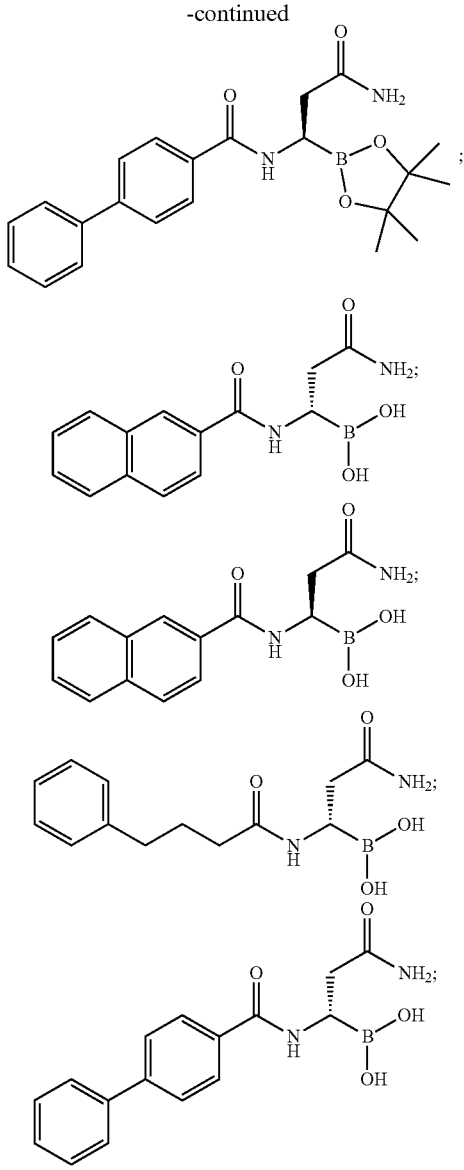

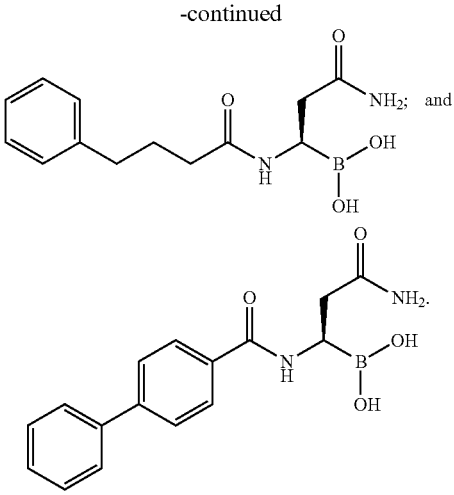

16. The method of claim 12, wherein the subject has a population and/or infection of pks+bacteria.

17. The method of claim 16, wherein the bacteria is a Proteobacteria.

18. The method of claim 12, whereby the level of genotoxin in the subject is reduced and/or the production of genotoxin in the subject is inhibited.

19. The method of claim 18, wherein the genotoxin is colibactin.

20. The method of claim 12, whereby the risk and/or progression of cancer in the subject is reduced or inhibited.

21. The method of claim 20, wherein the cancer is colorectal cancer, a urinary tract cancer, a squamous cell carcinoma, an oral squamous cell carcinoma, or a head-and-neck cancer.

22. The method of claim 7, wherein the Proteobacteria is *Citrobacter, Klebsiella,* Eshcerichia, or *E. coli*.

23. The method of claim 17, wherein the Proteobacteria is *Citrobacter, Klebsiella,* Eshcerichia, or *E. coli*.

* * * * *